US008715689B2

(12) United States Patent
Kinney et al.

(10) Patent No.: US 8,715,689 B2
(45) Date of Patent: May 6, 2014

(54) CHIMERIC WEST NILE/DENGUE VIRUSES

(75) Inventors: Claire Y. H. Kinney, Fort Collins, CO (US); Eric Thomas Beck, Whitefish Bay, WI (US); Richard M. Kinney, Fort Collins, CO (US)

(73) Assignee: The United States of America as represented by the Secretary of the Department of Health and Human Services, Centers for Disease Control and Prevention, Atlanta, GA (US)

( * ) Notice: Subject to any disclaimer, the term of this patent is extended or adjusted under 35 U.S.C. 154(b) by 515 days.

(21) Appl. No.: 12/990,322

(22) PCT Filed: Apr. 27, 2009

(86) PCT No.: PCT/US2009/041824
§ 371 (c)(1),
(2), (4) Date: Oct. 29, 2010

(87) PCT Pub. No.: WO2009/134717
PCT Pub. Date: Nov. 5, 2009

(65) Prior Publication Data
US 2011/0150771 A1 Jun. 23, 2011

Related U.S. Application Data

(60) Provisional application No. 61/049,342, filed on Apr. 30, 2008.

(51) Int. Cl.
*A61K 39/295* (2006.01)
*A61K 48/00* (2006.01)

(52) U.S. Cl.
USPC .................................. 424/202.1; 424/218.1

(58) Field of Classification Search
None
See application file for complete search history.

(56) References Cited

U.S. PATENT DOCUMENTS

| | | | |
|---|---|---|---|
| 6,682,883 B1 | 1/2004 | Monath et al. | |
| 6,696,281 B1 | 2/2004 | Chambers et al. | |
| 7,094,411 B2 | 8/2006 | Kinney et al. | |
| 7,641,909 B2 | 1/2010 | Kinney et al. | |
| 2007/0269458 A1 | 11/2007 | Guirakhoo et al. | |
| 2010/0255030 A1 | 10/2010 | Kinney et al. | |

FOREIGN PATENT DOCUMENTS

| | | |
|---|---|---|
| WO | WO 96/40933 | 12/1996 |
| WO | WO 03/059384 | 7/2003 |
| WO | WO 2006/116182 | 11/2006 |

OTHER PUBLICATIONS

Boroughs et al., "Fast Growth Dengue-Like Chimeric Viruses," *American Society of Tropical Medicine and Hygiene*, Annual Meeting, 2010.
Higgs et al., "Growth characteristics of chimerivax-den vaccine viruses in *Aedes aegypti* and *Aedes albopictus* from Thailand," *Am. J. Trop. Med. Hyg.*, vol. 75, No. 5, pp. 986-993, 2006.
Ishikawa et al., "Construction and evaluation of a chimeric pseudoinfectious virus vaccine to prevent Japanese encephalitis," *Vaccine*, vol. 26, pp. 2772-2781, 2008.
Kinney et al., "Avian virulence and Thermostable replication of the North American strain of *West Nile virus*," *Journal of General Virology*, vol. 87, pp. 3611-3622, 2006.
Arroyo et al., "ChimeriVax-West Nile Virus Live-Attenuated Vaccine: Preclinical Evaluation of Safety, Immunogenicity, and Efficacy," *Journal of Virology*, vol. 78, No. 22, pp. 12497-12507, 2004.
Beck et al., "Creation of a Chimeric West Nile Virus Containing Dengue-2 Pre-Membrane and Envelope Genes," *American Journal of Tropical Medicine and Hygiene*, vol. 79, No. 6. Suppl. S, p. 150, 2008.
Calvert et al., "Non-structural proteins of dengue 2 virus offer limited protection to interferon-deficient mice after dengue 2 virus challenge," *Journal of General Virology*, vol. 87, pp. 339-346, 2006.
Huang et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus," *Journal of Virology*, vol. 79, No. 12, pp. 7300-7310, 2005.
Mathenge et al., "Fusion PCR generated Japanese encephalitis virus/dengue 4 virus chimera exhibits lack of neuroinvasiveness, attenuated neurovirulence, and a dual-flavi immune response in mice," *Journal of General Virology*, vol. 85, pp. 2503-2513, 2004.
Pletnev et al., "West Nile virus/dengue type 4 virus chimeras that are reduced in neurovirulence and peripheral virulence without loss of immunogenicity or protective efficacy," *PNAS*, vol. 99, No. 5, pp. 3036-3041, 2002.
Suzuki et al., "Construction and Characterization of a Single-Cycle Chimeric Flavivirus Vaccine Candidate that Protects Mice against Lethal Challenge with Dengue Virus Type 2," *Journal of Virology*, vol. 83, No. 4, pp. 1870-1880, 2009.

*Primary Examiner* — Bao Li
(74) *Attorney, Agent, or Firm* — Klarquist Sparkman, LLP

(57) ABSTRACT

The disclosure provides chimeric West Nile/Dengue viruses comprising non-coding regions, non-structural proteins, and a C protein from a West Nile virus and prM and E proteins from a Dengue virus. Also disclosed are methods of using the chimeric viruses in diagnosis of Dengue viral infection, assessment of candidate Dengue virus vaccine efficacy, and production of Dengue prM and E proteins.

22 Claims, 9 Drawing Sheets

```
                                                                    (SEQ ID NO:  9)
                                                                    (SEQ ID NO: 10)

(SEQ ID NO: 11)
                                                                    (SEQ ID NO: 12)

(SEQ ID NO: 13)
                                                                    (SEQ ID NO: 14)
```

PrM Signal Sequence                    PrM Gene
               C gene                                              Signalase
D2 16681    AGACCAGA|TCTGCAGG-----------ATGATCATTATGCTGATTCCAACAGTGATGGCG|TTCCATTTAACCACACGTAACGGA
             R  R  R | S  A  G  -  -  -  M  I  I  M  L  I  P  T  V  M  A | F  H  L  T  T  R  N  G WN/D2       AAGAAAAGA|TCCGCGGGC-----------ATGATCATTATGCTGATTCCAACAGTGATGGCG|TTCCATTTAACCACACGTAACGGA
             K  K  R | S  A  G  -  -  -  M  I  I  M  L  I  P  T  V  M  A | F  H  L  T  T  R  N  G WN NY99     AAGAAAAGA|GGAGGAAAGACCGGAATTGCAGTAATGATTGGCCTGATCGCCAGCGTAGGAGCA|GTTACCCTCTCTAACTTCCAAGGG
             K  K  R | G  G  K  T  G  I  A  V  M  I  G  L  I  A  S  V  G  A | V  T  L  S  N  F  Q  G

FIG. 1

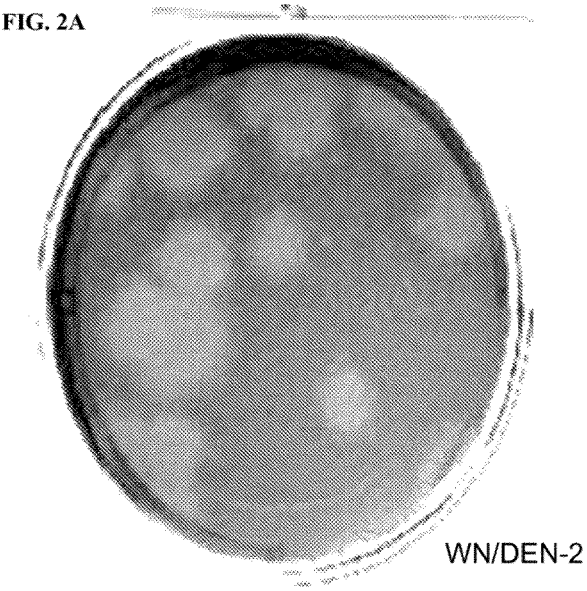
FIG. 2A  WN/DEN-2
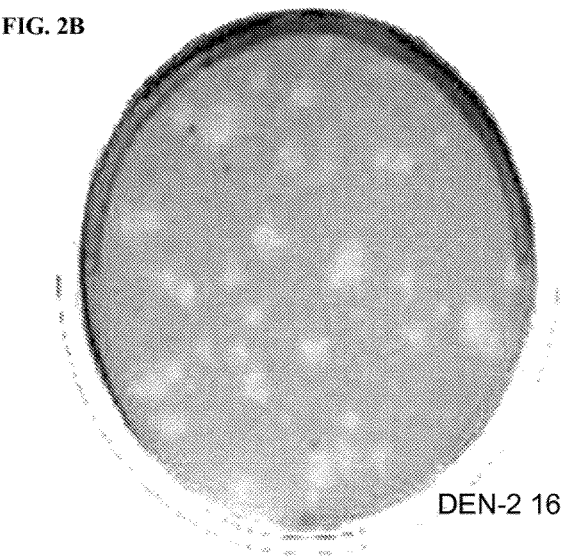
FIG. 2B  DEN-2 16681

```
        C gene    |          PrM Signal Sequence                          |   PrM Gene
WN/D1  AAGAAAAGA|TCCGTGACC---------------ATGCTCCTTATGCTGCTGCCCACAGCCCTGGCG|TTCCATCTGACGACAACGAGGGGA   (SEQ ID NO: 15)
        K  K  R | S  V  T  -  -  -  -  -  M  L  M  L  L  P  T  A  L  A  | F  H  L  T  T  R  G  G     (SEQ ID NO: 16)

WN/D3  AAGAAAAGA|ACATCGCTC---------------TGTCTCATGATGATGTTACCAGCAACACTTGCT|TTCCACTTAACTTCACGAGATGAA   (SEQ ID NO: 17)
        K  K  R | T  S  L  -  -  -  -  -  C  L  M  M  M  L  P  A  T  L  A| F  H  L  T  S  R  D  G    (SEQ ID NO: 18)

WN/D4  AAGAAAAGA|TCAACGATA---------------ACATTGCTGTGCTTGATTCCCACCGTAATGGCG|TTTCACTTGTCAACAAGAGATGGC   (SEQ ID NO: 19)
        K  K  R | S  T  I  -  -  -  -  -  T  L  L  C  L  I  P  T  V  M  A| F  H  L  S  T  R  D  G    (SEQ ID NO: 20)
```

FIG. 8

CHIMERIC WEST NILE/DENGUE VIRUSES

CROSS REFERENCE TO RELATED APPLICATIONS

This is the §371 U.S. National Stage of International Application No. PCT/US2009/041824, filed Apr. 27, 2009, which was published in English under PCT Article 21(2), which in turn claims the benefit of U.S. Provisional Application No. 61/049,342, filed Apr. 30, 2008, which is incorporated by reference herein in its entirety.

FIELD

The disclosure relates to chimeric flaviviruses, particularly chimeric West Nile virus/Dengue virus constructs. Further, it relates to methods of using these chimeras in diagnosis of flavivirus infection and assessing candidate Dengue virus vaccine efficacy.

BACKGROUND

Dengue virus (DENV) is the most important arboviral cause of morbidity and mortality throughout the world. There are currently 2.5 billion people living in dengue endemic regions with roughly 100 million annual cases of dengue fever and hundreds of thousands of cases of dengue hemorrhagic fever and dengue shock syndrome (Gubler, *Clin. Microbiol. Rev.* 11:480-496, 1998). No vaccines are currently commercially available against any of the four DENV serotypes (DENV 1-4) largely because vaccine production is hampered by the fact that neutralizing antibodies to one serotype do not effectively neutralize the remaining DENV serotypes (Halstead and O'Rourke, *J. Exp. Med.* 146:201-217, 1977). In fact, low levels of these antibodies may actually increase the risk for more severe disease during secondary infection due to a phenomenon known as antibody mediated enhancement, which occurs when antibodies against one DENV serotype bind in a non-neutralizing manner to DENV particles of another serotype. This binding allows increased infection of Fc receptor-bearing cells, such as macrophages, which can change the infection profile of the virus or cause a release of chemokines leading to dengue hemorrhagic fever or dengue shock syndrome (Halstead and O'Rourke, *J. Exp. Med.* 146:201-217, 1977).

West Nile virus (WNV) is a member of the Japanese encephalitis serocomplex in the genus Flavivirus, family Flaviviridae. Until the mid-1990s, WNV caused sporadic outbreaks of illness in Africa, the Middle East, and Western Asia. However, since 1996, WN encephalitis has been reported more frequently in Europe, the Middle East, northern and western Africa, and Russia. WNV emerged in the western hemisphere in 1999 and has become the leading cause of arboviral encephalitis in humans and equines in North America. There are two lineages of WNV. Lineage 1, of which the NY99 strain is a member, is the more virulent strain and is the predominant strain infecting humans and horses (Jordan et al., *Viral Immunol.* 13:435-446, 2000). There is currently no approved vaccine for WNV to protect at-risk human populations from WN illness.

SUMMARY

Disclosed herein are chimeric flaviviruses including non-coding regions, non-structural proteins, and a C protein from WNV, and at least a portion of a prM protein and E protein from DENV. In some embodiments, the chimera includes a first nucleic acid molecule including a 5' non-coding region, a nucleic acid encoding a C protein and non-structural proteins, and a 3' non-coding region from a West Nile virus and a second nucleic acid molecule operably linked to the first nucleic acid molecule, encoding at least a portion of a prM protein and E protein from a Dengue virus. In a particular example, the chimeric flavivirus includes nucleotide sequence(s) from DEN2 virus.

Also disclosed are chimeric flaviviruses including non-coding regions and non-structural proteins from WNV and at least a portion of a C protein, prM protein, and E protein from DENV. In some embodiments, the chimera includes a first nucleic acid molecule including a 5' non-coding region, a nucleic acid encoding non-structural proteins, and a 3' non-coding region from a WNV and a second nucleic acid molecule operably linked to the first nucleic acid molecule, encoding at least a portion of a C protein, a prM protein, and an E protein from a DENV.

In some examples, the chimeric flavivirus includes at least one nucleic acid or amino acid substitution which improves chimera characteristics (such as increased replication in cell culture or decreased infectivity or transmissibility in mosquitoes). In particular examples, the amino acid substitution is in the DENV prM protein, DENV E protein, WNV NS2A protein, or WNV NS4B protein. In additional examples, the chimeric flavivirus includes at least one nucleotide substitution in the 5' or 3' non-coding region.

In further examples, the chimeric flavivirus includes at least one amino acid substitution in the DENV E protein, wherein the substituted E protein exhibits measurably reduced antibody cross-reactivity.

Also disclosed herein are methods of using the chimeric flaviviruses in diagnosis of flavivirus infection. In a particular embodiment, the method includes detecting Dengue virus antibody in a sample, including contacting a sample from a subject with a chimeric flavivirus disclosed herein and detecting formation of an antibody-virus complex. In some embodiments methods of use of the chimeric flavivirus to evaluate efficacy of candidate Dengue virus vaccines are disclosed. Also disclosed are methods of producing Dengue virus structural proteins utilizing the chimeric flaviviruses described herein.

The foregoing and other features of the invention will become more apparent from the following detailed description, which proceeds with reference to the accompanying figures.

BRIEF DESCRIPTION OF THE DRAWINGS

FIG. 1 is a schematic diagram of a WN/DEN2 chimeric flavivirus. The chimera contains the prM signal sequence (between the NS2B-3 protease and signalase cleavage sites, arrow and triangle, respectively), prM, and E proteins of the DEN2 16681 virus in the WN NY99 virus backbone. The enlarged sequence alignment shows the SacII restriction site (underlined) that was introduced in the cDNA clone to create the splice site to engineer the chimera. The mutations introduced to create the SacII site do not change the DEN2 amino acid sequence.

FIGS. 2A and 2B show the plaque phenotype of virus seed recovered from C6/36 cells. The amplified virus seed was plated on Vero cells to visualize plaques. FIG. 2A shows plaques formed by the chimeric WN/DEN2 virus on day 8 post-infection (p.i). FIG. 2B shows plaques formed by DEN2 16681 virus on day 8 p.i.

FIG. 8 is a schematic diagram of a WN/DEN chimeric flavivirus. The chimera contains the prM signal sequence from the indicated DEN virus (between the NS2B-3 protease and signalase cleavage sites, arrow and triangle, respectively), and prM and E proteins of the DEN virus in the WN NY99 virus backbone. The enlarged sequence alignment shows junction between the WNV C protein and the DENV prM signal sequence in the WN/DEN1, WN/DEN3, and WN/DEN4 chimeras.

SEQUENCE LISTING

Figure 3A:
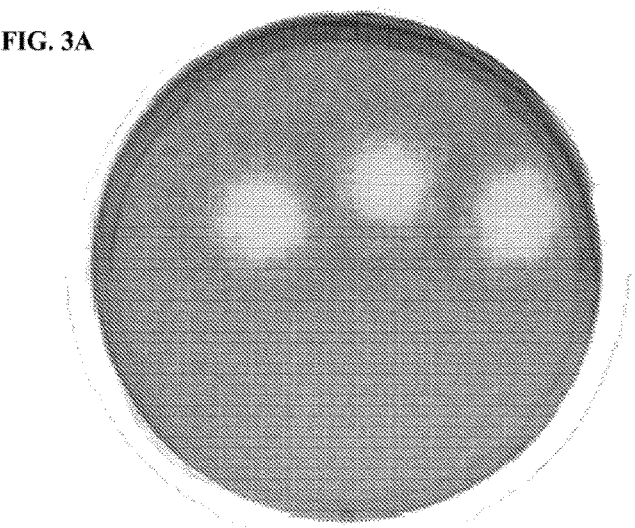
FIGS. 3A to 3F show the plaque phenotype of virus recovered from C6/36 cells or Vero cells on day 5 p.i. at the indicated passages. (A) wild type WNV NY99 (LLC-MK2-1); (B) wild type DEN2 16681 (C6-1); (C) WN/DEN2 (C6-1); (D) WN/DEN2 (C6-1/V-2); (E) WN/DEN2 (V-3); (F) WN/DEN2 (V-10).
Figure 3B:
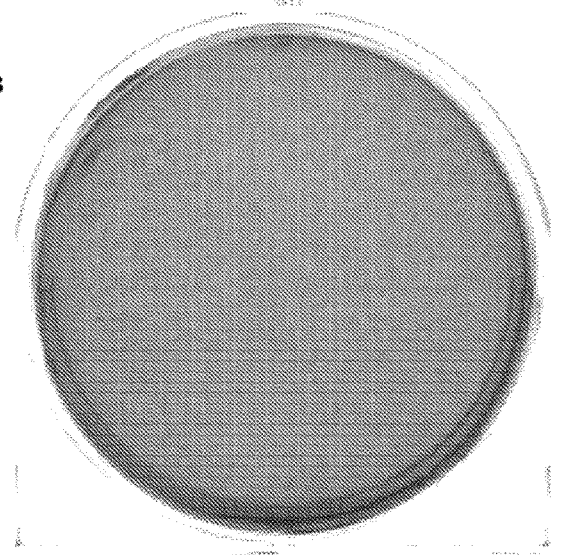
Figure 3C:
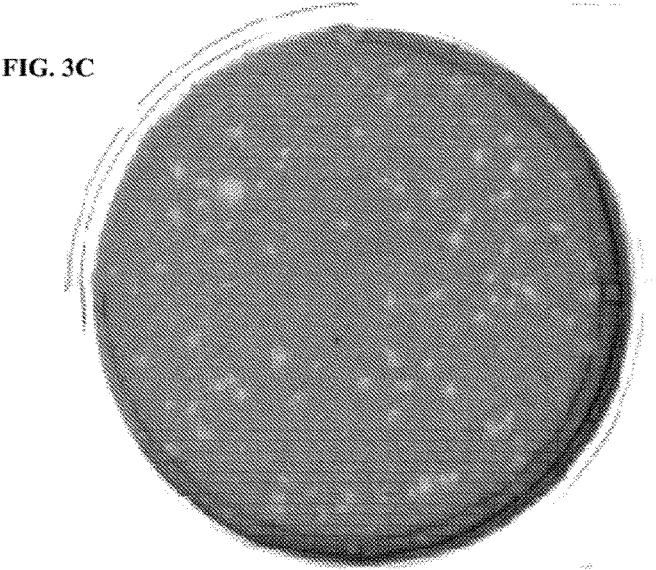
Figure 3D:
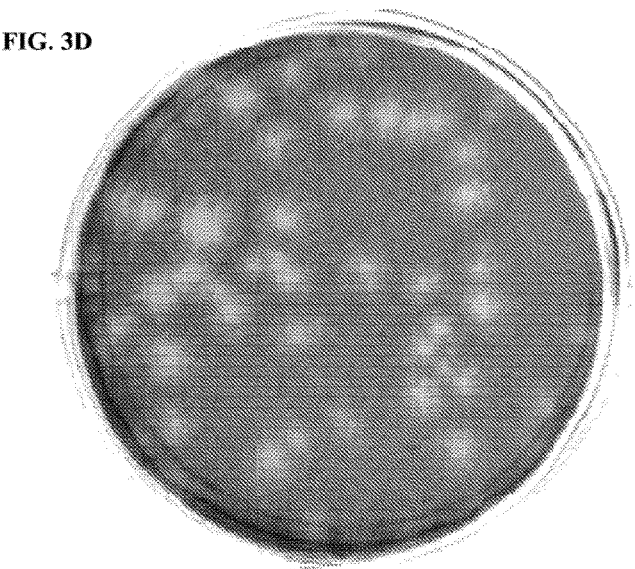
Figure 3E:
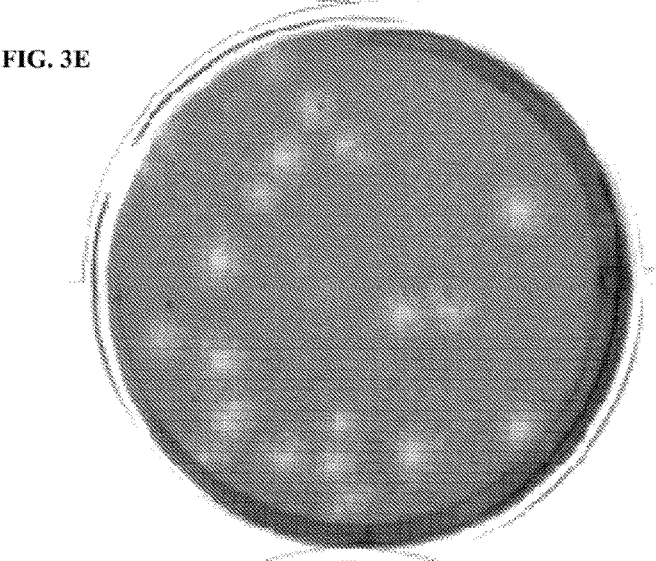
Figure 3F:
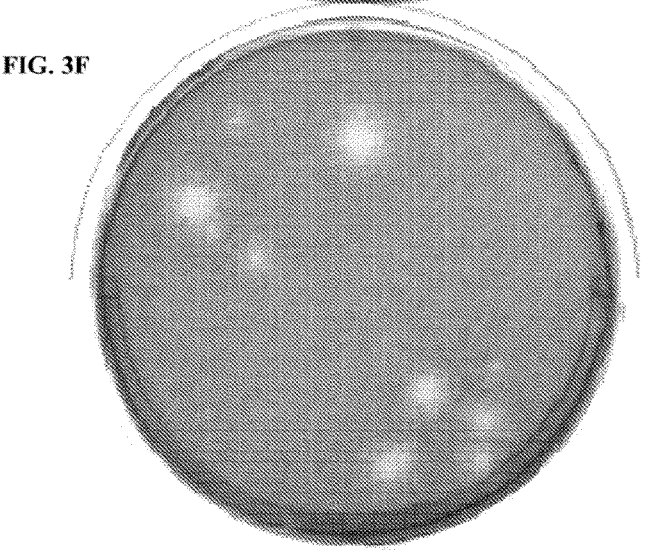

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 22, 2010, and is 339,010 bytes, which is incorporated by reference herein.

SEQ ID NOs: 1 and 2 show the nucleic acid and amino acid sequences, respectively, of a recombinant West Nile/Dengue-2 chimera WN/DEN2. The start and stop positions of the particular genes and proteins of the chimera are shown in Table 1.

SEQ ID NOs: 3 and 4 show the nucleic acid and amino acid sequences, respectively, of a recombinant West Nile/Dengue-1 chimera. The start and stop positions of the particular genes and proteins of this chimera are shown in Table 1.

SEQ ID NOs: 5 and 6 show the nucleic acid and amino acid sequences, respectively, of a recombinant West Nile/Dengue-3 chimera. The start and stop positions of the particular genes and proteins of the chimera are shown in Table 2.

SEQ ID NOs: 7 and 8 show the nucleic acid and amino acid sequences, respectively, of a recombinant West Nile/Dengue-4 chimera. The start and stop positions of the particular genes and proteins of this chimera are shown in Table 1.

TABLE 1

Start and stop positions of NCRs, structural proteins and nonstructural proteins in WN/DEN2, WN/DEN1, and WN/DEN4 chimeras

| Region | Nucleotide start/stop position (SEQ ID NOs: 1, 3, and 7) | Amino acid start/stop position (SEQ ID NOs: 2, 4, and 8) |
|---|---|---|
| 5' NCR | 1-96 | — |
| C | 97-453 | 1-119 |
| prM | 454-951 | 120-285 |
| M | 727-951 | 211-285 |
| E | 952-2436 | 286-780 |
| NS1 | 2437-3492 | 781-1132 |
| NS2A | 3493-4185 | 1133-1363 |
| NS2B | 4186-4578 | 1364-1494 |
| NS3 | 4579-6435 | 1495-2113 |
| NS4A | 6436-6882 | 2114-2262 |
| NS4B | 6883-7647 | 2263-2517 |
| NS5 | 7648-10362 | 2518-3422 |
| 3' NCR | 10363-10996 | — |

TABLE 2

Start and stop positions of NCRs, structural proteins and nonstructural proteins in SEQ ID NOs: 5 and 6. (WN/DEN3 chimera)

| Region | Nucleotide start/stop position (SEQ ID NO: 5) | Amino acid start/stop position (SEQ ID NO: 6) |
|---|---|---|
| 5' NCR | 1-96 | — |
| C | 97-453 | 1-119 |
| prM | 454-951 | 120-285 |
| M | 727-951 | 211-285 |
| E | 952-2430 | 286-778 |
| NS1 | 2431-3486 | 779-1130 |
| NS2A | 3487-4179 | 1131-1361 |
| NS2B | 4180-4572 | 1362-1492 |
| NS3 | 4573-6429 | 1493-2111 |
| NS4A | 6430-6876 | 2113-2260 |
| NS4B | 6877-7641 | 2261-2515 |
| NS5 | 7642-10356 | 2516-3420 |
| 3' NCR | 10357-10990 | — |

SEQ ID NOs: 9 and 10 show the nucleic acid and amino acid sequences, respectively, of the C protein/prM junction in a wild type DEN2 16681 virus.

SEQ ID NOs: 11 and 12 show the nucleic acid and amino acid sequences, respectively, of the WN/DEN2 chimeric virus.

SEQ ID NOs: 13 and 14 show the nucleic acid and amino acid sequences, respectively, of the C protein/prM junction in a wild type WN NY99 virus.

SEQ ID NOs: 15 and 16 show the nucleic acid and amino acid sequences, respectively, of the WN/DENT chimeric virus.

SEQ ID NOs: 17 and 18 show the nucleic acid and amino acid sequences, respectively, of the WN/DEN3 chimeric virus.

SEQ ID NOs: 19 and 20 show the nucleic acid and amino acid sequences, respectively, of the WN/DEN4 chimeric virus.

DETAILED DESCRIPTION

Lack of an ideal DEN animal model is a major obstacle in vaccine and therapeutic development for DENV. Immunocompetent outbred mice do not succumb to wild type DENV infection, so typical markers of protection, such as lethality and viremia, are not evident in mice after wild type DENV challenge. Transgenic and inbred mice have been used for DENV mouse models, but these animals are usually high cost, difficult to work with, and are not realistic for high-throughput or multiple dose experiments. Many animals are susceptible to WNV infection, and outbred mice, such as Swiss Webster and NIH Swiss, succumb to wild type WNV infection. Sickness, lethality, and viremia level have been successfully used as protection markers in WNV research using small animal models such as, mice, hamsters, and birds. Thus, chimeric WN/DEN viruses disclosed herein may be virulent and/or generate significant viremia in mice, therefore they can be used as the challenge dose to assess the efficacy of DENV candidate vaccines.

In addition, although both DENV and WNV are flaviviruses, DENV replicates much more slowly and to lower titers than WNV in cell cultures. This makes development of diagnostic viral antigen production and diagnostic tests for DENV more difficult than for WNV. The chimeric WN/DEN viruses described herein contain DENV antigenic structures on the surface of the virus particles while retaining certain WNV replication features (such as replication to high titer). The disclosed chimeras can thus be used as a DEN-like surrogate virus for testing DENV candidate vaccine efficacy and for development of faster or more effective DENV diagnostics.

I. Abbreviations

DEN: Dengue
DENY: Dengue virus
E: envelope glycoprotein
ELISA: enzyme-linked immunosorbent assay
HMAF: hyperimmune mouse ascitic fluid
IFA: immunofluorescence antibody assay
mAb: monoclonal antibody
MOI: multiplicity of infection
NCR: non-coding region
pfu: plaque forming unit
p.i.: post-infection
prM: premembrane protein
PRNT: plaque reduction neutralization test
$VD_{50}$: 50% virulent dose
WN: West Nile
WNV: West Nile virus
WN/DEN: West Nile/Dengue virus chimera II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

In one example, antibody binding affinity is measured by end-point titration in an Ag-ELISA assay. Antibody binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a flavivirus E protein.

Chimera: A molecule (e.g., gene, transcript or protein) composed of parts that are of different origin (such as at least two nucleic acid or amino acid sequences) that, while typically unjoined in their native state, are joined or linked to form a single continuous molecule. A chimera may include nucleotide or amino acid sequences that are joined end-to-end (for example, the amino-terminus of one sequence is joined to the carboxyl-terminus of a second sequence) or may include a sequence from one molecule that is embedded within that of another molecule (for example, the amino-terminus and carboxyl-terminus of the chimera are from one molecule, while an intervening sequence comes from another molecule).

A chimera may include a chimeric protein, for example a protein that is composed of amino acid sequences from more than one protein. A chimera may also include a chimeric nucleic acid sequence composed of nucleic acid sequences from more than one source, such as a chimeric nucleic acid which encodes a chimeric protein. In other examples, a chimera may include a chimeric genome, such as a flavivirus genome, which is composed of sequences from two or more flaviviruses. For example, a chimeric flavivirus genome may comprise nucleic acid sequences from more than one flavivirus genome, such as a West Nile virus and a Dengue virus. In some examples, a chimeric flavivirus includes nucleic acid sequences encoding one or more proteins from a first flavivirus and nucleic acid sequences encoding one or more proteins from a second flavivirus. In particular examples, a chimeric flavivirus is composed of a nucleotide sequence encoding the non-structural proteins and a C protein from a West Nile virus genome linked to a nucleotide sequence encoding at least a portion of a prM protein and E protein from a Dengue virus genome (such as DENT, DEN2, DEN3, or DEN4).

Conservative substitution: A substitution of one amino acid residue in a protein sequence for a different amino acid residue having similar biochemical properties. Typically, conservative substitutions have little to no impact on the activity of a resulting polypeptide. For example, ideally, a flavivirus protein (such as a prM, E, or non-structural protein) including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by infecting cells with a virus containing a variant protein and determining ability to replicate (for example as described in Example 2), by producing virus containing a variant protein and determining its neurovirulence or neuroinvasion properties (as described in Example 6), or by testing antibody cross-reactivity (as described in Example 10).

Envelope glycoprotein (E protein): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Flavivirus cross-reactive antibody: An antibody that recognizes (that is, specifically binds to) an epitope found on a peptide from more than one species of flavivirus. Flavivirus cross-reactive antibodies are classified as either complex cross-reactive or group cross-reactive antibodies. Complex cross-reactive antibodies recognize epitopes shared by all viruses within a complex, such as the JE virus complex or the DEN virus complex. Group cross-reactive antibodies recognize epitopes shared by all members of the genus Flavivirus.

Antibody cross-reactivity is further refined within the sub-complex and sub-group cross-reactive categories. Sub-complex cross-reactive antibodies recognize epitopes shared by most, but not all, members of a particular flavivirus complex (e.g., DEN-1, -2, and -3, but not DEN-4), while sub-group cross-reactive antibodies recognize epitopes shared by flaviviruses from several complexes, but not all members of the flavivirus group (e.g., all members of the DEN virus and JE virus complexes, but not all members of the tick-borne virus complex). Specific, non-limiting examples of flavivirus cross-reactive antibodies include the group cross-reactive mAbs 4G2 and 6B6C-1, the sub-group cross-reactive mAb 1B7-5, and the sub-complex cross-reactive mAb 10A1D-2. (see, e.g., Roehrig et al., *Virology* 246:317-28, 1998; Crill and Chang, *J. Virol.* 78:13975-13986, 2004).

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS 1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222: 159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B, with the function of NS2A remaining unknown. NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, PrM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., *The Togaviruses: Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Recombinant nucleic acid: A nucleic acid molecule that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (Gene, 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, at least 98%, or at least 99% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, 96%, 97%, 98%, or at least 99% depending on their similarity to the reference sequence. Sequence identity over such short windows can be determined using LFASTA; methods are described at the NCBI website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject: Living multi-cellular vertebrate organisms, a category that includes both human and non-human mammals (such as mice, rats, rabbits, sheep, horses, cows, and non-human primates).

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes. All GenBank Accession Nos. mentioned herein are incorporated by reference in their entirety. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. WN/DEN Chimeric Viruses

Disclosed herein are chimeric flaviviruses that include non-coding regions, non-structural proteins, and a C protein from WNV, and at least a portion of a prM protein and E protein from DENV. In some embodiments, the chimera includes a first nucleic acid molecule including a 5' non-coding region, a nucleic acid encoding a C protein and non-structural proteins, and a 3' non-coding region from a West Nile virus genome and a second nucleic acid molecule operably linked to the first nucleic acid molecule, encoding at least a portion of a prM protein and E protein from a Dengue virus genome. In particular examples, the nucleic acid molecules encoding the prM and E proteins of the WNV genome are replaced with molecules having the corresponding sequences from the DENV genome. In some examples, the prM signal sequence of the WNV C protein is also replaced with the prM signal sequence of the corresponding DENV genome.

Also disclosed are chimeric flaviviruses including non-coding regions and non-structural proteins from WNV and at least a portion of a C protein, prM protein, and E protein from DENV. In some embodiments, the chimera includes a first nucleic acid molecule including a 5' non-coding region, a nucleic acid encoding non-structural proteins, and a 3' non-coding region from a WNV genome and a second nucleic acid molecule operably linked to the first nucleic acid molecule, encoding at least a portion of a C protein, a prM protein, and an E protein from a DENV genome. In a particular example, the nucleic acid encoding the C, prM, and E proteins of the WNV genome are replaced with molecules having the corresponding sequences from the DENV genome.

In some examples disclosed herein, the WNV genome used in the chimera is derived from a particular WNV strain, such as NY99 or KEN-3829. Additional WNV strains are known in the art (see, e.g., Ebel et al. *Emerg. Infect. Dis.* 7:650-653, 2001; American Type Culture Collection (ATCC) catalog numbers VR-82, VR-1267, VR-1507, VR-1510). In particular examples, the WNV genome is WN/IC-P991 (such as GenBank Accession No. AF196835 (incorporated by reference as included in GenBank on Apr. 27, 2009) or with mutations as described in Kinney et al., *J. Gen. Virol.* 87:3611-3622, 2006).

WNV genome sequences are publicly available. For example, GenBank Accession Nos.: AF196835, AY278441, AF202541, AF404754, AF260967, AY660002, AF481864, AY268133, AF404757, AY268132, AF260969, AF317203, AY262283, AY490240, AF260968, AY603654, D00246, M12294, EU068667, AY765264, and AY277251 disclose WNV genomic nucleic acid sequences, all of which are incorporated by reference as included in GenBank on Apr. 27, 2009. In further examples, the WNV genome, or the non-coding regions, non-structural proteins, and/or C protein of the WNV genome are at least 95%, at least 96%, at least 97%, at least 98%, or at least 99% identical to a publicly available WNV genome sequence.

In the disclosed flavivirus chimeras, the DENV genome is from a Dengue 1 (DEN1), Dengue 2 (DEN2), Dengue 3 (DEN3), or Dengue 4 (DEN4) virus. In some examples, the DENV genome portion of the disclosed chimeras includes sequences from a single DENV genome, while in other examples, the DENV genome portion includes sequences from two or more DENV genomes. The DENV genome may be a wild type strain or an attenuated (or vaccine) strain. In some examples, the DENV genome is DEN2 (for example, wild type DEN2 16681 strain or attenuated DEN-2 PDK-53 strain), DEN1 (for example, wild type DEN1 16007 strain or attenuated DEN1 PDK-13 strain), DEN3 (for example, wild type DEN3 16562 strain or attenuated DEN3 PGMK-30/

FRhL-3) or DEN4 (for example, wild type DEN4 1036 or attenuated DEN4 PDK-48). Additional DENV strains are known in the art (see e.g., U.S. Pat. Nos. 5,939,254 and 6,793,488). In particular examples, the DENV genome is a wild type (non-attenuated) strain, for example DEN2 16681 (such as GenBank Accession No. U87411, incorporated by reference as included in GenBank on Apr. 27, 2009).

DENV sequences are publicly available. For example GenBank Accession Nos.: NC_001477, AF180817, and U88536 disclose DEN1 nucleic acid sequences; NC_001474 and U87411 disclose DEN2 nucleic acid sequences; NC_001475, AY099336, and AF317645 disclose DEN3 nucleic acid sequences; and NC_002640 and AF326825 disclose DEN4 nucleic acid sequences, all of which are incorporated by reference as included in GenBank on Apr. 27, 2009. In additional examples, the DENV genome (or the prM and/or E protein from the DENV genome) are at least 95%, at least 96%, at least 97%, at least 98%, or at least 99% identical to a publicly available DENV sequence.

In a particular embodiment, the chimeric flavivirus includes a nucleic acid molecule having a sequence including the 5' and 3' non-coding regions of the virus and encoding the non-structural proteins and C protein from a WN NY99 virus genome, operably linked to a nucleic acid molecule having a sequence encoding the prM signal sequence, the prM protein and the E protein from DEN2 16681 virus genome. In one example, the chimeric flavivirus is a WN/DEN2 chimera having the nucleic acid and amino acid sequence shown in SEQ ID NOs: 1 and 2, respectively. In additional examples, the disclosed chimeric virus has nucleic acid and amino acid sequences at least 95%, at least 96%, at least 97%, at least 98%, or at least 99% identical or more to the sequences disclosed in SEQ ID NOs: 1 and 2.

In other embodiments, the chimeric flaviviruses disclosed herein include a first nucleic acid molecule including the 5' and 3' non-coding regions and encoding the non-structural proteins and C protein from a WN NY99 virus genome operably linked to a second nucleic acid molecule encoding the prM and E proteins from a DEN1, DEN3, or DEN4 virus genome. In some examples, the second nucleic acid molecule encodes the prM signal sequence from a DEN1, DEN3, or DEN4 virus genome. Particular examples of WN/DEN1 (SEQ ID NOs: 3 and 4), WN/DEN3 (SEQ ID NOs: 5 and 6) and WN/DEN4 (SEQ ID NOs: 7 and 8) chimeras are disclosed herein. In additional examples, the disclosed chimeric viruses are at least 95%, at least 96%, at least 97%, at least 98%, or at least 99% identical or more to the sequences disclosed in SEQ ID NOs: 3-8.

The disclosed chimeric flaviviruses can readily be produced by replication in host cells in culture. Methods of producing viruses are well known in the art (see e.g. *Fields Virology*, Knipe and Howley, eds., Lippincott, Williams, and Wilkins, 2001; Flint et al., *Principles of Virology*, ASM Press, 2000). Host cell lines are preferably easy to infect with virus or transfect with viral genomic RNA, capable of stably maintaining foreign RNA with an unarranged sequence, and have the necessary cellular components for efficient transcription, translation, post-translation modification, virus assembly, and secretion of the protein or virus particle. Preferably, cells are those having simple media component requirements which can be adapted for growth in suspension culture. In some examples, the host cell line is a mammalian cell line that can be adapted to growth in low serum or serum-free medium. Suitable host cell lines include Vero (monkey), C6/36 (mosquito), BHK21 (hamster), LLC-MK2 (monkey) SK6 (swine), L292 (mouse), HeLa (human), HEK (human), 2fTGH cells (human), HepG2 (human), and PDK (dog). Suitable cell lines can be obtained from the American Type Culture Collection (ATCC), Manassas, Va.

In some examples, the disclosed chimeric WN/DEN viruses replicate in cell culture more rapidly that DEN viruses. For example, plaques formed by WN/DEN chimeric viruses may form on cell cultures (such as C6/36 or Vero cells) sooner than DEN viruses (such as at least one day, two days, three days, four days, or five days post-infection sooner). In other examples, WN/DEN chimeric viruses may form larger plaques than DEN viruses. For example, plaques formed by chimeric WN/DEN viruses disclosed herein may form plaques that are at least 25% larger to about 10 times larger than DEN viruses (such as at least 50% larger, two-fold, three-fold, four-fold, five-fold, or up to 10-fold larger).

IV. WN/DEN Chimeras and Variants Thereof

The disclosure also provides flavivirus chimeras having one or more nucleic acid or amino acid substitution, insertion, deletion, or combination thereof, such that the resulting chimera has improved characteristics. In some examples, the improved characteristic of the chimera including one or more substitution, insertion, and/or deletion includes, but is not limited to, increased virus titer, increased replication rate, increased plaque size, or increased stability in cell culture compared to a wild type virus. In additional examples, the improved characteristic of the chimera comprising one or more substitution, insertion, and/or deletion, includes increased infectivity or virulence in a subject (such as mice or non-human primates) or decreased infectivity or transmissibility in mosquitoes as compared to a wild type virus.

Manipulation of the nucleotide sequence of the disclosed chimeric flaviviruses using standard procedures, including for instance site-directed mutagenesis or PCR and M13 primer mutagenesis, can be used to produce variants with improved characteristics (such as increased virus titer or stability in cell culture). Details of these techniques are well known. For instances, protocols are provided in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The simplest modifications involve the substitution of one or more amino acids for amino acids having similar physiochemical and/or structural properties. These so-called conservative substitutions are likely to have minimal impact on the activity and/or structure of the resultant protein. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |

-continued

| Original Residue | Conservative Substitutions |
|---|---|
| Ser | Thr |
| Thr | Ser |
| Trp | Tyr |
| Tyr | Trp; Phe |
| Val | Ile; Leu |

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

In addition to targeted mutagenesis to produce variants of the disclosed WN/DENV chimeras, naturally occurring mutations may accrue upon passage in cell culture that result in variants, some with desirable characteristics. Nucleic acid and amino acid substitutions, insertions, or deletions that accrue in chimeric viruses during cell culture passages are readily determined by sequence analysis of the virus amplified from isolated plaques of the virus seed, and can be engineered into infectious clones to generate WN/DENV chimera variants that have improved characteristics (such as replication to high titer or production of uniform large plaques in cells). Consistent mutations identified from multiple seeds or isolated plaques are one indication of a desirable substitution of the chimera in the cell type. Previous studies have successfully identified substitutions which occurred in cell culture and engineered these into different chimeric virus constructs to produce chimeric viruses with improved characteristics (Huang et al., *J. Virol.* 77:11436-11447, 2003; Huang et al., *J. Virol.* 12:7300-7310, 2005).

In some embodiments, the chimeric flavivirus encodes a polypeptide that includes one or more amino acid substitution (or insertion or deletion) of one or more residues of the Dengue virus prM or E protein, such that the chimera has improved characteristics. In other examples, the chimeric flavivirus encodes a polypeptide that includes one or more amino acid substitution (or insertion or deletion) of one or more residues of a WNV non-structural and/or C protein, such that the resulting chimera has improved characteristics. In additional examples, the chimeric flavivirus includes one or more nucleic acid substitution, insertion, or deletion in the WNV 5' and/or 3' non-coding region, such that the chimera has improved characteristics.

Examples of a chimera encoding at least one substitution that improves chimeric virus characteristic are those encoding a polypeptide having one or more amino acid substitution in a DENV E protein. In particular embodiments, the substitution includes, but is not limited to, at least one substitution at DENV E protein amino acid position 64, 122, 186, or 203 of the DEN2 E protein, or a combination of two or more thereof. It is to be understood that substitutions at the equivalent E protein amino acid positions in DEN1, DEN3, or DEN4 are also contemplated. Furthermore, substitutions at the equivalent position are contemplated even in situations where the wild type amino acid is different from the amino acid in the wild type DEN2 (for example, DEN2 E protein includes Lys at position 64, while the equivalent amino acid in DEN4 E protein is Ser64). In some examples, the amino acid substitution alters a positively charged residue (such as Lys, Arg, or His; for example, Lys64 or Lys 122) to a non-charged residue (for example, Met, Ser, Thr, Gly, Ala, Val, Leu, Ile, or Val) or to a negatively charged residue (for example, Asp or Glu). The particular substitution (expressed as in DEN2) may include K64M, K64S, K64T, K122L, K122I, K122T, and/or K122E. In other examples, the amino acid substitution alters a polar residue (such as Ser or Thr; for example, Ser186 of DEN2) to a negatively charged residue (for example, Asp or Glu) or a hydrophobic residue (such as phenylalanine). In further examples, the amino acid substitution includes a substitution at amino acid position 203 of the E protein (expressed as in DEN2), for example N203D. In particular examples, the disclosed chimeric flavivirus encodes a DEN2 E protein including K122I, S186F, N203D, or a combination of two or more thereof.

In some embodiments, the disclosed chimeric flavivirus encodes at least one amino acid substitution in the DENV prM protein that improves virus characteristics. In one example, the substitution includes a substitution at amino acid position 149 of the DEN2 prM protein. It is to be understood that substitutions at the equivalent prM protein amino acid positions in DEN1, DEN3, or DEN4 are also contemplated. Furthermore, substitutions at the equivalent position are contemplated even in situations where the wild type amino acid is different from the amino acid in the wild type DEN2 (for example, DEN2 prM protein includes Phe at position 149, while the equivalent amino acid is Thr in DEN1 and DEN3 and is Ile in DEN4). In a particular example, the amino acid substitution alters Phe149 of DEN2 prM to an non-charged amino acid (for example, Met, Thr, Gly, or Ile), such as an amino acid residue that is found at the equivalent position in the Japanese encephalitis complex (for example, WNV, Japanese encephalitis virus, St. Louis encephalitis virus, or Murray Valley encephalitis virus).

In additional embodiments, the disclosed chimeric flavivirus may encode at least one amino acid substitution in each of the DENV prM and E proteins. In other examples, the chimeric flavivirus may encode two or more amino acid substitutions in the DEN prM protein or the E protein. For example, the chimeric flavivirus may include at least one amino acid substitution in the DEN E protein (such as Lys64, Lys122, Ser186, and/or Asn203) and at least one amino acid substitution in the DEN prM protein (such as Phe149).

In further examples, the disclosed chimeric flavivirus encodes at least one amino acid substitution, insertion, or deletion in at least one non-structural protein (for example, NS1, NS2A, NS2B, NS3, NS4A, NS4B, or NS5) or C protein of the WNV that improves virus characteristics. For example, the chimeric flavivirus may encode one or more amino acid substitutions in non-structural protein NS2A that may increase virus titer, replication rate, or plaque size, or may stabilize growth of the disclosed chimeras in cell culture. In some examples, the amino acid substitution may include substitutions at one or more of Val23 of NS2A (such as V23M or V23C), 11e49 of NS2A (such as I49T), and Phe94 (such as F94L). Other variant chimeras may encode one or more substitutions in non-structural protein NS1, NS3, and/or NS4A. These variants may alter virus characteristics, for example increasing temperature sensitivity or decreasing infectivity in mosquitoes. In particular examples, the substitution may include Gly53 of NS1 (for example G53D). In other examples the substitution may include amino acid positions 249 and/or 251 of NS3 (such as P249T, P249H, E251V, or E251Q). In still further examples, the flavivirus chimera may encode one or more substitution in non-structural protein NS4B (such as Thr241 of NS4B, for example T241I).

In some embodiments, the disclosed chimeras may include at least one nucleotide substitution, insertion, or deletion in the 5' and/or 3' non-coding region of the WNV backbone, such that the substitution, insertion, or deletion improves virus characteristics such as replication rate, virus titer, plaque size, stability in cell culture, or infectivity in mammals or mosquitoes. In one example, the chimera includes insertion of a microRNA (miRNA, such as miR-14 (Mead and Tu, *BMC Genomics* 9:244, 2008)) in the 5' or 3' non-coding region to decrease virus replication in mosquitoes. In other examples, the nucleic acid substitution, insertion, and/or deletion may decrease virus replication in mosquitoes or mice.

In additional examples, the chimeras include a combination of two or more nucleic acid substitutions in the non-coding regions, in the nucleic acid sequences encoding the C, prM, E, or non-structural proteins, or any combination thereof. For example, the chimera may include one, two, three, or more substitutions in the DEN prM or E proteins. The chimera may also include one, two, three, or more substitutions in the WNV C protein, non-structural proteins, or non-coding regions. In particular examples, the chimeric flavivirus encodes a DEN2 E protein including N203D and an NS2A protein including I49T and F94L. In other examples, the chimeric flavivirus encodes a DEN2 E protein including K122I, S186F, and N203D, a WNV NS2A protein including I49T and F94L, and a WNV NS4B protein including T241I.

The disclosure also provides WN/DEN chimeras encoding at least one amino acid substitution in the E protein, wherein antibody cross-reactivity of the E protein is measurably reduced. In some examples, the chimera encodes at least one amino acid substitution, for example at DEN2 E protein amino acid position 101, 106, 107, 108, 135, or a combination of two or more thereof. It is to be understood that substitutions at the equivalent E protein amino acid positions in DEN1, DEN3, or DEN4 are also contemplated. Furthermore, substitutions at the equivalent position are contemplated even in situations where the wild type amino acid is different from the amino acid in the wild type DEN2. Particular amino acid substitutions include, but are not limited to, W101F, G106A, G106L, L107F, F108W, F108M, F108V, F108L, L135W, or L135K. Additional examples of amino acid substitutions which reduce antibody cross-reactivity of flavivirus E proteins are known in the art (see e.g. WO06/025990; incorporated herein by reference). Chimeras that include mutations that reduce E protein antibody cross-reactivity may also include one or more additional mutations in the structural proteins, non-structural proteins, or NCRs, such as those described above.

Methods to assess the characteristics of the above-described WN/DEN chimeric viruses including sequence variants are well-known in the art. For example, methods of assessing viral titer, replication rate, plaque size, and stability in culture may be assessed as described in Example 2. See also, Obijeski et al., *J. Gen. Virol.* 22:21-33, 1974; Beaty et al., *Diagnostic Procedures for Viral, Ricksettial, and Chlamydial Infections*, pp. 189-212, Lennette et al. (eds.), 7$^{th}$ Edition, American Public Health Association, 1995; *Virology Methods Manual*, Mahy and Kangro (eds.), Academic Press, 1996; Huang et al., *J. Virol.* 77:11436-11447, 2003; Huang et al., *J. Virol.* 79:7300-7310, 2005. Methods to assess infectivity in mammals (such as mice) or mosquitoes can be carried out as described below (such as Examples 4, 6, and 7).

Reduction in antibody cross-reactivity can be determined by comparing antibody binding affinity of an antibody for the wild type E protein with antibody binding affinity for an E protein including one or more amino acid substitutions. A reduction in antibody binding affinity indicates a reduction in antibody cross-reactivity. Antibody binding affinities can be determined by many methods well known in the art, such as end-point titration in an Ag-ELISA assay, competition binding in an ELISA assay, a solid-phase radioimmunoassay, and the Biacore® surface plasmon resonance technique (Malmqvist, *Biochem. Soc. Trans.* 27:335-40, 1999; and Drake et al., *Anal. Biochem.* 328:35-43, 2004). In some embodiments the antibody is a polyclonal antibody or a mAb. A specific, non-limiting example of a polyclonal antibody is polyclonal anti-DEN2 murine hyperimmune ascitic fluid. Specific, non-limiting examples of mAbs include 4G2 (ATCC No. HB-112), 6B6C-1, 1B7-5, 1A1D-2, 1A5D-1, 1B4C-2, F4540, D1-11, 9F10, D2811, 2H3, 9A3D-8, 3H5, 1F1, 8A1, or 1H10 (see, e.g., Roehrig et al., *Virology* 246:317-28, 1998; Crill and Chang, *J. Virol.* 78:13975-13986, 2004). Antibody cross-reactivity may be assessed as described in Example 10.

V. Preparation of Viruses and Virus Particles

Methods of cell culture, viral replication, plaque titration, and virus or virus particle purification are well known in the art. See e.g. Obijeski et al., *J. Gen. Virol.* 22:21-33, 1974; Beaty et al., *Diagnostic Procedures for Viral, Ricksettial, and Chlamydial Infections*, pp. 189-212, Lennette et al. (eds.), 7$^{th}$ Edition, American Public Health Association, 1995; *Virology Methods Manual*, Mahy and Kangro (eds.), Academic Press, 1996.

The chimeric viruses of the present invention can be made using standard methods known and recognized in the art. For example, an RNA molecule corresponding to the genome of a virus, or a chimeric virus, can be introduced into primary cells, chick embryos, or diploid cell lines, from which (or the supernatants of which) progeny virus can then be purified. Another method that can be used to produce the viruses employs heteroploid cells, such as Vero cells (Yasumura et al., *Nihon Rinsho* 21:1201-1215, 1963). In this method, a nucleic acid molecule (e.g., an RNA molecule) corresponding to the genome of a virus or chimeric virus is introduced into the heteroploid cells, virus is harvested from the medium in which the cells have been cultured, and harvested virus is treated with a nuclease (e.g., an endonuclease that degrades both DNA and RNA, such as Benzonase; U.S. Pat. No. 5,173, 418). The nuclease-treated virus is then concentrated (e.g., by use of ultrafiltration using a filter having a molecular weight cut-off of, e.g., 500 kDa (e.g., a Pellicon-2 Mini ultrafilter cassette)), diafiltered against MEME without phenol red or FBS, formulated by the addition of lactose, and filtered into a sterile container. Details of a method of virus production are provided in WO 03/060088. Virus particles may be purified as discussed herein (see, e.g., section VIII), for example, by ultracentrifugation through a sucrose gradient and sucrose cushion.

VI. Detection of Flavivirus Antibodies

The present disclosure further provides a method of detecting a flavivirus-reactive antibody in a sample (such as a sample from a subject, for example, a blood sample), including contacting the sample with a chimeric virus of this disclosure under conditions whereby an antibody/polypeptide complex can form; and detecting formation of the complex, thereby detecting flavivirus antibody in a sample. An advantage of the disclosed WN/DEN chimeras is that they grow faster and to higher titers and produce larger plaques than wild type DENV. Therefore, the disclosure provides methods of detecting DENV-reactive antibody in a sample that are faster and more specific than methods utilizing wild type DENV. For example, the specificity of the assay (for example to distinguish between DENV serotypes) may be improved by use of the disclosed chimeras which include amino acid substitutions in the E protein which reduce antibody cross-reactivity.

The method of detecting flavivirus-reactive antibody in a sample can be performed, for example, by contacting a fluid or tissue sample from a subject with a chimeric virus of this disclosure and detecting the binding of at least one polypeptide encoded by the virus to the antibody. A fluid sample of this method can include any biological fluid which could contain the antibody, such as cerebrospinal fluid, blood, bile plasma, serum, saliva and urine. Other possible examples of body fluids include sputum, mucus and the like.

In one example, the presence of a Dengue virus antibody can be detected in a sample from a subject utilizing a disclosed chimeric flavivirus in a plaque-reduction neutralization test (PRNT) assay (see e.g., Example 9). In the PRNT assay, a sample is contacted with a virus encoded by a chimeric flavivirus disclosed herein (such as a WN/DEN2 virus). A suitable cell culture (such as Vero, C6/36, or BHK cells) is inoculated with the virus-sample mixture to infect the cells. The cell culture is incubated under conditions sufficient to allow plaque formation and the number of plaques formed in a culture inoculated with the chimeric virus-sample mixture is compared to the number of plaques formed in a control culture (such as cells inoculated with virus alone). A reduction in the number of plaques in the cell culture inoculated with the chimeric virus-sample mixture as compared to the control culture (for example a decrease of at least 50%, 60%, 70%, 80%, 90%, 95%, or 99% compared with the control sample) indicates the presence of a DENV neutralizing antibody in the sample.

Enzyme immunoassays such as IFA, ELISA and immunoblotting can be readily adapted to accomplish the detection of flavivirus antibodies in a sample according to the methods of this disclosure. An ELISA method effective for the detection of the antibodies can, for example, be as follows: 1) bind the chimeric virus or virus particles to a substrate; 2) contact the bound chimeric virus with a fluid or tissue sample containing the antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

The detectable moiety allows for visual detection of a precipitate or a color change, visual detection by microscopy (such as a chromogenic deposit or fluorescence), or automated detection by spectrometry, radiometric measurement or the like. Examples of detectable moieties include fluorescein, fluorescein isothiocyanate, rhodamine, Cy5, and Cy3 (for fluorescence microscopy and/or the microsphere-based immunoassay), horseradish peroxidase (for either light or electron microscopy and biochemical detection), biotin-streptavidin (for light or electron microscopy) and alkaline phosphatase (for biochemical detection by color change).

Another immunologic technique that can be useful in the detection of flavivirus antibodies uses mAbs for detection of antibodies specifically reactive with flavivirus polypeptides in a competitive inhibition assay. Briefly, a sample is contacted with a chimeric flavivirus or virus particle of this invention which is bound to a substrate (for example, a 96-well plate). Excess sample is thoroughly washed away. A labeled (for example, enzyme-linked, fluorescent, radioactive, etc.) mAb is then contacted with any previously formed polypeptide-antibody complexes and the amount of mAb binding is measured. The amount of inhibition of mAb binding is measured relative to a control (no antibody), allowing for detection and measurement of antibody in the sample. The degree of mAb binding inhibition can be a very specific assay for detecting a particular flavivirus variety or strain, when based on mAb binding specificity for a particular variety or strain of flavivirus. mAbs can also be used for direct detection of flavivirus in cells by, for example, IFA according to standard methods.

As a further example, a micro-agglutination test can be used to detect the presence of flavivirus antibodies in a sample. Briefly, latex beads, red blood cells or other agglutinable particles are coated with a chimeric flavivirus or virus particles of this disclosure and mixed with a sample, such that antibodies in the sample that are specifically reactive with the antigen crosslink with the antigen, causing agglutination. The agglutinated antigen-antibody complexes form a precipitate, visible with the naked eye or measurable by spectrophotometer.

In yet another example, a microsphere-based immunoassay can be used to detect the presence of flavivirus antibodies in a sample. Briefly, microsphere beads are coated with a chimeric flavivirus or virus particle of this disclosure and mixed with a sample, such that antibodies in the sample that are specifically reactive with an antigen encoded by the virus bind the antigen. The bead-bound virus-antibody complexes are allowed to react with fluorescent-dye labeled anti-species antibody (such as FITC-labeled goat anti-human IgM), and are measured using a microsphere reader (such as a Luminex instrument).

VII. Evaluation of Candidate Vaccine Efficacy

The chimeric flaviviruses disclosed herein may be used in methods to assess the efficacy of candidate vaccines, such as DENV vaccine candidates. A number of candidate DENV vaccines have been developed previously, such as attenuated vaccine strains (for example DEN2 PDK-53, DENT PDK-13, DEN3 PGMK-30/FRhL-3, and DEN4 PDK-48) and chimeric DENV constructs (see e.g. U.S. Pat. No. 7,094,411). However, currently there is no ideal mouse model for evaluation of candidate DENV vaccines, because outbred immune competent mice do not succumb to wild type DENV challenge and do not generate sufficient viremia for measuring a protective effect of a candidate vaccine.

The efficacy of candidate DENV vaccines may be tested by inoculating subjects (for example, mice or non-human primates (such as rhesus monkeys)) with a candidate vaccine, followed by challenge with a virulent DENV strain. The disclosed WN/DENV chimeras may be virulent and/or generate significant viremia in non-immunized mice, therefore they can be used as the challenge dose in previously inoculated subjects.

In one particular embodiment, a set of subjects (such as mice) is inoculated with a candidate DENV vaccine (for example, DENV2 PDK-53 strain). Administration of the candidate vaccine strain virus may be carried out by any suitable means, including both parenteral injection (such as intraperitoneal, subcutaneous, or intramuscular injection), by in ovo injection in birds, orally, and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally) or by inhalation administration, such as by creating respirable particles of a pharmaceutical formulation (including both solid particles and liquid particles) containing the virus as an aerosol suspension, and then causing the subject to inhale the respirable particles. In a particular example, the subjects are inoculated intraperitoneally with vaccine virus in a vehicle such as phosphate buffered saline. Multiple inoculations (such as boosters) may be carried out, separated by a suitable period of time, such as at least two weeks, four weeks, eight weeks, twelve weeks, or more.

Subjects that have been test vaccinated are challenged with a virulent or lethal dose (such as a lethal dose determined as in Example 8) of a flavivirus chimera disclosed herein (for example a WN/DEN chimera, such as that encoded by one of SEQ ID NOs: 1, 3, 5, or 7) following a suitable period of time to allow immunity based on the vaccination to develop (such as at least two weeks, four weeks, eight weeks, twelve weeks, or more). The challenge dose may be administered by any suitable route including those above, and optionally is administered by the same or a different route as the vaccinating dose. Following the challenge dose, subjects are monitored for development of morbidity (such as fever, rash, vomiting, loss of appetite, rough fur, hunched back, lethargy, unbalanced or irritable movement, dehydration, weight loss, or signs of paralysis) or mortality. In addition, blood is collected from subjects after challenge for measurement of viremia levels. A decrease in viremia levels, signs of morbidity and/or mortality compared to a set of control subjects which is not inoculated with the candidate vaccine (for example, a decrease of at least 10%, 20%, 30%, 40%, 50%, 60%, 70%, 80%, 90%, 95%, or 99% in a test vaccinated population compared with a control population) indicates the effectiveness of the candidate vaccine.

VIII. Production of Purified Virus Particles Containing Dengue prM and E Proteins The chimeras disclosed herein may also be used to rapidly produce quantities of virus particles containing DENV prM (or M) and E proteins, as wild type and attenuated DENV strains generally do not replicate efficiently in culture.

Methods of protein purification are well-known in the art (see e.g. Scopes, *Protein Purification: Principles and Practice*, 3$^{rd}$ edition, Springer, 1994). Examples of methods of protein purification include immunoaffinity purification, ultracentrifugation over a gradient, ion exchange chromatography, and gel filtration.

In one example, a method is disclosed of producing virus particles containing Dengue virus E and prM (or M) proteins. The method includes producing the chimeric flaviviruses disclosed herein in a cell culture system, such as Vero, C6/36, LLC-MK$_2$, or BHK cells. The cells are infected with a WN/DEN chimera and incubated for sufficient time for virus to be produced (for example, at least 2 days, 3 days, 4 days, 5 days, 8 days, or 10 days). A supernatant, such as the cell culture medium, containing the chimeric virus is collected and condensed by PEG-precipitation. The virus particles are then purified through ultracentrifugation over a gradient (such as sucrose or glycerol/potassium tartrate gradient). See e.g., Obijeski et al., *J. Gen. Virol.* 22:21-33, 1974. In a particular example, Vero or C6/36 cells are infected with the disclosed WN/DEN2 chimera and the viral particle with DEN2 prM and/or E protein is purified.

Purified virus particles containing DENV prM and E proteins are suitable for use in place of proteins prepared by other means (such as recombinant expression in mammalian cells, yeast, or *E. coli*). For example, purified virus particles of the disclosed chimeric viruses with DENV prM and/or E proteins may be used in methods of detecting antibodies against these proteins (such as diagnostic tests or assays to determine response to a candidate vaccine). For example, purified virus particles may be immobilized on a solid support and utilized in immunodetection methods such as ELISA, competitive inhibition assays, micro-agglutination test, or microsphere based immunoassays. Further, the purified virus particles are suitable for use in PRNT assays for detection of neutralizing DENV antibodies.

Further, because the disclosed WN/DEN chimeric viruses grow more rapidly in culture and to higher titers than DEN viruses, purified virus particles containing DENV prM and/or E proteins are useful for production of DENV antigens. Uses for these antigens include production and testing of vaccine candidates and use of virus particles for further study of protein folding, three-dimensional structure, and epitope mapping.

IX. Mosquito Infectivity and Transmissibility

*Aedes aegypti* mosquito is the major vector for DENV, while *Culex quinquefasciatus* and *Culex pipiens* mosquitoes are the natural vectors for WNV. The disclosed chimeric flaviviruses may have reduced or eliminated infectivity and/or transmissibility in one or more mosquito vectors. Methods for determining whether a virus can infect or be transmitted by a mosquito species or strain are known to one of skill in the art.

By way of example, to determine if the disclosed chimeric viruses can infect *A. aegypti, C. quinquefasciatus, C. pipiens*, or other mosquito species, mosquitoes can be fed bloodmeal containing virus (such as a 1:1 mixture of cell supernatant from infected cells and defibrinated calf or sheep blood) or by intrathoracic inoculation with medium containing virus (such as about $10^5$ to $10^7$ pfu).

Infected or control mosquitoes are cold anesthetized and dissected. Midguts and/or heads are collected and fixed in either acetone (heads) or 4% paraformaldehyde (midguts) and stained by immunofluorescence assay with a pan-flavivirus E protein antibody, such as 4G2, or serotype-specific antibodies, such as 3H5 (DEN2), 1F1 (DENT), 8A3 (DEN3), or 1H10 (DEN4). A fluorescein-conjugated antibody (such as goat anti-mouse IgG antibody) is used for secondary detection. Tissue immunofluorescence assays are read using a fluorescent microscope.

Decreased E protein immunofluorescence in mosquitoes infected with chimeric WN/DEN virus as compared to control samples (those infected with DENV or WNV) indicates that the chimeric virus has decreased infectivity and/or transmissibility in a particular mosquito species as compared to the wild type DENV or WNV. An increase in E protein immunofluorescence in mosquitoes infected with chimeric WN/DEN virus as compared to control samples (such as those infected with DENV or WNV) may indicate that the chimeric virus has increased infectivity and/or transmissibility in a particular mosquito species as compared to the wild type DENV or WNV.

The following examples are provided to illustrate certain particular features and/or embodiments. These examples should not be construed to limit the invention to the particular features or embodiments described.

EXAMPLES

Example 1

Construction of WN/DEN2 Chimeric Virus

This example describes construction of a chimeric West Nile/Dengue-2 virus consisting of the prM and E genes from DEN2 in a WNV backbone.

A WNV NY99 infectious clone (designated as WN/IC-P991 clone) in a two plasmid system was used. pWN-AB-Asc contained nucleotides 1 to 2495 and pWN-CG contained nucleotides 2495-11029 (described in Kinney et al., *J. Gen. Virol.* 87:3611-3622, 2006). Site-directed mutagenesis of pWN-AB-Asc was performed using the QuikChange® Multi site-directed mutagenesis kit (Stratagene, La Jolla, Calif.) to create a SacII site at nucleotides 412-418 and a BspEI site at nucleotides 2424-2429 of the WNV genome. Using similar site-directed mutagenesis, these sites were engineered in a DEN2 16681 infectious clone (D2/IC-30P-A; Kinney et al., *Virology* 230:300-308, 1997) to generate D2IC-30P-NBX clone. Restriction digestion with SacII and BspEI was used to cut the prM and E genes (bp 398-2430) out of both the DEN2 16681 and WNV infectious clones. The prM (including the DEN2 prM signal sequence at the end of the C gene, which serves as an anchor for the C protein during polyprotein processing) and E genes of DEN2 16681 was ligated in the pWN-AB-Asc plasmid, replacing the WNV prM and E genes with the DENV equivalents, to create pWN/D2-AB.

Full length genomic cDNA was prepared by cleaving pWN/D2-AB and pWN-CG at the natural NgoMIV site located at by 2495 of the WNV genome. The two plasmids were then ligated together at the NgoMIV site and transcribed using the AmpliScribe™ T7 kit (Epicentre Technologies, Madison, Wis.). FIG. 1 shows a schematic diagram of the WN/DEN2 chimera (WN/D2) and the junction between the WN C protein and the DEN2 prM signal sequence and prM protein.

In vitro transcription was carried out at 37° C. for 2-3 hours and C6/36 or Vero cells were transfected with the transcribed RNA by electroporation. Infectious virus was collected 4-7 days post transfection. Virus was designated as C6/36-0 seed when recovered from transfected C6/36 cells, and as Vero-0 when recovered from transfected Vero cells. The C6/36-0 and Vero-0 seeds were used to infect C6/36 and Vero cells, respectively, to obtain the C6-1 and V-1 working seeds. To verify the genome accuracy of the recovered chimeras, viral RNA was extracted from C6-1 virus using the QIAamp® Kit (Qiagen Inc, Valencia, Calif.) and cDNA products were generated using the Titan™ One-Tube RT-PCR system (Roche Applied Science, Indianapolis, Ind.). PCR products were directly sequenced to confirm the genome sequence of the chimeric WN/DEN2 virus (SEQ ID NO: 1).

Example 2

WN/DEN2 Chimeric Virus Replication and Titration in Cells

This example describes the replication of a WN/DEN2 chimeric virus in C6/36 and Vero cell lines.
Methods
Three T75 flasks of C6/36 and Vero cells were infected at a multiplicity of infection (MOI) of 0.001 with each of the following viruses: WN NY99, DEN2 681, or WN/DEN2 virus (produced as described in Example 1). Viruses in either 3 ml of Ye-Lah medium (10 g yeast extract and 50 g lactalbumin hydrolysate per 1000 ml water) containing 2% fetal calf serum (C6/36 cells) or 3 ml of Iscove's Modified DMEM (e.g. Gibco-Invitrogen, Carlsbad, Calif.) containing 2% fetal calf serum (Vero cells) were added to the monolayer when the cells were 95-100% confluent. Following infection, flasks were incubated at 28° C. and 37° C. for C6/36 and Vero cells, respectively. Flasks were rocked every 15 minutes for 1.5 hours for viral adsorption. After 1.5 hours, 27 ml of growth medium was added to each flask and the flasks were incubated at 28° C. for C6/36 cells or 37° C. for Vero cells for 10 days. Every 2 days an aliquot of 300 µL was removed from each flask and combined with 300 µL of Iscove's DMEM containing 35% fetal calf serum. All aliquots were stored at -80° C. until they could be titrated by plaque assay on Vero cells. After plaque titration of each aliquot, the viral growth kinetics in each cell type was established, and also used to determine the proper seed harvest day when producing chimera seeds. When producing chimeric virus seeds, the culture conditions were proportionally scaled up to larger tissue culture vessels.

Virus samples were titrated by plaque assay on Vero cells. Serial 10-fold dilutions of all virus samples were made in BA-1 diluent. 100 µL of each dilution was added to one well of a 6-well tissue culture plate containing a confluent monolayer of Vero cells. Following inoculation, plates were incubated at 37° C. in an atmosphere of 5% $CO_2$ for 1.5 hours to allow virus adsorption. Plates were rocked every 10 minutes to ensure that the monolayer did not dry out. After virus adsorption all wells were overlaid with 4 ml of 0.8% agarose overlay containing a balanced salt solution and Ye-Lah medium. Plates were incubated at 37° C. in an atmosphere of 5% $CO_2$ for the indicated times. Following incubation, wells were overlaid with another 2 ml of agarose overlay that also contains 1.5% neutral red to visualize plaques. Plates were read and plaques were counted the following day.

Plaque isolation and serial passage of the chimera in Vero cells was performed. One of the large plaques from the V-1 seed (as V-2) was isolated from the titration plate, and used to infect a flask of fresh Vero cells. The culture medium harvested from this flask was designated as V-3 seed, and was serially passaged through Vero cells seven more times to obtain the V-4 to V-10 seeds. Additionally, the plaques produced from the C6-1 working seed in the Vero plaque titration plate also showed a small portion of larger plaques among the pin-point size plaques. One large plaque was isolated from the plate (as C6-1V-1) and used to infect a flask of fresh Vero cells to obtain C6-1V-2 seed.

PRNT tests were performed by incubating viruses with serial dilutions of a WNV hyperimmune mouse ascitic fluid (HMAF; M28548), a WNV E protein-specific monoclonal antibody (MAb3.67G), a DEN2 HMAF (VS0090), or a DENV-2 E protein-specific monoclonal antibody (MAb3H5) at 4° C. overnight. The following day, samples were added to Vero cells in 6-well culture plates and followed by overlay procedure as in the plaque titration method described above. Neutralization titer was determined as the greatest antibody dilution that decreased plaques by at least 50% compared to the back titration results of the input virus in the same assay.
Results
The WN/DEN2 chimeric virus replicated efficiently and reached high titers in C6/36 cells (8.6 $\log_{10}$ pfu/ml for C6-1 seed). Plaque formation was also assessed in Vero cells. Titers of the working seed after one passage in Vero cells (V-1 seed) was about 4-5 $\log_{10}$ pfu/ml. Compared to the plaque size of the parental D2 16681 and WN NY 99 viruses in Vero cells, the chimeric WN/DEN2 virus formed plaques that were much larger than the D2 16681 virus on day 8 post-infection (p.i.) (FIG. 2), but still smaller than the fast growing WN NY99 virus, which would lyse the whole cell sheet on day 8 post infection.

Plaques were visualized and measured on day 5 p.i. after passage in C6 or Vero cells (FIG. 3). Wild type West Nile NY99 virus (WNV NY99) and DEN-2 16681 virus were included in the same experiment for comparison. WNV NY99 produced large plaques at day 5 p.i., while no plaques were visible for DEN-2 16681 at this time point. Plaque size increased following additional passages in Vero cells (Table 3).

Full genome sequence was obtained for the C6-1 working seed as well as the serial Vero passage seeds, V-3, V-10, and C6-1V2. The consensus sequence of the C6-1 seed showed no mutation compared to the parent West Nile and DEN-2 viruses from which it was derived. The C6-1V-2 seed contained two silent mutations (nucleotide 3291 of SEQ ID NO: 1 C>T and 8469 of SEQ ID NO: 1 A>G) and one missense mutation (nucleotide 1558 of SEQ ID NO: 1; A>G), resulting in an amino acid change from N to D at position 203 of the DEN2 E protein (amino acid 488 of SEQ ID NO: 2; E-N203D). The V-3 passage had two silent mutations (nucleotide 1566 of SEQ ID NO: 1 T>C and nucleotide 2973 of SEQ ID NO: 1 T>C) and three missense mutations, nucleotide 1558 of SEQ ID NO: 1 (A>G), nucleotide 3638 of SEQ ID NO: 1 (T>C), and nucleotide 3772 of SEQ ID NO: 1 (T>C). These missense mutations resulted in amino acid substitutions in the DEN2 E protein E-N203D (amino acid 488 of SEQ ID NO: 2) and the WNV NS2A protein, NS2A-I49T (amino acid 1181 of SEQ ID NO: 2) and NS2A-F94L (amino acid 1226 of SEQ ID NO: 2). The V-10 seed showed 4 silent mutations (nucleotide 1566 of SEQ ID NO: 1 T>C, nucleotide 2973 of SEQ ID NO: 1 T>C, nucleotide 3600 of SEQ ID NO: 1 T>T/C mix, and nucleotide 6181 of SEQ ID NO: 1 C>C/T mix) and 6 missense mutations (nucleotides 1316 A>T/A, 1508 C>T, 1558 A>G 3638 T>C, 3772 T>C, and 7604 C>T, all numbered as in SEQ ID NO: 1). The resulting amino acid changes are shown in Table 3. Two of the missense mutation loci had mixed nucleotides, resulting in a mixed genotype of E-K122I/K (amino acid 407 of SEQ ID NO: 2) and NS4B-T241T/I (amino acid 2503 of SEQ ID NO: 2).

The E-N203D mutation was found in two seeds (C6-1/V-2 and V-3) that were descendents from separate virus seeds derived from independent experiments. This indicates that this particular mutation may be critical for the chimera adapting to the Vero cell cultures. This mutation may also slightly increase the plaque size of the chimera in Vero cells, further supporting its effect on virus growth in Vero. In addition, the two NS2A mutations in the V-3 seed, NS2A-I49T and NS2A-F49L, also significantly increased the virus growth in Vero cells, resulting in larger plaques compared to the C6-1/V-2 seed. The E-K122I mutation (which eliminates the positive charge at E protein amino acid 122) may also be a Vero cell-adapting mutation for DEN2.

TABLE 3

Plaque size and sequence of successive passages of WN/DEN2

| Virus | Passage History | Amino Acid Mutations | | Plaque Size at Day 5 p.i. (mm)* |
| --- | --- | --- | --- | --- |
| | | Protein | Mutation | |
| WNV NY99 | LLC-MK2-1 | N/A | N/A | 5.18 +/− 0.37 |
| DENV-2 16681 | C6-1 | N/A | N/A | Could not be visualized |
| WN/D2 | C6-1 | None | None | 0.48 +/− 0.08 |
| WN/D2 | C6-1/V-2 | E | N203D | 1.05 +/− 0.16 |
| WN/D2 | V-3 | E | N203D | 1.55 +/− 0.20 |
| | | NS2A | 149T | |
| | | NS2A | F94L | |
| WN/D2 | V-10 | E | K122I/K | 1.78 +/− 0.43 |
| | | E | S186F | |
| | | E | N203D | |
| | | NS2A | I49T | |
| | | NS2A | F94L | |
| | | NS4B | T241T/I | |

*mean ± standard deviation
N/A: not applicable

Figure 4:
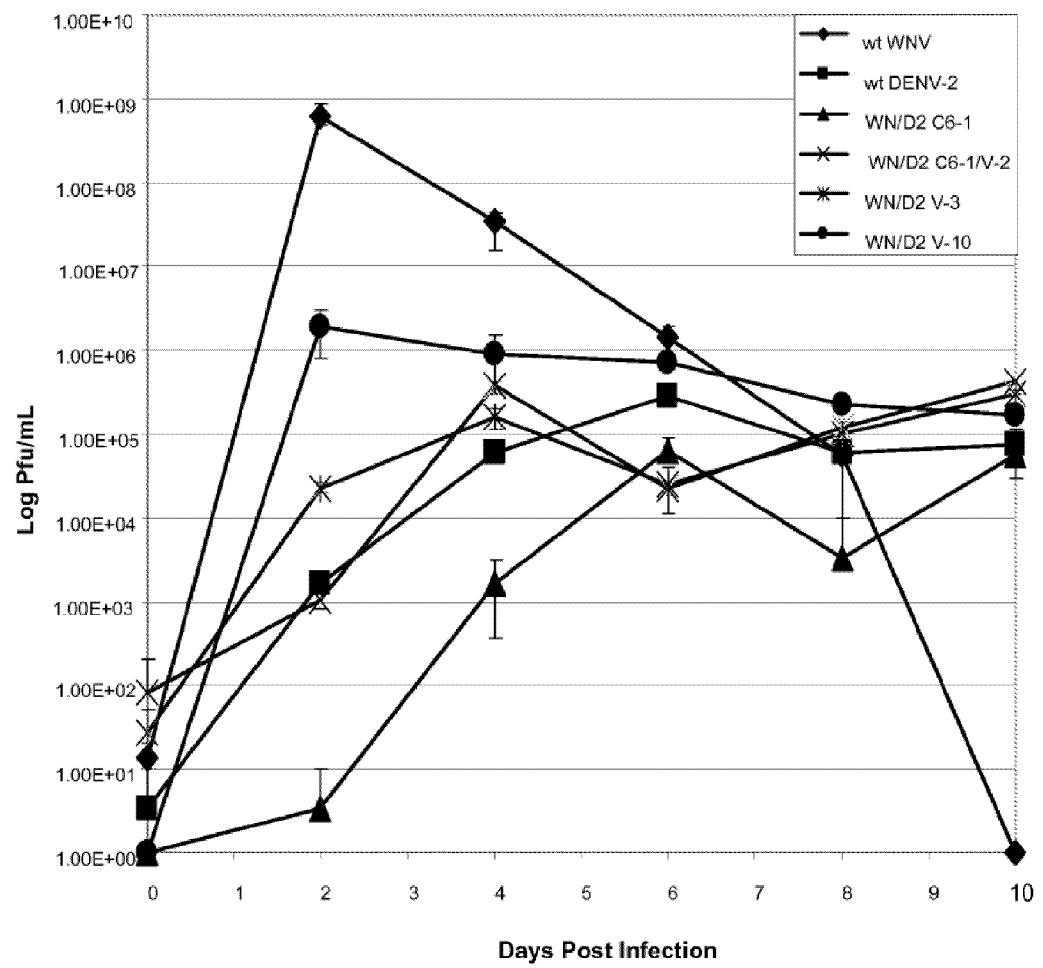
FIG. 4 shows growth curves in Vero cells of the wild type WNV NY99 (wt WNV), wild type DEN2 16681 virus (wt DENV-2), and successive passages of WN/DEN2 seeds (WN/DEN2 C6-1 seed, C6-1/V-2 seed, V-3 seed, and V-10 seed). Each point represents an average titer from three flasks, with the error bars showing the highest and lowest titers at each time point. ♦, wild type WNV; ■, wild type DEN2; ▲, WN/DEN2; C6-1 seed; x, WN/DEN2 C6-1/V-2 seed; *, WN/DEN2 V-3 seed; ●, WN/DEN2 V-10 seed.

The growth kinetics of the wild type and chimeric viruses were tested in both Vero and C6/36 cells. Vero cells were infected with chimeric WN/DEN2, WNV NY99, or DENV-2 16681 at the same multiplicity of infection (MOI) and titer was determined for 10 days (FIG. 4). Wild type WNV NY99 reached its maximum titer (8.8 $\log_{10}$ pfu/ml) by day 2 and the titer dropped rapidly in subsequent days. WN/DEN2 V-10 seed also reached its maximum titer by day 2 (6.3 $\log_{10}$ pfu/ml), but only decreased slightly in titer by day 10. WN/DEN2 V-3 and C6-1/V-2 seeds approached their maximum titers (5.5 $\log_{10}$ pfu/ml and 5.6 $\log_{10}$ pfu/ml, respectively) by day 4 and then remained fairly consistent (with a slight overall increase) through day 10. WN/DEN2 C6-1 grew more slowly, reaching its maximum titer at day 6 (84.8 $\log_{10}$ pfu/ml). DENV-2 16681 also reached its maximum titer (5.5 $\log_{10}$ pfu/ml) at day 6 and remained fairly consistent throughout the remaining days.

Figure 5:
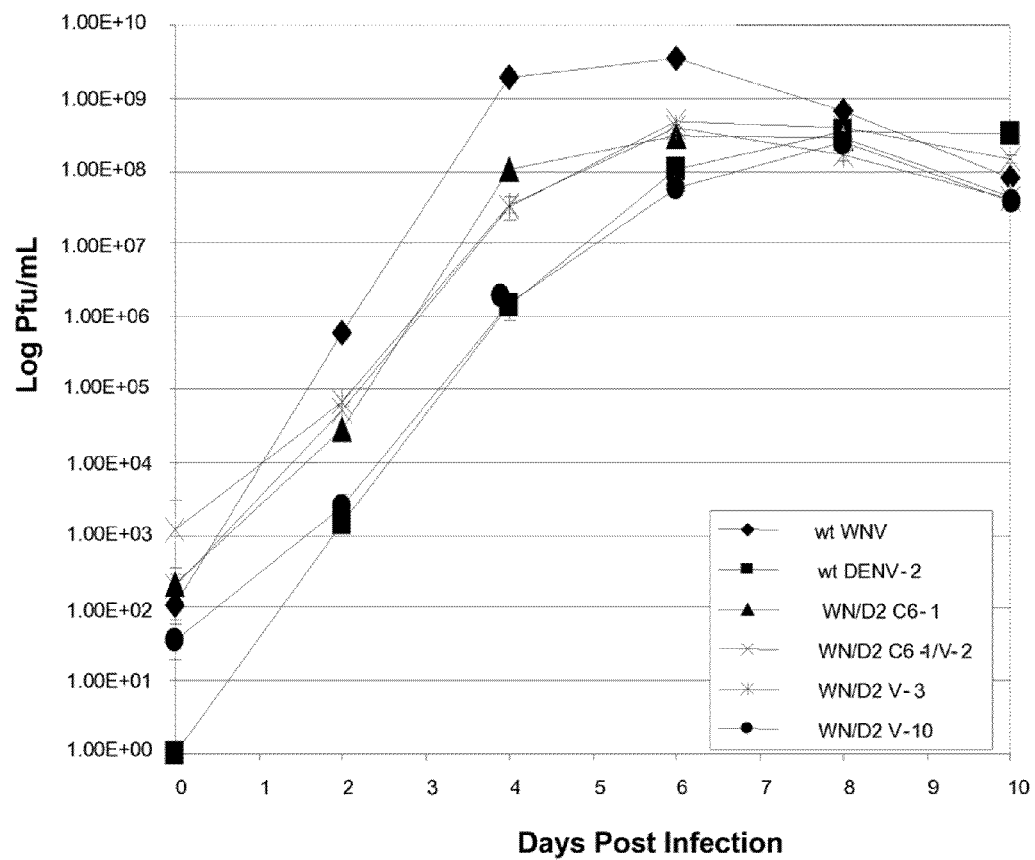
FIG. 5 shows growth curves in C6/36 cells of the wild type WNV NY99 (wt WNV), wild type DEN2 16681 virus (wt DENV-2), and successive passages of WN/DEN2 seeds (WN/DEN2 C6-1 seed, C6-1/V-2 seed, V-3 seed, and V-10 seed). ♦, wild type WNV; ■, wild type DEN2; ▲, WN/DEN2; C6-1 seed; x, WN/DEN2 C6-1/V-2 seed; *, WN/DEN2 V-3 seed; ●, WN/DEN2 V-10 seed.
Figure 6A:
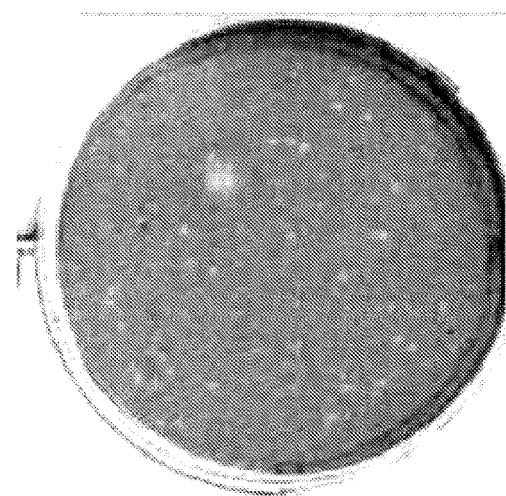
FIGS. 6A to 6D show plaque phenotype of WN/DEN2 chimeras engineered to include E-203, NS2A49, and/or NS2A94 mutants. (A) WN/DEN2 C6-1 seed; (B) WN/DEN2 E-N203D V-1 seed; (C) WN/DEN2 NS2A-I49T/F94L V-1 seed; (D) WN/DEN2 N203D, NS2A-I49T/F94L V-1 seed.
Figure 6B:
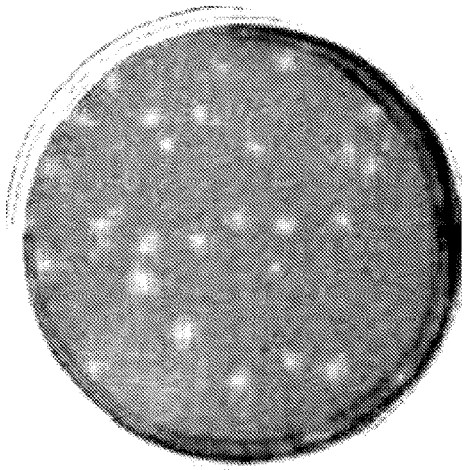
Figure 6C:
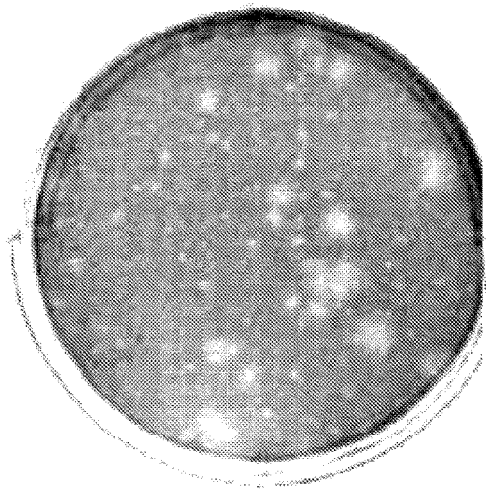
Figure 6D:
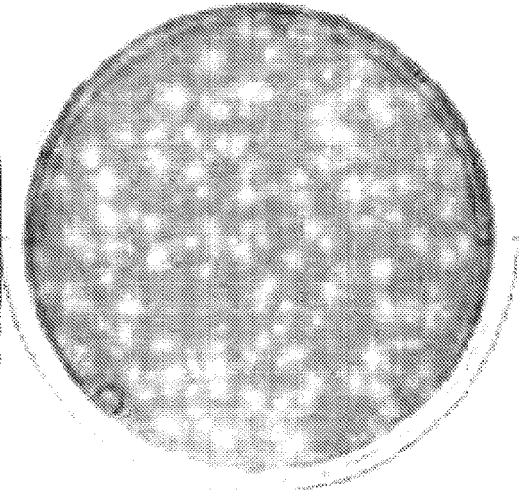

Virus replication in C6/36 cells showed that chimeric WN/DEN2 viruses all reached peak titers of approximately 8.5 $\log_{10}$ pfu/ml (FIG. 5), similar to that of DENV-2 16681. WNV NY99 reached a peak titer of 9.6 $\log_{10}$ pfu/ml. Except for the V-10 seed, all the chimeric viruses reached peak titers at day 6 p.i., similar to WNV NY99. The V-10 seed reached peak titer on day 8, and had a very similar growth profile to that of DENV-2 16681.

Plaque reduction neutralization (PRNT) tests were performed on WNV NY99, DENV-2 16681, WN/DEN2 C6-1, WN/DEN2 C6-1/V-2, WN/DEN2 V-3, and WN/DEN2 V-10 to determine their antigenic profile (Table 4). Although, the endpoint of some of the PRNT titers was not determined, all the chimeras had a similar neutralization pattern to the wt DENV-2 16681 by all 4 tested antibodies. The traditional PRNT of the DENV-2 16681 virus usually takes about 8-10 days due to the slow growth and tiny plaques produced by the virus. On the other hand, all the WN/D2 seeds tested showed plaques by day 5 p.i., resulting in faster PRNT. The similar PRNT patterns to those of wt DENV-2 and the rapid plaque forming ability make WN/D2 chimeras suitable as a surrogate DENV-2 virus in diagnosis by PRNT.

TABLE 4

PRNT assay of WN/DEN2 chimeric viruses

| | $PRNT_{50}$ Titer* | | | |
| --- | --- | --- | --- | --- |
| Virus | WNV HMAF (M28548) | WNV E-Specific MAb (MAb3.67G) | DENV-2 HMAF (VS0090) | DENV-2 E-Specific MAb (MAb3H5) |
| WNV NY99 | 10240 | >40960 | <160 | <80 |
| DENV-2 16681 | <640 | <1280 | 5120 | >2560 |
| WN/D2 C6-1 | <640 | <1280 | >5120 | >2560 |
| WN/D2 C6-1/V-2 | <640 | <1280 | 5120 | >2560 |
| WN/D2 V-3 | <640 | <1280 | 5120 | >2560 |
| WN/D2 V-10 | <640 | <1280 | >5120 | >2560 |

*Greatest antibody dilution that decreased plaques by at least 50%.

Example 3

Characteristics of WN/DEN2 Chimeras with Specific Mutations

This example describes the in vitro characteristics of WN/DEN2 chimeras containing specific introduced mutations.

Methods

To further modify the chimeric WN/DEN2 virus for adapting to mammalian cell cultures, chimeric constructs WN/D2-E203 (containing E-N203D; amino acid 488 of SEQ ID NO: 2), WN/D2-2A (containing NS2A-I49T and NS2A-F94L; amino acids 1181 and 1226 of SEQ ID NO: 2, respectively), and WN/D2-E-2A (containing E-N203D, NS2A-I49T and NS2A-F94L) were made. cDNA fragments containing the E-N203D mutation, or NS2A-I49T and NS2A-F94L mutations were RT-PCR amplified from the C6-1/V-2 seed or V-3 seed (described in Example 2), respectively. The fragment with E-N203D was cloned into the 5'-plasmid containing chimeric WN/DEN2 cDNA from nt 1-2445 (pWN/D2-AB) to obtain new mutant plasmid, pWN/D2-AB-E203. The NS2A mutant fragment (including the silent mutation at nucleotide 2973 of SEQ ID NO: 1 T>C) was cloned into the wt 3'-WN plasmid containing WNV cDNA nt 2440-10996 (pWN-CG) to obtain mutant pWN-CG-2A. WN/D2-E203 was constructed by ligating pWN/D2-AB-E203 with wt pWN-CG by NgoMIV junction (nt 2495 of WNV). WN/D2-2A was constructed by ligating wt pWN/D2-AB with pWN-CG-2A by NgoMIV junction. WN/D2-E2A was made by ligating pWN-AB-E203 with wt pWN-CG-2A by NgoMIV junction. Each chimeric virus was recovered from transfected Vero cells and the working seed (V-1) of each virus was made after one passage of the transfection seed to Vero cells.

Results

Full genome sequencing of the V-1 seed confirmed that no additional missense mutations accrued during replication in Vero cells. Only a silent mutation at nt 2973 of SEQ ID No 1: (T>C) was found in both WN/D2-2A and WN/D2-E2A virus; this mutation was introduced during the cloning of pWN-CG-2A plasmid used in the process of deriving these chimeras.

Plaque assays using each chimera showed that all produced larger plaques in Vero cells than the original WN/D2-C6-1 seed (FIG. 6). Plaques produced by these chimeras could be easily visualized by day 4 p.i. There was a mixed plaque phenotype in the WN/D2-2A seed, which may indicate this virus was still evolving in Vero cells. However, both chimeras with the E-N203D mutation appeared to be quite stable in Vero cells.

Example 4

Determination of Mosquito Infectivity of WN/DEN2 Chimera

This example describes the determination of the ability of WN/DEN2 chimera to infect DENV and WNV mosquito vectors.

Methods

Infectious bloodmeals were made using freshly prepared viruses with an approximate titer of $10^7$ pfu/ml in a 1:1 ratio with defibrinated sheep blood. *Aedes aegypti, Culex pipiens*, or *Culex quinquefasciatus* mosquitoes were allowed to feed on infectious bloodmeals provided in a HEMOTEK membrane feeder. Bloodfed mosquitoes were held at 28° C. for 10 days. Midguts and heads were dissected, fixed on slides, and stained via immunofluorescence using the pan-flaviviral monoclonal antibody 4G2.

Results

Figure 7:
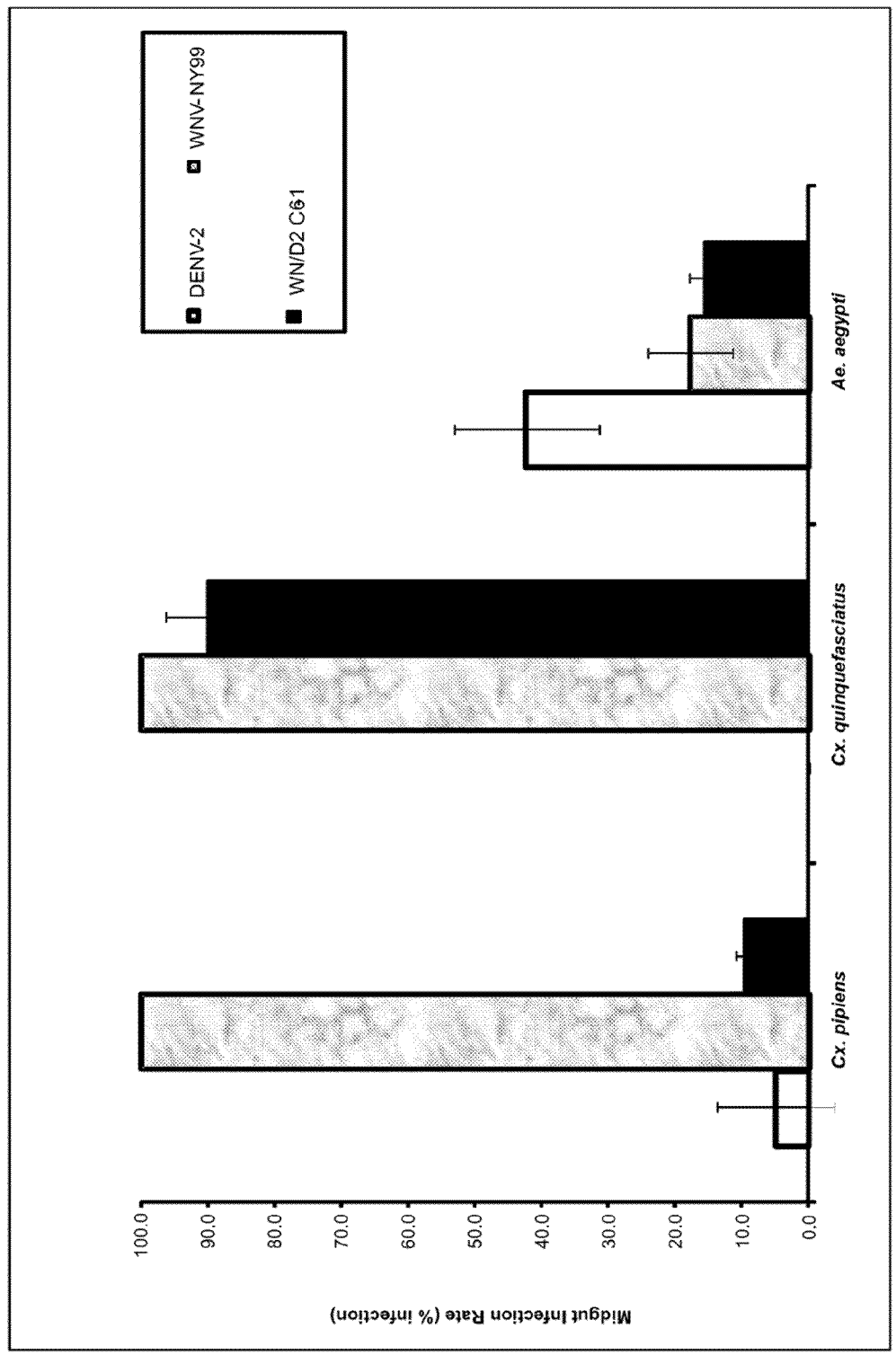
FIG. 7 shows the midgut infection rate of wild type WNV-NY99, wild type DENV-2 16681, and WN/DEN2 C6-1 seed in *Culex pipiens*, *Culex quinquefasciatus*, and *Aedes aegypti* mosquitoes. Open bars, DENV-2; shaded bars, WNV-NY99; solid bars, WN/D2 C6-1 seed.

*Aedes aegypti* mosquito is the major vector for DENV, while *Culex quinquefasciatus* and *Culex pipiens* are the natural vectors for WNV. The WN/DEN2 C6-1 chimera (which lacks any Vero cell-adapting mutations) infects the midgut of *Culex quinquefasciatus* and *Aedes aegypti* in a pattern more similar to that of wild type WNV than wild type DEN2 virus (FIG. 7), suggesting the WNV non-structural genes in the chimera virus have significant effects in infection of these mosquitoes. However, the WN/DEN2 C6-1 virus had similar low infection rate as the DENV-2 in the midgut of *Culex pipiens*, suggesting the structural DENV2 genes in the chimera were controlling the infection in *Culex pipiens*.

Example 5

Construction of Additional WN/DEN Chimeric Viruses

This example describes the construction of chimeric viruses containing the WNV backbone and prM and E protein from DEN1, DEN3, or DEN4.

The prM (including the DEN4 prM signal sequence) and E genes of DEN4, was ligated in the pWN-AB-Asc plasmid, replacing the WNV prM and E genes with the DENV equivalents, to create pWN/D4-AB. Two chimeras were constructed, one with wild type WNV components and one including the WNV NS2A mutations I49T and F94L. Full length genomic cDNA was prepared by cleaving pWN/D4-AB and pWN-CG (or WN-CG-2A) at the natural NgoMIV site located at by 2495 of the WNV genome. The two plasmids were then ligated together at the NgoMIV site and transcribed using the AmpliScribe™ T7 kit (Epicentre Technologies, Madison, Wis.). FIG. 8 shows a schematic diagram of the WN/DEN4 chimera (WN/D4) and the junction between the WN C protein and the DEN4 prM signal sequence and prM protein. The nucleic acid and amino acid sequences of a WN/DEN4 chimera are provided in SEQ ID NOs: 7 and 8, respectively. The WN/DEN4 chimera having the NS2A mutations had amino acid substitutions at amino acids 1181 and 1226 of SEQ ID NO: 8, respectively.

WN/DEN1 and WN/DEN3 chimeras are created as above and the junction between the WN C protein and the DEN prM signal sequence and prM protein is shown in FIG. 8. The nucleic acid and amino acid sequences of a WN/DEN1 chimera are provided in SEQ ID NOs: 3 and 4, respectively. The WN/DENT chimera having the NS2A mutations had amino acid substitutions at amino acids 1181 and 1226 of SEQ ID NO: 4, respectively. The nucleic acid and amino acid sequences of a WN/DEN3 chimera are provided in SEQ ID NOs: 5 and 6, respectively. The WN/DEN3 chimera having the NS2A mutations had amino acid substitutions at amino acids 1179 and 1224 of SEQ ID NO: 6, respectively.

Example 6

Assessment of Neurovirulence and Neuroinvasion Kinetics of Chimeric Virus

This example describes methods for assessing the neurovirulence and neuroinvasion kinetics of WN/DEN chimeric viruses (such as produced in Examples 1 or 5) in mice.

Neurovirulence

Groups of 10 mice (such as Swiss Webster, NIH Swiss, or ICR mice) are inoculated intracranially with ten-fold dilutions of WNV and WN/DEN chimeric virus from 0.1 pfu to 1000 pfu. One group of 10 mice is inoculated with 1000 pfu of DENV. The virus is diluted in 30 μL of sterile phosphate buffered saline (PBS) and is administered via intracranial inoculation. Mice are monitored daily for 4 weeks to determine the virulent dose. Mice showing signs of illness (such as rough fur, hunched back, lethargy, unbalanced or irritable movement, dehydration, 10% weight loss, or signs of paralysis) are euthanized. The results are used to calculate the 50% virulent dose ($VD_{50}$) of the WNV/DENV chimera. A decreased $VD_{50}$ compared to DEN wild type virus indicates higher neurovirulence than the wild type DENV.

Viremia/Neuroinvasion

Groups of 12 mice (such as Swiss Webster, NIH Swiss, or ICR mice) are inoculated with 1000 pfu of WNV, DENV, and WN/DEN chimera. Virus is inoculated intraperitoneally in 100 µl of PBS. At days 1, 3, 5, and 7 p.i., mice from each group are sacrificed and blood and brain samples are collected from each mouse. Brains are homogenized in DMEM and both blood and brain titers are determined by plaque assay on Vero cells, as described in Example 2. An increased number of pfu as compared to a control sample (such as a DENV or WNV) indicates increased neuroinvasion or virulence. A decreased number of pfu compared to a control sample (such as a DENV or WNV) indicates decreased neuroinvasion or virulence. Chimeras with higher neuroinvasion are further evaluated in 12-week-old mice for developing a surrogate DENV dose for virulence challenge study as described in Example 8.

Example 7

Determination of Antibody Response to WN/DEN Chimeras

This example describes methods for the determination of antibody responses in mice or other animals inoculated with WN/DEN chimeras. Antibodies to DENV prM and E proteins and WNV non-structural proteins, particularly NS 1, are measured. This example also describes a method for assessing the protective efficacy of immune response to WNV non-structural proteins.

Prior to virus inoculation, pre-immune serum blood samples are collected from all mice by nicking the tail vein. Groups of 10 mice (such as Swiss Webster, NIH Swiss, or ICR mice) are inoculated intraperitoneally with 100 µL of PBS containing serial ten-fold dilutions of WNV or WN/DEN chimeric virus ranging from 0.1 to 1000 pfu. One group of 10 mice is inoculated with 1000 pfu of DENV. Mice are monitored daily for four weeks and mice showing signs of illness will be euthanized. Four weeks after primary virus inoculation, blood is collected from all surviving mice by nicking the tail vein. Only low dose groups of WNV and chimeric WN/DEN inoculated mice, and mice inoculated with 1000 pfu of DENV are expected to survive. Serum samples from the collected blood are heat-inactivated at 56° C. for 30 minutes and antibodies in the serum are determined by ELISA and/or PRNT assays.

Two days after blood collection, all mice are inoculated with a lethal dose of WNV NY99 (1000 pfu). The virus is delivered in 100 µl of PBS via intraperitoneal inoculation. Mice are monitored daily and moribund mice are euthanized by overexposure to $CO_2$ gas. Blood is collected from mice surviving more than 21 days after WNV challenge and antibodies in serum are determined by ELISA and/or PRNT. Antibody responses and survival ratios in the groups that are first inoculated with chimeric WN/DEN virus are used to evaluate the protective efficacy of the immune response triggered by WNV non-structural proteins from the chimeric WN/DEN virus. Increased antibody response and/or survival ratio in animals inoculated with WN/DEN chimeric virus and challenged with WNV indicates that an antibody response and protective immunity are the result of WNV C protein or non-structural proteins.

Example 8

Determination of WN/DEN Lethal Dose and Evaluation of DENY Vaccine Efficacy

This example describes methods for using WN/DEN chimeric viruses to evaluate the efficacy of candidate DENV vaccines.

The lethal dose of WN/DEN chimeric virus is determined in mice by inoculating 12 week old mice (such as Swiss Webster, NIH Swiss, or ICR mice; 8 animals per group) with PBS as a control, or 10, 100, 1000, or 10,000 times the $VD_{50}$ calculated from the neuroinvasion experiment (described in Example 6) or $10^4$, $10^5$, $10^6$, or $10^7$ pfu, whichever is lower. Mice are inoculated intraperitoneally with virus in 100 µL of PBS. Mice are monitored for signs of clinical illness daily and moribund mice are euthanized by overexposure to $CO_2$ gas. The $VD_{50}$ (the dose causing sickness in 50% of the mice inoculated) is calculated and the lethal dose is generally $10\text{-}1000 \times VD_{50}$. Usually $100 \times VD_{50}$ is used. Alternatively, blood can be collected after virus challenge to determine the viremia levels from each group. Chimeric virus doses causing higher viremia compared to a wild type DENV control group (such as 100-fold, 1000-fold, 10000-fold or higher) may be used for vaccine efficacy study.

To assess candidate DENV vaccine efficacy, groups of 4 week old mice (such as Swiss Webster, NIH Swiss, or ICR mice) are inoculated intraperitoneally with wild type DENV, DENV vaccine strain, or PBS. Mice in each group are inoculated intraperitoneally with $10^5$ pfu of virus in 100 µl of PBS. Identical immunizations are given four to six weeks later. The mice are given WN/DEN chimeric virus at a lethal dose ($100 \times VD_{50}$) or a dose causing high viremia compared to wild type DENV when they are 12 weeks old. Mice are bled to determine viremia level and monitored daily for signs of morbidity after lethal virus challenge. Mice with the first sign of morbidity, such as rough fur, hunched back, lethargy, unbalanced or irritable movement, dehydration, 10% weight loss, or signs of paralysis are euthanized immediately by overexposure to $CO_2$ gas.

Blood is also collected prior to secondary immunization, lethal WN/DEN challenge, and from mice surviving 21-28 days after lethal challenge. Antibodies to DEN or WNV proteins in the serum are determined by PRNT. Protective efficacy of the vaccine is evaluated by comparing viremia levels or survival ratios of the vaccinated groups to the non-immunized control group. Increased survival, decreased viremia level, or increased anti-DENV antibody production of mice inoculated with a candidate vaccine as compared to a control group indicates a DENV vaccine candidate suitable for further testing. No increase in survival or no decrease in viremia level compared to a non-immunized control group indicates poor protective efficacy by the DENV vaccine candidate.

Example 9

Neutralizing Antibody Assays

This example describes methods of assessing neutralizing antibody response to DENV infection or WN/DEN virus chimeras using a plaque-reduction neutralization assay (PRNT) or immunostaining-based neutralization assay.

Serum samples are tested for neutralizing antibodies by serum-dilution PRNT. 60-100 pfu of WN/DEN virus chimera or wild type DENV is incubated with serial 2-fold dilutions of heat-inactivated (56° C. for 30 minutes) serum specimens overnight at 4° C. The virus-serum mixtures are inoculated in tissue culture plates containing a confluent monolayer of Vero cells. Following inoculation, plates are incubated at 37° C. in an atmosphere of 5% $CO_2$ for 1.5 hours to allow virus adsorption. Plates are rocked every 10 minutes to ensure the cell monolayer does not dry out. After virus adsorption, the cells are overlaid with 0.8% agarose containing balanced salt solution and Ye-Lah medium (10 g yeast extract and 50 g lactalbumin hydrolysate per 1000 ml water). Plates are incubated at 37° C. in an atmosphere of 5% $CO_2$ for 1-7 days. Following this incubation, wells are overlaid with another agarose overlay containing 1.5% neutral red to visualize plaques. Plaques are counted the following 1-3 days.

A reduction in the number of plaques in the cell culture inoculated with the virus-serum mixture as compared to the control culture (cells incubated with virus alone) indicates the presence of a DENV neutralizing antibody in the serum. The neutralizing antibody titer is identified as the highest serum dilution that reduces the number of virus plaques in the test by 50% or more.

In addition to PRNT assay, neutralizing antibody can also be measured by an immunostaining-based neutralization assay. The method is identical to the PRNT assay, up to the step of virus-antibody absorption on cell monolayer in a cell culture plate (6-well, 24-well, 48-well, or 96-well plate) at 37° C. $CO_2$ incubator. Instead of Ye-Lah medium with agarose overlay, liquid culture medium or medium mixed with Avicel overlay is added to the plates following the virus absorption. Medium or the Avicel overlay is removed after desired incubation periods (e.g. 2-5 days), and cells are fixed with acetone. DENV antibodies are added to the cell plates for 1 hour at 37° C. Plates are washed 3 times to remove unbound antibodies, and chemical or fluorescent conjugated secondary antibody is added to the plate and incubated for 30-60 min at 37° C. The immunostained virus foci in the Avicel overlay plates can be visualized and counted. In the case of using liquid medium in the experiment, the viral antigen produced in the infected cells can be measured by plate reader.

Example 10

Antibody Cross-Reactivity of Chimeric Flaviviruses

This example describes methods for determining reduction of antibody cross-reactivity for DENV E proteins including one or more amino acid substitutions.

DENV E protein (wild type or including one or more amino acid substitutions) is expressed either by infection of cells with a WN/DEN virus chimera encoding a DENV E protein, or by recombinant production of the DENV E proteins (for example by expression in mammalian cells, yeast, or E. coli). E protein antigen of the WN/DENV chimera or its variants containing different amino acid substitutions expressed in the chimera-infected C6/36 cells is analyzed with a panel of anti-flavivirus mAbs by IFA to determine mAb end point reactivity of the variant E proteins. Briefly, infected cells are fixed by acetone on microscopy optical slides or slide chambers. Serial diluted mAbs are added to different wells of the slide and incubated at 37° C. for 1 hour and unbound mAb is then rinsed away by PBS. Secondary goat- or rabbit-anti-mouse IgG conjugated with FITC is added and incubated at 37° for 30 min to bind the mouse mAb in the wells, and unbound conjugates is rinsed off by PBS. Positive wells are detected by fluorescent microscope.

Alternatively, purified WN/DENV virus particles are captured in native form by a rabbit anti-DEN polyclonal antibody coated on ELISA plates. The E protein and its variants on the virus particles are analyzed by ELISA with a panel of mouse anti-flavivirus mAbs to determine mAb end point reactivity of the variant viral particles, following the protocol of Roehrig et al. (*Virology* 246:317-28, 1998). The panel of the mAb can include 4G2 (ATCC No. HB-112), 6B6C-1, 1B7-5, 1A1D-2, 1A5D-1, 1B4C-2, F4540, D1-11, 9F-10, D2811, 2H3, 9A3D-8, 3H5, 1F1, 8A1, and/or 1H10.

WN/DEN chimeras including E protein variants that have reduced antibody cross-reactivity may be used for diagnosis of secondary flavivirus infection with a particular DENV serotype (i.e. DEN1, DEN2, DEN3, or DEN4), such as in a PRNT assay. These chimeras may also be included in a flavivirus diagnosis panel, which can reduce false positive results and enhance the speed and accuracy of flavivirus diagnostics.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A nucleic acid chimera comprising:
   a first nucleic acid molecule comprising a 5' non-coding region, a nucleic acid encoding a C protein and non-structural proteins, and a 3' non-coding region from a West Nile virus genome; and
   a second nucleic acid molecule operably linked to the first nucleic acid molecule, encoding at least a portion of a prM protein and E protein from a Dengue virus genome.

2. The chimera of claim 1, wherein the West Nile virus genome is a NY99 West Nile virus strain genome.

3. The chimera of claim 1, wherein the Dengue virus genome is a Dengue-1, Dengue-2, Dengue-3, or Dengue-4 genome.

4. The chimera of claim 1, wherein the Dengue virus genome comprises a 16681 Dengue-2 virus strain genome.

5. The chimera of claim 1, wherein the second nucleic acid molecule encodes at least one amino acid substitution in the E protein, wherein the substitution increases virus titer, replication rate, plaque size, or stability in cell culture.

6. The chimera of claim 5, wherein the at least one amino acid substitution in the E protein comprises a substitution at amino acid position 64, 122, 186, 203, or a combination of two or more thereof.

7. The chimera of claim 6, wherein the at least one amino acid substitution in the E protein is one or more of K122I, S186F, and N203D.

8. The chimera of claim 1, wherein the second nucleic acid molecule encodes at least one amino acid substitution in the prM protein, wherein the substitution increases virus titer, replication rate, plaque size, or stability in cell culture.

9. The chimera of claim 1, wherein the first nucleic acid molecule encodes at least one amino acid substitution in one or more of the non-structural proteins or the C protein, wherein the substitution increases virus titer, replication rate, plaque size, or stability in cell culture, or decreases infectivity in mosquitoes.

10. The chimera of claim 9, wherein the amino acid substitution is a substitution selected from the group consisting of position 49 of non-structural protein 2A (NS2A), position 94 of NS2A, position 241 of non-structural protein 4B (NS4B), and a combination of two or more thereof.

11. The chimera of claim 10, wherein the amino acid substitution is one or more of NS2A I49T, NS2A F94L, and NS4B T241I.

12. The chimera of claim 1, wherein the first nucleic acid molecule comprises at least one nucleic acid substitution in the 5' non-coding region or the 3' non-coding region of the West Nile virus genome, wherein the substitution increases virus titer, replication rate, plaque size, or stability in cell culture, or decreases infectivity in mosquitoes.

13. The chimera of claim 1, wherein the second nucleic acid molecule encodes at least one amino acid substitution in the E protein, wherein the substituted E-protein exhibits measurably reduced antibody cross-reactivity.

14. The chimera of claim 13, wherein the at least one amino acid substitution in the E protein comprises a substitution at amino acid position 101, 106, 107, 108, 135, or a combination of two or more thereof.

15. The chimera of claim 1, having a nucleic acid sequence selected from the group consisting of SEQ ID NOs: 1, 3, 5, 7, and nucleic acid sequences at least 95% identical to at least one of SEQ ID NOs: 1, 3, 5, or 7.

16. The chimera of claim 1, having an amino acid sequence selected from the group consisting of SEQ ID NOs: 2, 4, 6, 8, and amino acid sequences at least 95% identical to at least one of SEQ ID NOs: 2, 4, 6, or 8.

17. A method of detecting a Dengue virus antibody in a sample from a subject, comprising:
   contacting the sample with a virus encoded by the chimera of claim 1 to form a virus-sample mixture;
   inoculating a susceptible monolayer cell culture with the virus-sample mixture;
   incubating the cell culture under conditions sufficient to allow virus replication;
   counting plaques, counting immunostained foci, or measuring viral antigen level in the culture; and
   comparing the number of plaques, the number of foci, or the viral antigen level to a control culture, wherein a decrease in the number of plaques, number of foci, or viral antigen level as compared to the control culture indicates the Dengue virus antibody is present in the sample.

18. A method of evaluating efficacy of a candidate Dengue virus vaccine, comprising:
   immunizing a set of subjects with the candidate Dengue virus vaccine;
   waiting sufficient time for an immune response to develop;
   challenging the subjects by inoculating the subjects with a virus encoded by the chimera of claim 1;
   waiting sufficient time for viremia, morbidity and/or mortality to develop; and
   comparing viremia, morbidity and/or mortality of the subjects with a set of non-immunized control subjects which has not been immunized with the candidate Dengue virus vaccine, wherein a decrease in viremia, morbidity and/or mortality as compared with the control subjects indicates efficacy of the candidate Dengue virus vaccine.

19. A method of producing virus particles expressing Dengue virus prM, M, and E proteins, comprising:
   culturing a virus encoded by the chimera of claim 1 in a cell, wherein virus particles comprising one or more Dengue prM, M, or E proteins are produced;
   collecting a supernatant from the cell culture containing the chimera; and
   purifying the virus particles from the supernatant.

20. A chimeric flavivirus or virus particle comprising the nucleic acid chimera of claim 1.

21. A mouse inoculated with the nucleic acid chimera of claim 1.

22. A mouse inoculated with a chimeric flavivirus or virus particle comprising the nucleic acid chimera of claim 1.

* * * * *

SEQUENCE LISTING

```
<160> NUMBER OF SEQ ID NOS: 20

<210> SEQ ID NO 1
<211> LENGTH: 10996
<212> TYPE: DNA
<213> ORGANISM: Artificial Sequence
<220> FEATURE:
<223> OTHER INFORMATION: Recombinant West Nile virus/Dengue-2 virus
      chimera
<220> FEATURE:
<221> NAME/KEY: CDS
<222> LOCATION: (97)..(10362)

<400> SEQUENCE: 1
agtagttcgc ctgtgtgagc tgacaaactt agtagtgttt gtgaggatta acaacaatta       60
acacagtgcg agctgtttct tagcacgaag atctcg atg tct aag aaa cca gga      114
                                        Met Ser Lys Lys Pro Gly
                                        1               5 ggg ccc ggc aag agc cgg gct gtc aat atg cta aaa cgc gga atg ccc      162
Gly Pro Gly Lys Ser Arg Ala Val Asn Met Leu Lys Arg Gly Met Pro
         10                  15                  20
```

```
cgc gtg ttg tcc ttg att gga ctg aag agg gct atg ttg agc ctg atc      210
Arg Val Leu Ser Leu Ile Gly Leu Lys Arg Ala Met Leu Ser Leu Ile
        25                  30                  35 gac ggc aag ggg cca ata cga ttt gtg ttg gct ctc ttg gcg ttc ttc      258
Asp Gly Lys Gly Pro Ile Arg Phe Val Leu Ala Leu Leu Ala Phe Phe
40                  45                  50 agg ttc aca gca att gct ccg acc cga gca gtg ctg gat cga tgg aga      306
Arg Phe Thr Ala Ile Ala Pro Thr Arg Ala Val Leu Asp Arg Trp Arg
55                  60                  65                  70 ggt gtg aac aaa caa aca gcg atg aaa cac ctt ctg agt ttt aag aag      354
Gly Val Asn Lys Gln Thr Ala Met Lys His Leu Leu Ser Phe Lys Lys
            75                  80                  85 gaa cta ggg acc ttg acc agt gct atc aat cgg cgg agc tca aaa caa      402
Glu Leu Gly Thr Leu Thr Ser Ala Ile Asn Arg Arg Ser Ser Lys Gln
        90                  95                  100 aag aaa aga tcc gcg ggc atg atc att atg ctg att cca aca gtg atg      450
Lys Lys Arg Ser Ala Gly Met Ile Ile Met Leu Ile Pro Thr Val Met
        105                 110                 115 gcg ttc cat tta acc aca cgt aac gga gaa cca cac atg atc gtc agc      498
Ala Phe His Leu Thr Thr Arg Asn Gly Glu Pro His Met Ile Val Ser
120                 125                 130 aga caa gag aaa ggg aaa agt ctt ctg ttt aaa aca gag gat ggc gtg      546
Arg Gln Glu Lys Gly Lys Ser Leu Leu Phe Lys Thr Glu Asp Gly Val
135                 140                 145                 150 aac atg tgt acc ctc atg gcc atg gac ctt ggt gaa ttg tgt gaa gac      594
Asn Met Cys Thr Leu Met Ala Met Asp Leu Gly Glu Leu Cys Glu Asp
                155                 160                 165 aca atc acg tac aag tgt ccc ctt ctc agg cag aat gag cca gaa gac      642
Thr Ile Thr Tyr Lys Cys Pro Leu Leu Arg Gln Asn Glu Pro Glu Asp
                170                 175                 180 ata gac tgt tgg tgc aac tct acg tcc acg tgg gta act tat ggg acg      690
Ile Asp Cys Trp Cys Asn Ser Thr Ser Thr Trp Val Thr Tyr Gly Thr
            185                 190                 195 tgt acc acc atg gga gaa cat aga aga gaa aaa aga tca gtg gca ctc      738
Cys Thr Thr Met Gly Glu His Arg Arg Glu Lys Arg Ser Val Ala Leu
        200                 205                 210 gtt cca cat gtg gga atg gga ctg gag aca cga act gaa aca tgg atg      786
Val Pro His Val Gly Met Gly Leu Glu Thr Arg Thr Glu Thr Trp Met
215                 220                 225                 230 tca tca gaa ggg gcc tgg aaa cat gtc cag aga att gaa act tgg atc      834
Ser Ser Glu Gly Ala Trp Lys His Val Gln Arg Ile Glu Thr Trp Ile
                235                 240                 245 ttg aga cat cca ggc ttc acc atg atg gca gca atc ctg gca tac acc      882
Leu Arg His Pro Gly Phe Thr Met Met Ala Ala Ile Leu Ala Tyr Thr
            250                 255                 260 ata gga acg aca cat ttc caa aga gcc ctg att ttc atc tta ctg aca      930
Ile Gly Thr Thr His Phe Gln Arg Ala Leu Ile Phe Ile Leu Leu Thr
        265                 270                 275 gct gtc act cct tca atg aca atg cgt tgc ata gga atg tca aat aga      978
Ala Val Thr Pro Ser Met Thr Met Arg Cys Ile Gly Met Ser Asn Arg
280                 285                 290 gac ttt gtg gaa ggg gtt tca gga gga agc tgg gtt gac ata gtc tta     1026
Asp Phe Val Glu Gly Val Ser Gly Gly Ser Trp Val Asp Ile Val Leu
295                 300                 305                 310 gaa cat gga agc tgt gtg acg acg atg gca aaa aac aaa cca aca ttg     1074
Glu His Gly Ser Cys Val Thr Thr Met Ala Lys Asn Lys Pro Thr Leu
                315                 320                 325 gat ttt gaa ctg ata aaa aca gaa gcc aaa cag cct gcc acc tta agg     1122
Asp Phe Glu Leu Ile Lys Thr Glu Ala Lys Gln Pro Ala Thr Leu Arg
            330                 335                 340
```

```
aag tac tgt ata gag gca aag cta acc aac aca aca aca gaa tct cgc    1170
Lys Tyr Cys Ile Glu Ala Lys Leu Thr Asn Thr Thr Thr Glu Ser Arg
        345                 350                 355 tgc cca aca caa ggg gaa ccc agc cta aat gaa gag cag gac aaa agg    1218
Cys Pro Thr Gln Gly Glu Pro Ser Leu Asn Glu Glu Gln Asp Lys Arg
360                 365                 370 ttc gtc tgc aaa cac tcc atg gta gac aga gga tgg gga aat gga tgt    1266
Phe Val Cys Lys His Ser Met Val Asp Arg Gly Trp Gly Asn Gly Cys
375                 380                 385                 390 gga cta ttt gga aag gga ggc att gtg acc tgt gct atg ttc aga tgc    1314
Gly Leu Phe Gly Lys Gly Gly Ile Val Thr Cys Ala Met Phe Arg Cys
                395                 400                 405 aaa aag aac atg gaa gga aaa gtt gtg caa cca gaa aac ttg gaa tac    1362
Lys Lys Asn Met Glu Gly Lys Val Val Gln Pro Glu Asn Leu Glu Tyr
            410                 415                 420 acc att gtg ata aca cct cac tca ggg gaa gag cat gca gtc gga aat    1410
Thr Ile Val Ile Thr Pro His Ser Gly Glu Glu His Ala Val Gly Asn
        425                 430                 435 gac aca gga aaa cat ggc aag gaa atc aaa ata aca cca cag agt tcc    1458
Asp Thr Gly Lys His Gly Lys Glu Ile Lys Ile Thr Pro Gln Ser Ser
    440                 445                 450 atc aca gaa gca gaa ttg aca ggt tat ggc act gtc aca atg gag tgc    1506
Ile Thr Glu Ala Glu Leu Thr Gly Tyr Gly Thr Val Thr Met Glu Cys
455                 460                 465                 470 tct cca aga acg ggc ctc gac ttc aat gag atg gtg ttg ttg cag atg    1554
Ser Pro Arg Thr Gly Leu Asp Phe Asn Glu Met Val Leu Leu Gln Met
                475                 480                 485 gaa aat aaa gct tgg ctg gtg cac agg caa tgg ttc cta gac ctg ccg    1602
Glu Asn Lys Ala Trp Leu Val His Arg Gln Trp Phe Leu Asp Leu Pro
            490                 495                 500 tta cca tgg ttg ccc gga gcg gac aca caa ggg tca aat tgg ata cag    1650
Leu Pro Trp Leu Pro Gly Ala Asp Thr Gln Gly Ser Asn Trp Ile Gln
        505                 510                 515 aaa gag aca ttg gtc act ttc aaa aat ccc cat gcg aag aaa cag gat    1698
Lys Glu Thr Leu Val Thr Phe Lys Asn Pro His Ala Lys Lys Gln Asp
    520                 525                 530 gtt gtt gtt tta gga tcc caa gaa ggg gcc atg cac aca gca ctt aca    1746
Val Val Val Leu Gly Ser Gln Glu Gly Ala Met His Thr Ala Leu Thr
535                 540                 545                 550 ggg gcc aca gaa atc caa atg tca tca gga aac tta ctc ttc aca gga    1794
Gly Ala Thr Glu Ile Gln Met Ser Ser Gly Asn Leu Leu Phe Thr Gly
                555                 560                 565 cat ctc aag tgc agg ctg aga atg gac aag cta cag ctc aaa gga atg    1842
His Leu Lys Cys Arg Leu Arg Met Asp Lys Leu Gln Leu Lys Gly Met
            570                 575                 580 tca tac tct atg tgc aca gga aag ttt aaa gtt gtg aag gaa ata gca    1890
Ser Tyr Ser Met Cys Thr Gly Lys Phe Lys Val Val Lys Glu Ile Ala
        585                 590                 595 gaa aca caa cat gga aca ata gtt atc aga gtg caa tat gaa ggg gac    1938
Glu Thr Gln His Gly Thr Ile Val Ile Arg Val Gln Tyr Glu Gly Asp
    600                 605                 610 ggc tct cca tgc aag atc cct ttt gag ata atg gat ttg gaa aaa aga    1986
Gly Ser Pro Cys Lys Ile Pro Phe Glu Ile Met Asp Leu Glu Lys Arg
615                 620                 625                 630 cat gtc tta ggt cgc ctg att aca gtc aac cca att gtg aca gaa aaa    2034
His Val Leu Gly Arg Leu Ile Thr Val Asn Pro Ile Val Thr Glu Lys
                635                 640                 645 gat agc cca gtc aac ata gaa gca gaa cct cca ttc gga gac agc tac    2082
Asp Ser Pro Val Asn Ile Glu Ala Glu Pro Pro Phe Gly Asp Ser Tyr
            650                 655                 660
```

```
atc atc ata gga gta gag ccg gga caa ctg aag ctc aac tgg ttt aag     2130
Ile Ile Ile Gly Val Glu Pro Gly Gln Leu Lys Leu Asn Trp Phe Lys
            665             670                 675 aaa gga agt tct atc ggc caa atg ttt gag aca aca atg agg ggg gcg     2178
Lys Gly Ser Ser Ile Gly Gln Met Phe Glu Thr Thr Met Arg Gly Ala
        680             685             690 aag aga atg gcc att tta ggt gac aca gcc tgg gat ttt gga tcc ttg     2226
Lys Arg Met Ala Ile Leu Gly Asp Thr Ala Trp Asp Phe Gly Ser Leu
695             700             705             710 gga gga gtg ttt aca tct ata gga aag gct ctc cac caa gtc ttt gga     2274
Gly Gly Val Phe Thr Ser Ile Gly Lys Ala Leu His Gln Val Phe Gly
            715             720             725 gca atc tat gga gct gcc ttc agt ggg gtt tca tgg act atg aaa atc     2322
Ala Ile Tyr Gly Ala Ala Phe Ser Gly Val Ser Trp Thr Met Lys Ile
        730             735             740 ctc ata gga gtc att atc aca tgg ata gga atg aat tca cgc agc acc     2370
Leu Ile Gly Val Ile Ile Thr Trp Ile Gly Met Asn Ser Arg Ser Thr
            745             750             755 tca ctg tct gtg aca cta gta ttg gtg gga att gtg aca ctg tat ttg     2418
Ser Leu Ser Val Thr Leu Val Leu Val Gly Ile Val Thr Leu Tyr Leu
    760             765             770 gga gtc atg gtg cag gcc gat tcc gga tgt gcc ata gac atc agc cgg     2466
Gly Val Met Val Gln Ala Asp Ser Gly Cys Ala Ile Asp Ile Ser Arg
775             780             785             790 caa gag ctg aga tgt gga agt gga gtg ttc ata cac aat gat gtg gag     2514
Gln Glu Leu Arg Cys Gly Ser Gly Val Phe Ile His Asn Asp Val Glu
            795             800             805 gct tgg atg gac cgg tac aag tat tac cct gaa acg cca caa ggc cta     2562
Ala Trp Met Asp Arg Tyr Lys Tyr Tyr Pro Glu Thr Pro Gln Gly Leu
        810             815             820 gcc aag atc att cag aaa gct cat aag gaa gga gtg tgc ggt cta cga     2610
Ala Lys Ile Ile Gln Lys Ala His Lys Glu Gly Val Cys Gly Leu Arg
            825             830             835 tca gtt tcc aga ctg gag cat caa atg tgg gaa gca gtg aag gac gag     2658
Ser Val Ser Arg Leu Glu His Gln Met Trp Glu Ala Val Lys Asp Glu
        840             845             850 ctg aac act ctt ttg aag gag aat ggt gtg gac ctt agt gtc gtg gtt     2706
Leu Asn Thr Leu Leu Lys Glu Asn Gly Val Asp Leu Ser Val Val Val
855             860             865             870 gag aaa cag gag gga atg tac aag tca gca cct aaa cgc ctc acc gcc     2754
Glu Lys Gln Glu Gly Met Tyr Lys Ser Ala Pro Lys Arg Leu Thr Ala
            875             880             885 acc acg gaa aaa ttg gaa att ggc tgg aag gcc tgg gga aag agt att     2802
Thr Thr Glu Lys Leu Glu Ile Gly Trp Lys Ala Trp Gly Lys Ser Ile
        890             895             900 tta ttt gca cca gaa ctc gcc aac aac acc ttt gtg gtt gat ggt ccg     2850
Leu Phe Ala Pro Glu Leu Ala Asn Asn Thr Phe Val Val Asp Gly Pro
            905             910             915 gag acc aag gaa tgt ccg act cag aat cgc gct tgg aat agc tta gaa     2898
Glu Thr Lys Glu Cys Pro Thr Gln Asn Arg Ala Trp Asn Ser Leu Glu
        920             925             930 gtg gag gat ttt gga ttt ggt ctc acc agc act cgg atg ttc ctg aag     2946
Val Glu Asp Phe Gly Phe Gly Leu Thr Ser Thr Arg Met Phe Leu Lys
935             940             945             950 gtc aga gag agc aac aca act gaa tgt gac tcg aag atc att gga acg     2994
Val Arg Glu Ser Asn Thr Thr Glu Cys Asp Ser Lys Ile Ile Gly Thr
            955             960             965 gct gtc aag aac aac ttg gcg atc cac agt gac ctg tcc tat tgg att     3042
Ala Val Lys Asn Asn Leu Ala Ile His Ser Asp Leu Ser Tyr Trp Ile
            970             975             980
```

-continued

```
gaa agc agg ctc aat gat acg tgg aag ctt gaa agg gca gtt ctg ggt      3090
Glu Ser Arg Leu Asn Asp Thr Trp Lys Leu Glu Arg Ala Val Leu Gly
            985                 990                 995 gaa gtc aaa tca tgt acg tgg cct gag acg cat acc ttg tgg ggc          3135
Glu Val Lys Ser Cys Thr Trp Pro Glu Thr His Thr Leu Trp Gly
        1000                1005                1010 gat gga atc ctt gag agt gac ttg ata ata cca gtc aca ctg gcg          3180
Asp Gly Ile Leu Glu Ser Asp Leu Ile Ile Pro Val Thr Leu Ala
        1015                1020                1025 gga cca cga agc aat cac aat cgg aga cct ggg tac aag aca caa          3225
Gly Pro Arg Ser Asn His Asn Arg Arg Pro Gly Tyr Lys Thr Gln
        1030                1035                1040 aac cag ggc cca tgg gac gaa ggc cgg gta gag att gac ttc gat          3270
Asn Gln Gly Pro Trp Asp Glu Gly Arg Val Glu Ile Asp Phe Asp
        1045                1050                1055 tac tgc cca gga act acg gtc acc ctg agt gag agc tgc gga cac          3315
Tyr Cys Pro Gly Thr Thr Val Thr Leu Ser Glu Ser Cys Gly His
        1060                1065                1070 cgt gga cct gcc act cgc acc acc aca gag agc gga aag ttg ata          3360
Arg Gly Pro Ala Thr Arg Thr Thr Thr Glu Ser Gly Lys Leu Ile
        1075                1080                1085 aca gat tgg tgc tgc agg agc tgc acc tta cca cca ctg cgc tac          3405
Thr Asp Trp Cys Cys Arg Ser Cys Thr Leu Pro Pro Leu Arg Tyr
        1090                1095                1100 caa act gac agc ggc tgt tgg tat ggt atg gag atc aga cca cag          3450
Gln Thr Asp Ser Gly Cys Trp Tyr Gly Met Glu Ile Arg Pro Gln
        1105                1110                1115 aga cat gat gaa aag acc ctc gtg cag tca caa gtg aat gct tat          3495
Arg His Asp Glu Lys Thr Leu Val Gln Ser Gln Val Asn Ala Tyr
        1120                1125                1130 aat gct gat atg att gac cct ttt cag ttg ggc ctt ctg gtc gtg          3540
Asn Ala Asp Met Ile Asp Pro Phe Gln Leu Gly Leu Leu Val Val
        1135                1140                1145 ttc ttg gcc acc cag gag gtc ctt cgc aag agg tgg aca gcc aag          3585
Phe Leu Ala Thr Gln Glu Val Leu Arg Lys Arg Trp Thr Ala Lys
        1150                1155                1160 atc agc atg cca gct ata ctg att gct ctg cta gtc ctg gtg ttt          3630
Ile Ser Met Pro Ala Ile Leu Ile Ala Leu Leu Val Leu Val Phe
        1165                1170                1175 ggg ggc att act tac act gat gtg tta cgc tat gtc atc ttg gtg          3675
Gly Gly Ile Thr Tyr Thr Asp Val Leu Arg Tyr Val Ile Leu Val
        1180                1185                1190 ggg gca gct ttc gca gaa tct aat tcg gga gga gac gtg gta cac          3720
Gly Ala Ala Phe Ala Glu Ser Asn Ser Gly Gly Asp Val Val His
        1195                1200                1205 ttg gcg ctc atg gcg acc ttc aag ata caa cca gtg ttt atg gtg          3765
Leu Ala Leu Met Ala Thr Phe Lys Ile Gln Pro Val Phe Met Val
        1210                1215                1220 gca tcg ttt ctc aaa gcg aga tgg acc aac cag gag aac att ttg          3810
Ala Ser Phe Leu Lys Ala Arg Trp Thr Asn Gln Glu Asn Ile Leu
        1225                1230                1235 ttg atg ttg gcg gct gtt ttc ttt caa atg gct tat tac gat gcc          3855
Leu Met Leu Ala Ala Val Phe Phe Gln Met Ala Tyr Tyr Asp Ala
        1240                1245                1250 cgc caa att ctg ctc tgg gag atc cct gat gtg ttg aat tca ctg          3900
Arg Gln Ile Leu Leu Trp Glu Ile Pro Asp Val Leu Asn Ser Leu
        1255                1260                1265 gcg gta gct tgg atg ata ctg aga gcc ata aca ttc aca acg aca          3945
Ala Val Ala Trp Met Ile Leu Arg Ala Ile Thr Phe Thr Thr Thr
        1270                1275                1280
```

-continued

```
tca aac gtg gtt gtt ccg ctg cta gcc ctg cta aca ccc ggg ctg      3990
Ser Asn Val Val Val Pro Leu Leu Ala Leu Leu Thr Pro Gly Leu
    1285            1290                1295 aga tgc ttg aat ctg gat gtg tac agg ata ctg ctg ttg atg gtc      4035
Arg Cys Leu Asn Leu Asp Val Tyr Arg Ile Leu Leu Leu Met Val
    1300            1305                1310 gga ata ggc agc ttg atc agg gag aag agg agt gca gct gca aaa      4080
Gly Ile Gly Ser Leu Ile Arg Glu Lys Arg Ser Ala Ala Ala Lys
    1315            1320                1325 aag aaa gga gca agt ctg cta tgc ttg gct cta gcc tca aca gga      4125
Lys Lys Gly Ala Ser Leu Leu Cys Leu Ala Leu Ala Ser Thr Gly
    1330            1335                1340 ctt ttc aac ccc atg atc ctt gct gct gga ctg att gca tgt gat      4170
Leu Phe Asn Pro Met Ile Leu Ala Ala Gly Leu Ile Ala Cys Asp
    1345            1350                1355 ccc aac cgt aaa cgc gga tgg ccc gca act gaa gtg atg aca gct      4215
Pro Asn Arg Lys Arg Gly Trp Pro Ala Thr Glu Val Met Thr Ala
    1360            1365                1370 gtc ggc cta atg ttt gcc atc gtc gga ggg ctg gca gag ctt gac      4260
Val Gly Leu Met Phe Ala Ile Val Gly Gly Leu Ala Glu Leu Asp
    1375            1380                1385 att gac tcc atg gcc att cca atg act atc gcg ggg ctc atg ttt      4305
Ile Asp Ser Met Ala Ile Pro Met Thr Ile Ala Gly Leu Met Phe
    1390            1395                1400 gct gct ttc gtg att tct ggg aaa tca aca gat atg tgg att gag      4350
Ala Ala Phe Val Ile Ser Gly Lys Ser Thr Asp Met Trp Ile Glu
    1405            1410                1415 aga acg gcg gac att tcc tgg gaa agt gat gca gaa att aca ggc      4395
Arg Thr Ala Asp Ile Ser Trp Glu Ser Asp Ala Glu Ile Thr Gly
    1420            1425                1430 tcg agc gaa aga gtt gat gtg cgg ctt gat gat gat gga aac ttc      4440
Ser Ser Glu Arg Val Asp Val Arg Leu Asp Asp Asp Gly Asn Phe
    1435            1440                1445 cag ctc atg aat gat cca gga gca cct tgg aag ata tgg atg ctc      4485
Gln Leu Met Asn Asp Pro Gly Ala Pro Trp Lys Ile Trp Met Leu
    1450            1455                1460 aga atg gtc tgt ctc gcg att agt gcg tac acc ccc tgg gca atc      4530
Arg Met Val Cys Leu Ala Ile Ser Ala Tyr Thr Pro Trp Ala Ile
    1465            1470                1475 ttg ccc tca gta gtt gga ttt tgg ata act ctc caa tac aca aag      4575
Leu Pro Ser Val Val Gly Phe Trp Ile Thr Leu Gln Tyr Thr Lys
    1480            1485                1490 aga gga ggc gtg ttg tgg gac act ccc tca cca aag gag tac aaa      4620
Arg Gly Gly Val Leu Trp Asp Thr Pro Ser Pro Lys Glu Tyr Lys
    1495            1500                1505 aag ggg gac acg acc acc ggc gtc tac agg atc atg act cgt ggg      4665
Lys Gly Asp Thr Thr Thr Gly Val Tyr Arg Ile Met Thr Arg Gly
    1510            1515                1520 ctg ctc ggc agt tat caa gca gga gcg ggc gtg atg gtt gaa ggt      4710
Leu Leu Gly Ser Tyr Gln Ala Gly Ala Gly Val Met Val Glu Gly
    1525            1530                1535 gtt ttc cac acc ctt tgg cat aca aca aaa gga gcc gct ttg atg      4755
Val Phe His Thr Leu Trp His Thr Thr Lys Gly Ala Ala Leu Met
    1540            1545                1550 agc gga gag ggc cgc ctg gac cca tac tgg ggc agt gtc aag gag      4800
Ser Gly Glu Gly Arg Leu Asp Pro Tyr Trp Gly Ser Val Lys Glu
    1555            1560                1565 gat cga ctt tgt tac gga gga ccc tgg aaa ttg cag cac aag tgg      4845
Asp Arg Leu Cys Tyr Gly Gly Pro Trp Lys Leu Gln His Lys Trp
    1570            1575                1580
```

```
aac  ggg  cag  gat  gag  gtg  cag  atg  att  gtg  gtg  gaa  cct  ggc  agg        4890
Asn  Gly  Gln  Asp  Glu  Val  Gln  Met  Ile  Val  Val  Glu  Pro  Gly  Arg
1585                universal 1590                1595 aac  gtt  aag  aac  gtc  cag  acg  aaa  cca  ggg  gtg  ttc  aaa  aca  cct        4935
Asn  Val  Lys  Asn  Val  Gln  Thr  Lys  Pro  Gly  Val  Phe  Lys  Thr  Pro
    1600                1605                1610 gaa  gga  gaa  atc  ggg  gcc  gtg  act  ttg  gac  ttc  ccc  act  gga  aca        4980
Glu  Gly  Glu  Ile  Gly  Ala  Val  Thr  Leu  Asp  Phe  Pro  Thr  Gly  Thr
        1615                1620                1625 tca  ggc  tca  cca  ata  gtg  gac  aaa  aac  ggt  gat  gtg  att  ggg  ctt        5025
Ser  Gly  Ser  Pro  Ile  Val  Asp  Lys  Asn  Gly  Asp  Val  Ile  Gly  Leu
            1630                1635                1640 tat  ggc  aat  gga  gtc  ata  atg  ccc  aac  ggc  tca  tac  ata  agc  gcg        5070
Tyr  Gly  Asn  Gly  Val  Ile  Met  Pro  Asn  Gly  Ser  Tyr  Ile  Ser  Ala
            1645                1650                1655 ata  gtg  cag  ggt  gaa  agg  atg  gat  gag  cca  atc  cca  gcc  gga  ttc        5115
Ile  Val  Gln  Gly  Glu  Arg  Met  Asp  Glu  Pro  Ile  Pro  Ala  Gly  Phe
        1660                1665                1670 gaa  cct  gag  atg  ctg  agg  aaa  aaa  cag  atc  act  gta  ctg  gat  ctc        5160
Glu  Pro  Glu  Met  Leu  Arg  Lys  Lys  Gln  Ile  Thr  Val  Leu  Asp  Leu
    1675                1680                1685 cat  ccc  ggc  gcc  ggt  aaa  aca  agg  agg  att  ctg  cca  cag  atc  atc        5205
His  Pro  Gly  Ala  Gly  Lys  Thr  Arg  Arg  Ile  Leu  Pro  Gln  Ile  Ile
        1690                1695                1700 aaa  gag  gcc  ata  aac  aga  aga  ctg  aga  aca  gcc  gtg  cta  gca  cca        5250
Lys  Glu  Ala  Ile  Asn  Arg  Arg  Leu  Arg  Thr  Ala  Val  Leu  Ala  Pro
1705                1710                1715 acc  agg  gtt  gtg  gct  gct  gag  atg  gct  gaa  gca  ctg  aga  gga  ctg        5295
Thr  Arg  Val  Val  Ala  Ala  Glu  Met  Ala  Glu  Ala  Leu  Arg  Gly  Leu
        1720                1725                1730 ccc  atc  cgg  tac  cag  aca  tcc  gca  gtg  ccc  aga  gaa  cat  aat  gga        5340
Pro  Ile  Arg  Tyr  Gln  Thr  Ser  Ala  Val  Pro  Arg  Glu  His  Asn  Gly
            1735                1740                1745 aat  gag  att  gtt  gat  gtc  atg  tgt  cat  gct  acc  ctc  acc  cac  agg        5385
Asn  Glu  Ile  Val  Asp  Val  Met  Cys  His  Ala  Thr  Leu  Thr  His  Arg
    1750                1755                1760 ctg  atg  tct  cct  cac  agg  gtg  ccg  aac  tac  aac  ctg  ttc  gtg  atg        5430
Leu  Met  Ser  Pro  His  Arg  Val  Pro  Asn  Tyr  Asn  Leu  Phe  Val  Met
1765                1770                1775 gat  gag  gct  cat  ttc  acc  gac  cca  gct  agc  att  gca  gca  aga  ggt        5475
Asp  Glu  Ala  His  Phe  Thr  Asp  Pro  Ala  Ser  Ile  Ala  Ala  Arg  Gly
        1780                1785                1790 tac  att  tcc  aca  aag  gtc  gag  cta  ggg  gag  gcg  gcg  gca  ata  ttc        5520
Tyr  Ile  Ser  Thr  Lys  Val  Glu  Leu  Gly  Glu  Ala  Ala  Ala  Ile  Phe
            1795                1800                1805 atg  aca  gcc  acc  cca  cca  ggc  act  tca  gat  cca  ttc  cca  gag  tcc        5565
Met  Thr  Ala  Thr  Pro  Pro  Gly  Thr  Ser  Asp  Pro  Phe  Pro  Glu  Ser
    1810                1815                1820 aat  tca  cca  att  tcc  gac  tta  cag  act  gag  atc  ccg  gat  cga  gct        5610
Asn  Ser  Pro  Ile  Ser  Asp  Leu  Gln  Thr  Glu  Ile  Pro  Asp  Arg  Ala
1825                1830                1835 tgg  aac  tct  gga  tac  gaa  tgg  atc  aca  gaa  tac  acc  ggg  aag  acg        5655
Trp  Asn  Ser  Gly  Tyr  Glu  Trp  Ile  Thr  Glu  Tyr  Thr  Gly  Lys  Thr
        1840                1845                1850 gtt  tgg  ttt  gtg  cct  agt  gtc  aag  atg  ggg  aat  gag  att  gcc  ctt        5700
Val  Trp  Phe  Val  Pro  Ser  Val  Lys  Met  Gly  Asn  Glu  Ile  Ala  Leu
            1855                1860                1865 tgc  cta  caa  cgt  gct  gga  aag  aaa  gta  gtc  caa  ttg  aac  aga  aag        5745
Cys  Leu  Gln  Arg  Ala  Gly  Lys  Lys  Val  Val  Gln  Leu  Asn  Arg  Lys
    1870                1875                1880
```

```
tcg tac gag acg gag tac cca aaa tgt aag aac gat gat tgg gac      5790
Ser Tyr Glu Thr Glu Tyr Pro Lys Cys Lys Asn Asp Asp Trp Asp
    1885            1890                1895 ttt gtt atc aca aca gac ata tct gaa atg ggg gct aac ttc aag      5835
Phe Val Ile Thr Thr Asp Ile Ser Glu Met Gly Ala Asn Phe Lys
1900            1905                1910 gcg agc agg gtg att gac agc cgg aag agt gtg aaa cca acc atc      5880
Ala Ser Arg Val Ile Asp Ser Arg Lys Ser Val Lys Pro Thr Ile
    1915            1920                1925 ata aca gaa gga gaa ggg aga gtg atc ctg gga gaa cca tct gca      5925
Ile Thr Glu Gly Glu Gly Arg Val Ile Leu Gly Glu Pro Ser Ala
1930            1935                1940 gtg aca gca gct agt gcc gcc cag aga cgt gga cgt atc ggt aga      5970
Val Thr Ala Ala Ser Ala Ala Gln Arg Arg Gly Arg Ile Gly Arg
    1945            1950                1955 aat ccg tcg caa gtt ggt gat gag tac tgt tat ggg ggg cac acg      6015
Asn Pro Ser Gln Val Gly Asp Glu Tyr Cys Tyr Gly Gly His Thr
1960            1965                1970 aat gaa gac gac tcg aac ttc gcc cat tgg act gag gca cga atc      6060
Asn Glu Asp Asp Ser Asn Phe Ala His Trp Thr Glu Ala Arg Ile
    1975            1980                1985 atg ctg gac aac atc aac atg cca aac gga ctg atc gct caa ttc      6105
Met Leu Asp Asn Ile Asn Met Pro Asn Gly Leu Ile Ala Gln Phe
1990            1995                2000 tac caa cca gag cgt gag aag gta tat acc atg gat ggg gaa tac      6150
Tyr Gln Pro Glu Arg Glu Lys Val Tyr Thr Met Asp Gly Glu Tyr
    2005            2010                2015 cgg ctc aga gga gaa gag aga aaa aac ttt ctg gaa ctg ttg agg      6195
Arg Leu Arg Gly Glu Glu Arg Lys Asn Phe Leu Glu Leu Leu Arg
2020            2025                2030 act gca gat ctg cca gtt tgg ctg gct tac aag gtt gca gcg gct      6240
Thr Ala Asp Leu Pro Val Trp Leu Ala Tyr Lys Val Ala Ala Ala
    2035            2040                2045 gga gtg tca tac cac gac cgg agg tgg tgc ttt gat ggt cct agg      6285
Gly Val Ser Tyr His Asp Arg Arg Trp Cys Phe Asp Gly Pro Arg
2050            2055                2060 aca aac aca att tta gaa gac aac aac gaa gtg gaa gtc atc acg      6330
Thr Asn Thr Ile Leu Glu Asp Asn Asn Glu Val Glu Val Ile Thr
    2065            2070                2075 aag ctt ggt gaa agg aag att ctg agg ccg cgc tgg att gac gcc      6375
Lys Leu Gly Glu Arg Lys Ile Leu Arg Pro Arg Trp Ile Asp Ala
2080            2085                2090 agg gtg tac tcg gat cac cag gca cta aag gcg ttc aag gac ttc      6420
Arg Val Tyr Ser Asp His Gln Ala Leu Lys Ala Phe Lys Asp Phe
    2095            2100                2105 gcc tcg gga aaa cgt tct cag ata ggg ctc att gag gtt ctg gga      6465
Ala Ser Gly Lys Arg Ser Gln Ile Gly Leu Ile Glu Val Leu Gly
2110            2115                2120 aag atg cct gag cac ttc atg ggg aag aca tgg gaa gca ctt gac      6510
Lys Met Pro Glu His Phe Met Gly Lys Thr Trp Glu Ala Leu Asp
    2125            2130                2135 acc atg tac gtt gtg gcc act gca gag aaa gga gga aga gct cac      6555
Thr Met Tyr Val Val Ala Thr Ala Glu Lys Gly Gly Arg Ala His
2140            2145                2150 aga atg gcc ctg gag gaa ctg cca gat gct ctt cag aca att gcc      6600
Arg Met Ala Leu Glu Glu Leu Pro Asp Ala Leu Gln Thr Ile Ala
    2155            2160                2165 ttg att gcc tta ttg agt gtg atg acc atg gga gta ttc ttc ctc      6645
Leu Ile Ala Leu Leu Ser Val Met Thr Met Gly Val Phe Phe Leu
2170            2175                2180
```

```
ctc atg cag cgg aag ggc att gga aag ata ggt ttg gga ggc gct      6690
Leu Met Gln Arg Lys Gly Ile Gly Lys Ile Gly Leu Gly Gly Ala
    2185            2190            2195 gtc ttg gga gtc gcg acc ttt ttc tgt tgg atg gct gaa gtt cca      6735
Val Leu Gly Val Ala Thr Phe Phe Cys Trp Met Ala Glu Val Pro
    2200            2205            2210 gga acg aag atc gcc gga atg ttg ctg ctc tcc ctt ctc ttg atg      6780
Gly Thr Lys Ile Ala Gly Met Leu Leu Leu Ser Leu Leu Leu Met
    2215            2220            2225 att gtg cta att cct gag cca gag aag caa cgt tcg cag aca gac      6825
Ile Val Leu Ile Pro Glu Pro Glu Lys Gln Arg Ser Gln Thr Asp
    2230            2235            2240 aac cag cta gcc gtg ttc ctg att tgt gtc atg acc ctt gtg agc      6870
Asn Gln Leu Ala Val Phe Leu Ile Cys Val Met Thr Leu Val Ser
    2245            2250            2255 gca gtg gca gcc aac gag atg ggt tgg cta gat aag acc aag agt      6915
Ala Val Ala Ala Asn Glu Met Gly Trp Leu Asp Lys Thr Lys Ser
    2260            2265            2270 gac ata agc agt ttg ttt ggg caa aga att gag gtc aag gag aat      6960
Asp Ile Ser Ser Leu Phe Gly Gln Arg Ile Glu Val Lys Glu Asn
    2275            2280            2285 ttc agc atg gga gag ttt ctt ttg gac ttg agg cct gca aca gcc      7005
Phe Ser Met Gly Glu Phe Leu Leu Asp Leu Arg Pro Ala Thr Ala
    2290            2295            2300 tgg tca ctg tac gct gtg aca aca gcg gtc ctc act cca ctg cta      7050
Trp Ser Leu Tyr Ala Val Thr Thr Ala Val Leu Thr Pro Leu Leu
    2305            2310            2315 aag cat ttg atc acg tca gat tac atc aac acc tca ttg acc tca      7095
Lys His Leu Ile Thr Ser Asp Tyr Ile Asn Thr Ser Leu Thr Ser
    2320            2325            2330 ata aac gtt cag gca agt gca cta ttc aca ctc gcg cga ggc ttc      7140
Ile Asn Val Gln Ala Ser Ala Leu Phe Thr Leu Ala Arg Gly Phe
    2335            2340            2345 ccc ttc gtc gat gtt gga gtg tcg gct ctc ctg cta gca gcc gga      7185
Pro Phe Val Asp Val Gly Val Ser Ala Leu Leu Leu Ala Ala Gly
    2350            2355            2360 tgc tgg gga caa gtc acc ctc acc gtt acg gta aca gcg gca aca      7230
Cys Trp Gly Gln Val Thr Leu Thr Val Thr Val Thr Ala Ala Thr
    2365            2370            2375 ctc ctt ttt tgc cac tat gcc tac atg gtt ccc ggt tgg caa gct      7275
Leu Leu Phe Cys His Tyr Ala Tyr Met Val Pro Gly Trp Gln Ala
    2380            2385            2390 gag gca atg cgc tca gcc cag cgg cgg aca gcg gcc gga atc atg      7320
Glu Ala Met Arg Ser Ala Gln Arg Arg Thr Ala Ala Gly Ile Met
    2395            2400            2405 aag aac gct gta gtg gat ggc atc gtg gcc acg gac gtc cca gaa      7365
Lys Asn Ala Val Val Asp Gly Ile Val Ala Thr Asp Val Pro Glu
    2410            2415            2420 tta gag cgc acc aca ccc atc atg cag aag aaa gtt gga cag atc      7410
Leu Glu Arg Thr Thr Pro Ile Met Gln Lys Lys Val Gly Gln Ile
    2425            2430            2435 atg ctg atc ttg gtg tct cta gct gca gta gta gtg aac ccg tct      7455
Met Leu Ile Leu Val Ser Leu Ala Ala Val Val Val Asn Pro Ser
    2440            2445            2450 gtg aag aca gta cga gaa gcc gga att ttg atc acg gcc gca gcg      7500
Val Lys Thr Val Arg Glu Ala Gly Ile Leu Ile Thr Ala Ala Ala
    2455            2460            2465 gtg acg ctt tgg gag aat gga gca agc tct gtt tgg aac gca aca      7545
Val Thr Leu Trp Glu Asn Gly Ala Ser Ser Val Trp Asn Ala Thr
    2470            2475            2480
```

| | | | | | | | | | | | | |
|---|---|---|---|---|---|---|---|---|---|---|---|---|
| act | gcc | atc | gga | ctc | tgc | cac | atc | atg | cgt | ggg | ggt | tgg | ttg | tca | 7590 |
| Thr | Ala | Ile | Gly | Leu | Cys | His | Ile | Met | Arg | Gly | Gly | Trp | Leu | Ser | |
| | 2485 | | | | 2490 | | | | | 2495 | | | | | |

```
act gcc atc gga ctc tgc cac atc atg cgt ggg ggt tgg ttg tca         7590
Thr Ala Ile Gly Leu Cys His Ile Met Arg Gly Gly Trp Leu Ser
    2485                2490                2495 tgt cta tcc ata aca tgg aca ctc ata aag aac atg gaa aaa cca         7635
Cys Leu Ser Ile Thr Trp Thr Leu Ile Lys Asn Met Glu Lys Pro
2500                2505                2510 gga cta aaa aga ggt ggg gca aaa gga cgc acc ttg gga gag gtt         7680
Gly Leu Lys Arg Gly Gly Ala Lys Gly Arg Thr Leu Gly Glu Val
    2515                2520                2525 tgg aaa gaa aga ctc aac cag atg aca aaa gaa gag ttc act agg         7725
Trp Lys Glu Arg Leu Asn Gln Met Thr Lys Glu Glu Phe Thr Arg
2530                2535                2540 tac cgc aaa gag gcc atc atc gaa gtc gat cgc tca gcg gca aaa         7770
Tyr Arg Lys Glu Ala Ile Ile Glu Val Asp Arg Ser Ala Ala Lys
    2545                2550                2555 cac gcc agg aaa gaa ggc aat gtc act gga ggg cat cca gtc tct         7815
His Ala Arg Lys Glu Gly Asn Val Thr Gly Gly His Pro Val Ser
2560                2565                2570 agg ggc aca gca aaa ctg aga tgg ctg gtc gaa cgg agg ttt ctc         7860
Arg Gly Thr Ala Lys Leu Arg Trp Leu Val Glu Arg Arg Phe Leu
    2575                2580                2585 gaa ccg gtc gga aaa gtg att gac ctt gga tgt gga aga ggc ggt         7905
Glu Pro Val Gly Lys Val Ile Asp Leu Gly Cys Gly Arg Gly Gly
2590                2595                2600 tgg tgt tac tat atg gca acc caa aaa aga gtc caa gaa gtc aga         7950
Trp Cys Tyr Tyr Met Ala Thr Gln Lys Arg Val Gln Glu Val Arg
    2605                2610                2615 ggg tac aca aag ggc ggt ccc gga cat gaa gag ccc caa cta gtg         7995
Gly Tyr Thr Lys Gly Gly Pro Gly His Glu Glu Pro Gln Leu Val
2620                2625                2630 caa agt tat gga tgg aac att gtc acc atg aag agt gga gtg gat         8040
Gln Ser Tyr Gly Trp Asn Ile Val Thr Met Lys Ser Gly Val Asp
    2635                2640                2645 gtg ttc tac aga cct tct gag tgt tgt gac acc ctc ctt tgt gac         8085
Val Phe Tyr Arg Pro Ser Glu Cys Cys Asp Thr Leu Leu Cys Asp
2650                2655                2660 atc gga gag tcc tcg tca agt gct gag gtt gaa gag cat agg acg         8130
Ile Gly Glu Ser Ser Ser Ser Ala Glu Val Glu Glu His Arg Thr
    2665                2670                2675 att cgg gtc ctt gaa atg gtt gag gac tgg ctg cac cga ggg cca         8175
Ile Arg Val Leu Glu Met Val Glu Asp Trp Leu His Arg Gly Pro
2680                2685                2690 agg gaa ttt tgc gtg aag gtg ctc tgc ccc tac atg ccg aaa gtc         8220
Arg Glu Phe Cys Val Lys Val Leu Cys Pro Tyr Met Pro Lys Val
    2695                2700                2705 ata gag aag atg gag ctg ctc caa gcc gga tat ggg ggg gga ctg         8265
Ile Glu Lys Met Glu Leu Leu Gln Arg Arg Tyr Gly Gly Gly Leu
2710                2715                2720 gtc aga aac cca ctc tca cgg aat tcc acg cac gag atg tat tgg         8310
Val Arg Asn Pro Leu Ser Arg Asn Ser Thr His Glu Met Tyr Trp
    2725                2730                2735 gtg agt cga gct tca ggc aat gtg gta cat tca gtg aat atg acc         8355
Val Ser Arg Ala Ser Gly Asn Val Val His Ser Val Asn Met Thr
2740                2745                2750 agc cag gtg ctc cta gga aga atg gaa aaa agg acc tgg aag gga         8400
Ser Gln Val Leu Leu Gly Arg Met Glu Lys Arg Thr Trp Lys Gly
    2755                2760                2765 ccc caa tac gag gaa gat gta aac ttg gga agt gga acc agg gcg         8445
Pro Gln Tyr Glu Glu Asp Val Asn Leu Gly Ser Gly Thr Arg Ala
2770                2775                2780
```

| | | | | | | | | | | | | | |
|---|---|---|---|---|---|---|---|---|---|---|---|---|---|
| gtg | gga | aaa | ccc | ctg | ctc | aac | tca | gac | acc | agt | aaa | atc | aag | aac | 8490 |
| Val | Gly | Lys | Pro | Leu | Leu | Asn | Ser | Asp | Thr | Ser | Lys | Ile | Lys | Asn | |
| | 2785 | | | | 2790 | | | | | 2795 | | | | | |
| agg | att | gaa | cga | ctc | agg | cgt | gag | tac | agt | tcg | acg | tgg | cac | cac | 8535 |
| Arg | Ile | Glu | Arg | Leu | Arg | Arg | Glu | Tyr | Ser | Ser | Thr | Trp | His | His | |
| | 2800 | | | | 2805 | | | | | 2810 | | | | | |
| gat | gag | aac | cac | cca | tat | aga | acc | tgg | aac | tat | cac | ggc | agt | tat | 8580 |
| Asp | Glu | Asn | His | Pro | Tyr | Arg | Thr | Trp | Asn | Tyr | His | Gly | Ser | Tyr | |
| | 2815 | | | | 2820 | | | | | 2825 | | | | | |
| gat | gtg | aag | ccc | aca | ggc | tcc | gcc | agt | tcg | ctg | gtc | aat | gga | gtg | 8625 |
| Asp | Val | Lys | Pro | Thr | Gly | Ser | Ala | Ser | Ser | Leu | Val | Asn | Gly | Val | |
| | 2830 | | | | 2835 | | | | | 2840 | | | | | |
| gtc | agg | ctc | ctc | tca | aaa | cca | tgg | gac | acc | atc | acg | aat | gtt | acc | 8670 |
| Val | Arg | Leu | Leu | Ser | Lys | Pro | Trp | Asp | Thr | Ile | Thr | Asn | Val | Thr | |
| | 2845 | | | | 2850 | | | | | 2855 | | | | | |
| acc | atg | gcc | atg | act | gac | act | act | ccc | ttc | ggg | cag | cag | cga | gtg | 8715 |
| Thr | Met | Ala | Met | Thr | Asp | Thr | Thr | Pro | Phe | Gly | Gln | Gln | Arg | Val | |
| | 2860 | | | | 2865 | | | | | 2870 | | | | | |
| ttc | aaa | gag | aag | gtg | gac | acg | aaa | gct | cct | gaa | ccg | cca | gaa | gga | 8760 |
| Phe | Lys | Glu | Lys | Val | Asp | Thr | Lys | Ala | Pro | Glu | Pro | Pro | Glu | Gly | |
| | 2875 | | | | 2880 | | | | | 2885 | | | | | |
| gtg | aag | tac | gtg | ctc | aac | gag | acc | acc | aac | tgg | ttg | tgg | gcg | ttt | 8805 |
| Val | Lys | Tyr | Val | Leu | Asn | Glu | Thr | Thr | Asn | Trp | Leu | Trp | Ala | Phe | |
| | 2890 | | | | 2895 | | | | | 2900 | | | | | |
| ttg | gcc | aga | gaa | aaa | cgt | ccc | aga | atg | tgc | tct | cga | gag | gaa | ttc | 8850 |
| Leu | Ala | Arg | Glu | Lys | Arg | Pro | Arg | Met | Cys | Ser | Arg | Glu | Glu | Phe | |
| | 2905 | | | | 2910 | | | | | 2915 | | | | | |
| ata | aga | aag | gtc | aac | agc | aat | gca | gct | ttg | ggt | gcc | atg | ttt | gaa | 8895 |
| Ile | Arg | Lys | Val | Asn | Ser | Asn | Ala | Ala | Leu | Gly | Ala | Met | Phe | Glu | |
| | 2920 | | | | 2925 | | | | | 2930 | | | | | |
| gag | cag | aat | caa | tgg | agg | agc | gcc | aga | gaa | gca | gtt | gaa | gat | cca | 8940 |
| Glu | Gln | Asn | Gln | Trp | Arg | Ser | Ala | Arg | Glu | Ala | Val | Glu | Asp | Pro | |
| | 2935 | | | | 2940 | | | | | 2945 | | | | | |
| aaa | ttt | tgg | gag | atg | gtg | gat | gag | gag | cgc | gag | gca | cat | ctg | cgg | 8985 |
| Lys | Phe | Trp | Glu | Met | Val | Asp | Glu | Glu | Arg | Glu | Ala | His | Leu | Arg | |
| | 2950 | | | | 2955 | | | | | 2960 | | | | | |
| ggg | gaa | tgt | cac | act | tgc | att | tac | aac | atg | atg | gga | aag | aga | gag | 9030 |
| Gly | Glu | Cys | His | Thr | Cys | Ile | Tyr | Asn | Met | Met | Gly | Lys | Arg | Glu | |
| | 2965 | | | | 2970 | | | | | 2975 | | | | | |
| aaa | aaa | ccc | gga | gag | ttc | gga | aag | gcc | aag | gga | agc | aga | gcc | att | 9075 |
| Lys | Lys | Pro | Gly | Glu | Phe | Gly | Lys | Ala | Lys | Gly | Ser | Arg | Ala | Ile | |
| | 2980 | | | | 2985 | | | | | 2990 | | | | | |
| tgg | ttc | atg | tgg | ctc | gga | gct | cgc | ttt | ctg | gag | ttc | gag | gct | ctg | 9120 |
| Trp | Phe | Met | Trp | Leu | Gly | Ala | Arg | Phe | Leu | Glu | Phe | Glu | Ala | Leu | |
| | 2995 | | | | 3000 | | | | | 3005 | | | | | |
| ggt | ttt | ctc | aat | gaa | gac | cac | tgg | ctt | gga | aga | aag | aac | tca | gga | 9165 |
| Gly | Phe | Leu | Asn | Glu | Asp | His | Trp | Leu | Gly | Arg | Lys | Asn | Ser | Gly | |
| | 3010 | | | | 3015 | | | | | 3020 | | | | | |
| gga | ggt | gtc | gag | ggc | ttg | ggc | ctc | caa | aaa | ctg | ggt | tac | atc | ctg | 9210 |
| Gly | Gly | Val | Glu | Gly | Leu | Gly | Leu | Gln | Lys | Leu | Gly | Tyr | Ile | Leu | |
| | 3025 | | | | 3030 | | | | | 3035 | | | | | |
| cgt | gaa | gtt | ggc | acc | cgg | cct | ggg | ggc | aag | atc | tat | gct | gat | gac | 9255 |
| Arg | Glu | Val | Gly | Thr | Arg | Pro | Gly | Gly | Lys | Ile | Tyr | Ala | Asp | Asp | |
| | 3040 | | | | 3045 | | | | | 3050 | | | | | |
| aca | gct | ggc | tgg | gac | acc | cgc | atc | acg | aga | gct | gac | ttg | gaa | aat | 9300 |
| Thr | Ala | Gly | Trp | Asp | Thr | Arg | Ile | Thr | Arg | Ala | Asp | Leu | Glu | Asn | |
| | 3055 | | | | 3060 | | | | | 3065 | | | | | |
| gaa | gct | aag | gtg | ctt | gag | ctg | ctt | gat | ggg | gaa | cat | cgg | cgt | ctt | 9345 |
| Glu | Ala | Lys | Val | Leu | Glu | Leu | Leu | Asp | Gly | Glu | His | Arg | Arg | Leu | |
| | 3070 | | | | 3075 | | | | | 3080 | | | | | |

```
gcc agg gcc atc att gag ctc acc tat cgt cac aaa gtt gtg aaa       9390
Ala Arg Ala Ile Ile Glu Leu Thr Tyr Arg His Lys Val Val Lys
3085              3090                3095 gtg atg cgc ccg gct gct gat gga aga acc gtc atg gat gtt atc       9435
Val Met Arg Pro Ala Ala Asp Gly Arg Thr Val Met Asp Val Ile
3100              3105                3110 tcc aga gaa gat cag agg ggg agt gga caa gtt gtc acc tac gcc       9480
Ser Arg Glu Asp Gln Arg Gly Ser Gly Gln Val Val Thr Tyr Ala
3115              3120                3125 cta aac act ttc acc aac ctg gcc gtc cag ctg gtg agg atg atg       9525
Leu Asn Thr Phe Thr Asn Leu Ala Val Gln Leu Val Arg Met Met
3130              3135                3140 gaa ggg gaa gga gtg att ggc cca gat gat gtg gag aaa ctc aca       9570
Glu Gly Glu Gly Val Ile Gly Pro Asp Asp Val Glu Lys Leu Thr
3145              3150                3155 aaa ggg aaa gga ccc aaa gtc agg acc tgg ctg ttt gag aat ggg       9615
Lys Gly Lys Gly Pro Lys Val Arg Thr Trp Leu Phe Glu Asn Gly
3160              3165                3170 gaa gaa aga ctc agc cgc atg gct gtc agt gga gat gac tgt gtg       9660
Glu Glu Arg Leu Ser Arg Met Ala Val Ser Gly Asp Asp Cys Val
3175              3180                3185 gta aag ccc ctg gac gat cgc ttt gcc acc tcg ctc cac ttc ctc       9705
Val Lys Pro Leu Asp Asp Arg Phe Ala Thr Ser Leu His Phe Leu
3190              3195                3200 aat gct atg tca aag gtt cgc aaa gac atc caa gag tgg aaa ccg       9750
Asn Ala Met Ser Lys Val Arg Lys Asp Ile Gln Glu Trp Lys Pro
3205              3210                3215 tca act gga tgg tat gat tgg cag cag gtt cca ttt tgc tca aac       9795
Ser Thr Gly Trp Tyr Asp Trp Gln Gln Val Pro Phe Cys Ser Asn
3220              3225                3230 cat ttc act gaa ttg atc atg aaa gat gga aga aca ctg gtg gtt       9840
His Phe Thr Glu Leu Ile Met Lys Asp Gly Arg Thr Leu Val Val
3235              3240                3245 cca tgc cga gga cag gat gaa ttg gta ggc aga gct cgc ata tct       9885
Pro Cys Arg Gly Gln Asp Glu Leu Val Gly Arg Ala Arg Ile Ser
3250              3255                3260 cca ggg gcc gga tgg aac gtc cgc gac act gct tgt ctg gct aag       9930
Pro Gly Ala Gly Trp Asn Val Arg Asp Thr Ala Cys Leu Ala Lys
3265              3270                3275 tct tat gcc cag atg tgg ctg ctt ctg tac ttc cac aga aga gac       9975
Ser Tyr Ala Gln Met Trp Leu Leu Leu Tyr Phe His Arg Arg Asp
3280              3285                3290 ctg cgg ctc atg gcc aac gcc att tgc tcc gct gtc cct gtg aat      10020
Leu Arg Leu Met Ala Asn Ala Ile Cys Ser Ala Val Pro Val Asn
3295              3300                3305 tgg gtc cct acc gga aga acc acg tgg tcc atc cat gca gga gga      10065
Trp Val Pro Thr Gly Arg Thr Thr Trp Ser Ile His Ala Gly Gly
3310              3315                3320 gag tgg atg aca aca gag gac atg ttg gag gtc tgg aac cgt gtt      10110
Glu Trp Met Thr Thr Glu Asp Met Leu Glu Val Trp Asn Arg Val
3325              3330                3335 tgg ata gag gag aat gaa tgg atg gaa gac aaa acc cca gtg gag      10155
Trp Ile Glu Glu Asn Glu Trp Met Glu Asp Lys Thr Pro Val Glu
3340              3345                3350 aaa tgg agt gac gtc cca tat tca gga aaa cga gag gac atc tgg      10200
Lys Trp Ser Asp Val Pro Tyr Ser Gly Lys Arg Glu Asp Ile Trp
3355              3360                3365 tgt ggc agc ctg att ggc aca aga gcc cga gcc acg tgg gca gaa      10245
Cys Gly Ser Leu Ile Gly Thr Arg Ala Arg Ala Thr Trp Ala Glu
3370              3375                3380
```

-continued

```
aac atc cag gtg gct atc aac caa gtc aga gca atc atc gga gat       10290
Asn Ile Gln Val Ala Ile Asn Gln Val Arg Ala Ile Ile Gly Asp
    3385                3390                3395 gag aag tat gtg gat tac atg agt tca cta aag aga tat gaa gac       10335
Glu Lys Tyr Val Asp Tyr Met Ser Ser Leu Lys Arg Tyr Glu Asp
3400                3405                3410 aca act ttg gtt gag gac aca gta ctg tagatattta atcaattgta         10382
Thr Thr Leu Val Glu Asp Thr Val Leu
    3415                3420 aatagacaat ataagtatgc ataaaagtgt agttttatag tagtatttag tggtgttagt 10442
gtaaatagtt aagaaaattt tgaggagaaa gtcaggccgg gaagttcccg ccaccggaag 10502
ttgagtagac ggtgctgcct gcgactcaac cccaggagga ctgggtgaac aaagccgcga 10562
agtgatccat gtaagccctc agaaccgtct cggaaggagg accccacatg ttgtaacttc 10622
aaagcccaat gtcagaccac gctacggcgt gctactctgc ggagagtgca gtctgcgata 10682
gtgccccagg aggactgggt taacaaaggc aaaccaacgc cccacgcggc cctagccccg 10742
gtaatggtgt taaccagggc gaaaggacta gaggttagag gagacccgc ggtttaaagt  10802
gcacggccca gcctggctga agctgtaggt caggggaagg actagaggtt agtgagacc  10862
ccgtgccaca aaacaccaca acaaaacagc atattgacac ctgggataga ctaggagatc 10922
ttctgctctg cacaaccagc cacacggcac agtgcgccga caatggtggc tggtggtgcg 10982
agaacacagg atct                                                   10996
```

<210> SEQ ID NO 2
<211> LENGTH: 3422
<212> TYPE: PRT
<213> ORGANISM: Artificial Sequence
<220> FEATURE:
<223> OTHER INFORMATION: Synthetic Construct

<400> SEQUENCE: 2

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Ser Ala Gly Met Ile Ile Met
            100                 105                 110

Leu Ile Pro Thr Val Met Ala Phe His Leu Thr Thr Arg Asn Gly Glu
        115                 120                 125

Pro His Met Ile Val Ser Arg Gln Glu Lys Gly Lys Ser Leu Leu Phe
    130                 135                 140

Lys Thr Glu Asp Gly Val Asn Met Cys Thr Leu Met Ala Met Asp Leu
145                 150                 155                 160

Gly Glu Leu Cys Glu Asp Thr Ile Thr Tyr Lys Cys Pro Leu Leu Arg
                165                 170                 175

Gln Asn Glu Pro Glu Asp Ile Asp Cys Trp Cys Asn Ser Thr Ser Thr
            180                 185                 190
```

```
Trp Val Thr Tyr Gly Thr Cys Thr Met Gly Glu His Arg Arg Glu
        195                 200                 205

Lys Arg Ser Val Ala Leu Val Pro His Val Gly Met Gly Leu Glu Thr
210                 215                 220

Arg Thr Glu Thr Trp Met Ser Ser Glu Gly Ala Trp Lys His Val Gln
225                 230                 235                 240

Arg Ile Glu Thr Trp Ile Leu Arg His Pro Gly Phe Thr Met Met Ala
                245                 250                 255

Ala Ile Leu Ala Tyr Thr Ile Gly Thr Thr His Phe Gln Arg Ala Leu
                260                 265                 270

Ile Phe Ile Leu Leu Thr Ala Val Thr Pro Ser Met Thr Met Arg Cys
            275                 280                 285

Ile Gly Met Ser Asn Arg Asp Phe Val Glu Gly Val Ser Gly Gly Ser
        290                 295                 300

Trp Val Asp Ile Val Leu Glu His Gly Ser Cys Val Thr Thr Met Ala
305                 310                 315                 320

Lys Asn Lys Pro Thr Leu Asp Phe Glu Leu Ile Lys Thr Glu Ala Lys
                325                 330                 335

Gln Pro Ala Thr Leu Arg Lys Tyr Cys Ile Glu Ala Lys Leu Thr Asn
                340                 345                 350

Thr Thr Thr Glu Ser Arg Cys Pro Thr Gln Gly Glu Pro Ser Leu Asn
            355                 360                 365

Glu Glu Gln Asp Lys Arg Phe Val Cys Lys His Ser Met Val Asp Arg
        370                 375                 380

Gly Trp Gly Asn Gly Cys Gly Leu Phe Gly Lys Gly Ile Val
385                 390                 395                 400

Cys Ala Met Phe Arg Cys Lys Lys Asn Met Glu Gly Lys Val Val Gln
                405                 410                 415

Pro Glu Asn Leu Glu Tyr Thr Ile Val Ile Thr Pro His Ser Gly Glu
                420                 425                 430

Glu His Ala Val Gly Asn Asp Thr Gly Lys His Gly Lys Glu Ile Lys
            435                 440                 445

Ile Thr Pro Gln Ser Ser Ile Thr Glu Ala Glu Leu Thr Gly Tyr Gly
        450                 455                 460

Thr Val Thr Met Glu Cys Ser Pro Arg Thr Gly Leu Asp Phe Asn Glu
465                 470                 475                 480

Met Val Leu Leu Gln Met Glu Asn Lys Ala Trp Leu Val His Arg Gln
                485                 490                 495

Trp Phe Leu Asp Leu Pro Leu Pro Trp Leu Pro Gly Ala Asp Thr Gln
                500                 505                 510

Gly Ser Asn Trp Ile Gln Lys Glu Thr Leu Val Thr Phe Lys Asn Pro
            515                 520                 525

His Ala Lys Lys Gln Asp Val Val Val Leu Gly Ser Gln Glu Gly Ala
        530                 535                 540

Met His Thr Ala Leu Thr Gly Ala Thr Glu Ile Gln Met Ser Ser Gly
545                 550                 555                 560

Asn Leu Leu Phe Thr Gly His Leu Lys Cys Arg Leu Arg Met Asp Lys
                565                 570                 575

Leu Gln Leu Lys Gly Met Ser Tyr Ser Met Cys Thr Gly Lys Phe Lys
                580                 585                 590

Val Val Lys Glu Ile Ala Glu Thr Gln His Gly Thr Ile Val Ile Arg
            595                 600                 605

Val Gln Tyr Glu Gly Asp Gly Ser Pro Cys Lys Ile Pro Phe Glu Ile
        610                 615                 620
```

```
Met Asp Leu Glu Lys Arg His Val Leu Gly Arg Leu Ile Thr Val Asn
625                 630                 635                 640

Pro Ile Val Thr Glu Lys Asp Ser Pro Val Asn Ile Glu Ala Glu Pro
                645                 650                 655

Pro Phe Gly Asp Ser Tyr Ile Ile Gly Val Glu Pro Gly Gln Leu
            660                 665                 670

Lys Leu Asn Trp Phe Lys Gly Ser Ser Ile Gly Gln Met Phe Glu
        675                 680                 685

Thr Thr Met Arg Gly Ala Lys Arg Met Ala Ile Leu Gly Asp Thr Ala
    690                 695                 700

Trp Asp Phe Gly Ser Leu Gly Gly Val Phe Thr Ser Ile Gly Lys Ala
705                 710                 715                 720

Leu His Gln Val Phe Gly Ala Ile Tyr Gly Ala Phe Ser Gly Val
            725                 730                 735

Ser Trp Thr Met Lys Ile Leu Ile Gly Val Ile Ile Thr Trp Ile Gly
                740                 745                 750

Met Asn Ser Arg Ser Thr Ser Leu Ser Val Thr Leu Val Leu Val Gly
            755                 760                 765

Ile Val Thr Leu Tyr Leu Gly Val Met Val Gln Ala Asp Ser Gly Cys
770                 775                 780

Ala Ile Asp Ile Ser Arg Gln Glu Leu Arg Cys Gly Ser Gly Val Phe
785                 790                 795                 800

Ile His Asn Asp Val Glu Ala Trp Met Asp Arg Tyr Lys Tyr Tyr Pro
                805                 810                 815

Glu Thr Pro Gln Gly Leu Ala Lys Ile Ile Gln Lys Ala His Lys Glu
            820                 825                 830

Gly Val Cys Gly Leu Arg Ser Val Ser Arg Leu Glu His Gln Met Trp
        835                 840                 845

Glu Ala Val Lys Asp Glu Leu Asn Thr Leu Leu Lys Glu Asn Gly Val
850                 855                 860

Asp Leu Ser Val Val Glu Lys Gln Glu Gly Met Tyr Lys Ser Ala
865                 870                 875                 880

Pro Lys Arg Leu Thr Ala Thr Thr Glu Lys Leu Glu Ile Gly Trp Lys
                885                 890                 895

Ala Trp Gly Lys Ser Ile Leu Phe Ala Pro Glu Leu Ala Asn Asn Thr
            900                 905                 910

Phe Val Val Asp Gly Pro Glu Thr Lys Glu Cys Pro Thr Gln Asn Arg
        915                 920                 925

Ala Trp Asn Ser Leu Glu Val Glu Asp Phe Gly Phe Gly Leu Thr Ser
    930                 935                 940

Thr Arg Met Phe Leu Lys Val Arg Glu Ser Asn Thr Thr Glu Cys Asp
945                 950                 955                 960

Ser Lys Ile Ile Gly Thr Ala Val Lys Asn Asn Leu Ala Ile His Ser
            965                 970                 975

Asp Leu Ser Tyr Trp Ile Glu Ser Arg Leu Asn Asp Thr Trp Lys Leu
        980                 985                 990

Glu Arg Ala Val Leu Gly Glu Val Lys Ser Cys Thr Trp Pro Glu Thr
    995                 1000                1005

His Thr Leu Trp Gly Asp Gly Ile Leu Glu Ser Asp Leu Ile Ile
        1010                1015                1020

Pro Val Thr Leu Ala Gly Pro Arg Ser Asn His Asn Arg Arg Pro
    1025                1030                1035

Gly Tyr Lys Thr Gln Asn Gln Gly Pro Trp Asp Glu Gly Arg Val
```

-continued

```
                1040                1045                1050

Glu Ile Asp Phe Asp Tyr Cys Pro Gly Thr Thr Val Thr Leu Ser
    1055                1060                1065

Glu Ser Cys Gly His Arg Gly Pro Ala Thr Arg Thr Thr Thr Glu
    1070                1075                1080

Ser Gly Lys Leu Ile Thr Asp Trp Cys Cys Arg Ser Cys Thr Leu
    1085                1090                1095

Pro Pro Leu Arg Tyr Gln Thr Asp Ser Gly Cys Trp Tyr Gly Met
    1100                1105                1110

Glu Ile Arg Pro Gln Arg His Asp Glu Lys Thr Leu Val Gln Ser
    1115                1120                1125

Gln Val Asn Ala Tyr Asn Ala Asp Met Ile Asp Pro Phe Gln Leu
    1130                1135                1140

Gly Leu Leu Val Val Phe Leu Ala Thr Gln Glu Val Leu Arg Lys
    1145                1150                1155

Arg Trp Thr Ala Lys Ile Ser Met Pro Ala Ile Leu Ile Ala Leu
    1160                1165                1170

Leu Val Leu Val Phe Gly Gly Ile Thr Tyr Thr Asp Val Leu Arg
    1175                1180                1185

Tyr Val Ile Leu Val Gly Ala Ala Phe Ala Glu Ser Asn Ser Gly
    1190                1195                1200

Gly Asp Val Val His Leu Ala Leu Met Ala Thr Phe Lys Ile Gln
    1205                1210                1215

Pro Val Phe Met Val Ala Ser Phe Leu Lys Ala Arg Trp Thr Asn
    1220                1225                1230

Gln Glu Asn Ile Leu Leu Met Leu Ala Ala Val Phe Phe Gln Met
    1235                1240                1245

Ala Tyr Tyr Asp Ala Arg Gln Ile Leu Leu Trp Glu Ile Pro Asp
    1250                1255                1260

Val Leu Asn Ser Leu Ala Val Ala Trp Met Ile Leu Arg Ala Ile
    1265                1270                1275

Thr Phe Thr Thr Thr Ser Asn Val Val Val Pro Leu Leu Ala Leu
    1280                1285                1290

Leu Thr Pro Gly Leu Arg Cys Leu Asn Leu Asp Val Tyr Arg Ile
    1295                1300                1305

Leu Leu Leu Met Val Gly Ile Gly Ser Leu Ile Arg Glu Lys Arg
    1310                1315                1320

Ser Ala Ala Lys Lys Lys Gly Ala Ser Leu Leu Cys Leu Ala
    1325                1330                1335

Leu Ala Ser Thr Gly Leu Phe Asn Pro Met Ile Leu Ala Ala Gly
    1340                1345                1350

Leu Ile Ala Cys Asp Pro Asn Arg Lys Arg Gly Trp Pro Ala Thr
    1355                1360                1365

Glu Val Met Thr Ala Val Gly Leu Met Phe Ala Ile Val Gly Gly
    1370                1375                1380

Leu Ala Glu Leu Asp Ile Asp Ser Met Ala Ile Pro Met Thr Ile
    1385                1390                1395

Ala Gly Leu Met Phe Ala Ala Phe Val Ile Ser Gly Lys Ser Thr
    1400                1405                1410

Asp Met Trp Ile Glu Arg Thr Ala Asp Ile Ser Trp Glu Ser Asp
    1415                1420                1425

Ala Glu Ile Thr Gly Ser Ser Glu Arg Val Asp Val Arg Leu Asp
    1430                1435                1440
```

-continued

Asp Asp Gly Asn Phe Gln Leu Met Asn Asp Pro Gly Ala Pro Trp
1445                 1450                1455

Lys Ile Trp Met Leu Arg Met Val Cys Leu Ala Ile Ser Ala Tyr
1460                1465                1470

Thr Pro Trp Ala Ile Leu Pro Ser Val Val Gly Phe Trp Ile Thr
1475                1480                1485

Leu Gln Tyr Thr Lys Arg Gly Gly Val Leu Trp Asp Thr Pro Ser
1490                1495                1500

Pro Lys Glu Tyr Lys Lys Gly Asp Thr Thr Thr Gly Val Tyr Arg
1505                1510                1515

Ile Met Thr Arg Gly Leu Leu Gly Ser Tyr Gln Ala Gly Ala Gly
1520                1525                1530

Val Met Val Glu Gly Val Phe His Thr Leu Trp His Thr Thr Lys
1535                1540                1545

Gly Ala Ala Leu Met Ser Gly Glu Gly Arg Leu Asp Pro Tyr Trp
1550                1555                1560

Gly Ser Val Lys Glu Asp Arg Leu Cys Tyr Gly Gly Pro Trp Lys
1565                1570                1575

Leu Gln His Lys Trp Asn Gly Gln Asp Glu Val Gln Met Ile Val
1580                1585                1590

Val Glu Pro Gly Arg Asn Val Lys Asn Val Gln Thr Lys Pro Gly
1595                1600                1605

Val Phe Lys Thr Pro Glu Gly Glu Ile Gly Ala Val Thr Leu Asp
1610                1615                1620

Phe Pro Thr Gly Thr Ser Gly Ser Pro Ile Val Asp Lys Asn Gly
1625                1630                1635

Asp Val Ile Gly Leu Tyr Gly Asn Gly Val Ile Met Pro Asn Gly
1640                1645                1650

Ser Tyr Ile Ser Ala Ile Val Gln Gly Glu Arg Met Asp Glu Pro
1655                1660                1665

Ile Pro Ala Gly Phe Glu Pro Glu Met Leu Arg Lys Lys Gln Ile
1670                1675                1680

Thr Val Leu Asp Leu His Pro Gly Ala Gly Lys Thr Arg Arg Ile
1685                1690                1695

Leu Pro Gln Ile Ile Lys Glu Ala Ile Asn Arg Arg Leu Arg Thr
1700                1705                1710

Ala Val Leu Ala Pro Thr Arg Val Val Ala Ala Glu Met Ala Glu
1715                1720                1725

Ala Leu Arg Gly Leu Pro Ile Arg Tyr Gln Thr Ser Ala Val Pro
1730                1735                1740

Arg Glu His Asn Gly Asn Glu Ile Val Asp Val Met Cys His Ala
1745                1750                1755

Thr Leu Thr His Arg Leu Met Ser Pro His Arg Val Pro Asn Tyr
1760                1765                1770

Asn Leu Phe Val Met Asp Glu Ala His Phe Thr Asp Pro Ala Ser
1775                1780                1785

Ile Ala Ala Arg Gly Tyr Ile Ser Thr Lys Val Glu Leu Gly Glu
1790                1795                1800

Ala Ala Ala Ile Phe Met Thr Ala Thr Pro Pro Gly Thr Ser Asp
1805                1810                1815

Pro Phe Pro Glu Ser Asn Ser Pro Ile Ser Asp Leu Gln Thr Glu
1820                1825                1830

Ile Pro Asp Arg Ala Trp Asn Ser Gly Tyr Glu Trp Ile Thr Glu
1835                1840                1845

```
Tyr Thr Gly Lys Thr Val Trp Phe Val Pro Ser Val Lys Met Gly
    1850            1855            1860

Asn Glu Ile Ala Leu Cys Leu Gln Arg Ala Gly Lys Lys Val Val
    1865            1870            1875

Gln Leu Asn Arg Lys Ser Tyr Glu Thr Glu Tyr Pro Lys Cys Lys
    1880            1885            1890

Asn Asp Asp Trp Asp Phe Val Ile Thr Thr Asp Ile Ser Glu Met
    1895            1900            1905

Gly Ala Asn Phe Lys Ala Ser Arg Val Ile Asp Ser Arg Lys Ser
    1910            1915            1920

Val Lys Pro Thr Ile Ile Thr Glu Gly Glu Gly Arg Val Ile Leu
    1925            1930            1935

Gly Glu Pro Ser Ala Val Thr Ala Ala Ser Ala Ala Gln Arg Arg
    1940            1945            1950

Gly Arg Ile Gly Arg Asn Pro Ser Gln Val Gly Asp Glu Tyr Cys
    1955            1960            1965

Tyr Gly Gly His Thr Asn Glu Asp Asp Ser Asn Phe Ala His Trp
    1970            1975            1980

Thr Glu Ala Arg Ile Met Leu Asp Asn Ile Asn Met Pro Asn Gly
    1985            1990            1995

Leu Ile Ala Gln Phe Tyr Gln Pro Glu Arg Glu Lys Val Tyr Thr
    2000            2005            2010

Met Asp Gly Glu Tyr Arg Leu Arg Gly Glu Glu Arg Lys Asn Phe
    2015            2020            2025

Leu Glu Leu Leu Arg Thr Ala Asp Leu Pro Val Trp Leu Ala Tyr
    2030            2035            2040

Lys Val Ala Ala Ala Gly Val Ser Tyr His Asp Arg Arg Trp Cys
    2045            2050            2055

Phe Asp Gly Pro Arg Thr Asn Thr Ile Leu Glu Asp Asn Asn Glu
    2060            2065            2070

Val Glu Val Ile Thr Lys Leu Gly Glu Arg Lys Ile Leu Arg Pro
    2075            2080            2085

Arg Trp Ile Asp Ala Arg Val Tyr Ser Asp His Gln Ala Leu Lys
    2090            2095            2100

Ala Phe Lys Asp Phe Ala Ser Gly Lys Arg Ser Gln Ile Gly Leu
    2105            2110            2115

Ile Glu Val Leu Gly Lys Met Pro Glu His Phe Met Gly Lys Thr
    2120            2125            2130

Trp Glu Ala Leu Asp Thr Met Tyr Val Val Ala Thr Ala Glu Lys
    2135            2140            2145

Gly Gly Arg Ala His Arg Met Ala Leu Glu Glu Leu Pro Asp Ala
    2150            2155            2160

Leu Gln Thr Ile Ala Leu Ile Ala Leu Leu Ser Val Met Thr Met
    2165            2170            2175

Gly Val Phe Phe Leu Leu Met Gln Arg Lys Gly Ile Gly Lys Ile
    2180            2185            2190

Gly Leu Gly Gly Ala Val Leu Gly Val Ala Thr Phe Phe Cys Trp
    2195            2200            2205

Met Ala Glu Val Pro Gly Thr Lys Ile Ala Gly Met Leu Leu Leu
    2210            2215            2220

Ser Leu Leu Leu Met Ile Val Leu Ile Pro Glu Pro Glu Lys Gln
    2225            2230            2235

Arg Ser Gln Thr Asp Asn Gln Leu Ala Val Phe Leu Ile Cys Val
```

```
            2240              2245              2250
Met Thr Leu Val Ser Ala Val Ala Ala Asn Glu Met Gly Trp Leu
    2255              2260              2265

Asp Lys Thr Lys Ser Asp Ile Ser Ser Leu Phe Gly Gln Arg Ile
    2270              2275              2280

Glu Val Lys Glu Asn Phe Ser Met Gly Glu Phe Leu Leu Asp Leu
    2285              2290              2295

Arg Pro Ala Thr Ala Trp Ser Leu Tyr Ala Val Thr Thr Ala Val
    2300              2305              2310

Leu Thr Pro Leu Leu Lys His Leu Ile Thr Ser Asp Tyr Ile Asn
    2315              2320              2325

Thr Ser Leu Thr Ser Ile Asn Val Gln Ala Ser Ala Leu Phe Thr
    2330              2335              2340

Leu Ala Arg Gly Phe Pro Phe Val Asp Val Gly Val Ser Ala Leu
    2345              2350              2355

Leu Leu Ala Ala Gly Cys Trp Gly Gln Val Thr Leu Thr Val Thr
    2360              2365              2370

Val Thr Ala Ala Thr Leu Leu Phe Cys His Tyr Ala Tyr Met Val
    2375              2380              2385

Pro Gly Trp Gln Ala Glu Ala Met Arg Ser Ala Gln Arg Arg Thr
    2390              2395              2400

Ala Ala Gly Ile Met Lys Asn Ala Val Val Asp Gly Ile Val Ala
    2405              2410              2415

Thr Asp Val Pro Glu Leu Glu Arg Thr Thr Pro Ile Met Gln Lys
    2420              2425              2430

Lys Val Gly Gln Ile Met Leu Ile Leu Val Ser Leu Ala Ala Val
    2435              2440              2445

Val Val Asn Pro Ser Val Lys Thr Val Arg Glu Ala Gly Ile Leu
    2450              2455              2460

Ile Thr Ala Ala Ala Val Thr Leu Trp Glu Asn Gly Ala Ser Ser
    2465              2470              2475

Val Trp Asn Ala Thr Thr Ala Ile Gly Leu Cys His Ile Met Arg
    2480              2485              2490

Gly Gly Trp Leu Ser Cys Leu Ser Ile Thr Trp Thr Leu Ile Lys
    2495              2500              2505

Asn Met Glu Lys Pro Gly Leu Lys Arg Gly Gly Ala Lys Gly Arg
    2510              2515              2520

Thr Leu Gly Glu Val Trp Lys Glu Arg Leu Asn Gln Met Thr Lys
    2525              2530              2535

Glu Glu Phe Thr Arg Tyr Arg Lys Glu Ala Ile Ile Glu Val Asp
    2540              2545              2550

Arg Ser Ala Ala Lys His Ala Arg Lys Glu Gly Asn Val Thr Gly
    2555              2560              2565

Gly His Pro Val Ser Arg Gly Thr Ala Lys Leu Arg Trp Leu Val
    2570              2575              2580

Glu Arg Arg Phe Leu Glu Pro Val Gly Lys Val Ile Asp Leu Gly
    2585              2590              2595

Cys Gly Arg Gly Gly Trp Cys Tyr Tyr Met Ala Thr Gln Lys Arg
    2600              2605              2610

Val Gln Glu Val Arg Gly Tyr Thr Lys Gly Gly Pro Gly His Glu
    2615              2620              2625

Glu Pro Gln Leu Val Gln Ser Tyr Gly Trp Asn Ile Val Thr Met
    2630              2635              2640
```

-continued

```
Lys Ser Gly Val Asp Val Phe Tyr Arg Pro Ser Glu Cys Cys Asp
    2645                2650                2655

Thr Leu Leu Cys Asp Ile Gly Glu Ser Ser Ser Ala Glu Val
    2660                2665                2670

Glu Glu His Arg Thr Ile Arg Val Leu Glu Met Val Glu Asp Trp
    2675                2680                2685

Leu His Arg Gly Pro Arg Glu Phe Cys Val Lys Val Leu Cys Pro
    2690                2695                2700

Tyr Met Pro Lys Val Ile Glu Lys Met Glu Leu Leu Gln Arg Arg
    2705                2710                2715

Tyr Gly Gly Gly Leu Val Arg Asn Pro Leu Ser Arg Asn Ser Thr
    2720                2725                2730

His Glu Met Tyr Trp Val Ser Arg Ala Ser Gly Asn Val Val His
    2735                2740                2745

Ser Val Asn Met Thr Ser Gln Val Leu Leu Gly Arg Met Glu Lys
    2750                2755                2760

Arg Thr Trp Lys Gly Pro Gln Tyr Glu Glu Asp Val Asn Leu Gly
    2765                2770                2775

Ser Gly Thr Arg Ala Val Gly Lys Pro Leu Leu Asn Ser Asp Thr
    2780                2785                2790

Ser Lys Ile Lys Asn Arg Ile Glu Arg Leu Arg Arg Glu Tyr Ser
    2795                2800                2805

Ser Thr Trp His His Asp Glu Asn His Pro Tyr Arg Thr Trp Asn
    2810                2815                2820

Tyr His Gly Ser Tyr Asp Val Lys Pro Thr Gly Ser Ala Ser Ser
    2825                2830                2835

Leu Val Asn Gly Val Val Arg Leu Leu Ser Lys Pro Trp Asp Thr
    2840                2845                2850

Ile Thr Asn Val Thr Thr Met Ala Met Thr Asp Thr Thr Pro Phe
    2855                2860                2865

Gly Gln Gln Arg Val Phe Lys Glu Lys Val Asp Thr Lys Ala Pro
    2870                2875                2880

Glu Pro Pro Glu Gly Val Lys Tyr Val Leu Asn Glu Thr Thr Asn
    2885                2890                2895

Trp Leu Trp Ala Phe Leu Ala Arg Glu Lys Arg Pro Arg Met Cys
    2900                2905                2910

Ser Arg Glu Glu Phe Ile Arg Lys Val Asn Ser Asn Ala Ala Leu
    2915                2920                2925

Gly Ala Met Phe Glu Glu Gln Asn Gln Trp Arg Ser Ala Arg Glu
    2930                2935                2940

Ala Val Glu Asp Pro Lys Phe Trp Glu Met Val Asp Glu Glu Arg
    2945                2950                2955

Glu Ala His Leu Arg Gly Glu Cys His Thr Cys Ile Tyr Asn Met
    2960                2965                2970

Met Gly Lys Arg Glu Lys Lys Pro Gly Glu Phe Gly Lys Ala Lys
    2975                2980                2985

Gly Ser Arg Ala Ile Trp Phe Met Trp Leu Gly Ala Arg Phe Leu
    2990                2995                3000

Glu Phe Glu Ala Leu Gly Phe Leu Asn Glu Asp His Trp Leu Gly
    3005                3010                3015

Arg Lys Asn Ser Gly Gly Gly Val Glu Gly Leu Gly Leu Gln Lys
    3020                3025                3030

Leu Gly Tyr Ile Leu Arg Glu Val Gly Thr Arg Pro Gly Gly Lys
    3035                3040                3045
```

```
Ile Tyr Ala Asp Asp Thr Ala Gly Trp Asp Thr Arg Ile Thr Arg
    3050                3055                3060
Ala Asp Leu Glu Asn Glu Ala Lys Val Leu Glu Leu Leu Asp Gly
    3065                3070                3075
Glu His Arg Arg Leu Ala Arg Ala Ile Ile Glu Leu Thr Tyr Arg
    3080                3085                3090
His Lys Val Val Lys Val Met Arg Pro Ala Ala Asp Gly Arg Thr
    3095                3100                3105
Val Met Asp Val Ile Ser Arg Glu Asp Gln Arg Gly Ser Gly Gln
    3110                3115                3120
Val Val Thr Tyr Ala Leu Asn Thr Phe Thr Asn Leu Ala Val Gln
    3125                3130                3135
Leu Val Arg Met Met Glu Gly Glu Gly Val Ile Gly Pro Asp Asp
    3140                3145                3150
Val Glu Lys Leu Thr Lys Gly Lys Gly Pro Lys Val Arg Thr Trp
    3155                3160                3165
Leu Phe Glu Asn Gly Glu Glu Arg Leu Ser Arg Met Ala Val Ser
    3170                3175                3180
Gly Asp Asp Cys Val Val Lys Pro Leu Asp Asp Arg Phe Ala Thr
    3185                3190                3195
Ser Leu His Phe Leu Asn Ala Met Ser Lys Val Arg Lys Asp Ile
    3200                3205                3210
Gln Glu Trp Lys Pro Ser Thr Gly Trp Tyr Asp Trp Gln Gln Val
    3215                3220                3225
Pro Phe Cys Ser Asn His Phe Thr Glu Leu Ile Met Lys Asp Gly
    3230                3235                3240
Arg Thr Leu Val Val Pro Cys Arg Gly Gln Asp Glu Leu Val Gly
    3245                3250                3255
Arg Ala Arg Ile Ser Pro Gly Ala Gly Trp Asn Val Arg Asp Thr
    3260                3265                3270
Ala Cys Leu Ala Lys Ser Tyr Ala Gln Met Trp Leu Leu Leu Tyr
    3275                3280                3285
Phe His Arg Arg Asp Leu Arg Leu Met Ala Asn Ala Ile Cys Ser
    3290                3295                3300
Ala Val Pro Val Asn Trp Val Pro Thr Gly Arg Thr Thr Trp Ser
    3305                3310                3315
Ile His Ala Gly Gly Glu Trp Met Thr Thr Glu Asp Met Leu Glu
    3320                3325                3330
Val Trp Asn Arg Val Trp Ile Glu Glu Asn Glu Trp Met Glu Asp
    3335                3340                3345
Lys Thr Pro Val Glu Lys Trp Ser Asp Val Pro Tyr Ser Gly Lys
    3350                3355                3360
Arg Glu Asp Ile Trp Cys Gly Ser Leu Ile Gly Thr Arg Ala Arg
    3365                3370                3375
Ala Thr Trp Ala Glu Asn Ile Gln Val Ala Ile Asn Gln Val Arg
    3380                3385                3390
Ala Ile Ile Gly Asp Glu Lys Tyr Val Asp Tyr Met Ser Ser Leu
    3395                3400                3405
Lys Arg Tyr Glu Asp Thr Thr Leu Val Glu Asp Thr Val Leu
    3410                3415                3420

<210> SEQ ID NO 3
<211> LENGTH: 10996
<212> TYPE: DNA
```

<213> ORGANISM: Artificial Sequence
<220> FEATURE:
<223> OTHER INFORMATION: Recombinant West Nile virus/Dengue-1 virus
        chimera
<220> FEATURE:
<221> NAME/KEY: CDS
<222> LOCATION: (97)..(10362)

<400> SEQUENCE: 3

```
agtagttcgc ctgtgtgagc tgacaaactt agtagtgttt gtgaggatta acaacaatta       60
acacagtgcg agctgtttct tagcacgaag atctcg atg tct aag aaa cca gga         114
                                        Met Ser Lys Lys Pro Gly
                                          1               5 ggg ccc ggc aag agc cgg gct gtc aat atg cta aaa cgc gga atg ccc         162
Gly Pro Gly Lys Ser Arg Ala Val Asn Met Leu Lys Arg Gly Met Pro
         10                  15                  20 cgc gtg ttg tcc ttg att gga ctg aag agg gct atg ttg agc ctg atc         210
Arg Val Leu Ser Leu Ile Gly Leu Lys Arg Ala Met Leu Ser Leu Ile
 25                  30                  35 gac ggc aag ggg cca ata cga ttt gtg ttg gct ctc ttg gcg ttc ttc         258
Asp Gly Lys Gly Pro Ile Arg Phe Val Leu Ala Leu Leu Ala Phe Phe
         40                  45                  50 agg ttc aca gca att gct ccg acc cga gca gtg ctg gat cga tgg aga         306
Arg Phe Thr Ala Ile Ala Pro Thr Arg Ala Val Leu Asp Arg Trp Arg
 55                  60                  65                  70 ggt gtg aac aaa caa aca gcg atg aaa cac ctt ctg agt ttt aag aag         354
Gly Val Asn Lys Gln Thr Ala Met Lys His Leu Leu Ser Phe Lys Lys
                 75                  80                  85 gaa cta ggg acc ttg acc agt gct atc aat cgg cgg agc tca aaa caa         402
Glu Leu Gly Thr Leu Thr Ser Ala Ile Asn Arg Arg Ser Ser Lys Gln
             90                  95                 100 aag aaa aga tcc gtg acc atg ctc ctt atg ctg ctg ccc aca gcc ctg         450
Lys Lys Arg Ser Val Thr Met Leu Leu Met Leu Leu Pro Thr Ala Leu
        105                 110                 115 gcg ttc cat ctg acg aca cga ggg gga gag ccg cat atg ata gtt agc         498
Ala Phe His Leu Thr Thr Arg Gly Gly Glu Pro His Met Ile Val Ser
120                 125                 130 aag cag gaa aga gga aag tca ctt ctg ttc aag acc tct gca ggt gtc         546
Lys Gln Glu Arg Gly Lys Ser Leu Leu Phe Lys Thr Ser Ala Gly Val
135                 140                 145                 150 aac atg tgc acc ctc att gcg atg gat ttg gga gag ttg tgt gag gac         594
Asn Met Cys Thr Leu Ile Ala Met Asp Leu Gly Glu Leu Cys Glu Asp
                155                 160                 165 acg atg acc tac aaa tgc ccc cgg atc act gag gcg gaa cca gat gac         642
Thr Met Thr Tyr Lys Cys Pro Arg Ile Thr Glu Ala Glu Pro Asp Asp
            170                 175                 180 gtt gac tgt tgg tgc aat gcc acg gac aca tgg gtg acc tat gga acg         690
Val Asp Cys Trp Cys Asn Ala Thr Asp Thr Trp Val Thr Tyr Gly Thr
        185                 190                 195 tgc tct caa act ggc gaa cac cga cga gac aaa cgt tcc gtc gca ttg         738
Cys Ser Gln Thr Gly Glu His Arg Arg Asp Lys Arg Ser Val Ala Leu
200                 205                 210 gcc cca cac gtg ggg ctt ggc cta gaa aca aga gcc gaa acg tgg atg         786
Ala Pro His Val Gly Leu Gly Leu Glu Thr Arg Ala Glu Thr Trp Met
215                 220                 225                 230 tcc tct gaa ggt gct tgg aaa cag ata caa aaa gta gag act tgg gct         834
Ser Ser Glu Gly Ala Trp Lys Gln Ile Gln Lys Val Glu Thr Trp Ala
                235                 240                 245 ctg aga cat cca gga ttc acg gtg ata gcc ctt ttt cta gca cat gcc         882
Leu Arg His Pro Gly Phe Thr Val Ile Ala Leu Phe Leu Ala His Ala
            250                 255                 260
```

```
ata gga aca tcc atc acc cag aaa ggg atc att ttc att ttg ctg atg    930
Ile Gly Thr Ser Ile Thr Gln Lys Gly Ile Ile Phe Ile Leu Leu Met
    265                 270                 275 ctg gta aca cca tct atg gcc atg cga tgc gtg gga ata ggc aac aga    978
Leu Val Thr Pro Ser Met Ala Met Arg Cys Val Gly Ile Gly Asn Arg
280                 285                 290 gac ttc gtg gaa gga ctg tca gga gca aca tgg gtg gat gtg gta ctg   1026
Asp Phe Val Glu Gly Leu Ser Gly Ala Thr Trp Val Asp Val Val Leu
295                 300                 305                 310 gag cat gga agt tgc gtc acc acc atg gca aaa aac aaa cca aca ctg   1074
Glu His Gly Ser Cys Val Thr Thr Met Ala Lys Asn Lys Pro Thr Leu
                315                 320                 325 gac att gaa ctc ttg aag acg gag gtc aca aac cct gca gtt ctg cgt   1122
Asp Ile Glu Leu Leu Lys Thr Glu Val Thr Asn Pro Ala Val Leu Arg
        330                 335                 340 aaa ttg tgc att gaa gct aaa ata tca aac acc acc acc gat tcg aga   1170
Lys Leu Cys Ile Glu Ala Lys Ile Ser Asn Thr Thr Thr Asp Ser Arg
            345                 350                 355 tgt cca aca caa gga gaa gcc aca ctg gtg gaa gaa caa gac gcg aac   1218
Cys Pro Thr Gln Gly Glu Ala Thr Leu Val Glu Glu Gln Asp Ala Asn
    360                 365                 370 ttt gtg tgc cga cga acg ttc gtg gac aga ggc tgg ggc aat ggc tgt   1266
Phe Val Cys Arg Arg Thr Phe Val Asp Arg Gly Trp Gly Asn Gly Cys
375                 380                 385                 390 ggg cta ttc gga aaa ggt agt cta ata acg tgt gcc aag ttt aag tgt   1314
Gly Leu Phe Gly Lys Gly Ser Leu Ile Thr Cys Ala Lys Phe Lys Cys
                395                 400                 405 gtg aca aaa cta gaa gga aag ata gtt caa tat gaa aac cta aaa tat   1362
Val Thr Lys Leu Glu Gly Lys Ile Val Gln Tyr Glu Asn Leu Lys Tyr
        410                 415                 420 tca gtg ata gtc acc gtc cac act gga gat cag cac cag gtg gga aat   1410
Ser Val Ile Val Thr Val His Thr Gly Asp Gln His Gln Val Gly Asn
            425                 430                 435 gag act aca gaa cat gga aca act gca acc ata aca cct caa gct cct   1458
Glu Thr Thr Glu His Gly Thr Thr Ala Thr Ile Thr Pro Gln Ala Pro
    440                 445                 450 acg tcg gaa ata cag ctg acc gac tac gga acc ctt aca tta gat tgt   1506
Thr Ser Glu Ile Gln Leu Thr Asp Tyr Gly Thr Leu Thr Leu Asp Cys
455                 460                 465                 470 tca cct agg aca ggg cta gat ttt aac gag atg gtg ttg ctg aca atg   1554
Ser Pro Arg Thr Gly Leu Asp Phe Asn Glu Met Val Leu Leu Thr Met
                475                 480                 485 aaa gaa aga tca tgg ctt gtc cac aaa caa tgg ttt cca gac tta cca   1602
Lys Glu Arg Ser Trp Leu Val His Lys Gln Trp Phe Pro Asp Leu Pro
        490                 495                 500 ctg cct tgg acc tct ggg gct tca aca tcc caa gag act tgg aac aga   1650
Leu Pro Trp Thr Ser Gly Ala Ser Thr Ser Gln Glu Thr Trp Asn Arg
            505                 510                 515 caa gat tta ctg gtc aca ttt aag aca gct cat gca aag aag cag gaa   1698
Gln Asp Leu Leu Val Thr Phe Lys Thr Ala His Ala Lys Lys Gln Glu
    520                 525                 530 gta gtc gta cta gga tca caa gaa gga gca atg cac act gcg ctg act   1746
Val Val Val Leu Gly Ser Gln Glu Gly Ala Met His Thr Ala Leu Thr
535                 540                 545                 550 gga gcg aca gaa atc caa acg tca gga acg aca aca att ttc gca gga   1794
Gly Ala Thr Glu Ile Gln Thr Ser Gly Thr Thr Thr Ile Phe Ala Gly
                555                 560                 565 cac cta aaa tgc aga cta aaa atg gac aaa cta act tta aaa ggg atg   1842
His Leu Lys Cys Arg Leu Lys Met Asp Lys Leu Thr Leu Lys Gly Met
        570                 575                 580
```

| | | |
|---|---|---|
| tca tat gtg atg tgc aca ggc tca ttc aag tta gag aaa gaa gtg gct<br>Ser Tyr Val Met Cys Thr Gly Ser Phe Lys Leu Glu Lys Glu Val Ala<br>585 590 595 | 1890 | |
| gag acc cag cat gga act gtt ctg gtg cag gtt aaa tat gaa gga aca<br>Glu Thr Gln His Gly Thr Val Leu Val Gln Val Lys Tyr Glu Gly Thr<br>600 605 610 | 1938 | |
| gac gca cca tgc aag att ccc ttt tcg acc caa gat gag aaa gga gca<br>Asp Ala Pro Cys Lys Ile Pro Phe Ser Thr Gln Asp Glu Lys Gly Ala<br>615 620 625 630 | 1986 | |
| acc cag aat ggg aga tta ata aca gcc aac ccc ata gtc act gac aaa<br>Thr Gln Asn Gly Arg Leu Ile Thr Ala Asn Pro Ile Val Thr Asp Lys<br>635 640 645 | 2034 | |
| gaa aaa cca gtc aat att gag gca gaa cca ccc ttt ggt gag agc tac<br>Glu Lys Pro Val Asn Ile Glu Ala Glu Pro Pro Phe Gly Glu Ser Tyr<br>650 655 660 | 2082 | |
| atc gtg gta gga gca ggt gaa aaa gct ttg aaa cta agc tgg ttc aag<br>Ile Val Val Gly Ala Gly Glu Lys Ala Leu Lys Leu Ser Trp Phe Lys<br>665 670 675 | 2130 | |
| aaa gga agc agc ata ggg aaa atg ttt gaa gca act gcc cga gga gca<br>Lys Gly Ser Ser Ile Gly Lys Met Phe Glu Ala Thr Ala Arg Gly Ala<br>680 685 690 | 2178 | |
| cga agg atg gcc att ctg gga gac acc gca tgg gac ttc ggt tct ata<br>Arg Arg Met Ala Ile Leu Gly Asp Thr Ala Trp Asp Phe Gly Ser Ile<br>695 700 705 710 | 2226 | |
| gga gga gtg ttc acg tct atg gga aaa ctg gta cac cag gtt ttt gga<br>Gly Gly Val Phe Thr Ser Met Gly Lys Leu Val His Gln Val Phe Gly<br>715 720 725 | 2274 | |
| act gca tat gga gtt ttg ttt agc gga gtt tct tgg acc atg aaa ata<br>Thr Ala Tyr Gly Val Leu Phe Ser Gly Val Ser Trp Thr Met Lys Ile<br>730 735 740 | 2322 | |
| gga ata ggg att ctg ctg aca tgg cta gga tta aat tca agg aac acg<br>Gly Ile Gly Ile Leu Leu Thr Trp Leu Gly Leu Asn Ser Arg Asn Thr<br>745 750 755 | 2370 | |
| tcc ctt tcg atg atg tgc atc gca gtt ggc atg gtc aca ctg tac cta<br>Ser Leu Ser Met Met Cys Ile Ala Val Gly Met Val Thr Leu Tyr Leu<br>760 765 770 | 2418 | |
| gga gtc atg gtt cag gca gat tcc gga tgt gcc ata gac atc agc cgg<br>Gly Val Met Val Gln Ala Asp Ser Gly Cys Ala Ile Asp Ile Ser Arg<br>775 780 785 790 | 2466 | |
| caa gag ctg aga tgt gga agt gga gtg ttc ata cac aat gat gtg gag<br>Gln Glu Leu Arg Cys Gly Ser Gly Val Phe Ile His Asn Asp Val Glu<br>795 800 805 | 2514 | |
| gct tgg atg gac cgg tac aag tat tac cct gaa acg cca caa ggc cta<br>Ala Trp Met Asp Arg Tyr Lys Tyr Tyr Pro Glu Thr Pro Gln Gly Leu<br>810 815 820 | 2562 | |
| gcc aag atc att cag aaa gct cat aag gaa gga gtg tgc ggt cta cga<br>Ala Lys Ile Ile Gln Lys Ala His Lys Glu Gly Val Cys Gly Leu Arg<br>825 830 835 | 2610 | |
| tca gtt tcc aga ctg gag cat caa atg tgg gaa gca gtg aag gac gag<br>Ser Val Ser Arg Leu Glu His Gln Met Trp Glu Ala Val Lys Asp Glu<br>840 845 850 | 2658 | |
| ctg aac act ctt ttg aag gag aat ggt gtg gac ctt agt gtc gtg gtt<br>Leu Asn Thr Leu Leu Lys Glu Asn Gly Val Asp Leu Ser Val Val Val<br>855 860 865 870 | 2706 | |
| gag aaa cag gag gga atg tac aag tca gca cct aaa cgc ctc acc gcc<br>Glu Lys Gln Glu Gly Met Tyr Lys Ser Ala Pro Lys Arg Leu Thr Ala<br>875 880 885 | 2754 | |
| acc acg gaa aaa ttg gaa att ggc tgg aag gcc tgg gga aag agt att<br>Thr Thr Glu Lys Leu Glu Ile Gly Trp Lys Ala Trp Gly Lys Ser Ile<br>890 895 900 | 2802 | |

```
tta ttt gca cca gaa ctc gcc aac aac acc ttt gtg gtt gat ggt ccg    2850
Leu Phe Ala Pro Glu Leu Ala Asn Asn Thr Phe Val Val Asp Gly Pro
            905                 910                 915 gag acc aag gaa tgt ccg act cag aat cgc gct tgg aat agc tta gaa    2898
Glu Thr Lys Glu Cys Pro Thr Gln Asn Arg Ala Trp Asn Ser Leu Glu
920                 925                 930 gtg gag gat ttt gga ttt ggt ctc acc agc act cgg atg ttc ctg aag    2946
Val Glu Asp Phe Gly Phe Gly Leu Thr Ser Thr Arg Met Phe Leu Lys
935                 940                 945                 950 gtc aga gag agc aac aca act gaa tgt gac tcg aag atc att gga acg    2994
Val Arg Glu Ser Asn Thr Thr Glu Cys Asp Ser Lys Ile Ile Gly Thr
            955                 960                 965 gct gtc aag aac aac ttg gcg atc cac agt gac ctg tcc tat tgg att    3042
Ala Val Lys Asn Asn Leu Ala Ile His Ser Asp Leu Ser Tyr Trp Ile
        970                 975                 980 gaa agc agg ctc aat gat acg tgg aag ctt gaa agg gca gtt ctg ggt    3090
Glu Ser Arg Leu Asn Asp Thr Trp Lys Leu Glu Arg Ala Val Leu Gly
985                 990                 995 gaa gtc aaa tca tgt acg tgg cct gag acg cat acc ttg tgg ggc        3135
Glu Val Lys Ser Cys Thr Trp Pro Glu Thr His Thr Leu Trp Gly
    1000                1005                1010 gat gga atc ctt gag agt gac ttg ata ata cca gtc aca ctg gcg        3180
Asp Gly Ile Leu Glu Ser Asp Leu Ile Ile Pro Val Thr Leu Ala
1015                1020                1025 gga cca cga agc aat cac aat cgg aga cct ggg tac aag aca caa        3225
Gly Pro Arg Ser Asn His Asn Arg Arg Pro Gly Tyr Lys Thr Gln
    1030                1035                1040 aac cag ggc cca tgg gac gaa ggc cgg gta gag att gac ttc gat        3270
Asn Gln Gly Pro Trp Asp Glu Gly Arg Val Glu Ile Asp Phe Asp
1045                1050                1055 tac tgc cca gga act acg gtc acc ctg agt gag agc tgc gga cac        3315
Tyr Cys Pro Gly Thr Thr Val Thr Leu Ser Glu Ser Cys Gly His
    1060                1065                1070 cgt gga cct gcc act cgc acc acc aca gag agc gga aag ttg ata        3360
Arg Gly Pro Ala Thr Arg Thr Thr Thr Glu Ser Gly Lys Leu Ile
1075                1080                1085 aca gat tgg tgc tgc agg agc tgc acc tta cca cca ctg cgc tac        3405
Thr Asp Trp Cys Cys Arg Ser Cys Thr Leu Pro Pro Leu Arg Tyr
    1090                1095                1100 caa act gac agc ggc tgt tgg tat ggt atg gag atc aga cca cag        3450
Gln Thr Asp Ser Gly Cys Trp Tyr Gly Met Glu Ile Arg Pro Gln
1105                1110                1115 aga cat gat gaa aag acc ctc gtg cag tca caa gtg aat gct tat        3495
Arg His Asp Glu Lys Thr Leu Val Gln Ser Gln Val Asn Ala Tyr
    1120                1125                1130 aat gct gat atg att gac cct ttt cag ttg ggc ctt ctg gtc gtg        3540
Asn Ala Asp Met Ile Asp Pro Phe Gln Leu Gly Leu Leu Val Val
1135                1140                1145 ttc ttg gcc acc cag gag gtc ctt cgc aag agg tgg aca gcc aag        3585
Phe Leu Ala Thr Gln Glu Val Leu Arg Lys Arg Trp Thr Ala Lys
    1150                1155                1160 atc agc atg cca gct ata ctg att gct ctg cta gtc ctg gtg ttt        3630
Ile Ser Met Pro Ala Ile Leu Ile Ala Leu Leu Val Leu Val Phe
1165                1170                1175 ggg ggc att act tac act gat gtg tta cgc tat gtc atc ttg gtg        3675
Gly Gly Ile Thr Tyr Thr Asp Val Leu Arg Tyr Val Ile Leu Val
    1180                1185                1190 ggg gca gct ttc gca gaa tct aat tcg gga gga gac gtg gta cac        3720
Gly Ala Ala Phe Ala Glu Ser Asn Ser Gly Gly Asp Val Val His
1195                1200                1205
```

| | | | | | | | | | | |
|---|---|---|---|---|---|---|---|---|---|---|
| ttg<br>Leu<br>1210 | gcg<br>Ala | ctc<br>Leu | atg<br>Met | gcg<br>Ala | acc<br>Thr | ttc<br>Phe<br>1215 | aag<br>Lys | ata<br>Ile | caa<br>Gln | cca<br>Pro | gtg<br>Val<br>1220 | ttt<br>Phe | atg<br>Met | gtg<br>Val | 3765 |
| gca<br>Ala | tcg<br>Ser<br>1225 | ttt<br>Phe | ctc<br>Leu | aaa<br>Lys | gcg<br>Ala | aga<br>Arg<br>1230 | tgg<br>Trp | acc<br>Thr | aac<br>Asn | cag<br>Gln | gag<br>Glu<br>1235 | aac<br>Asn | att<br>Ile | ttg<br>Leu | 3810 |
| ttg<br>Leu | atg<br>Met<br>1240 | ttg<br>Leu | gcg<br>Ala | gct<br>Ala | gtt<br>Val | ttc<br>Phe<br>1245 | ttt<br>Phe | caa<br>Gln | atg<br>Met | gct<br>Ala | tat<br>Tyr<br>1250 | tac<br>Tyr | gat<br>Asp | gcc<br>Ala | 3855 |
| cgc<br>Arg | caa<br>Gln<br>1255 | att<br>Ile | ctg<br>Leu | ctc<br>Leu | tgg<br>Trp | gag<br>Glu<br>1260 | atc<br>Ile | cct<br>Pro | gat<br>Asp | gtg<br>Val | ttg<br>Leu<br>1265 | aat<br>Asn | tca<br>Ser | ctg<br>Leu | 3900 |
| gcg<br>Ala | gta<br>Val<br>1270 | gct<br>Ala | tgg<br>Trp | atg<br>Met | ata<br>Ile | ctg<br>Leu<br>1275 | aga<br>Arg | gcc<br>Ala | ata<br>Ile | aca<br>Thr | ttc<br>Phe<br>1280 | aca<br>Thr | acg<br>Thr | aca<br>Thr | 3945 |
| tca<br>Ser | aac<br>Asn<br>1285 | gtg<br>Val | gtt<br>Val | gtt<br>Val | ccg<br>Pro | ctg<br>Leu<br>1290 | cta<br>Leu | gcc<br>Ala | ctg<br>Leu | cta<br>Leu | aca<br>Thr<br>1295 | ccc<br>Pro | ggg<br>Gly | ctg<br>Leu | 3990 |
| aga<br>Arg | tgc<br>Cys<br>1300 | ttg<br>Leu | aat<br>Asn | ctg<br>Leu | gat<br>Asp | gtg<br>Val<br>1305 | tac<br>Tyr | agg<br>Arg | ata<br>Ile | ctg<br>Leu | ctg<br>Leu<br>1310 | ttg<br>Leu | atg<br>Met | gtc<br>Val | 4035 |
| gga<br>Gly | ata<br>Ile<br>1315 | ggc<br>Gly | agc<br>Ser | ttg<br>Leu | atc<br>Ile | agg<br>Arg<br>1320 | gag<br>Glu | aag<br>Lys | agg<br>Arg | agt<br>Ser | gca<br>Ala<br>1325 | gct<br>Ala | gca<br>Ala | aaa<br>Lys | 4080 |
| aag<br>Lys | aaa<br>Lys<br>1330 | gga<br>Gly | gca<br>Ala | agt<br>Ser | ctg<br>Leu | cta<br>Leu<br>1335 | tgc<br>Cys | ttg<br>Leu | gct<br>Ala | cta<br>Leu | gcc<br>Ala<br>1340 | tca<br>Ser | aca<br>Thr | gga<br>Gly | 4125 |
| ctt<br>Leu | ttc<br>Phe<br>1345 | aac<br>Asn | ccc<br>Pro | atg<br>Met | atc<br>Ile | ctt<br>Leu<br>1350 | gct<br>Ala | gct<br>Ala | gga<br>Gly | ctg<br>Leu | att<br>Ile<br>1355 | gca<br>Ala | tgt<br>Cys | gat<br>Asp | 4170 |
| ccc<br>Pro | aac<br>Asn<br>1360 | cgt<br>Arg | aaa<br>Lys | cgc<br>Arg | gga<br>Gly | tgg<br>Trp<br>1365 | ccc<br>Pro | gca<br>Ala | act<br>Thr | gaa<br>Glu | gtg<br>Val<br>1370 | atg<br>Met | aca<br>Thr | gct<br>Ala | 4215 |
| gtc<br>Val | ggc<br>Gly<br>1375 | cta<br>Leu | atg<br>Met | ttt<br>Phe | gcc<br>Ala | atc<br>Ile<br>1380 | gtc<br>Val | gga<br>Gly | ggg<br>Gly | ctg<br>Leu | gca<br>Ala<br>1385 | gag<br>Glu | ctt<br>Leu | gac<br>Asp | 4260 |
| att<br>Ile | gac<br>Asp<br>1390 | tcc<br>Ser | atg<br>Met | gcc<br>Ala | att<br>Ile | cca<br>Pro<br>1395 | atg<br>Met | act<br>Thr | atc<br>Ile | gcg<br>Ala | ggg<br>Gly<br>1400 | ctc<br>Leu | atg<br>Met | ttt<br>Phe | 4305 |
| gct<br>Ala | gct<br>Ala<br>1405 | ttc<br>Phe | gtg<br>Val | att<br>Ile | tct<br>Ser | ggg<br>Gly<br>1410 | aaa<br>Lys | tca<br>Ser | aca<br>Thr | gat<br>Asp | atg<br>Met<br>1415 | tgg<br>Trp | att<br>Ile | gag<br>Glu | 4350 |
| aga<br>Arg | acg<br>Thr<br>1420 | gcg<br>Ala | gac<br>Asp | att<br>Ile | tcc<br>Ser | tgg<br>Trp<br>1425 | gaa<br>Glu | agt<br>Ser | gat<br>Asp | gca<br>Ala | gaa<br>Glu<br>1430 | att<br>Ile | aca<br>Thr | ggc<br>Gly | 4395 |
| tcg<br>Ser | agc<br>Ser<br>1435 | gaa<br>Glu | aga<br>Arg | gtt<br>Val | gat<br>Asp | gtg<br>Val<br>1440 | cgg<br>Arg | ctt<br>Leu | gat<br>Asp | gat<br>Asp | gat<br>Asp<br>1445 | gga<br>Gly | aac<br>Asn | ttc<br>Phe | 4440 |
| cag<br>Gln | ctc<br>Leu<br>1450 | atg<br>Met | aat<br>Asn | gat<br>Asp | cca<br>Pro | gga<br>Gly<br>1455 | gca<br>Ala | cct<br>Pro | tgg<br>Trp | aag<br>Lys | ata<br>Ile<br>1460 | tgg<br>Trp | atg<br>Met | ctc<br>Leu | 4485 |
| aga<br>Arg | atg<br>Met<br>1465 | gtc<br>Val | tgt<br>Cys | ctc<br>Leu | gcg<br>Ala | att<br>Ile<br>1470 | agt<br>Ser | gcg<br>Ala | tac<br>Tyr | acc<br>Thr | ccc<br>Pro<br>1475 | tgg<br>Trp | gca<br>Ala | atc<br>Ile | 4530 |
| ttg<br>Leu | ccc<br>Pro<br>1480 | tca<br>Ser | gta<br>Val | gtt<br>Val | gga<br>Gly | ttt<br>Phe<br>1485 | tgg<br>Trp | ata<br>Ile | act<br>Thr | ctc<br>Leu | caa<br>Gln<br>1490 | tac<br>Tyr | aca<br>Thr | aag<br>Lys | 4575 |
| aga<br>Arg | gga<br>Gly<br>1495 | ggc<br>Gly | gtg<br>Val | ttg<br>Leu | tgg<br>Trp | gac<br>Asp<br>1500 | act<br>Thr | ccc<br>Pro | tca<br>Ser | cca<br>Pro | aag<br>Lys<br>1505 | gag<br>Glu | tac<br>Tyr | aaa<br>Lys | 4620 |

```
aag ggg gac acg acc acc ggc gtc tac agg atc atg act cgt ggg      4665
Lys Gly Asp Thr Thr Thr Gly Val Tyr Arg Ile Met Thr Arg Gly
    1510                1515                1520 ctg ctc ggc agt tat caa gca gga gcg ggc gtg atg gtt gaa ggt      4710
Leu Leu Gly Ser Tyr Gln Ala Gly Ala Gly Val Met Val Glu Gly
    1525                1530                1535 gtt ttc cac acc ctt tgg cat aca aca aaa gga gcc gct ttg atg      4755
Val Phe His Thr Leu Trp His Thr Thr Lys Gly Ala Ala Leu Met
    1540                1545                1550 agc gga gag ggc cgc ctg gac cca tac tgg ggc agt gtc aag gag      4800
Ser Gly Glu Gly Arg Leu Asp Pro Tyr Trp Gly Ser Val Lys Glu
    1555                1560                1565 gat cga ctt tgt tac gga gga ccc tgg aaa ttg cag cac aag tgg      4845
Asp Arg Leu Cys Tyr Gly Gly Pro Trp Lys Leu Gln His Lys Trp
    1570                1575                1580 aac ggg cag gat gag gtg cag atg att gtg gtg gaa cct ggc agg      4890
Asn Gly Gln Asp Glu Val Gln Met Ile Val Val Glu Pro Gly Arg
    1585                1590                1595 aac gtt aag aac gtc cag acg aaa cca ggg gtg ttc aaa aca cct      4935
Asn Val Lys Asn Val Gln Thr Lys Pro Gly Val Phe Lys Thr Pro
    1600                1605                1610 gaa gga gaa atc ggg gcc gtg act ttg gac ttc ccc act gga aca      4980
Glu Gly Glu Ile Gly Ala Val Thr Leu Asp Phe Pro Thr Gly Thr
    1615                1620                1625 tca ggc tca cca ata gtg gac aaa aac ggt gat gtg att ggg ctt      5025
Ser Gly Ser Pro Ile Val Asp Lys Asn Gly Asp Val Ile Gly Leu
    1630                1635                1640 tat ggc aat gga gtc ata atg ccc aac ggc tca tac ata agc gcg      5070
Tyr Gly Asn Gly Val Ile Met Pro Asn Gly Ser Tyr Ile Ser Ala
    1645                1650                1655 ata gtg cag ggt gaa agg atg gat gag cca atc cca gcc gga ttc      5115
Ile Val Gln Gly Glu Arg Met Asp Glu Pro Ile Pro Ala Gly Phe
    1660                1665                1670 gaa cct gag atg ctg agg aaa aaa cag atc act gta ctg gat ctc      5160
Glu Pro Glu Met Leu Arg Lys Lys Gln Ile Thr Val Leu Asp Leu
    1675                1680                1685 cat ccc ggc gcc ggt aaa aca agg agg att ctg cca cag atc atc      5205
His Pro Gly Ala Gly Lys Thr Arg Arg Ile Leu Pro Gln Ile Ile
    1690                1695                1700 aaa gag gcc ata aac aga aga ctg aga aca gcc gtg cta gca cca      5250
Lys Glu Ala Ile Asn Arg Arg Leu Arg Thr Ala Val Leu Ala Pro
    1705                1710                1715 acc agg gtt gtg gct gct gag atg gct gaa gca ctg aga gga ctg      5295
Thr Arg Val Val Ala Ala Glu Met Ala Glu Ala Leu Arg Gly Leu
    1720                1725                1730 ccc atc cgg tac cag aca tcc gca gtg ccc aga gaa cat aat gga      5340
Pro Ile Arg Tyr Gln Thr Ser Ala Val Pro Arg Glu His Asn Gly
    1735                1740                1745 aat gag att gtt gat gtc atg tgt cat gct acc ctc acc cac agg      5385
Asn Glu Ile Val Asp Val Met Cys His Ala Thr Leu Thr His Arg
    1750                1755                1760 ctg atg tct cct cac agg gtg ccg aac tac aac ctg ttc gtg atg      5430
Leu Met Ser Pro His Arg Val Pro Asn Tyr Asn Leu Phe Val Met
    1765                1770                1775 gat gag gct cat ttc acc gac cca gct agc att gca gca aga ggt      5475
Asp Glu Ala His Phe Thr Asp Pro Ala Ser Ile Ala Ala Arg Gly
    1780                1785                1790 tac att tcc aca aag gtc gag cta ggg gag gcg gcg gca ata ttc      5520
Tyr Ile Ser Thr Lys Val Glu Leu Gly Glu Ala Ala Ala Ile Phe
    1795                1800                1805
```

```
atg aca gcc acc cca cca ggc act tca gat cca ttc cca gag tcc        5565
Met Thr Ala Thr Pro Pro Gly Thr Ser Asp Pro Phe Pro Glu Ser
    1810            1815                1820 aat tca cca att tcc gac tta cag act gag atc ccg gat cga gct        5610
Asn Ser Pro Ile Ser Asp Leu Gln Thr Glu Ile Pro Asp Arg Ala
    1825            1830                1835 tgg aac tct gga tac gaa tgg atc aca gaa tac acc ggg aag acg        5655
Trp Asn Ser Gly Tyr Glu Trp Ile Thr Glu Tyr Thr Gly Lys Thr
    1840            1845                1850 gtt tgg ttt gtg cct agt gtc aag atg ggg aat gag att gcc ctt        5700
Val Trp Phe Val Pro Ser Val Lys Met Gly Asn Glu Ile Ala Leu
    1855            1860                1865 tgc cta caa cgt gct gga aag aaa gta gtc caa ttg aac aga aag        5745
Cys Leu Gln Arg Ala Gly Lys Lys Val Val Gln Leu Asn Arg Lys
    1870            1875                1880 tcg tac gag acg gag tac cca aaa tgt aag aac gat gat tgg gac        5790
Ser Tyr Glu Thr Glu Tyr Pro Lys Cys Lys Asn Asp Asp Trp Asp
    1885            1890                1895 ttt gtt atc aca aca gac ata tct gaa atg ggg gct aac ttc aag        5835
Phe Val Ile Thr Thr Asp Ile Ser Glu Met Gly Ala Asn Phe Lys
    1900            1905                1910 gcg agc agg gtg att gac agc cgg aag agt gtg aaa cca acc atc        5880
Ala Ser Arg Val Ile Asp Ser Arg Lys Ser Val Lys Pro Thr Ile
    1915            1920                1925 ata aca gaa gga gaa ggg aga gtg atc ctg gga gaa cca tct gca        5925
Ile Thr Glu Gly Glu Gly Arg Val Ile Leu Gly Glu Pro Ser Ala
    1930            1935                1940 gtg aca gca gct agt gcc gcc cag aga cgt gga cgt atc ggt aga        5970
Val Thr Ala Ala Ser Ala Ala Gln Arg Arg Gly Arg Ile Gly Arg
    1945            1950                1955 aat ccg tcg caa gtt ggt gat gag tac tgt tat ggg ggg cac acg        6015
Asn Pro Ser Gln Val Gly Asp Glu Tyr Cys Tyr Gly Gly His Thr
    1960            1965                1970 aat gaa gac gac tcg aac ttc gcc cat tgg act gag gca cga atc        6060
Asn Glu Asp Asp Ser Asn Phe Ala His Trp Thr Glu Ala Arg Ile
    1975            1980                1985 atg ctg gac aac atc aac atg cca aac gga ctg atc gct caa ttc        6105
Met Leu Asp Asn Ile Asn Met Pro Asn Gly Leu Ile Ala Gln Phe
    1990            1995                2000 tac caa cca gag cgt gag aag gta tat acc atg gat ggg gaa tac        6150
Tyr Gln Pro Glu Arg Glu Lys Val Tyr Thr Met Asp Gly Glu Tyr
    2005            2010                2015 cgg ctc aga gga gaa gag aga aaa aac ttt ctg gaa ctg ttg agg        6195
Arg Leu Arg Gly Glu Glu Arg Lys Asn Phe Leu Glu Leu Leu Arg
    2020            2025                2030 act gca gat ctg cca gtt tgg ctg gct tac aag gtt gca gcg gct        6240
Thr Ala Asp Leu Pro Val Trp Leu Ala Tyr Lys Val Ala Ala Ala
    2035            2040                2045 gga gtg tca tac cac gac cgg agg tgg tgc ttt gat ggt cct agg        6285
Gly Val Ser Tyr His Asp Arg Arg Trp Cys Phe Asp Gly Pro Arg
    2050            2055                2060 aca aac aca att tta gaa gac aac aac gaa gtg gaa gtc atc acg        6330
Thr Asn Thr Ile Leu Glu Asp Asn Asn Glu Val Glu Val Ile Thr
    2065            2070                2075 aag ctt ggt gaa agg aag att ctg agg ccg cgc tgg att gac gcc        6375
Lys Leu Gly Glu Arg Lys Ile Leu Arg Pro Arg Trp Ile Asp Ala
    2080            2085                2090 agg gtg tac tcg gat cac cag gca cta aag gcg ttc aag gac ttc        6420
Arg Val Tyr Ser Asp His Gln Ala Leu Lys Ala Phe Lys Asp Phe
    2095            2100                2105
```

```
gcc tcg gga aaa cgt tct cag ata ggg ctc att gag gtt ctg gga      6465
Ala Ser Gly Lys Arg Ser Gln Ile Gly Leu Ile Glu Val Leu Gly
    2110            2115                2120 aag atg cct gag cac ttc atg ggg aag aca tgg gaa gca ctt gac      6510
Lys Met Pro Glu His Phe Met Gly Lys Thr Trp Glu Ala Leu Asp
    2125            2130                2135 acc atg tac gtt gtg gcc act gca gag aaa gga gga aga gct cac      6555
Thr Met Tyr Val Val Ala Thr Ala Glu Lys Gly Gly Arg Ala His
    2140            2145                2150 aga atg gcc ctg gag gaa ctg cca gat gct ctt cag aca att gcc      6600
Arg Met Ala Leu Glu Glu Leu Pro Asp Ala Leu Gln Thr Ile Ala
    2155            2160                2165 ttg att gcc tta ttg agt gtg atg acc atg gga gta ttc ttc ctc      6645
Leu Ile Ala Leu Leu Ser Val Met Thr Met Gly Val Phe Phe Leu
    2170            2175                2180 ctc atg cag cgg aag ggc att gga aag ata ggt ttg gga ggc gct      6690
Leu Met Gln Arg Lys Gly Ile Gly Lys Ile Gly Leu Gly Gly Ala
    2185            2190                2195 gtc ttg gga gtc gcg acc ttt ttc tgt tgg atg gct gaa gtt cca      6735
Val Leu Gly Val Ala Thr Phe Phe Cys Trp Met Ala Glu Val Pro
    2200            2205                2210 gga acg aag atc gcc gga atg ttg ctg ctc tcc ctt ctc ttg atg      6780
Gly Thr Lys Ile Ala Gly Met Leu Leu Leu Ser Leu Leu Leu Met
    2215            2220                2225 att gtg cta att cct gag cca gag aag caa cgt tcg cag aca gac      6825
Ile Val Leu Ile Pro Glu Pro Glu Lys Gln Arg Ser Gln Thr Asp
    2230            2235                2240 aac cag cta gcc gtg ttc ctg att tgt gtc atg acc ctt gtg agc      6870
Asn Gln Leu Ala Val Phe Leu Ile Cys Val Met Thr Leu Val Ser
    2245            2250                2255 gca gtg gca gcc aac gag atg ggt tgg cta gat aag acc aag agt      6915
Ala Val Ala Ala Asn Glu Met Gly Trp Leu Asp Lys Thr Lys Ser
    2260            2265                2270 gac ata agc agt ttg ttt ggg caa aga att gag gtc aag gag aat      6960
Asp Ile Ser Ser Leu Phe Gly Gln Arg Ile Glu Val Lys Glu Asn
    2275            2280                2285 ttc agc atg gga gag ttt ctt ttg gac ttg agg cct gca aca gcc      7005
Phe Ser Met Gly Glu Phe Leu Leu Asp Leu Arg Pro Ala Thr Ala
    2290            2295                2300 tgg tca ctg tac gct gtg aca aca gcg gtc ctc act cca ctg cta      7050
Trp Ser Leu Tyr Ala Val Thr Thr Ala Val Leu Thr Pro Leu Leu
    2305            2310                2315 aag cat ttg atc acg tca gat tac atc aac acc tca ttg acc tca      7095
Lys His Leu Ile Thr Ser Asp Tyr Ile Asn Thr Ser Leu Thr Ser
    2320            2325                2330 ata aac gtt cag gca agt gca cta ttc aca ctc gcg cga ggc ttc      7140
Ile Asn Val Gln Ala Ser Ala Leu Phe Thr Leu Ala Arg Gly Phe
    2335            2340                2345 ccc ttc gtc gat gtt gga gtg tcg gct ctc ctg cta gca gcc gga      7185
Pro Phe Val Asp Val Gly Val Ser Ala Leu Leu Leu Ala Ala Gly
    2350            2355                2360 tgc tgg gga caa gtc acc ctc acc gtt acg gta aca gcg gca aca      7230
Cys Trp Gly Gln Val Thr Leu Thr Val Thr Val Thr Ala Ala Thr
    2365            2370                2375 ctc ctt ttt tgc cac tat gcc tac atg gtt ccc ggt tgg caa gct      7275
Leu Leu Phe Cys His Tyr Ala Tyr Met Val Pro Gly Trp Gln Ala
    2380            2385                2390 gag gca atg cgc tca gcc cag cgg cgg aca gcg gcc gga atc atg      7320
Glu Ala Met Arg Ser Ala Gln Arg Arg Thr Ala Ala Gly Ile Met
    2395            2400                2405
```

| | | | | | | | | | | | | |
|---|---|---|---|---|---|---|---|---|---|---|---|---|
| aag | aac | gct | gta | gtg | gat | ggc | atc | gtg | gcc | acg | gac | gtc | cca | gaa | 7365 |
| Lys | Asn | Ala | Val | Val | Asp | Gly | Ile | Val | Ala | Thr | Asp | Val | Pro | Glu | |
| | 2410 | | | | 2415 | | | | 2420 | | | | | | |

| tta | gag | cgc | acc | aca | ccc | atc | atg | cag | aag | aaa | gtt | gga | cag | atc | 7410 |
| Leu | Glu | Arg | Thr | Thr | Pro | Ile | Met | Gln | Lys | Lys | Val | Gly | Gln | Ile | |
| 2425 | | | | | 2430 | | | | | 2435 | | | | | |

| atg | ctg | atc | ttg | gtg | tct | cta | gct | gca | gta | gta | gtg | aac | ccg | tct | 7455 |
| Met | Leu | Ile | Leu | Val | Ser | Leu | Ala | Ala | Val | Val | Val | Asn | Pro | Ser | |
| 2440 | | | | | 2445 | | | | | 2450 | | | | | |

| gtg | aag | aca | gta | cga | gaa | gcc | gga | att | ttg | atc | acg | gcc | gca | gcg | 7500 |
| Val | Lys | Thr | Val | Arg | Glu | Ala | Gly | Ile | Leu | Ile | Thr | Ala | Ala | Ala | |
| | 2455 | | | | 2460 | | | | | 2465 | | | | | |

| gtg | acg | ctt | tgg | gag | aat | gga | gca | agc | tct | gtt | tgg | aac | gca | aca | 7545 |
| Val | Thr | Leu | Trp | Glu | Asn | Gly | Ala | Ser | Ser | Val | Trp | Asn | Ala | Thr | |
| | 2470 | | | | 2475 | | | | | 2480 | | | | | |

| act | gcc | atc | gga | ctc | tgc | cac | atc | atg | cgt | ggg | ggt | tgg | ttg | tca | 7590 |
| Thr | Ala | Ile | Gly | Leu | Cys | His | Ile | Met | Arg | Gly | Gly | Trp | Leu | Ser | |
| | 2485 | | | | 2490 | | | | | 2495 | | | | | |

| tgt | cta | tcc | ata | aca | tgg | aca | ctc | ata | aag | aac | atg | gaa | aaa | cca | 7635 |
| Cys | Leu | Ser | Ile | Thr | Trp | Thr | Leu | Ile | Lys | Asn | Met | Glu | Lys | Pro | |
| | 2500 | | | | 2505 | | | | | 2510 | | | | | |

| gga | cta | aaa | aga | ggt | ggg | gca | aaa | gga | cgc | acc | ttg | gga | gag | gtt | 7680 |
| Gly | Leu | Lys | Arg | Gly | Gly | Ala | Lys | Gly | Arg | Thr | Leu | Gly | Glu | Val | |
| | 2515 | | | | 2520 | | | | | 2525 | | | | | |

| tgg | aaa | gaa | aga | ctc | aac | cag | atg | aca | aaa | gaa | gag | ttc | act | agg | 7725 |
| Trp | Lys | Glu | Arg | Leu | Asn | Gln | Met | Thr | Lys | Glu | Glu | Phe | Thr | Arg | |
| | 2530 | | | | 2535 | | | | | 2540 | | | | | |

| tac | cgc | aaa | gag | gcc | atc | atc | gaa | gtc | gat | cgc | tca | gcg | gca | aaa | 7770 |
| Tyr | Arg | Lys | Glu | Ala | Ile | Ile | Glu | Val | Asp | Arg | Ser | Ala | Ala | Lys | |
| | 2545 | | | | 2550 | | | | | 2555 | | | | | |

| cac | gcc | agg | aaa | gaa | ggc | aat | gtc | act | gga | ggg | cat | cca | gtc | tct | 7815 |
| His | Ala | Arg | Lys | Glu | Gly | Asn | Val | Thr | Gly | Gly | His | Pro | Val | Ser | |
| | 2560 | | | | 2565 | | | | | 2570 | | | | | |

| agg | ggc | aca | gca | aaa | ctg | aga | tgg | ctg | gtc | gaa | cgg | agg | ttt | ctc | 7860 |
| Arg | Gly | Thr | Ala | Lys | Leu | Arg | Trp | Leu | Val | Glu | Arg | Arg | Phe | Leu | |
| | 2575 | | | | 2580 | | | | | 2585 | | | | | |

| gaa | ccg | gtc | gga | aaa | gtg | att | gac | ctt | gga | tgt | gga | aga | ggc | ggt | 7905 |
| Glu | Pro | Val | Gly | Lys | Val | Ile | Asp | Leu | Gly | Cys | Gly | Arg | Gly | Gly | |
| | 2590 | | | | 2595 | | | | | 2600 | | | | | |

| tgg | tgt | tac | tat | atg | gca | acc | caa | aaa | aga | gtc | caa | gaa | gtc | aga | 7950 |
| Trp | Cys | Tyr | Tyr | Met | Ala | Thr | Gln | Lys | Arg | Val | Gln | Glu | Val | Arg | |
| | 2605 | | | | 2610 | | | | | 2615 | | | | | |

| ggg | tac | aca | aag | ggc | ggt | ccc | gga | cat | gaa | gag | ccc | caa | cta | gtg | 7995 |
| Gly | Tyr | Thr | Lys | Gly | Gly | Pro | Gly | His | Glu | Glu | Pro | Gln | Leu | Val | |
| | 2620 | | | | 2625 | | | | | 2630 | | | | | |

| caa | agt | tat | gga | tgg | aac | att | gtc | acc | atg | aag | agt | gga | gtg | gat | 8040 |
| Gln | Ser | Tyr | Gly | Trp | Asn | Ile | Val | Thr | Met | Lys | Ser | Gly | Val | Asp | |
| | 2635 | | | | 2640 | | | | | 2645 | | | | | |

| gtg | ttc | tac | aga | cct | tct | gag | tgt | tgt | gac | acc | ctc | ctt | tgt | gac | 8085 |
| Val | Phe | Tyr | Arg | Pro | Ser | Glu | Cys | Cys | Asp | Thr | Leu | Leu | Cys | Asp | |
| | 2650 | | | | 2655 | | | | | 2660 | | | | | |

| atc | gga | gag | tcc | tcg | tca | agt | gct | gag | gtt | gaa | gag | cat | agg | acg | 8130 |
| Ile | Gly | Glu | Ser | Ser | Ser | Ser | Ala | Glu | Val | Glu | Glu | His | Arg | Thr | |
| | 2665 | | | | 2670 | | | | | 2675 | | | | | |

| att | cgg | gtc | ctt | gaa | atg | gtt | gag | gac | tgg | ctg | cac | cga | ggg | cca | 8175 |
| Ile | Arg | Val | Leu | Glu | Met | Val | Glu | Asp | Trp | Leu | His | Arg | Gly | Pro | |
| | 2680 | | | | 2685 | | | | | 2690 | | | | | |

| agg | gaa | ttt | tgc | gtg | aag | gtg | ctc | tgc | ccc | tac | atg | ccg | aaa | gtc | 8220 |
| Arg | Glu | Phe | Cys | Val | Lys | Val | Leu | Cys | Pro | Tyr | Met | Pro | Lys | Val | |
| | 2695 | | | | 2700 | | | | | 2705 | | | | | |

-continued

| | | | | | | | | | | | |
|---|---|---|---|---|---|---|---|---|---|---|---|
| ata | gag | aag | atg | gag | ctg | ctc | caa | cgc | cgg | tat | ggg | ggg | gga | ctg | 8265 |
| Ile | Glu | Lys | Met | Glu | Leu | Leu | Gln | Arg | Arg | Tyr | Gly | Gly | Gly | Leu | |
| | 2710 | | | | 2715 | | | | | 2720 | | | | | |

| gtc | aga | aac | cca | ctc | tca | cgg | aat | tcc | acg | cac | gag | atg | tat | tgg | 8310 |
| Val | Arg | Asn | Pro | Leu | Ser | Arg | Asn | Ser | Thr | His | Glu | Met | Tyr | Trp | |
| | 2725 | | | | 2730 | | | | | 2735 | | | | | |

| gtg | agt | cga | gct | tca | ggc | aat | gtg | gta | cat | tca | gtg | aat | atg | acc | 8355 |
| Val | Ser | Arg | Ala | Ser | Gly | Asn | Val | Val | His | Ser | Val | Asn | Met | Thr | |
| | 2740 | | | | 2745 | | | | | 2750 | | | | | |

| agc | cag | gtg | ctc | cta | gga | aga | atg | gaa | aaa | agg | acc | tgg | aag | gga | 8400 |
| Ser | Gln | Val | Leu | Leu | Gly | Arg | Met | Glu | Lys | Arg | Thr | Trp | Lys | Gly | |
| 2755 | | | | | 2760 | | | | | 2765 | | | | | |

| ccc | caa | tac | gag | gaa | gat | gta | aac | ttg | gga | agt | gga | acc | agg | gcg | 8445 |
| Pro | Gln | Tyr | Glu | Glu | Asp | Val | Asn | Leu | Gly | Ser | Gly | Thr | Arg | Ala | |
| 2770 | | | | | 2775 | | | | | 2780 | | | | | |

| gtg | gga | aaa | ccc | ctg | ctc | aac | tca | gac | acc | agt | aaa | atc | aag | aac | 8490 |
| Val | Gly | Lys | Pro | Leu | Leu | Asn | Ser | Asp | Thr | Ser | Lys | Ile | Lys | Asn | |
| 2785 | | | | | 2790 | | | | | 2795 | | | | | |

| agg | att | gaa | cga | ctc | agg | cgt | gag | tac | agt | tcg | acg | tgg | cac | cac | 8535 |
| Arg | Ile | Glu | Arg | Leu | Arg | Arg | Glu | Tyr | Ser | Ser | Thr | Trp | His | His | |
| 2800 | | | | | 2805 | | | | | 2810 | | | | | |

| gat | gag | aac | cac | cca | tat | aga | acc | tgg | aac | tat | cac | ggc | agt | tat | 8580 |
| Asp | Glu | Asn | His | Pro | Tyr | Arg | Thr | Trp | Asn | Tyr | His | Gly | Ser | Tyr | |
| 2815 | | | | | 2820 | | | | | 2825 | | | | | |

| gat | gtg | aag | ccc | aca | ggc | tcc | gcc | agt | tcg | ctg | gtc | aat | gga | gtg | 8625 |
| Asp | Val | Lys | Pro | Thr | Gly | Ser | Ala | Ser | Ser | Leu | Val | Asn | Gly | Val | |
| | 2830 | | | | 2835 | | | | | 2840 | | | | | |

| gtc | agg | ctc | ctc | tca | aaa | cca | tgg | gac | acc | atc | acg | aat | gtt | acc | 8670 |
| Val | Arg | Leu | Leu | Ser | Lys | Pro | Trp | Asp | Thr | Ile | Thr | Asn | Val | Thr | |
| 2845 | | | | | 2850 | | | | | 2855 | | | | | |

| acc | atg | gcc | atg | act | gac | act | act | ccc | ttc | ggg | cag | cag | cga | gtg | 8715 |
| Thr | Met | Ala | Met | Thr | Asp | Thr | Thr | Pro | Phe | Gly | Gln | Gln | Arg | Val | |
| 2860 | | | | | 2865 | | | | | 2870 | | | | | |

| ttc | aaa | gag | aag | gtg | gac | acg | aaa | gct | cct | gaa | ccg | cca | gaa | gga | 8760 |
| Phe | Lys | Glu | Lys | Val | Asp | Thr | Lys | Ala | Pro | Glu | Pro | Pro | Glu | Gly | |
| | 2875 | | | | 2880 | | | | | 2885 | | | | | |

| gtg | aag | tac | gtg | ctc | aac | gag | acc | acc | aac | tgg | ttg | tgg | gcg | ttt | 8805 |
| Val | Lys | Tyr | Val | Leu | Asn | Glu | Thr | Thr | Asn | Trp | Leu | Trp | Ala | Phe | |
| | 2890 | | | | 2895 | | | | | 2900 | | | | | |

| ttg | gcc | aga | gaa | aaa | cgt | ccc | aga | atg | tgc | tct | cga | gag | gaa | ttc | 8850 |
| Leu | Ala | Arg | Glu | Lys | Arg | Pro | Arg | Met | Cys | Ser | Arg | Glu | Glu | Phe | |
| | 2905 | | | | 2910 | | | | | 2915 | | | | | |

| ata | aga | aag | gtc | aac | agc | aat | gca | gct | ttg | ggt | gcc | atg | ttt | gaa | 8895 |
| Ile | Arg | Lys | Val | Asn | Ser | Asn | Ala | Ala | Leu | Gly | Ala | Met | Phe | Glu | |
| | 2920 | | | | 2925 | | | | | 2930 | | | | | |

| gag | cag | aat | caa | tgg | agg | agc | gcc | aga | gaa | gca | gtt | gaa | gat | cca | 8940 |
| Glu | Gln | Asn | Gln | Trp | Arg | Ser | Ala | Arg | Glu | Ala | Val | Glu | Asp | Pro | |
| | 2935 | | | | 2940 | | | | | 2945 | | | | | |

| aaa | ttt | tgg | gag | atg | gtg | gat | gag | gag | cgc | gag | gca | cat | ctg | cgg | 8985 |
| Lys | Phe | Trp | Glu | Met | Val | Asp | Glu | Glu | Arg | Glu | Ala | His | Leu | Arg | |
| | 2950 | | | | 2955 | | | | | 2960 | | | | | |

| ggg | gaa | tgt | cac | act | tgc | att | tac | aac | atg | atg | gga | aag | aga | gag | 9030 |
| Gly | Glu | Cys | His | Thr | Cys | Ile | Tyr | Asn | Met | Met | Gly | Lys | Arg | Glu | |
| | 2965 | | | | 2970 | | | | | 2975 | | | | | |

| aaa | aaa | ccc | gga | gag | ttc | gga | aag | gcc | aag | gga | agc | aga | gcc | att | 9075 |
| Lys | Lys | Pro | Gly | Glu | Phe | Gly | Lys | Ala | Lys | Gly | Ser | Arg | Ala | Ile | |
| | 2980 | | | | 2985 | | | | | 2990 | | | | | |

| tgg | ttc | atg | tgg | ctc | gga | gct | cgc | ttt | ctg | gag | ttc | gag | gct | ctg | 9120 |
| Trp | Phe | Met | Trp | Leu | Gly | Ala | Arg | Phe | Leu | Glu | Phe | Glu | Ala | Leu | |
| | 2995 | | | | 3000 | | | | | 3005 | | | | | |

```
ggt ttt ctc aat gaa gac cac tgg ctt gga aga aag aac tca gga        9165
Gly Phe Leu Asn Glu Asp His Trp Leu Gly Arg Lys Asn Ser Gly
    3010            3015                3020 gga ggt gtc gag ggc ttg ggc ctc caa aaa ctg ggt tac atc ctg        9210
Gly Gly Val Glu Gly Leu Gly Leu Gln Lys Leu Gly Tyr Ile Leu
3025                3030                3035 cgt gaa gtt ggc acc cgg cct ggg ggc aag atc tat gct gat gac        9255
Arg Glu Val Gly Thr Arg Pro Gly Gly Lys Ile Tyr Ala Asp Asp
    3040                3045                3050 aca gct ggc tgg gac acc cgc atc acg aga gct gac ttg gaa aat        9300
Thr Ala Gly Trp Asp Thr Arg Ile Thr Arg Ala Asp Leu Glu Asn
3055                3060                3065 gaa gct aag gtg ctt gag ctg ctt gat ggg gaa cat cgg cgt ctt        9345
Glu Ala Lys Val Leu Glu Leu Leu Asp Gly Glu His Arg Arg Leu
    3070                3075                3080 gcc agg gcc atc att gag ctc acc tat cgt cac aaa gtt gtg aaa        9390
Ala Arg Ala Ile Ile Glu Leu Thr Tyr Arg His Lys Val Val Lys
3085                3090                3095 gtg atg cgc ccg gct gct gat gga aga acc gtc atg gat gtt atc        9435
Val Met Arg Pro Ala Ala Asp Gly Arg Thr Val Met Asp Val Ile
    3100                3105                3110 tcc aga gaa gat cag agg ggg agt gga caa gtt gtc acc tac gcc        9480
Ser Arg Glu Asp Gln Arg Gly Ser Gly Gln Val Val Thr Tyr Ala
3115                3120                3125 cta aac act ttc acc aac ctg gcc gtc cag ctg gtg agg atg atg        9525
Leu Asn Thr Phe Thr Asn Leu Ala Val Gln Leu Val Arg Met Met
    3130                3135                3140 gaa ggg gaa gga gtg att ggc cca gat gat gtg gag aaa ctc aca        9570
Glu Gly Glu Gly Val Ile Gly Pro Asp Asp Val Glu Lys Leu Thr
3145                3150                3155 aaa ggg aaa gga ccc aaa gtc agg acc tgg ctg ttt gag aat ggg        9615
Lys Gly Lys Gly Pro Lys Val Arg Thr Trp Leu Phe Glu Asn Gly
    3160                3165                3170 gaa gaa aga ctc agc cgc atg gct gtc agt gga gat gac tgt gtg        9660
Glu Glu Arg Leu Ser Arg Met Ala Val Ser Gly Asp Asp Cys Val
3175                3180                3185 gta aag ccc ctg gac gat cgc ttt gcc acc tcg ctc cac ttc ctc        9705
Val Lys Pro Leu Asp Asp Arg Phe Ala Thr Ser Leu His Phe Leu
    3190                3195                3200 aat gct atg tca aag gtt cgc aaa gac atc caa gag tgg aaa ccg        9750
Asn Ala Met Ser Lys Val Arg Lys Asp Ile Gln Glu Trp Lys Pro
3205                3210                3215 tca act gga tgg tat gat tgg cag cag gtt cca ttt tgc tca aac        9795
Ser Thr Gly Trp Tyr Asp Trp Gln Gln Val Pro Phe Cys Ser Asn
    3220                3225                3230 cat ttc act gaa ttg atc atg aaa gat gga aga aca ctg gtg gtt        9840
His Phe Thr Glu Leu Ile Met Lys Asp Gly Arg Thr Leu Val Val
3235                3240                3245 cca tgc cga gga cag gat gaa ttg gta ggc aga gct cgc ata tct        9885
Pro Cys Arg Gly Gln Asp Glu Leu Val Gly Arg Ala Arg Ile Ser
    3250                3255                3260 cca ggg gcc gga tgg aac gtc cgc gac act gct tgt ctg gct aag        9930
Pro Gly Ala Gly Trp Asn Val Arg Asp Thr Ala Cys Leu Ala Lys
3265                3270                3275 tct tat gcc cag atg tgg ctt ctg tac ttc cac aga aga gac        9975
Ser Tyr Ala Gln Met Trp Leu Leu Leu Tyr Phe His Arg Arg Asp
    3280                3285                3290 ctg cgg ctc atg gcc aac gcc att tgc tcc gct gtc cct gtg aat        10020
Leu Arg Leu Met Ala Asn Ala Ile Cys Ser Ala Val Pro Val Asn
3295                3300                3305
```

```
tgg gtc cct acc gga aga acc acg tgg tcc atc cat gca gga gga        10065
Trp Val Pro Thr Gly Arg Thr Thr Trp Ser Ile His Ala Gly Gly
    3310                3315                3320 gag tgg atg aca aca gag gac atg ttg gag gtc tgg aac cgt gtt        10110
Glu Trp Met Thr Thr Glu Asp Met Leu Glu Val Trp Asn Arg Val
3325                3330                3335 tgg ata gag gag aat gaa tgg atg gaa gac aaa acc cca gtg gag        10155
Trp Ile Glu Glu Asn Glu Trp Met Glu Asp Lys Thr Pro Val Glu
    3340                3345                3350 aaa tgg agt gac gtc cca tat tca gga aaa cga gag gac atc tgg        10200
Lys Trp Ser Asp Val Pro Tyr Ser Gly Lys Arg Glu Asp Ile Trp
3355                3360                3365 tgt ggc agc ctg att ggc aca aga gcc cga gcc acg tgg gca gaa        10245
Cys Gly Ser Leu Ile Gly Thr Arg Ala Arg Ala Thr Trp Ala Glu
    3370                3375                3380 aac atc cag gtg gct atc aac caa gtc aga gca atc atc gga gat        10290
Asn Ile Gln Val Ala Ile Asn Gln Val Arg Ala Ile Ile Gly Asp
3385                3390                3395 gag aag tat gtg gat tac atg agt tca cta aag aga tat gaa gac        10335
Glu Lys Tyr Val Asp Tyr Met Ser Ser Leu Lys Arg Tyr Glu Asp
    3400                3405                3410 aca act ttg gtt gag gac aca gta ctg tagatattta atcaattgta          10382
Thr Thr Leu Val Glu Asp Thr Val Leu
3415                3420 aatagacaat ataagtatgc ataaaagtgt agttttatag tagtatttag tggtgttagt  10442
gtaaatagtt aagaaaattt tgaggagaaa gtcaggccgg gaagttcccg ccaccggaag  10502
ttgagtagac ggtgctgcct gcgactcaac cccaggagga ctgggtgaac aaagccgcga  10562
agtgatccat gtaagccctc agaaccgtct cggaaggagg accccacatg ttgtaacttc  10622
aaagcccaat gtcagaccac gctacggcgt gctactctgc ggagagtgca gtctgcgata  10682
gtgccccagg aggactgggt taacaaaggc aaaccaacgc cccacgcggc cctagccccg  10742
gtaatggtgt taaccagggc gaaaggacta gaggttagag gagaccccgc ggtttaaagt  10802
gcacggccca gcctggctga agctgtaggt caggggaagg actagaggtt agtggagacc  10862
ccgtgccaca aaacaccaca acaaaacagc atattgacac ctgggataga ctaggagatc  10922
ttctgctctg cacaaccagc cacacggcac agtgcgccga caatggtggc tggtggtgcg  10982
agaacacagg atct                                                   10996
```

<210> SEQ ID NO 4
<211> LENGTH: 3422
<212> TYPE: PRT
<213> ORGANISM: Artificial Sequence
<220> FEATURE:
<223> OTHER INFORMATION: Synthetic Construct

<400> SEQUENCE: 4

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn 85                  90                  95
Arg Arg Ser Ser Lys Gln Lys Lys Arg Ser Val Thr Met Leu Leu Met
                100                 105                 110

Leu Leu Pro Thr Ala Leu Ala Phe His Leu Thr Thr Arg Gly Gly Glu
                115                 120                 125

Pro His Met Ile Val Ser Lys Gln Glu Arg Gly Lys Ser Leu Leu Phe
                130                 135                 140

Lys Thr Ser Ala Gly Val Asn Met Cys Thr Leu Ile Ala Met Asp Leu
145                 150                 155                 160

Gly Glu Leu Cys Glu Asp Thr Met Thr Tyr Lys Cys Pro Arg Ile Thr
                165                 170                 175

Glu Ala Glu Pro Asp Asp Val Asp Cys Trp Cys Asn Ala Thr Asp Thr
                180                 185                 190

Trp Val Thr Tyr Gly Thr Cys Ser Gln Thr Gly Glu His Arg Arg Asp
                195                 200                 205

Lys Arg Ser Val Ala Leu Ala Pro His Val Gly Leu Gly Leu Glu Thr
                210                 215                 220

Arg Ala Glu Thr Trp Met Ser Ser Glu Gly Ala Trp Lys Gln Ile Gln
225                 230                 235                 240

Lys Val Glu Thr Trp Ala Leu Arg His Pro Gly Phe Thr Val Ile Ala
                245                 250                 255

Leu Phe Leu Ala His Ala Ile Gly Thr Ser Ile Thr Gln Lys Gly Ile
                260                 265                 270

Ile Phe Ile Leu Leu Met Leu Val Thr Pro Ser Met Ala Met Arg Cys
                275                 280                 285

Val Gly Ile Gly Asn Arg Asp Phe Val Glu Gly Leu Ser Gly Ala Thr
                290                 295                 300

Trp Val Asp Val Val Leu Glu His Gly Ser Cys Val Thr Thr Met Ala
305                 310                 315                 320

Lys Asn Lys Pro Thr Leu Asp Ile Glu Leu Leu Lys Thr Glu Val Thr
                325                 330                 335

Asn Pro Ala Val Leu Arg Lys Leu Cys Ile Glu Ala Lys Ile Ser Asn
                340                 345                 350

Thr Thr Thr Asp Ser Arg Cys Pro Thr Gln Gly Glu Ala Thr Leu Val
                355                 360                 365

Glu Glu Gln Asp Ala Asn Phe Val Cys Arg Arg Thr Phe Val Asp Arg
                370                 375                 380

Gly Trp Gly Asn Gly Cys Gly Leu Phe Gly Lys Gly Ser Leu Ile Thr
385                 390                 395                 400

Cys Ala Lys Phe Lys Cys Val Thr Lys Leu Glu Gly Lys Ile Val Gln
                405                 410                 415

Tyr Glu Asn Leu Lys Tyr Ser Val Ile Val Thr Val His Thr Gly Asp
                420                 425                 430

Gln His Gln Val Gly Asn Glu Thr Thr Glu His Gly Thr Thr Ala Thr
                435                 440                 445

Ile Thr Pro Gln Ala Pro Thr Ser Glu Ile Gln Leu Thr Asp Tyr Gly
                450                 455                 460

Thr Leu Thr Leu Asp Cys Ser Pro Arg Thr Gly Leu Asp Phe Asn Glu
465                 470                 475                 480

Met Val Leu Leu Thr Met Lys Glu Arg Ser Trp Leu Val His Lys Gln
                485                 490                 495

Trp Phe Pro Asp Leu Pro Leu Pro Trp Thr Ser Gly Ala Ser Thr Ser
                500                 505                 510

```
Gln Glu Thr Trp Asn Arg Gln Asp Leu Leu Val Thr Phe Lys Thr Ala
        515                 520                 525

His Ala Lys Lys Gln Glu Val Val Leu Gly Ser Gln Glu Gly Ala
        530                 535                 540

Met His Thr Ala Leu Thr Gly Ala Thr Glu Ile Gln Thr Ser Gly Thr
545                 550                 555                 560

Thr Thr Ile Phe Ala Gly His Leu Lys Cys Arg Leu Lys Met Asp Lys
                565                 570                 575

Leu Thr Leu Lys Gly Met Ser Tyr Val Met Cys Thr Gly Ser Phe Lys
            580                 585                 590

Leu Glu Lys Glu Val Ala Glu Thr Gln His Gly Thr Val Leu Val Gln
        595                 600                 605

Val Lys Tyr Glu Gly Thr Asp Ala Pro Cys Lys Ile Pro Phe Ser Thr
    610                 615                 620

Gln Asp Glu Lys Gly Ala Thr Gln Asn Gly Arg Leu Ile Thr Ala Asn
625                 630                 635                 640

Pro Ile Val Thr Asp Lys Glu Lys Pro Val Asn Ile Glu Ala Glu Pro
                645                 650                 655

Pro Phe Gly Glu Ser Tyr Ile Val Val Gly Ala Gly Glu Lys Ala Leu
            660                 665                 670

Lys Leu Ser Trp Phe Lys Lys Gly Ser Ser Ile Gly Lys Met Phe Glu
        675                 680                 685

Ala Thr Ala Arg Gly Ala Arg Arg Met Ala Ile Leu Gly Asp Thr Ala
    690                 695                 700

Trp Asp Phe Gly Ser Ile Gly Gly Val Phe Thr Ser Met Gly Lys Leu
705                 710                 715                 720

Val His Gln Val Phe Gly Thr Ala Tyr Gly Val Leu Phe Ser Gly Val
                725                 730                 735

Ser Trp Thr Met Lys Ile Gly Ile Gly Ile Leu Leu Thr Trp Leu Gly
            740                 745                 750

Leu Asn Ser Arg Asn Thr Ser Leu Ser Met Met Cys Ile Ala Val Gly
        755                 760                 765

Met Val Thr Leu Tyr Leu Gly Val Met Val Gln Ala Asp Ser Gly Cys
    770                 775                 780

Ala Ile Asp Ile Ser Arg Gln Glu Leu Arg Cys Gly Ser Gly Val Phe
785                 790                 795                 800

Ile His Asn Asp Val Glu Ala Trp Met Asp Arg Tyr Lys Tyr Tyr Pro
                805                 810                 815

Glu Thr Pro Gln Gly Leu Ala Lys Ile Ile Gln Lys Ala His Lys Glu
            820                 825                 830

Gly Val Cys Gly Leu Arg Ser Val Ser Arg Leu Glu His Gln Met Trp
        835                 840                 845

Glu Ala Val Lys Asp Glu Leu Asn Thr Leu Leu Lys Glu Asn Gly Val
    850                 855                 860

Asp Leu Ser Val Val Val Glu Lys Gln Glu Gly Met Tyr Lys Ser Ala
865                 870                 875                 880

Pro Lys Arg Leu Thr Ala Thr Thr Glu Lys Leu Glu Ile Gly Trp Lys
                885                 890                 895

Ala Trp Gly Lys Ser Ile Leu Phe Ala Pro Glu Leu Ala Asn Asn Thr
            900                 905                 910

Phe Val Val Asp Gly Pro Glu Thr Lys Glu Cys Pro Thr Gln Asn Arg
        915                 920                 925

Ala Trp Asn Ser Leu Glu Val Glu Asp Phe Gly Phe Gly Leu Thr Ser
    930                 935                 940
```

```
Thr Arg Met Phe Leu Lys Val Arg Glu Ser Asn Thr Thr Glu Cys Asp
945                 950                 955                 960

Ser Lys Ile Ile Gly Thr Ala Val Lys Asn Asn Leu Ala Ile His Ser
            965                 970                 975

Asp Leu Ser Tyr Trp Ile Glu Ser Arg Leu Asn Asp Thr Trp Lys Leu
            980                 985                 990

Glu Arg Ala Val Leu Gly Glu Val  Lys Ser Cys Thr Trp Pro Glu Thr
            995                 1000                1005

His Thr Leu Trp Gly Asp Gly  Ile Leu Glu Ser Asp  Leu Ile Ile
1010                1015                1020

Pro Val Thr Leu Ala Gly Pro  Arg Ser Asn His Asn  Arg Arg Pro
1025                1030                1035

Gly Tyr Lys Thr Gln Asn Gln  Gly Pro Trp Asp Glu  Gly Arg Val
1040                1045                1050

Glu Ile Asp Phe Asp Tyr Cys  Pro Gly Thr Thr Val  Thr Leu Ser
1055                1060                1065

Glu Ser Cys Gly His Arg Gly  Pro Ala Thr Arg Thr  Thr Thr Glu
1070                1075                1080

Ser Gly Lys Leu Ile Thr Asp  Trp Cys Cys Arg Ser  Cys Thr Leu
1085                1090                1095

Pro Pro Leu Arg Tyr Gln Thr  Asp Ser Gly Cys Trp  Tyr Gly Met
1100                1105                1110

Glu Ile Arg Pro Gln Arg His  Asp Glu Lys Thr Leu  Val Gln Ser
1115                1120                1125

Gln Val Asn Ala Tyr Asn Ala  Asp Met Ile Asp Pro  Phe Gln Leu
1130                1135                1140

Gly Leu Leu Val Val Phe Leu  Ala Thr Gln Glu Val  Leu Arg Lys
1145                1150                1155

Arg Trp Thr Ala Lys Ile Ser  Met Pro Ala Ile Leu  Ile Ala Leu
1160                1165                1170

Leu Val Leu Val Phe Gly Gly  Ile Thr Tyr Thr Asp  Val Leu Arg
1175                1180                1185

Tyr Val Ile Leu Val Gly Ala  Ala Phe Ala Glu Ser  Asn Ser Gly
1190                1195                1200

Gly Asp Val Val His Leu Ala  Leu Met Ala Thr Phe  Lys Ile Gln
1205                1210                1215

Pro Val Phe Met Val Ala Ser  Phe Leu Lys Ala Arg  Trp Thr Asn
1220                1225                1230

Gln Glu Asn Ile Leu Leu Met  Leu Ala Ala Val Phe  Phe Gln Met
1235                1240                1245

Ala Tyr Tyr Asp Ala Arg Gln  Ile Leu Leu Trp Glu  Ile Pro Asp
1250                1255                1260

Val Leu Asn Ser Leu Ala Val  Ala Trp Met Ile Leu  Arg Ala Ile
1265                1270                1275

Thr Phe Thr Thr Thr Ser Asn  Val Val Val Pro Leu  Leu Ala Leu
1280                1285                1290

Leu Thr Pro Gly Leu Arg Cys  Leu Asn Leu Asp Val  Tyr Arg Ile
1295                1300                1305

Leu Leu Leu Met Val Gly Ile  Gly Ser Leu Ile Arg  Glu Lys Arg
1310                1315                1320

Ser Ala Ala Ala Lys Lys Lys  Gly Ala Ser Leu Leu  Cys Leu Ala
1325                1330                1335

Leu Ala Ser Thr Gly Leu Phe  Asn Pro Met Ile Leu  Ala Ala Gly
```

-continued

```
             1340                1345                1350

Leu Ile Ala Cys Asp Pro Asn Arg Lys Arg Gly Trp Pro Ala Thr
    1355                1360                1365

Glu Val Met Thr Ala Val Gly Leu Met Phe Ala Ile Val Gly Gly
    1370                1375                1380

Leu Ala Glu Leu Asp Ile Asp Ser Met Ala Ile Pro Met Thr Ile
    1385                1390                1395

Ala Gly Leu Met Phe Ala Ala Phe Val Ile Ser Gly Lys Ser Thr
    1400                1405                1410

Asp Met Trp Ile Glu Arg Thr Ala Asp Ile Ser Trp Glu Ser Asp
    1415                1420                1425

Ala Glu Ile Thr Gly Ser Ser Glu Arg Val Asp Val Arg Leu Asp
    1430                1435                1440

Asp Asp Gly Asn Phe Gln Leu Met Asn Asp Pro Gly Ala Pro Trp
    1445                1450                1455

Lys Ile Trp Met Leu Arg Met Val Cys Leu Ala Ile Ser Ala Tyr
    1460                1465                1470

Thr Pro Trp Ala Ile Leu Pro Ser Val Val Gly Phe Trp Ile Thr
    1475                1480                1485

Leu Gln Tyr Thr Lys Arg Gly Gly Val Leu Trp Asp Thr Pro Ser
    1490                1495                1500

Pro Lys Glu Tyr Lys Lys Gly Asp Thr Thr Gly Val Tyr Arg
    1505                1510                1515

Ile Met Thr Arg Gly Leu Leu Gly Ser Tyr Gln Ala Gly Ala Gly
    1520                1525                1530

Val Met Val Glu Gly Val Phe His Thr Leu Trp His Thr Thr Lys
    1535                1540                1545

Gly Ala Ala Leu Met Ser Gly Glu Gly Arg Leu Asp Pro Tyr Trp
    1550                1555                1560

Gly Ser Val Lys Glu Asp Arg Leu Cys Tyr Gly Gly Pro Trp Lys
    1565                1570                1575

Leu Gln His Lys Trp Asn Gly Gln Asp Glu Val Gln Met Ile Val
    1580                1585                1590

Val Glu Pro Gly Arg Asn Val Lys Asn Val Gln Thr Lys Pro Gly
    1595                1600                1605

Val Phe Lys Thr Pro Glu Gly Glu Ile Gly Ala Val Thr Leu Asp
    1610                1615                1620

Phe Pro Thr Gly Thr Ser Gly Ser Pro Ile Val Asp Lys Asn Gly
    1625                1630                1635

Asp Val Ile Gly Leu Tyr Gly Asn Gly Val Ile Met Pro Asn Gly
    1640                1645                1650

Ser Tyr Ile Ser Ala Ile Val Gln Gly Glu Arg Met Asp Glu Pro
    1655                1660                1665

Ile Pro Ala Gly Phe Glu Pro Glu Met Leu Arg Lys Lys Gln Ile
    1670                1675                1680

Thr Val Leu Asp Leu His Pro Gly Ala Gly Lys Thr Arg Arg Ile
    1685                1690                1695

Leu Pro Gln Ile Ile Lys Glu Ala Ile Asn Arg Arg Leu Arg Thr
    1700                1705                1710

Ala Val Leu Ala Pro Thr Arg Val Val Ala Ala Glu Met Ala Glu
    1715                1720                1725

Ala Leu Arg Gly Leu Pro Ile Arg Tyr Gln Thr Ser Ala Val Pro
    1730                1735                1740
```

```
Arg Glu His Asn Gly Asn Glu Ile Val Asp Val Met Cys His Ala
1745                1750                1755

Thr Leu Thr His Arg Leu Met Ser Pro His Arg Val Pro Asn Tyr
1760                1765                1770

Asn Leu Phe Val Met Asp Glu Ala His Phe Thr Asp Pro Ala Ser
1775                1780                1785

Ile Ala Ala Arg Gly Tyr Ile Ser Thr Lys Val Glu Leu Gly Glu
1790                1795                1800

Ala Ala Ala Ile Phe Met Thr Ala Thr Pro Pro Gly Thr Ser Asp
1805                1810                1815

Pro Phe Pro Glu Ser Asn Ser Pro Ile Ser Asp Leu Gln Thr Glu
1820                1825                1830

Ile Pro Asp Arg Ala Trp Asn Ser Gly Tyr Glu Trp Ile Thr Glu
1835                1840                1845

Tyr Thr Gly Lys Thr Val Trp Phe Val Pro Ser Val Lys Met Gly
1850                1855                1860

Asn Glu Ile Ala Leu Cys Leu Gln Arg Ala Gly Lys Lys Val Val
1865                1870                1875

Gln Leu Asn Arg Lys Ser Tyr Glu Thr Glu Tyr Pro Lys Cys Lys
1880                1885                1890

Asn Asp Asp Trp Asp Phe Val Ile Thr Thr Asp Ile Ser Glu Met
1895                1900                1905

Gly Ala Asn Phe Lys Ala Ser Arg Val Ile Asp Ser Arg Lys Ser
1910                1915                1920

Val Lys Pro Thr Ile Ile Thr Glu Gly Glu Gly Arg Val Ile Leu
1925                1930                1935

Gly Glu Pro Ser Ala Val Thr Ala Ala Ser Ala Ala Gln Arg Arg
1940                1945                1950

Gly Arg Ile Gly Arg Asn Pro Ser Gln Val Gly Asp Glu Tyr Cys
1955                1960                1965

Tyr Gly Gly His Thr Asn Glu Asp Asp Ser Asn Phe Ala His Trp
1970                1975                1980

Thr Glu Ala Arg Ile Met Leu Asp Asn Ile Asn Met Pro Asn Gly
1985                1990                1995

Leu Ile Ala Gln Phe Tyr Gln Pro Glu Arg Glu Lys Val Tyr Thr
2000                2005                2010

Met Asp Gly Glu Tyr Arg Leu Arg Gly Glu Glu Arg Lys Asn Phe
2015                2020                2025

Leu Glu Leu Leu Arg Thr Ala Asp Leu Pro Val Trp Leu Ala Tyr
2030                2035                2040

Lys Val Ala Ala Ala Gly Val Ser Tyr His Asp Arg Arg Trp Cys
2045                2050                2055

Phe Asp Gly Pro Arg Thr Asn Thr Ile Leu Glu Asp Asn Asn Glu
2060                2065                2070

Val Glu Val Ile Thr Lys Leu Gly Glu Arg Lys Ile Leu Arg Pro
2075                2080                2085

Arg Trp Ile Asp Ala Arg Val Tyr Ser Asp His Gln Ala Leu Lys
2090                2095                2100

Ala Phe Lys Asp Phe Ala Ser Gly Lys Arg Ser Gln Ile Gly Leu
2105                2110                2115

Ile Glu Val Leu Gly Lys Met Pro Glu His Phe Met Gly Lys Thr
2120                2125                2130

Trp Glu Ala Leu Asp Thr Met Tyr Val Val Ala Thr Ala Glu Lys
2135                2140                2145
```

-continued

```
Gly Gly Arg Ala His Arg Met Ala Leu Glu Glu Leu Pro Asp Ala
    2150                2155                2160

Leu Gln Thr Ile Ala Leu Ile Ala Leu Leu Ser Val Met Thr Met
    2165                2170                2175

Gly Val Phe Phe Leu Leu Met Gln Arg Lys Gly Ile Gly Lys Ile
    2180                2185                2190

Gly Leu Gly Gly Ala Val Leu Gly Val Ala Thr Phe Phe Cys Trp
    2195                2200                2205

Met Ala Glu Val Pro Gly Thr Lys Ile Ala Gly Met Leu Leu Leu
    2210                2215                2220

Ser Leu Leu Leu Met Ile Val Leu Ile Pro Glu Pro Glu Lys Gln
    2225                2230                2235

Arg Ser Gln Thr Asp Asn Gln Leu Ala Val Phe Leu Ile Cys Val
    2240                2245                2250

Met Thr Leu Val Ser Ala Val Ala Ala Asn Glu Met Gly Trp Leu
    2255                2260                2265

Asp Lys Thr Lys Ser Asp Ile Ser Ser Leu Phe Gly Gln Arg Ile
    2270                2275                2280

Glu Val Lys Glu Asn Phe Ser Met Gly Glu Phe Leu Leu Asp Leu
    2285                2290                2295

Arg Pro Ala Thr Ala Trp Ser Leu Tyr Ala Val Thr Thr Ala Val
    2300                2305                2310

Leu Thr Pro Leu Leu Lys His Leu Ile Thr Ser Asp Tyr Ile Asn
    2315                2320                2325

Thr Ser Leu Thr Ser Ile Asn Val Gln Ala Ser Ala Leu Phe Thr
    2330                2335                2340

Leu Ala Arg Gly Phe Pro Phe Val Asp Val Gly Val Ser Ala Leu
    2345                2350                2355

Leu Leu Ala Ala Gly Cys Trp Gly Gln Val Thr Leu Thr Val Thr
    2360                2365                2370

Val Thr Ala Ala Thr Leu Leu Phe Cys His Tyr Ala Tyr Met Val
    2375                2380                2385

Pro Gly Trp Gln Ala Glu Ala Met Arg Ser Ala Gln Arg Arg Thr
    2390                2395                2400

Ala Ala Gly Ile Met Lys Asn Ala Val Val Asp Gly Ile Val Ala
    2405                2410                2415

Thr Asp Val Pro Glu Leu Glu Arg Thr Thr Pro Ile Met Gln Lys
    2420                2425                2430

Lys Val Gly Gln Ile Met Leu Ile Leu Val Ser Leu Ala Ala Val
    2435                2440                2445

Val Val Asn Pro Ser Val Lys Thr Val Arg Glu Ala Gly Ile Leu
    2450                2455                2460

Ile Thr Ala Ala Ala Val Thr Leu Trp Glu Asn Gly Ala Ser Ser
    2465                2470                2475

Val Trp Asn Ala Thr Thr Ala Ile Gly Leu Cys His Ile Met Arg
    2480                2485                2490

Gly Gly Trp Leu Ser Cys Leu Ser Ile Thr Trp Thr Leu Ile Lys
    2495                2500                2505

Asn Met Glu Lys Pro Gly Leu Lys Arg Gly Gly Ala Lys Gly Arg
    2510                2515                2520

Thr Leu Gly Glu Val Trp Lys Glu Arg Leu Asn Gln Met Thr Lys
    2525                2530                2535

Glu Glu Phe Thr Arg Tyr Arg Lys Glu Ala Ile Ile Glu Val Asp
```

|     |     |     |     |     |     |     |     |     |     |     |     |
|-----|-----|-----|-----|-----|-----|-----|-----|-----|-----|-----|-----|
|     |     | 2540 |     |     | 2545 |     |     | 2550 |     |     |     |
| Arg | Ser | Ala | Ala | Lys | His | Ala | Arg | Lys | Glu | Gly | Asn | Val | Thr | Gly |
|     | 2555 |     |     |     | 2560 |     |     |     | 2565 |     |     |
| Gly | His | Pro | Val | Ser | Arg | Gly | Thr | Ala | Lys | Leu | Arg | Trp | Leu | Val |
|     | 2570 |     |     |     | 2575 |     |     |     | 2580 |     |     |
| Glu | Arg | Arg | Phe | Leu | Glu | Pro | Val | Gly | Lys | Val | Ile | Asp | Leu | Gly |
|     | 2585 |     |     |     | 2590 |     |     |     | 2595 |     |     |
| Cys | Gly | Arg | Gly | Gly | Trp | Cys | Tyr | Tyr | Met | Ala | Thr | Gln | Lys | Arg |
|     | 2600 |     |     |     | 2605 |     |     |     | 2610 |     |     |
| Val | Gln | Glu | Val | Arg | Gly | Tyr | Thr | Lys | Gly | Gly | Pro | Gly | His | Glu |
|     | 2615 |     |     |     | 2620 |     |     |     | 2625 |     |     |
| Glu | Pro | Gln | Leu | Val | Gln | Ser | Tyr | Gly | Trp | Asn | Ile | Val | Thr | Met |
|     | 2630 |     |     |     | 2635 |     |     |     | 2640 |     |     |
| Lys | Ser | Gly | Val | Asp | Val | Phe | Tyr | Arg | Pro | Ser | Glu | Cys | Cys | Asp |
|     | 2645 |     |     |     | 2650 |     |     |     | 2655 |     |     |
| Thr | Leu | Leu | Cys | Asp | Ile | Gly | Glu | Ser | Ser | Ser | Ala | Glu | Val |
|     | 2660 |     |     |     | 2665 |     |     |     | 2670 |     |     |
| Glu | Glu | His | Arg | Thr | Ile | Arg | Val | Leu | Glu | Met | Val | Glu | Asp | Trp |
|     | 2675 |     |     |     | 2680 |     |     |     | 2685 |     |     |
| Leu | His | Arg | Gly | Pro | Arg | Glu | Phe | Cys | Val | Lys | Val | Leu | Cys | Pro |
|     | 2690 |     |     |     | 2695 |     |     |     | 2700 |     |     |
| Tyr | Met | Pro | Lys | Val | Ile | Glu | Lys | Met | Glu | Leu | Leu | Gln | Arg | Arg |
|     | 2705 |     |     |     | 2710 |     |     |     | 2715 |     |     |
| Tyr | Gly | Gly | Gly | Leu | Val | Arg | Asn | Pro | Leu | Ser | Arg | Asn | Ser | Thr |
|     | 2720 |     |     |     | 2725 |     |     |     | 2730 |     |     |
| His | Glu | Met | Tyr | Trp | Val | Ser | Arg | Ala | Ser | Gly | Asn | Val | Val | His |
|     | 2735 |     |     |     | 2740 |     |     |     | 2745 |     |     |
| Ser | Val | Asn | Met | Thr | Ser | Gln | Val | Leu | Leu | Gly | Arg | Met | Glu | Lys |
|     | 2750 |     |     |     | 2755 |     |     |     | 2760 |     |     |
| Arg | Thr | Trp | Lys | Gly | Pro | Gln | Tyr | Glu | Glu | Asp | Val | Asn | Leu | Gly |
|     | 2765 |     |     |     | 2770 |     |     |     | 2775 |     |     |
| Ser | Gly | Thr | Arg | Ala | Val | Gly | Lys | Pro | Leu | Leu | Asn | Ser | Asp | Thr |
|     | 2780 |     |     |     | 2785 |     |     |     | 2790 |     |     |
| Ser | Lys | Ile | Lys | Asn | Arg | Ile | Glu | Arg | Leu | Arg | Arg | Glu | Tyr | Ser |
|     | 2795 |     |     |     | 2800 |     |     |     | 2805 |     |     |
| Ser | Thr | Trp | His | His | Asp | Glu | Asn | His | Pro | Tyr | Arg | Thr | Trp | Asn |
|     | 2810 |     |     |     | 2815 |     |     |     | 2820 |     |     |
| Tyr | His | Gly | Ser | Tyr | Asp | Val | Lys | Pro | Thr | Gly | Ser | Ala | Ser | Ser |
|     | 2825 |     |     |     | 2830 |     |     |     | 2835 |     |     |
| Leu | Val | Asn | Gly | Val | Val | Arg | Leu | Leu | Ser | Lys | Pro | Trp | Asp | Thr |
|     | 2840 |     |     |     | 2845 |     |     |     | 2850 |     |     |
| Ile | Thr | Asn | Val | Thr | Thr | Met | Ala | Met | Thr | Asp | Thr | Thr | Pro | Phe |
|     | 2855 |     |     |     | 2860 |     |     |     | 2865 |     |     |
| Gly | Gln | Gln | Arg | Val | Phe | Lys | Glu | Lys | Val | Asp | Thr | Lys | Ala | Pro |
|     | 2870 |     |     |     | 2875 |     |     |     | 2880 |     |     |
| Glu | Pro | Pro | Glu | Gly | Val | Lys | Tyr | Val | Leu | Asn | Glu | Thr | Thr | Asn |
|     | 2885 |     |     |     | 2890 |     |     |     | 2895 |     |     |
| Trp | Leu | Trp | Ala | Phe | Leu | Ala | Arg | Glu | Lys | Arg | Pro | Arg | Met | Cys |
|     | 2900 |     |     |     | 2905 |     |     |     | 2910 |     |     |
| Ser | Arg | Glu | Glu | Phe | Ile | Arg | Lys | Val | Asn | Ser | Asn | Ala | Ala | Leu |
|     | 2915 |     |     |     | 2920 |     |     |     | 2925 |     |     |
| Gly | Ala | Met | Phe | Glu | Glu | Gln | Asn | Gln | Trp | Arg | Ser | Ala | Arg | Glu |
|     | 2930 |     |     |     | 2935 |     |     |     | 2940 |     |     |

-continued

```
Ala Val Glu Asp Pro Lys Phe Trp Glu Met Val Asp Glu Glu Arg
    2945                2950                2955

Glu Ala His Leu Arg Gly Glu Cys His Thr Cys Ile Tyr Asn Met
    2960                2965                2970

Met Gly Lys Arg Glu Lys Lys Pro Gly Glu Phe Gly Lys Ala Lys
    2975                2980                2985

Gly Ser Arg Ala Ile Trp Phe Met Trp Leu Gly Ala Arg Phe Leu
    2990                2995                3000

Glu Phe Glu Ala Leu Gly Phe Leu Asn Glu Asp His Trp Leu Gly
    3005                3010                3015

Arg Lys Asn Ser Gly Gly Gly Val Glu Gly Leu Gly Leu Gln Lys
    3020                3025                3030

Leu Gly Tyr Ile Leu Arg Glu Val Gly Thr Arg Pro Gly Gly Lys
    3035                3040                3045

Ile Tyr Ala Asp Asp Thr Ala Gly Trp Asp Thr Arg Ile Thr Arg
    3050                3055                3060

Ala Asp Leu Glu Asn Glu Ala Lys Val Leu Glu Leu Leu Asp Gly
    3065                3070                3075

Glu His Arg Arg Leu Ala Arg Ala Ile Ile Glu Leu Thr Tyr Arg
    3080                3085                3090

His Lys Val Val Lys Val Met Arg Pro Ala Ala Asp Gly Arg Thr
    3095                3100                3105

Val Met Asp Val Ile Ser Arg Glu Asp Gln Arg Gly Ser Gly Gln
    3110                3115                3120

Val Val Thr Tyr Ala Leu Asn Thr Phe Thr Asn Leu Ala Val Gln
    3125                3130                3135

Leu Val Arg Met Met Glu Gly Glu Gly Val Ile Gly Pro Asp Asp
    3140                3145                3150

Val Glu Lys Leu Thr Lys Gly Lys Gly Pro Lys Val Arg Thr Trp
    3155                3160                3165

Leu Phe Glu Asn Gly Glu Glu Arg Leu Ser Arg Met Ala Val Ser
    3170                3175                3180

Gly Asp Asp Cys Val Val Lys Pro Leu Asp Asp Arg Phe Ala Thr
    3185                3190                3195

Ser Leu His Phe Leu Asn Ala Met Ser Lys Val Arg Lys Asp Ile
    3200                3205                3210

Gln Glu Trp Lys Pro Ser Thr Gly Trp Tyr Asp Trp Gln Gln Val
    3215                3220                3225

Pro Phe Cys Ser Asn His Phe Thr Glu Leu Ile Met Lys Asp Gly
    3230                3235                3240

Arg Thr Leu Val Val Pro Cys Arg Gly Gln Asp Glu Leu Val Gly
    3245                3250                3255

Arg Ala Arg Ile Ser Pro Gly Ala Gly Trp Asn Val Arg Asp Thr
    3260                3265                3270

Ala Cys Leu Ala Lys Ser Tyr Ala Gln Met Trp Leu Leu Leu Tyr
    3275                3280                3285

Phe His Arg Arg Asp Leu Arg Leu Met Ala Asn Ala Ile Cys Ser
    3290                3295                3300

Ala Val Pro Val Asn Trp Val Pro Thr Gly Arg Thr Thr Trp Ser
    3305                3310                3315

Ile His Ala Gly Gly Glu Trp Met Thr Thr Glu Asp Met Leu Glu
    3320                3325                3330

Val Trp Asn Arg Val Trp Ile Glu Glu Asn Glu Trp Met Glu Asp
    3335                3340                3345
```

```
Lys Thr Pro Val Glu Lys Trp Ser Asp Val Pro Tyr Ser Gly Lys
    3350                3355                3360

Arg Glu Asp Ile Trp Cys Gly Ser Leu Ile Gly Thr Arg Ala Arg
    3365                3370                3375

Ala Thr Trp Ala Glu Asn Ile Gln Val Ala Ile Asn Gln Val Arg
    3380                3385                3390

Ala Ile Ile Gly Asp Glu Lys Tyr Val Asp Tyr Met Ser Ser Leu
    3395                3400                3405

Lys Arg Tyr Glu Asp Thr Thr Leu Val Glu Asp Thr Val Leu
    3410                3415                3420

<210> SEQ ID NO 5
<211> LENGTH: 10990
<212> TYPE: DNA
<213> ORGANISM: Artificial Sequence
<220> FEATURE:
<223> OTHER INFORMATION: Recombinant West Nile virus/Dengue-3 virus
      chimera
<220> FEATURE:
<221> NAME/KEY: CDS
<222> LOCATION: (97)..(10356)

<400> SEQUENCE: 5
agtagttcgc ctgtgtgagc tgacaaactt agtagtgttt gtgaggatta acaacaatta      60
acacagtgcg agctgtttct tagcacgaag atctcg atg tct aag aaa cca gga      114
                                        Met Ser Lys Lys Pro Gly
                                          1               5 ggg ccc ggc aag agc cgg gct gtc aat atg cta aaa cgc gga atg ccc      162
Gly Pro Gly Lys Ser Arg Ala Val Asn Met Leu Lys Arg Gly Met Pro
             10                  15                  20 cgc gtg ttg tcc ttg att gga ctg aag agg gct atg ttg agc ctg atc      210
Arg Val Leu Ser Leu Ile Gly Leu Lys Arg Ala Met Leu Ser Leu Ile
         25                  30                  35 gac ggc aag ggg cca ata cga ttt gtg ttg gct ctc ttg gcg ttc ttc      258
Asp Gly Lys Gly Pro Ile Arg Phe Val Leu Ala Leu Leu Ala Phe Phe
     40                  45                  50 agg ttc aca gca att gct ccg acc cga gca gtg ctg gat cga tgg aga      306
Arg Phe Thr Ala Ile Ala Pro Thr Arg Ala Val Leu Asp Arg Trp Arg
 55                  60                  65                  70 ggt gtg aac aaa caa aca gcg atg aaa cac ctt ctg agt ttt aag aag      354
Gly Val Asn Lys Gln Thr Ala Met Lys His Leu Leu Ser Phe Lys Lys
                 75                  80                  85 gaa cta ggg acc ttg acc agt gct atc aat cgg cgg agt tcg aaa caa      402
Glu Leu Gly Thr Leu Thr Ser Ala Ile Asn Arg Arg Ser Ser Lys Gln
             90                  95                 100 aag aaa aga aca tcg ctc tgt ctc atg atg atg tta cca gca aca ctt      450
Lys Lys Arg Thr Ser Leu Cys Leu Met Met Met Leu Pro Ala Thr Leu
        105                 110                 115 gct ttc cac tta act tca cga gat gga gag ccg cgc atg att gtg ggg      498
Ala Phe His Leu Thr Ser Arg Asp Gly Glu Pro Arg Met Ile Val Gly
    120                 125                 130 aag aat gaa aga gga aaa tcc cta ctt ttc aag aca gcc tct gga atc      546
Lys Asn Glu Arg Gly Lys Ser Leu Leu Phe Lys Thr Ala Ser Gly Ile
135                 140                 145                 150 aac atg tgc aca ctc ata gcc atg gat ctg gga gag atg tgt gat gac      594
Asn Met Cys Thr Leu Ile Ala Met Asp Leu Gly Glu Met Cys Asp Asp
                155                 160                 165 acg gtc act tac aaa tgc ccc cac att acc gaa gtg gag cct gaa gac      642
Thr Val Thr Tyr Lys Cys Pro His Ile Thr Glu Val Glu Pro Glu Asp
            170                 175                 180
```

| | | |
|---|---|---|
| att gac tgc tgg tgc aac ctt aca tcg aca tgg gtg act tat gga aca<br>Ile Asp Cys Trp Cys Asn Leu Thr Ser Thr Trp Val Thr Tyr Gly Thr<br>185 190 195 | | 690 |
| tgc aat caa gct gga gag cat aga cgc gat aag aga tca gtg gcg tta<br>Cys Asn Gln Ala Gly Glu His Arg Arg Asp Lys Arg Ser Val Ala Leu<br>200 205 210 | | 738 |
| gct ccc cat gtt ggc atg gga ctg gac aca cgc act caa acc tgg atg<br>Ala Pro His Val Gly Met Gly Leu Asp Thr Arg Thr Gln Thr Trp Met<br>215 220 225 230 | | 786 |
| tcg gct gaa gga gct tgg aga caa gtc gag aag gta gag aca tgg gcc<br>Ser Ala Glu Gly Ala Trp Arg Gln Val Glu Lys Val Glu Thr Trp Ala<br>235 240 245 | | 834 |
| ctt agg cac cca ggg ttt acc ata cta gcc cta ttt ctt gcc cat tac<br>Leu Arg His Pro Gly Phe Thr Ile Leu Ala Leu Phe Leu Ala His Tyr<br>250 255 260 | | 882 |
| ata ggc act tcc ttg acc cag aaa gtg gtt att ttt ata cta tta atg<br>Ile Gly Thr Ser Leu Thr Gln Lys Val Val Ile Phe Ile Leu Leu Met<br>265 270 275 | | 930 |
| ctg gtt acc cca tcc atg aca atg aga tgt gta gga gta gga aac aga<br>Leu Val Thr Pro Ser Met Thr Met Arg Cys Val Gly Val Gly Asn Arg<br>280 285 290 | | 978 |
| gat ttt gtg gaa ggc cta tcg gga gct acg tgg gtt gac gtg gtg ctc<br>Asp Phe Val Glu Gly Leu Ser Gly Ala Thr Trp Val Asp Val Val Leu<br>295 300 305 310 | | 1026 |
| gag cac ggt ggg tgt gtg act acc atg gct aag aac aag ccc acg ctg<br>Glu His Gly Gly Cys Val Thr Thr Met Ala Lys Asn Lys Pro Thr Leu<br>315 320 325 | | 1074 |
| gac ata gag ctt cag aag acc gag gcc acc caa ctg gcg acc cta agg<br>Asp Ile Glu Leu Gln Lys Thr Glu Ala Thr Gln Leu Ala Thr Leu Arg<br>330 335 340 | | 1122 |
| aag cta tgc att gag gga aaa att acc aac ata aca acc gac tca aga<br>Lys Leu Cys Ile Glu Gly Lys Ile Thr Asn Ile Thr Thr Asp Ser Arg<br>345 350 355 | | 1170 |
| tgt ccc acc caa ggg gaa gcg att tta cct gag gag cag gac cag aac<br>Cys Pro Thr Gln Gly Glu Ala Ile Leu Pro Glu Glu Gln Asp Gln Asn<br>360 365 370 | | 1218 |
| tac gtg tgt aag cat aca tac gtg gac aga ggc tgg gga aac ggt tgt<br>Tyr Val Cys Lys His Thr Tyr Val Asp Arg Gly Trp Gly Asn Gly Cys<br>375 380 385 390 | | 1266 |
| ggt ttg ttt ggc aag gga agc ttg gtg aca tgc gcg aaa ttt caa tgt<br>Gly Leu Phe Gly Lys Gly Ser Leu Val Thr Cys Ala Lys Phe Gln Cys<br>395 400 405 | | 1314 |
| tta gaa tca ata gag gga aaa gtg gtg caa cat gag aac ctc aaa tac<br>Leu Glu Ser Ile Glu Gly Lys Val Val Gln His Glu Asn Leu Lys Tyr<br>410 415 420 | | 1362 |
| acc gtc atc atc aca gtg cac aca gga gac caa cac cag gtg gga aat<br>Thr Val Ile Ile Thr Val His Thr Gly Asp Gln His Gln Val Gly Asn<br>425 430 435 | | 1410 |
| gaa acg cag gga gtc acg gct gag ata aca ccc cag gca tca acc gct<br>Glu Thr Gln Gly Val Thr Ala Glu Ile Thr Pro Gln Ala Ser Thr Ala<br>440 445 450 | | 1458 |
| gaa gcc att tta cct gaa tat gga acc ctc ggg cta gaa tgc tca cca<br>Glu Ala Ile Leu Pro Glu Tyr Gly Thr Leu Gly Leu Glu Cys Ser Pro<br>455 460 465 470 | | 1506 |
| cgg aca ggt ttg gat ttc aat gaa atg atc tca ttg aca atg aag aac<br>Arg Thr Gly Leu Asp Phe Asn Glu Met Ile Ser Leu Thr Met Lys Asn<br>475 480 485 | | 1554 |
| aaa gca tgg atg gta cat aga caa tgg ttc ttt gac tta ccc cta cca<br>Lys Ala Trp Met Val His Arg Gln Trp Phe Phe Asp Leu Pro Leu Pro<br>490 495 500 | | 1602 |

```
tgg aca tca gga gct aca gca gaa aca cca act tgg aac agg aaa gag    1650
Trp Thr Ser Gly Ala Thr Ala Glu Thr Pro Thr Trp Asn Arg Lys Glu
        505                 510                 515 ctt ctt gtg aca ttt aaa aat gca cat gca aaa aag caa gaa gta gtt    1698
Leu Leu Val Thr Phe Lys Asn Ala His Ala Lys Lys Gln Glu Val Val
520                 525                 530 gtt ctt gga tca caa gag gga gca atg cat aca gca ctg aca gga gct    1746
Val Leu Gly Ser Gln Glu Gly Ala Met His Thr Ala Leu Thr Gly Ala
535                 540                 545                 550 aca gag atc caa acc tca gga ggc aca agt atc ttt gcg ggg cac tta    1794
Thr Glu Ile Gln Thr Ser Gly Gly Thr Ser Ile Phe Ala Gly His Leu
                555                 560                 565 aaa tgt aga ctc aag atg gac aaa ttg gaa ctc aag ggg atg agc tat    1842
Lys Cys Arg Leu Lys Met Asp Lys Leu Glu Leu Lys Gly Met Ser Tyr
            570                 575                 580 gca atg tgc ttg agt agc ttt gtg ttg aag aaa gaa gtc tcc gaa acg    1890
Ala Met Cys Leu Ser Ser Phe Val Leu Lys Lys Glu Val Ser Glu Thr
                585                 590                 595 cag cat ggg aca ata ctc att aag gtt gag tac aaa ggg gaa gat gca    1938
Gln His Gly Thr Ile Leu Ile Lys Val Glu Tyr Lys Gly Glu Asp Ala
        600                 605                 610 ccc tgc aag att cct ttc tcc acg gag gat gga caa gga aaa gct cac    1986
Pro Cys Lys Ile Pro Phe Ser Thr Glu Asp Gly Gln Gly Lys Ala His
615                 620                 625                 630 aat ggc aga ctg atc aca gcc aat cca gtg gtg acc aag aag gag gag    2034
Asn Gly Arg Leu Ile Thr Ala Asn Pro Val Val Thr Lys Lys Glu Glu
                635                 640                 645 cct gtc aac att gag gct gaa cct cct ttt gga gaa agt aac ata gta    2082
Pro Val Asn Ile Glu Ala Glu Pro Pro Phe Gly Glu Ser Asn Ile Val
            650                 655                 660 att gga att gga gac aaa gcc ctg aaa atc aac tgg tac aag aag gga    2130
Ile Gly Ile Gly Asp Lys Ala Leu Lys Ile Asn Trp Tyr Lys Lys Gly
                665                 670                 675 agc tcg att ggg aag atg ttc gag gcc act gcc aga ggt gca agg cgc    2178
Ser Ser Ile Gly Lys Met Phe Glu Ala Thr Ala Arg Gly Ala Arg Arg
        680                 685                 690 atg gcc atc ttg gga gac aca gcc tgg gac ttt gga tca gtg ggt ggt    2226
Met Ala Ile Leu Gly Asp Thr Ala Trp Asp Phe Gly Ser Val Gly Gly
695                 700                 705                 710 gtt ttg aat tca tta ggg aaa atg gtc cac caa ata ttt ggg agt gct    2274
Val Leu Asn Ser Leu Gly Lys Met Val His Gln Ile Phe Gly Ser Ala
                715                 720                 725 tac aca gcc cta ttt ggt gga gtc tcc tgg atg atg aaa att gga ata    2322
Tyr Thr Ala Leu Phe Gly Gly Val Ser Trp Met Met Lys Ile Gly Ile
            730                 735                 740 ggt gtc ctc tta acc tgg ata ggg ttg aac tca aaa aat act tct atg    2370
Gly Val Leu Leu Thr Trp Ile Gly Leu Asn Ser Lys Asn Thr Ser Met
                745                 750                 755 tca ttt tca tgc atc gcg ata gga atc att aca ctc tat ctg gga gcc    2418
Ser Phe Ser Cys Ile Ala Ile Gly Ile Ile Thr Leu Tyr Leu Gly Ala
        760                 765                 770 gtg gtg caa gct gac tcc gga tgt gcc ata gac atc agc cgg caa gag    2466
Val Val Gln Ala Asp Ser Gly Cys Ala Ile Asp Ile Ser Arg Gln Glu
775                 780                 785                 790 ctg aga tgt gga agt gga gtg ttc ata cac aat gat gtg gag gct tgg    2514
Leu Arg Cys Gly Ser Gly Val Phe Ile His Asn Asp Val Glu Ala Trp
                795                 800                 805 atg gac cgg tac aag tat tac cct gaa acg cca caa ggc cta gcc aag    2562
Met Asp Arg Tyr Lys Tyr Tyr Pro Glu Thr Pro Gln Gly Leu Ala Lys
            810                 815                 820
```

```
atc att cag aaa gct cat aag gaa gga gtg tgc ggt cta cga tca gtt      2610
Ile Ile Gln Lys Ala His Lys Glu Gly Val Cys Gly Leu Arg Ser Val
        825                 830                 835 tcc aga ctg gag cat caa atg tgg gaa gca gtg aag gac gag ctg aac      2658
Ser Arg Leu Glu His Gln Met Trp Glu Ala Val Lys Asp Glu Leu Asn
    840                 845                 850 act ctt ttg aag gag aat ggt gtg gac ctt agt gtc gtg gtt gag aaa      2706
Thr Leu Leu Lys Glu Asn Gly Val Asp Leu Ser Val Val Glu Lys
855                 860                 865                 870 cag gag gga atg tac aag tca gca cct aaa cgc ctc acc gcc acc acg      2754
Gln Glu Gly Met Tyr Lys Ser Ala Pro Lys Arg Leu Thr Ala Thr Thr
                875                 880                 885 gaa aaa ttg gaa att ggc tgg aag gcc tgg gga aag agt att tta ttt      2802
Glu Lys Leu Glu Ile Gly Trp Lys Ala Trp Gly Lys Ser Ile Leu Phe
    890                 895                 900 gca cca gaa ctc gcc aac aac acc ttt gtg gtt gat ggt ccg gag acc      2850
Ala Pro Glu Leu Ala Asn Asn Thr Phe Val Val Asp Gly Pro Glu Thr
905                 910                 915 aag gaa tgt ccg act cag aat cgc gct tgg aat agc tta gaa gtg gag      2898
Lys Glu Cys Pro Thr Gln Asn Arg Ala Trp Asn Ser Leu Glu Val Glu
    920                 925                 930 gat ttt gga ttt ggt ctc acc agc act cgg atg ttc ctg aag gtc aga      2946
Asp Phe Gly Phe Gly Leu Thr Ser Thr Arg Met Phe Leu Lys Val Arg
935                 940                 945                 950 gag agc aac aca act gaa tgt gac tcg aag atc att gga acg gct gtc      2994
Glu Ser Asn Thr Thr Glu Cys Asp Ser Lys Ile Ile Gly Thr Ala Val
                955                 960                 965 aag aac aac ttg gcg atc cac agt gac ctg tcc tat tgg att gaa agc      3042
Lys Asn Asn Leu Ala Ile His Ser Asp Leu Ser Tyr Trp Ile Glu Ser
    970                 975                 980 agg ctc aat gat acg tgg aag ctt gaa agg gca gtt ctg ggt gaa gtc      3090
Arg Leu Asn Asp Thr Trp Lys Leu Glu Arg Ala Val Leu Gly Glu Val
                985                 990                 995 aaa tca tgt acg tgg cct gag  acg cat acc ttg tgg  ggc gat gga        3135
Lys Ser Cys Thr Trp Pro Glu  Thr His Thr Leu Trp  Gly Asp Gly
1000                1005                          1010 atc ctt  gag agt gac ttg ata  ata cca gtc aca ctg  gcg gga cca       3180
Ile Leu  Glu Ser Asp Leu Ile  Ile Pro Val Thr Leu  Ala Gly Pro
1015                 1020                          1025 cga agc  aat cac aat cgg aga  cct ggg tac aag aca  caa aac cag       3225
Arg Ser  Asn His Asn Arg Arg  Pro Gly Tyr Lys Thr  Gln Asn Gln
1030                 1035                          1040 ggc cca  tgg gac gaa ggc cgg  gta gag att gac ttc  gat tac tgc       3270
Gly Pro  Trp Asp Glu Gly Arg  Val Glu Ile Asp Phe  Asp Tyr Cys
1045                 1050                          1055 cca gga  act acg gtc acc ctg  agt gag agc tgc gga  cac cgt gga       3315
Pro Gly  Thr Thr Val Thr Leu  Ser Glu Ser Cys Gly  His Arg Gly
1060                 1065                          1070 cct gcc  act cgc acc acc aca  gag agc gga aag ttg  ata aca gat       3360
Pro Ala  Thr Arg Thr Thr Thr  Glu Ser Gly Lys Leu  Ile Thr Asp
1075                 1080                          1085 tgg tgc  tgc agg agc tgc acc  tta cca cca ctg cgc  tac caa act       3405
Trp Cys  Cys Arg Ser Cys Thr  Leu Pro Pro Leu Arg  Tyr Gln Thr
1090                 1095                          1100 gac agc  ggc tgt tgg tat ggt  atg gag atc aga cca  cag aga cat       3450
Asp Ser  Gly Cys Trp Tyr Gly  Met Glu Ile Arg Pro  Gln Arg His
1105                 1110                          1115 gat gaa  aag acc ctc gtg cag  tca caa gtg aat gct  tat aat gct       3495
Asp Glu  Lys Thr Leu Val Gln  Ser Gln Val Asn Ala  Tyr Asn Ala
1120                 1125                          1130
```

```
gat atg att gac cct ttt cag ttg ggc ctt ctg gtc gtg ttc ttg    3540
Asp Met Ile Asp Pro Phe Gln Leu Gly Leu Leu Val Val Phe Leu
    1135            1140                1145 gcc acc cag gag gtc ctt cgc aag agg tgg aca gcc aag atc agc    3585
Ala Thr Gln Glu Val Leu Arg Lys Arg Trp Thr Ala Lys Ile Ser
1150                1155                1160 atg cca gct ata ctg att gct ctg cta gtc ctg gtg ttt ggg ggc    3630
Met Pro Ala Ile Leu Ile Ala Leu Leu Val Leu Val Phe Gly Gly
    1165            1170                1175 att act tac act gat gtg tta cgc tat gtc atc ttg gtg ggg gca    3675
Ile Thr Tyr Thr Asp Val Leu Arg Tyr Val Ile Leu Val Gly Ala
1180                1185                1190 gct ttc gca gaa tct aat tcg gga gga gac gtg gta cac ttg gcg    3720
Ala Phe Ala Glu Ser Asn Ser Gly Gly Asp Val Val His Leu Ala
    1195            1200                1205 ctc atg gcg acc ttc aag ata caa cca gtg ttt atg gtg gca tcg    3765
Leu Met Ala Thr Phe Lys Ile Gln Pro Val Phe Met Val Ala Ser
1210                1215                1220 ttt ctc aaa gcg aga tgg acc aac cag gag aac att ttg ttg atg    3810
Phe Leu Lys Ala Arg Trp Thr Asn Gln Glu Asn Ile Leu Leu Met
    1225            1230                1235 ttg gcg gct gtt ttc ttt caa atg gct tat tac gat gcc cgc caa    3855
Leu Ala Ala Val Phe Phe Gln Met Ala Tyr Tyr Asp Ala Arg Gln
1240                1245                1250 att ctg ctc tgg gag atc cct gat gtg tta aat tca ctg gcg gta    3900
Ile Leu Leu Trp Glu Ile Pro Asp Val Leu Asn Ser Leu Ala Val
    1255            1260                1265 gct tgg atg ata ctg aga gcc ata aca ttc aca acg aca tca aac    3945
Ala Trp Met Ile Leu Arg Ala Ile Thr Phe Thr Thr Thr Ser Asn
1270                1275                1280 gtg gtt gtt ccg ctg cta gcc ctg cta aca ccc ggg ctg aga tgc    3990
Val Val Val Pro Leu Leu Ala Leu Leu Thr Pro Gly Leu Arg Cys
    1285            1290                1295 ttg aat ctg gat gtg tac agg ata ctg ctg ttg atg gtc gga ata    4035
Leu Asn Leu Asp Val Tyr Arg Ile Leu Leu Leu Met Val Gly Ile
1300                1305                1310 ggc agc ttg atc agg gag aag agg agt gca gct gca aaa aag aaa    4080
Gly Ser Leu Ile Arg Glu Lys Arg Ser Ala Ala Ala Lys Lys Lys
    1315            1320                1325 gga gca agt ctg cta tgc ttg gct cta gcc tca aca gga ctt ttc    4125
Gly Ala Ser Leu Leu Cys Leu Ala Leu Ala Ser Thr Gly Leu Phe
1330                1335                1340 aac ccc atg atc ctt gct gct gga ctg att gca tgt gat ccc aac    4170
Asn Pro Met Ile Leu Ala Ala Gly Leu Ile Ala Cys Asp Pro Asn
    1345            1350                1355 cgt aaa cgc gga tgg ccc gca act gaa gtg atg aca gct gtc ggc    4215
Arg Lys Arg Gly Trp Pro Ala Thr Glu Val Met Thr Ala Val Gly
1360                1365                1370 cta atg ttt gcc atc gtc gga ggg ctg gca gag ctt gac att gac    4260
Leu Met Phe Ala Ile Val Gly Gly Leu Ala Glu Leu Asp Ile Asp
    1375            1380                1385 tcc atg gcc att cca atg act atc gcg ggg ctc atg ttt gct gct    4305
Ser Met Ala Ile Pro Met Thr Ile Ala Gly Leu Met Phe Ala Ala
1390                1395                1400 ttc gtg att tct ggg aaa tca aca gat atg tgg att gag aga acg    4350
Phe Val Ile Ser Gly Lys Ser Thr Asp Met Trp Ile Glu Arg Thr
    1405            1410                1415 gcg gac att tcc tgg gaa agt gat gca gaa att aca ggc tcg agc    4395
Ala Asp Ile Ser Trp Glu Ser Asp Ala Glu Ile Thr Gly Ser Ser
1420                1425                1430
```

-continued

| | | |
|---|---|---|
| gaa aga gtt gat gtg cgg ctt gat gat gat gga aac ttc cag ctc<br>Glu Arg Val Asp Val Arg Leu Asp Asp Asp Gly Asn Phe Gln Leu<br>1435                    1440                   1445 | | 4440 |
| atg aat gat cca gga gca cct tgg aag ata tgg atg ctc aga atg<br>Met Asn Asp Pro Gly Ala Pro Trp Lys Ile Trp Met Leu Arg Met<br>1450                    1455                   1460 | | 4485 |
| gtc tgt ctc gcg att agt gcg tac acc ccc tgg gca atc ttg ccc<br>Val Cys Leu Ala Ile Ser Ala Tyr Thr Pro Trp Ala Ile Leu Pro<br>1465                    1470                   1475 | | 4530 |
| tca gta gtt gga ttt tgg ata act ctc caa tac aca aag aga gga<br>Ser Val Val Gly Phe Trp Ile Thr Leu Gln Tyr Thr Lys Arg Gly<br>1480                    1485                   1490 | | 4575 |
| ggc gtg ttg tgg gac act ccc tca cca aag gag tac aaa aag ggg<br>Gly Val Leu Trp Asp Thr Pro Ser Pro Lys Glu Tyr Lys Lys Gly<br>1495                    1500                   1505 | | 4620 |
| gac acg acc acc ggc gtc tac agg atc atg act cgt ggg ctg ctc<br>Asp Thr Thr Thr Gly Val Tyr Arg Ile Met Thr Arg Gly Leu Leu<br>1510                    1515                   1520 | | 4665 |
| ggc agt tat caa gca gga gcg ggc gtg atg gtt gaa ggt gtt ttc<br>Gly Ser Tyr Gln Ala Gly Ala Gly Val Met Val Glu Gly Val Phe<br>1525                    1530                   1535 | | 4710 |
| cac acc ctt tgg cat aca aca aaa gga gcc gct ttg atg agc gga<br>His Thr Leu Trp His Thr Thr Lys Gly Ala Ala Leu Met Ser Gly<br>1540                    1545                   1550 | | 4755 |
| gag ggc cgc ctg gac cca tac tgg gga agt gtc aag gag gat cga<br>Glu Gly Arg Leu Asp Pro Tyr Trp Gly Ser Val Lys Glu Asp Arg<br>1555                    1560                   1565 | | 4800 |
| ctt tgt tac gga gga ccc tgg aaa ttg cag cac aag tgg aac ggg<br>Leu Cys Tyr Gly Gly Pro Trp Lys Leu Gln His Lys Trp Asn Gly<br>1570                    1575                   1580 | | 4845 |
| cag gat gag gtg cag atg att gtg gtg gaa cct ggc agg aac gtt<br>Gln Asp Glu Val Gln Met Ile Val Val Glu Pro Gly Arg Asn Val<br>1585                    1590                   1595 | | 4890 |
| aag aac gtc cag acg aaa cca ggg gtg ttc aaa aca cct gaa gga<br>Lys Asn Val Gln Thr Lys Pro Gly Val Phe Lys Thr Pro Glu Gly<br>1600                    1605                   1610 | | 4935 |
| gaa atc ggg gcc gtg act ttg gac ttc ccc act gga aca tca ggc<br>Glu Ile Gly Ala Val Thr Leu Asp Phe Pro Thr Gly Thr Ser Gly<br>1615                    1620                   1625 | | 4980 |
| tca cca ata gtg gac aaa aac ggt gat gtg att ggg ctt tat ggc<br>Ser Pro Ile Val Asp Lys Asn Gly Asp Val Ile Gly Leu Tyr Gly<br>1630                    1635                   1640 | | 5025 |
| aat gga gtc ata atg ccc aac ggc tca tac ata agc gcg ata gtg<br>Asn Gly Val Ile Met Pro Asn Gly Ser Tyr Ile Ser Ala Ile Val<br>1645                    1650                   1655 | | 5070 |
| cag ggt gaa agg atg gat gag cca atc cca gcc gga ttc gaa cct<br>Gln Gly Glu Arg Met Asp Glu Pro Ile Pro Ala Gly Phe Glu Pro<br>1660                    1665                   1670 | | 5115 |
| gag atg ctg agg aaa aaa cag atc act gta ctg gat ctc cat ccc<br>Glu Met Leu Arg Lys Lys Gln Ile Thr Val Leu Asp Leu His Pro<br>1675                    1680                   1685 | | 5160 |
| ggc gcc ggt aaa aca agg agg att ctg cca cag atc atc aaa gag<br>Gly Ala Gly Lys Thr Arg Arg Ile Leu Pro Gln Ile Ile Lys Glu<br>1690                    1695                   1700 | | 5205 |
| gcc ata aac aga aga ctg aga aca gcc gtg cta gca cca acc agg<br>Ala Ile Asn Arg Arg Leu Arg Thr Ala Val Leu Ala Pro Thr Arg<br>1705                    1710                   1715 | | 5250 |
| gtt gtg gct gct gag atg gct gaa gca ctg aga gga ctg ccc atc<br>Val Val Ala Ala Glu Met Ala Glu Ala Leu Arg Gly Leu Pro Ile<br>1720                    1725                   1730 | | 5295 |

```
cgg tac cag aca tcc gca gtg ccc aga gaa cat aat gga aat gag      5340
Arg Tyr Gln Thr Ser Ala Val Pro Arg Glu His Asn Gly Asn Glu
    1735                1740                1745 att gtt gat gtc atg tgt cat gct acc ctc acc cac agg ctg atg      5385
Ile Val Asp Val Met Cys His Ala Thr Leu Thr His Arg Leu Met
    1750                1755                1760 tct cct cac agg gtg ccg aac tac aac ctg ttc gtg atg gat gag      5430
Ser Pro His Arg Val Pro Asn Tyr Asn Leu Phe Val Met Asp Glu
    1765                1770                1775 gct cat ttc acc gac cca gct agc att gca gca aga ggt tac att      5475
Ala His Phe Thr Asp Pro Ala Ser Ile Ala Ala Arg Gly Tyr Ile
    1780                1785                1790 tcc aca aag gtc gag cta ggg gag gcg gcg gca ata ttc atg aca      5520
Ser Thr Lys Val Glu Leu Gly Glu Ala Ala Ala Ile Phe Met Thr
    1795                1800                1805 gcc acc cca cca ggc act tca gat cca ttc cca gag tcc aat tca      5565
Ala Thr Pro Pro Gly Thr Ser Asp Pro Phe Pro Glu Ser Asn Ser
    1810                1815                1820 cca att tcc gac tta cag act gag atc ccg gat cga gct tgg aac      5610
Pro Ile Ser Asp Leu Gln Thr Glu Ile Pro Asp Arg Ala Trp Asn
    1825                1830                1835 tct gga tac gaa tgg atc aca gaa tac acc ggg aag acg gtt tgg      5655
Ser Gly Tyr Glu Trp Ile Thr Glu Tyr Thr Gly Lys Thr Val Trp
    1840                1845                1850 ttt gtg cct agt gtc aag atg ggg aat gag att gcc ctt tgc cta      5700
Phe Val Pro Ser Val Lys Met Gly Asn Glu Ile Ala Leu Cys Leu
    1855                1860                1865 caa cgt gct gga aag aaa gta gtc caa ttg aac aga aag tcg tac      5745
Gln Arg Ala Gly Lys Lys Val Val Gln Leu Asn Arg Lys Ser Tyr
    1870                1875                1880 gag acg gag tac cca aaa tgt aag aac gat gat tgg gac ttt gtt      5790
Glu Thr Glu Tyr Pro Lys Cys Lys Asn Asp Asp Trp Asp Phe Val
    1885                1890                1895 atc aca aca gac ata tct gaa atg ggg gct aac ttc aag gcg agc      5835
Ile Thr Thr Asp Ile Ser Glu Met Gly Ala Asn Phe Lys Ala Ser
    1900                1905                1910 agg gtg att gac agc cgg aag agt gtg aaa cca acc atc ata aca      5880
Arg Val Ile Asp Ser Arg Lys Ser Val Lys Pro Thr Ile Ile Thr
    1915                1920                1925 gaa gga gaa ggg aga gtg atc ctg gga gaa cca tct gca gtg aca      5925
Glu Gly Glu Gly Arg Val Ile Leu Gly Glu Pro Ser Ala Val Thr
    1930                1935                1940 gca gct agt gcc gcc cag aga cgt gga cgt atc ggt aga aat ccg      5970
Ala Ala Ser Ala Ala Gln Arg Arg Gly Arg Ile Gly Arg Asn Pro
    1945                1950                1955 tcg caa gtt ggt gat gag tac tgt tat ggg ggg cac acg aat gaa      6015
Ser Gln Val Gly Asp Glu Tyr Cys Tyr Gly Gly His Thr Asn Glu
    1960                1965                1970 gac gac tcg aac ttc gcc cat tgg act gag gca cga atc atg ctg      6060
Asp Asp Ser Asn Phe Ala His Trp Thr Glu Ala Arg Ile Met Leu
    1975                1980                1985 gac aac atc aac atg cca aac gga ctg atc gct caa ttc tac caa      6105
Asp Asn Ile Asn Met Pro Asn Gly Leu Ile Ala Gln Phe Tyr Gln
    1990                1995                2000 cca gag cgt gag aag gta tat acc atg gat ggg gaa tac cgg ctc      6150
Pro Glu Arg Glu Lys Val Tyr Thr Met Asp Gly Glu Tyr Arg Leu
    2005                2010                2015 aga gga gaa gag aga aaa aac ttt ctg gaa ctg ttg agg act gca      6195
Arg Gly Glu Glu Arg Lys Asn Phe Leu Glu Leu Leu Arg Thr Ala
    2020                2025                2030
```

```
gat ctg cca gtt tgg ctg gct tac aag gtt gca gcg gct gga gtg      6240
Asp Leu Pro Val Trp Leu Ala Tyr Lys Val Ala Ala Ala Gly Val
    2035                2040                2045 tca tac cac gac cgg agg tgg tgc ttt gat ggt cct agg aca aac      6285
Ser Tyr His Asp Arg Arg Trp Cys Phe Asp Gly Pro Arg Thr Asn
    2050                2055                2060 aca att tta gaa gac aac aac gaa gtg gaa gtc atc acg aag ctt      6330
Thr Ile Leu Glu Asp Asn Asn Glu Val Glu Val Ile Thr Lys Leu
    2065                2070                2075 ggt gaa agg aag att ctg agg ccg cgc tgg att gac gcc agg gtg      6375
Gly Glu Arg Lys Ile Leu Arg Pro Arg Trp Ile Asp Ala Arg Val
    2080                2085                2090 tac tcg gat cac cag gca cta aag gcg ttc aag gac ttc gcc tcg      6420
Tyr Ser Asp His Gln Ala Leu Lys Ala Phe Lys Asp Phe Ala Ser
    2095                2100                2105 gga aaa cgt tct cag ata ggg ctc att gag gtt ctg gga aag atg      6465
Gly Lys Arg Ser Gln Ile Gly Leu Ile Glu Val Leu Gly Lys Met
    2110                2115                2120 cct gag cac ttc atg ggg aag aca tgg gaa gca ctt gac acc atg      6510
Pro Glu His Phe Met Gly Lys Thr Trp Glu Ala Leu Asp Thr Met
    2125                2130                2135 tac gtt gtg gcc act gca gag aaa gga gga aga gct cac aga atg      6555
Tyr Val Val Ala Thr Ala Glu Lys Gly Gly Arg Ala His Arg Met
    2140                2145                2150 gcc ctg gag gaa ctg cca gat gct ctt cag aca att gcc ttg att      6600
Ala Leu Glu Glu Leu Pro Asp Ala Leu Gln Thr Ile Ala Leu Ile
    2155                2160                2165 gcc tta ttg agt gtg atg acc atg gga gta ttc ttc ctc ctc atg      6645
Ala Leu Leu Ser Val Met Thr Met Gly Val Phe Phe Leu Leu Met
    2170                2175                2180 cag cgg aag ggc att gga aag ata ggt ttg gga ggc gct gtc ttg      6690
Gln Arg Lys Gly Ile Gly Lys Ile Gly Leu Gly Gly Ala Val Leu
    2185                2190                2195 gga gtc gcg acc ttt ttc tgt tgg atg gct gaa gtt cca gga acg      6735
Gly Val Ala Thr Phe Phe Cys Trp Met Ala Glu Val Pro Gly Thr
    2200                2205                2210 aag atc gcc gga atg ttg ctc ctc tcc ctt ctc ttg atg att gtg      6780
Lys Ile Ala Gly Met Leu Leu Leu Ser Leu Leu Leu Met Ile Val
    2215                2220                2225 cta att cct gag cca gag aag caa cgt tcg cag aca gac aac cag      6825
Leu Ile Pro Glu Pro Glu Lys Gln Arg Ser Gln Thr Asp Asn Gln
    2230                2235                2240 cta gcc gtg ttc ctg att tgt gtc atg acc ctt gtg agc gca gtg      6870
Leu Ala Val Phe Leu Ile Cys Val Met Thr Leu Val Ser Ala Val
    2245                2250                2255 gca gcc aac gag atg ggt tgg cta gat aag acc aag agt gac ata      6915
Ala Ala Asn Glu Met Gly Trp Leu Asp Lys Thr Lys Ser Asp Ile
    2260                2265                2270 agc agt ttg ttt ggg caa aga att gag gtc aag gag aat ttc agc      6960
Ser Ser Leu Phe Gly Gln Arg Ile Glu Val Lys Glu Asn Phe Ser
    2275                2280                2285 atg gga gag ttt ctt ttg gac ttg agg cct gca aca gcc tgg tca      7005
Met Gly Glu Phe Leu Leu Asp Leu Arg Pro Ala Thr Ala Trp Ser
    2290                2295                2300 ctg tac gct gtg aca aca gcg gtc ctc act cca ctg cta aag cat      7050
Leu Tyr Ala Val Thr Thr Ala Val Leu Thr Pro Leu Leu Lys His
    2305                2310                2315 ttg atc acg tca gat tac atc aac acc tca ttg acc tca ata aac      7095
Leu Ile Thr Ser Asp Tyr Ile Asn Thr Ser Leu Thr Ser Ile Asn
    2320                2325                2330
```

```
gtt cag gca agt gca cta ttc aca ctc gcg cga ggc ttc ccc ttc      7140
Val Gln Ala Ser Ala Leu Phe Thr Leu Ala Arg Gly Phe Pro Phe
    2335            2340            2345 gtc gat gtt gga gtg tcg gct ctc ctg cta gca gcc gga tgc tgg      7185
Val Asp Val Gly Val Ser Ala Leu Leu Leu Ala Ala Gly Cys Trp
2350            2355            2360 gga caa gtc acc ctc acc gtt acg gta aca gcg gca aca ctc ctt      7230
Gly Gln Val Thr Leu Thr Val Thr Val Thr Ala Ala Thr Leu Leu
2365            2370            2375 ttt tgc cac tat gcc tac atg gtt ccc ggt tgg caa gct gag gca      7275
Phe Cys His Tyr Ala Tyr Met Val Pro Gly Trp Gln Ala Glu Ala
2380            2385            2390 atg cgc tca gcc cag cgg cgg aca gcg gcc gga atc atg aag aac      7320
Met Arg Ser Ala Gln Arg Arg Thr Ala Ala Gly Ile Met Lys Asn
2395            2400            2405 gct gta gtg gat ggc atc gtg gcc acg gac gtc cca gaa tta gag      7365
Ala Val Val Asp Gly Ile Val Ala Thr Asp Val Pro Glu Leu Glu
2410            2415            2420 cgc acc aca ccc atc atg cag aag aaa gtt gga cag atc atg ctg      7410
Arg Thr Thr Pro Ile Met Gln Lys Lys Val Gly Gln Ile Met Leu
2425            2430            2435 atc ttg gtg tct cta gct gca gta gta gtg aac ccg tct gtg aag      7455
Ile Leu Val Ser Leu Ala Ala Val Val Val Asn Pro Ser Val Lys
2440            2445            2450 aca gta cga gaa gcc gga att ttg atc acg gcc gcg gtg acg      7500
Thr Val Arg Glu Ala Gly Ile Leu Ile Thr Ala Ala Ala Val Thr
2455            2460            2465 ctt tgg gag aat gga gca agc tct gtt tgg aac gca aca act gcc      7545
Leu Trp Glu Asn Gly Ala Ser Ser Val Trp Asn Ala Thr Thr Ala
2470            2475            2480 atc gga ctc tgc cac atc atg cgt ggg ggt tgg ttg tca tgt cta      7590
Ile Gly Leu Cys His Ile Met Arg Gly Gly Trp Leu Ser Cys Leu
2485            2490            2495 tcc ata aca tgg aca ctc ata aag aac atg gaa aaa cca gga cta      7635
Ser Ile Thr Trp Thr Leu Ile Lys Asn Met Glu Lys Pro Gly Leu
2500            2505            2510 aaa aga ggt ggg gca aaa gga cgc acc ttg gga gag gtt tgg aaa      7680
Lys Arg Gly Gly Ala Lys Gly Arg Thr Leu Gly Glu Val Trp Lys
2515            2520            2525 gaa aga ctc aac cag atg aca aaa gaa gag ttc act agg tac cgc      7725
Glu Arg Leu Asn Gln Met Thr Lys Glu Glu Phe Thr Arg Tyr Arg
2530            2535            2540 aaa gag gcc atc atc gaa gtc gat cgc tca gcg gca aaa cac gcc      7770
Lys Glu Ala Ile Ile Glu Val Asp Arg Ser Ala Ala Lys His Ala
2545            2550            2555 agg aaa gaa ggc aat gtc act gga ggg cat cca gtc tct agg ggc      7815
Arg Lys Glu Gly Asn Val Thr Gly Gly His Pro Val Ser Arg Gly
2560            2565            2570 aca gca aaa ctg aga tgg ctg gtc gaa cgg agg ttt ctc gaa ccg      7860
Thr Ala Lys Leu Arg Trp Leu Val Glu Arg Arg Phe Leu Glu Pro
2575            2580            2585 gtc gga aaa gtg att gac ctt gga tgt gga aga ggc ggt tgg tgt      7905
Val Gly Lys Val Ile Asp Leu Gly Cys Gly Arg Gly Gly Trp Cys
2590            2595            2600 tac tat atg gca acc caa aaa aga gtc caa gaa gtc aga ggg tac      7950
Tyr Tyr Met Ala Thr Gln Lys Arg Val Gln Glu Val Arg Gly Tyr
2605            2610            2615 aca aag ggc ggt ccc gga cat gaa gag ccc caa cta gtg caa agt      7995
Thr Lys Gly Gly Pro Gly His Glu Glu Pro Gln Leu Val Gln Ser
2620            2625            2630
```

```
tat gga tgg aac att gtc acc atg aag agt gga gtg gat gtg ttc    8040
Tyr Gly Trp Asn Ile Val Thr Met Lys Ser Gly Val Asp Val Phe
    2635                2640                2645 tac aga cct tct gag tgt tgt gac acc ctc ctt tgt gac atc gga    8085
Tyr Arg Pro Ser Glu Cys Cys Asp Thr Leu Leu Cys Asp Ile Gly
    2650                2655                2660 gag tcc tcg tca agt gct gag gtt gaa gag cat agg acg att cgg    8130
Glu Ser Ser Ser Ser Ala Glu Val Glu Glu His Arg Thr Ile Arg
    2665                2670                2675 gtc ctt gaa atg gtt gag gac tgg ctg cac cga ggg cca agg gaa    8175
Val Leu Glu Met Val Glu Asp Trp Leu His Arg Gly Pro Arg Glu
    2680                2685                2690 ttt tgc gtg aag gtg ctc tgc ccc tac atg ccg aaa gtc ata gag    8220
Phe Cys Val Lys Val Leu Cys Pro Tyr Met Pro Lys Val Ile Glu
    2695                2700                2705 aag atg gag ctg ctc caa cgc cgg tat ggg ggg gga ctg gtc aga    8265
Lys Met Glu Leu Leu Gln Arg Arg Tyr Gly Gly Gly Leu Val Arg
    2710                2715                2720 aac cca ctc tca cgg aat tcc acg cac gag atg tat tgg gtg agt    8310
Asn Pro Leu Ser Arg Asn Ser Thr His Glu Met Tyr Trp Val Ser
    2725                2730                2735 cga gct tca ggc aat gtg gta cat tca gtg aat atg acc agc cag    8355
Arg Ala Ser Gly Asn Val Val His Ser Val Asn Met Thr Ser Gln
    2740                2745                2750 gtg ctc cta gga aga atg gaa aaa agg acc tgg aag gga ccc caa    8400
Val Leu Leu Gly Arg Met Glu Lys Arg Thr Trp Lys Gly Pro Gln
    2755                2760                2765 tac gag gaa gat gta aac ttg gga agt gga acc agg gcg gtg gga    8445
Tyr Glu Glu Asp Val Asn Leu Gly Ser Gly Thr Arg Ala Val Gly
    2770                2775                2780 aaa ccc ctg ctc aac tca gac acc agt aaa atc aag aac agg att    8490
Lys Pro Leu Leu Asn Ser Asp Thr Ser Lys Ile Lys Asn Arg Ile
    2785                2790                2795 gaa cga ctc agg cgt gag tac agt tcg acg tgg cac cac gat gag    8535
Glu Arg Leu Arg Arg Glu Tyr Ser Ser Thr Trp His His Asp Glu
    2800                2805                2810 aac cac cca tat aga acc tgg aac tat cac ggc agt tat gat gtg    8580
Asn His Pro Tyr Arg Thr Trp Asn Tyr His Gly Ser Tyr Asp Val
    2815                2820                2825 aag ccc aca ggc tcc gcc agt tcg ctg gtc aat gga gtg gtc agg    8625
Lys Pro Thr Gly Ser Ala Ser Ser Leu Val Asn Gly Val Val Arg
    2830                2835                2840 ctc ctc tca aaa cca tgg gac acc atc acg aat gtt acc acc atg    8670
Leu Leu Ser Lys Pro Trp Asp Thr Ile Thr Asn Val Thr Thr Met
    2845                2850                2855 gcc atg act gac act act ccc ttc ggg cag cag cga gtg ttc aaa    8715
Ala Met Thr Asp Thr Thr Pro Phe Gly Gln Gln Arg Val Phe Lys
    2860                2865                2870 gag aag gtg gac acg aaa gct cct gaa ccg cca gaa gga gtg aag    8760
Glu Lys Val Asp Thr Lys Ala Pro Glu Pro Pro Glu Gly Val Lys
    2875                2880                2885 tac gtg ctc aac gag acc acc aac tgg ttg tgg gcg ttt ttg gcc    8805
Tyr Val Leu Asn Glu Thr Thr Asn Trp Leu Trp Ala Phe Leu Ala
    2890                2895                2900 aga gaa aaa cgt ccc aga atg tgc tct cga gag gaa ttc ata aga    8850
Arg Glu Lys Arg Pro Arg Met Cys Ser Arg Glu Glu Phe Ile Arg
    2905                2910                2915 aag gtc aac agc aat gca gct ttg ggt gcc atg ttt gaa gag cag    8895
Lys Val Asn Ser Asn Ala Ala Leu Gly Ala Met Phe Glu Glu Gln
    2920                2925                2930
```

```
aat caa tgg agg agc gcc aga gaa gca gtt gaa gat cca aaa ttt      8940
Asn Gln Trp Arg Ser Ala Arg Glu Ala Val Glu Asp Pro Lys Phe
    2935            2940                2945 tgg gag atg gtg gat gag gag cgc gag gca cat ctg cgg ggg gaa      8985
Trp Glu Met Val Asp Glu Glu Arg Glu Ala His Leu Arg Gly Glu
2950            2955                2960 tgt cac act tgc att tac aac atg atg gga aag aga gag aaa aaa      9030
Cys His Thr Cys Ile Tyr Asn Met Met Gly Lys Arg Glu Lys Lys
2965            2970                2975 ccc gga gag ttc gga aag gcc aag gga agc aga gcc att tgg ttc      9075
Pro Gly Glu Phe Gly Lys Ala Lys Gly Ser Arg Ala Ile Trp Phe
2980            2985                2990 atg tgg ctc gga gct cgc ttt ctg gag ttc gag gct ctg ggt ttt      9120
Met Trp Leu Gly Ala Arg Phe Leu Glu Phe Glu Ala Leu Gly Phe
2995            3000                3005 ctc aat gaa gac cac tgg ctt gga aga aag aac tca gga gga ggt      9165
Leu Asn Glu Asp His Trp Leu Gly Arg Lys Asn Ser Gly Gly Gly
    3010            3015                3020 gtc gag ggc ttg ggc ctc caa aaa ctg ggt tac atc ctg cgt gaa      9210
Val Glu Gly Leu Gly Leu Gln Lys Leu Gly Tyr Ile Leu Arg Glu
3025            3030                3035 gtt ggc acc cgg cct ggg ggc aag atc tat gct gat gac aca gct      9255
Val Gly Thr Arg Pro Gly Gly Lys Ile Tyr Ala Asp Asp Thr Ala
3040            3045                3050 ggc tgg gac acc cgc atc acg aga gct gac ttg gaa aat gaa gct      9300
Gly Trp Asp Thr Arg Ile Thr Arg Ala Asp Leu Glu Asn Glu Ala
3055            3060                3065 aag gtg ctt gag ctg ctt gat ggg gaa cat cgg cgt ctt gcc agg      9345
Lys Val Leu Glu Leu Leu Asp Gly Glu His Arg Arg Leu Ala Arg
    3070            3075                3080 gcc atc att gag ctc acc tat cgt cac aaa gtt gtg aaa gtg atg      9390
Ala Ile Ile Glu Leu Thr Tyr Arg His Lys Val Val Lys Val Met
3085            3090                3095 cgc ccg gct gct gat gga aga acc gtc atg gat gtt atc tcc aga      9435
Arg Pro Ala Ala Asp Gly Arg Thr Val Met Asp Val Ile Ser Arg
3100            3105                3110 gaa gat cag agg ggg agt gga caa gtt gtc acc tac gcc cta aac      9480
Glu Asp Gln Arg Gly Ser Gly Gln Val Val Thr Tyr Ala Leu Asn
    3115            3120                3125 act ttc acc aac ctg gcc gtc cag ctg gtg agg atg atg gaa ggg      9525
Thr Phe Thr Asn Leu Ala Val Gln Leu Val Arg Met Met Glu Gly
3130            3135                3140 gaa gga gtg att ggc cca gat gat gtg gag aaa ctc aca aaa ggg      9570
Glu Gly Val Ile Gly Pro Asp Asp Val Glu Lys Leu Thr Lys Gly
3145            3150                3155 aaa gga ccc aaa gtc agg acc tgg ctg ttt gag aat ggg gaa gaa      9615
Lys Gly Pro Lys Val Arg Thr Trp Leu Phe Glu Asn Gly Glu Glu
3160            3165                3170 aga ctc agc cgc atg gct gtc agt gga gat gac tgt gtg gta aag      9660
Arg Leu Ser Arg Met Ala Val Ser Gly Asp Asp Cys Val Val Lys
    3175            3180                3185 ccc ctg gac gat cgc ttt gcc acc tcg ctc cac ttc ctc aat gct      9705
Pro Leu Asp Asp Arg Phe Ala Thr Ser Leu His Phe Leu Asn Ala
3190            3195                3200 atg tca aag gtt cgc aaa gac atc caa gag tgg aaa ccg tca act      9750
Met Ser Lys Val Arg Lys Asp Ile Gln Glu Trp Lys Pro Ser Thr
3205            3210                3215 gga tgg tat gat tgg cag cag gtt cca ttt tgc tca aac cat ttc      9795
Gly Trp Tyr Asp Trp Gln Gln Val Pro Phe Cys Ser Asn His Phe
3220            3225                3230
```

| | | | | | | | | | | | | |
|---|---|---|---|---|---|---|---|---|---|---|---|---|
| act | gaa | ttg | atc | atg | aaa | gat | gga | aga | aca | ctg | gtg | gtt | cca | tgc | 9840 |
| Thr | Glu | Leu | Ile | Met | Lys | Asp | Gly | Arg | Thr | Leu | Val | Val | Pro | Cys | |
| | 3235 | | | | 3240 | | | | | 3245 | | | | | |

| cga | gga | cag | gat | gaa | ttg | gta | ggc | aga | gct | cgc | ata | tct | cca | ggg | 9885 |
| Arg | Gly | Gln | Asp | Glu | Leu | Val | Gly | Arg | Ala | Arg | Ile | Ser | Pro | Gly | |
| 3250 | | | | | 3255 | | | | | 3260 | | | | | |

| gcc | gga | tgg | aac | gtc | cgc | gac | act | gct | tgt | ctg | gct | aag | tct | tat | 9930 |
| Ala | Gly | Trp | Asn | Val | Arg | Asp | Thr | Ala | Cys | Leu | Ala | Lys | Ser | Tyr | |
| 3265 | | | | | 3270 | | | | | 3275 | | | | | |

| gcc | cag | atg | tgg | ctg | ctt | ctg | tac | ttc | cac | aga | aga | gac | ctg | cgg | 9975 |
| Ala | Gln | Met | Trp | Leu | Leu | Leu | Tyr | Phe | His | Arg | Arg | Asp | Leu | Arg | |
| 3280 | | | | | 3285 | | | | | 3290 | | | | | |

| ctc | atg | gcc | aac | gcc | att | tgc | tcc | gct | gtc | cct | gtg | aat | tgg | gtc | 10020 |
| Leu | Met | Ala | Asn | Ala | Ile | Cys | Ser | Ala | Val | Pro | Val | Asn | Trp | Val | |
| 3295 | | | | | 3300 | | | | | 3305 | | | | | |

| cct | acc | gga | aga | acc | acg | tgg | tcc | atc | cat | gca | gga | gga | gag | tgg | 10065 |
| Pro | Thr | Gly | Arg | Thr | Thr | Trp | Ser | Ile | His | Ala | Gly | Gly | Glu | Trp | |
| 3310 | | | | | 3315 | | | | | 3320 | | | | | |

| atg | aca | aca | gag | gac | atg | ttg | gag | gtc | tgg | aac | cgt | gtt | tgg | ata | 10110 |
| Met | Thr | Thr | Glu | Asp | Met | Leu | Glu | Val | Trp | Asn | Arg | Val | Trp | Ile | |
| 3325 | | | | | 3330 | | | | | 3335 | | | | | |

| gag | gag | aat | gaa | tgg | atg | gaa | gac | aaa | acc | cca | gtg | gag | aaa | tgg | 10155 |
| Glu | Glu | Asn | Glu | Trp | Met | Glu | Asp | Lys | Thr | Pro | Val | Glu | Lys | Trp | |
| 3340 | | | | | 3345 | | | | | 3350 | | | | | |

| agt | gac | gtc | cca | tat | tca | gga | aaa | cga | gag | gac | atc | tgg | tgt | ggc | 10200 |
| Ser | Asp | Val | Pro | Tyr | Ser | Gly | Lys | Arg | Glu | Asp | Ile | Trp | Cys | Gly | |
| 3355 | | | | | 3360 | | | | | 3365 | | | | | |

| agc | ctg | att | ggc | aca | aga | gcc | cga | gcc | acg | tgg | gca | gaa | aac | atc | 10245 |
| Ser | Leu | Ile | Gly | Thr | Arg | Ala | Arg | Ala | Thr | Trp | Ala | Glu | Asn | Ile | |
| 3370 | | | | | 3375 | | | | | 3380 | | | | | |

| cag | gtg | gct | atc | aac | caa | gtc | aga | gca | atc | atc | gga | gat | gag | aag | 10290 |
| Gln | Val | Ala | Ile | Asn | Gln | Val | Arg | Ala | Ile | Ile | Gly | Asp | Glu | Lys | |
| 3385 | | | | | 3390 | | | | | 3395 | | | | | |

| tat | gtg | gat | tac | atg | agt | tca | cta | aag | aga | tat | gaa | gac | aca | act | 10335 |
| Tyr | Val | Asp | Tyr | Met | Ser | Ser | Leu | Lys | Arg | Tyr | Glu | Asp | Thr | Thr | |
| 3400 | | | | | 3405 | | | | | 3410 | | | | | |

| ttg | gtt | gag | gac | aca | gta | ctg | tagatattta atcaattgta aatagacaat | 10386 |
| Leu | Val | Glu | Asp | Thr | Val | Leu | | |
| 3415 | | | | | 3420 | | | |

```
ataagtatgc ataaaagtgt agttttatag tagtatttag tggtgttagt gtaaatagtt   10446
aagaaatttt tgaggagaaa gtcaggccgg gaagttcccg ccaccggaag ttgagtagac   10506
ggtgctgcct gcgactcaac cccaggagga ctgggtgaac aaagccgcga agtgatccat   10566
gtaagccctc agaaccgtct cggaaggagg accccacatg ttgtaacttc aaagcccaat   10626
gtcagaccac gctacggcgt gctactctgc ggagagtgca gtctgcgata gtgccccagg   10686
aggactgggt taacaaaggc aaaccaacgc cccacgcggc cctagccccg gtaatggtgt   10746
taaccagggc gaaaggacta gaggttagag gagacccgc ggtttaaagt gcacggccca    10806
gcctggctga agctgtaggt caggggaagg actagaggtt agtggagacc ccgtgccaca   10866
aaacaccaca acaaaacagc atattgacac ctgggataga ctaggagatc ttctgctctg   10926
cacaaccagc cacacggcac agtgcgccga caatggtggc tggtggtgcg agaacacagg   10986
atct                                                                10990
```

<210> SEQ ID NO 6
<211> LENGTH: 3420
<212> TYPE: PRT
<213> ORGANISM: Artificial Sequence
<220> FEATURE:

<223> OTHER INFORMATION: Synthetic Construct

<400> SEQUENCE: 6

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
            85                  90                  95

Arg Arg Ser Ser Lys Gln Lys Lys Arg Thr Ser Leu Cys Leu Met Met
            100                 105                 110

Met Leu Pro Ala Thr Leu Ala Phe His Leu Thr Ser Arg Asp Gly Glu
        115                 120                 125

Pro Arg Met Ile Val Gly Lys Asn Glu Arg Gly Lys Ser Leu Leu Phe
    130                 135                 140

Lys Thr Ala Ser Gly Ile Asn Met Cys Thr Leu Ile Ala Met Asp Leu
145                 150                 155                 160

Gly Glu Met Cys Asp Asp Thr Val Thr Tyr Lys Cys Pro His Ile Thr
            165                 170                 175

Glu Val Glu Pro Glu Asp Ile Asp Cys Trp Cys Asn Leu Thr Ser Thr
            180                 185                 190

Trp Val Thr Tyr Gly Thr Cys Asn Gln Ala Gly Glu His Arg Arg Asp
        195                 200                 205

Lys Arg Ser Val Ala Leu Ala Pro His Val Gly Met Gly Leu Asp Thr
    210                 215                 220

Arg Thr Gln Thr Trp Met Ser Ala Glu Gly Ala Trp Arg Gln Val Glu
225                 230                 235                 240

Lys Val Glu Thr Trp Ala Leu Arg His Pro Gly Phe Thr Ile Leu Ala
            245                 250                 255

Leu Phe Leu Ala His Tyr Ile Gly Thr Ser Leu Thr Gln Lys Val Val
        260                 265                 270

Ile Phe Ile Leu Leu Met Leu Val Thr Pro Ser Met Thr Met Arg Cys
    275                 280                 285

Val Gly Val Gly Asn Arg Asp Phe Val Glu Gly Leu Ser Gly Ala Thr
    290                 295                 300

Trp Val Asp Val Val Leu Glu His Gly Gly Cys Val Thr Thr Met Ala
305                 310                 315                 320

Lys Asn Lys Pro Thr Leu Asp Ile Glu Leu Gln Lys Thr Glu Ala Thr
            325                 330                 335

Gln Leu Ala Thr Leu Arg Lys Leu Cys Ile Glu Gly Lys Ile Thr Asn
        340                 345                 350

Ile Thr Thr Asp Ser Arg Cys Pro Thr Gln Gly Glu Ala Ile Leu Pro
    355                 360                 365

Glu Glu Gln Asp Gln Asn Tyr Val Cys Lys His Thr Tyr Val Asp Arg
    370                 375                 380

Gly Trp Gly Asn Gly Cys Gly Leu Phe Gly Lys Gly Ser Leu Val Thr
385                 390                 395                 400

Cys Ala Lys Phe Gln Cys Leu Glu Ser Ile Glu Gly Lys Val Val Gln
```

```
                405                 410                 415
His Glu Asn Leu Lys Tyr Thr Val Ile Ile Thr Val His Thr Gly Asp
            420                 425                 430

Gln His Gln Val Gly Asn Glu Thr Gln Gly Val Thr Ala Glu Ile Thr
        435                 440                 445

Pro Gln Ala Ser Thr Ala Glu Ala Ile Leu Pro Glu Tyr Gly Thr Leu
    450                 455                 460

Gly Leu Glu Cys Ser Pro Arg Thr Gly Leu Asp Phe Asn Glu Met Ile
465                 470                 475                 480

Ser Leu Thr Met Lys Asn Lys Ala Trp Met Val His Arg Gln Trp Phe
            485                 490                 495

Phe Asp Leu Pro Leu Pro Trp Thr Ser Gly Ala Thr Ala Glu Thr Pro
        500                 505                 510

Thr Trp Asn Arg Lys Glu Leu Val Thr Phe Lys Asn Ala His Ala
    515                 520                 525

Lys Lys Gln Glu Val Val Leu Gly Ser Gln Glu Gly Ala Met His
530                 535                 540

Thr Ala Leu Thr Gly Ala Thr Glu Ile Gln Thr Ser Gly Gly Thr Ser
545                 550                 555                 560

Ile Phe Ala Gly His Leu Lys Cys Arg Leu Lys Met Asp Lys Leu Glu
            565                 570                 575

Leu Lys Gly Met Ser Tyr Ala Met Cys Leu Ser Ser Phe Val Leu Lys
        580                 585                 590

Lys Glu Val Ser Glu Thr Gln His Gly Thr Ile Leu Ile Lys Val Glu
    595                 600                 605

Tyr Lys Gly Glu Asp Ala Pro Cys Lys Ile Pro Phe Ser Thr Glu Asp
610                 615                 620

Gly Gln Gly Lys Ala His Asn Gly Arg Leu Ile Thr Ala Asn Pro Val
625                 630                 635                 640

Val Thr Lys Lys Glu Glu Pro Val Asn Ile Glu Ala Glu Pro Pro Phe
            645                 650                 655

Gly Glu Ser Asn Ile Val Ile Gly Ile Gly Asp Lys Ala Leu Lys Ile
        660                 665                 670

Asn Trp Tyr Lys Lys Gly Ser Ser Ile Gly Lys Met Phe Glu Ala Thr
    675                 680                 685

Ala Arg Gly Ala Arg Arg Met Ala Ile Leu Gly Asp Thr Ala Trp Asp
690                 695                 700

Phe Gly Ser Val Gly Gly Val Leu Asn Ser Leu Gly Lys Met Val His
705                 710                 715                 720

Gln Ile Phe Gly Ser Ala Tyr Thr Ala Leu Phe Gly Gly Val Ser Trp
            725                 730                 735

Met Met Lys Ile Gly Ile Gly Val Leu Leu Thr Trp Ile Gly Leu Asn
        740                 745                 750

Ser Lys Asn Thr Ser Met Ser Phe Ser Cys Ile Ala Ile Gly Ile Ile
    755                 760                 765

Thr Leu Tyr Leu Gly Ala Val Val Gln Ala Asp Ser Gly Cys Ala Ile
770                 775                 780

Asp Ile Ser Arg Gln Glu Leu Arg Cys Gly Ser Gly Val Phe Ile His
785                 790                 795                 800

Asn Asp Val Glu Ala Trp Met Asp Arg Tyr Lys Tyr Pro Glu Thr
            805                 810                 815

Pro Gln Gly Leu Ala Lys Ile Ile Gln Lys Ala His Lys Glu Gly Val
        820                 825                 830
```

-continued

Cys Gly Leu Arg Ser Val Ser Arg Leu Glu His Gln Met Trp Glu Ala
        835                 840                 845

Val Lys Asp Glu Leu Asn Thr Leu Leu Lys Glu Asn Gly Val Asp Leu
850                 855                 860

Ser Val Val Glu Lys Gln Glu Gly Met Tyr Lys Ser Ala Pro Lys
865                 870                 875                 880

Arg Leu Thr Ala Thr Thr Glu Lys Leu Glu Ile Gly Trp Lys Ala Trp
                885                 890                 895

Gly Lys Ser Ile Leu Phe Ala Pro Glu Leu Ala Asn Asn Thr Phe Val
                900                 905                 910

Val Asp Gly Pro Glu Thr Lys Glu Cys Pro Thr Gln Asn Arg Ala Trp
                915                 920                 925

Asn Ser Leu Glu Val Glu Asp Phe Gly Phe Gly Leu Thr Ser Thr Arg
930                 935                 940

Met Phe Leu Lys Val Arg Glu Ser Asn Thr Thr Glu Cys Asp Ser Lys
945                 950                 955                 960

Ile Ile Gly Thr Ala Val Lys Asn Asn Leu Ala Ile His Ser Asp Leu
                965                 970                 975

Ser Tyr Trp Ile Glu Ser Arg Leu Asn Asp Thr Trp Lys Leu Glu Arg
                980                 985                 990

Ala Val Leu Gly Glu Val Lys Ser Cys Thr Trp Pro Glu Thr His Thr
                995                 1000                1005

Leu Trp Gly Asp Gly Ile Leu Glu Ser Asp Leu Ile Ile Pro Val
    1010                1015                1020

Thr Leu Ala Gly Pro Arg Ser Asn His Asn Arg Arg Pro Gly Tyr
    1025                1030                1035

Lys Thr Gln Asn Gln Gly Pro Trp Asp Glu Gly Arg Val Glu Ile
    1040                1045                1050

Asp Phe Asp Tyr Cys Pro Gly Thr Thr Val Thr Leu Ser Glu Ser
    1055                1060                1065

Cys Gly His Arg Gly Pro Ala Thr Arg Thr Thr Thr Glu Ser Gly
    1070                1075                1080

Lys Leu Ile Thr Asp Trp Cys Cys Arg Ser Cys Thr Leu Pro Pro
    1085                1090                1095

Leu Arg Tyr Gln Thr Asp Ser Gly Cys Trp Tyr Gly Met Glu Ile
    1100                1105                1110

Arg Pro Gln Arg His Asp Glu Lys Thr Leu Val Gln Ser Gln Val
    1115                1120                1125

Asn Ala Tyr Asn Ala Asp Met Ile Asp Pro Phe Gln Leu Gly Leu
    1130                1135                1140

Leu Val Val Phe Leu Ala Thr Gln Glu Val Leu Arg Lys Arg Trp
    1145                1150                1155

Thr Ala Lys Ile Ser Met Pro Ala Ile Leu Ile Ala Leu Leu Val
    1160                1165                1170

Leu Val Phe Gly Gly Ile Thr Tyr Thr Asp Val Leu Arg Tyr Val
    1175                1180                1185

Ile Leu Val Gly Ala Ala Phe Ala Glu Ser Asn Ser Gly Gly Asp
    1190                1195                1200

Val Val His Leu Ala Leu Met Ala Thr Phe Lys Ile Gln Pro Val
    1205                1210                1215

Phe Met Val Ala Ser Phe Leu Lys Ala Arg Trp Thr Asn Gln Glu
    1220                1225                1230

Asn Ile Leu Leu Met Leu Ala Ala Val Phe Phe Gln Met Ala Tyr
    1235                1240                1245

```
Tyr Asp Ala Arg Gln Ile Leu Leu Trp Glu Ile Pro Asp Val Leu
1250                1255                1260

Asn Ser Leu Ala Val Ala Trp Met Ile Leu Arg Ala Ile Thr Phe
1265                1270                1275

Thr Thr Thr Ser Asn Val Val Val Pro Leu Leu Ala Leu Leu Thr
1280                1285                1290

Pro Gly Leu Arg Cys Leu Asn Leu Asp Val Tyr Arg Ile Leu Leu
1295                1300                1305

Leu Met Val Gly Ile Gly Ser Leu Ile Arg Glu Lys Arg Ser Ala
1310                1315                1320

Ala Ala Lys Lys Lys Gly Ala Ser Leu Leu Cys Leu Ala Leu Ala
1325                1330                1335

Ser Thr Gly Leu Phe Asn Pro Met Ile Leu Ala Ala Gly Leu Ile
1340                1345                1350

Ala Cys Asp Pro Asn Arg Lys Arg Gly Trp Pro Ala Thr Glu Val
1355                1360                1365

Met Thr Ala Val Gly Leu Met Phe Ala Ile Val Gly Gly Leu Ala
1370                1375                1380

Glu Leu Asp Ile Asp Ser Met Ala Ile Pro Met Thr Ile Ala Gly
1385                1390                1395

Leu Met Phe Ala Ala Phe Val Ile Ser Gly Lys Ser Thr Asp Met
1400                1405                1410

Trp Ile Glu Arg Thr Ala Asp Ile Ser Trp Glu Ser Asp Ala Glu
1415                1420                1425

Ile Thr Gly Ser Ser Glu Arg Val Asp Val Arg Leu Asp Asp Asp
1430                1435                1440

Gly Asn Phe Gln Leu Met Asn Asp Pro Gly Ala Pro Trp Lys Ile
1445                1450                1455

Trp Met Leu Arg Met Val Cys Leu Ala Ile Ser Ala Tyr Thr Pro
1460                1465                1470

Trp Ala Ile Leu Pro Ser Val Val Gly Phe Trp Ile Thr Leu Gln
1475                1480                1485

Tyr Thr Lys Arg Gly Gly Val Leu Trp Asp Thr Pro Ser Pro Lys
1490                1495                1500

Glu Tyr Lys Lys Gly Asp Thr Thr Thr Gly Val Tyr Arg Ile Met
1505                1510                1515

Thr Arg Gly Leu Leu Gly Ser Tyr Gln Ala Gly Ala Gly Val Met
1520                1525                1530

Val Glu Gly Val Phe His Thr Leu Trp His Thr Thr Lys Gly Ala
1535                1540                1545

Ala Leu Met Ser Gly Glu Gly Arg Leu Asp Pro Tyr Trp Gly Ser
1550                1555                1560

Val Lys Glu Asp Arg Leu Cys Tyr Gly Gly Pro Trp Lys Leu Gln
1565                1570                1575

His Lys Trp Asn Gly Gln Asp Glu Val Gln Met Ile Val Val Glu
1580                1585                1590

Pro Gly Arg Asn Val Lys Asn Val Gln Thr Lys Pro Gly Val Phe
1595                1600                1605

Lys Thr Pro Glu Gly Glu Ile Gly Ala Val Thr Leu Asp Phe Pro
1610                1615                1620

Thr Gly Thr Ser Gly Ser Pro Ile Val Asp Lys Asn Gly Asp Val
1625                1630                1635

Ile Gly Leu Tyr Gly Asn Gly Val Ile Met Pro Asn Gly Ser Tyr
```

-continued

```
                1640                1645                1650

Ile Ser Ala Ile Val Gln Gly Glu Arg Met Asp Glu Pro Ile Pro
    1655                1660                1665

Ala Gly Phe Glu Pro Glu Met Leu Arg Lys Lys Gln Ile Thr Val
    1670                1675                1680

Leu Asp Leu His Pro Gly Ala Gly Lys Thr Arg Arg Ile Leu Pro
    1685                1690                1695

Gln Ile Ile Lys Glu Ala Ile Asn Arg Arg Leu Arg Thr Ala Val
    1700                1705                1710

Leu Ala Pro Thr Arg Val Val Ala Ala Glu Met Ala Glu Ala Leu
    1715                1720                1725

Arg Gly Leu Pro Ile Arg Tyr Gln Thr Ser Ala Val Pro Arg Glu
    1730                1735                1740

His Asn Gly Asn Glu Ile Val Asp Val Met Cys His Ala Thr Leu
    1745                1750                1755

Thr His Arg Leu Met Ser Pro His Arg Val Pro Asn Tyr Asn Leu
    1760                1765                1770

Phe Val Met Asp Glu Ala His Phe Thr Asp Pro Ala Ser Ile Ala
    1775                1780                1785

Ala Arg Gly Tyr Ile Ser Thr Lys Val Glu Leu Gly Glu Ala Ala
    1790                1795                1800

Ala Ile Phe Met Thr Ala Thr Pro Pro Gly Thr Ser Asp Pro Phe
    1805                1810                1815

Pro Glu Ser Asn Ser Pro Ile Ser Asp Leu Gln Thr Glu Ile Pro
    1820                1825                1830

Asp Arg Ala Trp Asn Ser Gly Tyr Glu Trp Ile Thr Glu Tyr Thr
    1835                1840                1845

Gly Lys Thr Val Trp Phe Val Pro Ser Val Lys Met Gly Asn Glu
    1850                1855                1860

Ile Ala Leu Cys Leu Gln Arg Ala Gly Lys Lys Val Val Gln Leu
    1865                1870                1875

Asn Arg Lys Ser Tyr Glu Thr Glu Tyr Pro Lys Cys Lys Asn Asp
    1880                1885                1890

Asp Trp Asp Phe Val Ile Thr Thr Asp Ile Ser Glu Met Gly Ala
    1895                1900                1905

Asn Phe Lys Ala Ser Arg Val Ile Asp Ser Arg Lys Ser Val Lys
    1910                1915                1920

Pro Thr Ile Ile Thr Glu Gly Glu Gly Arg Val Ile Leu Gly Glu
    1925                1930                1935

Pro Ser Ala Val Thr Ala Ala Ser Ala Ala Gln Arg Arg Gly Arg
    1940                1945                1950

Ile Gly Arg Asn Pro Ser Gln Val Gly Asp Glu Tyr Cys Tyr Gly
    1955                1960                1965

Gly His Thr Asn Glu Asp Asp Ser Asn Phe Ala His Trp Thr Glu
    1970                1975                1980

Ala Arg Ile Met Leu Asp Asn Ile Asn Met Pro Asn Gly Leu Ile
    1985                1990                1995

Ala Gln Phe Tyr Gln Pro Glu Arg Glu Lys Val Tyr Thr Met Asp
    2000                2005                2010

Gly Glu Tyr Arg Leu Arg Gly Glu Glu Arg Lys Asn Phe Leu Glu
    2015                2020                2025

Leu Leu Arg Thr Ala Asp Leu Pro Val Trp Leu Ala Tyr Lys Val
    2030                2035                2040
```

```
Ala Ala Ala Gly Val Ser Tyr His Asp Arg Arg Trp Cys Phe Asp
2045                2050                2055

Gly Pro Arg Thr Asn Thr Ile Leu Glu Asp Asn Asn Glu Val Glu
2060                2065                2070

Val Ile Thr Lys Leu Gly Glu Arg Lys Ile Leu Arg Pro Arg Trp
2075                2080                2085

Ile Asp Ala Arg Val Tyr Ser Asp His Gln Ala Leu Lys Ala Phe
2090                2095                2100

Lys Asp Phe Ala Ser Gly Lys Arg Ser Gln Ile Gly Leu Ile Glu
2105                2110                2115

Val Leu Gly Lys Met Pro Glu His Phe Met Gly Lys Thr Trp Glu
2120                2125                2130

Ala Leu Asp Thr Met Tyr Val Val Ala Thr Ala Glu Lys Gly Gly
2135                2140                2145

Arg Ala His Arg Met Ala Leu Glu Glu Leu Pro Asp Ala Leu Gln
2150                2155                2160

Thr Ile Ala Leu Ile Ala Leu Leu Ser Val Met Thr Met Gly Val
2165                2170                2175

Phe Phe Leu Leu Met Gln Arg Lys Gly Ile Gly Lys Ile Gly Leu
2180                2185                2190

Gly Gly Ala Val Leu Gly Val Ala Thr Phe Phe Cys Trp Met Ala
2195                2200                2205

Glu Val Pro Gly Thr Lys Ile Ala Gly Met Leu Leu Leu Ser Leu
2210                2215                2220

Leu Leu Met Ile Val Leu Ile Pro Glu Pro Glu Lys Gln Arg Ser
2225                2230                2235

Gln Thr Asp Asn Gln Leu Ala Val Phe Leu Ile Cys Val Met Thr
2240                2245                2250

Leu Val Ser Ala Val Ala Ala Asn Glu Met Gly Trp Leu Asp Lys
2255                2260                2265

Thr Lys Ser Asp Ile Ser Ser Leu Phe Gly Gln Arg Ile Glu Val
2270                2275                2280

Lys Glu Asn Phe Ser Met Gly Glu Phe Leu Leu Asp Leu Arg Pro
2285                2290                2295

Ala Thr Ala Trp Ser Leu Tyr Ala Val Thr Thr Ala Val Leu Thr
2300                2305                2310

Pro Leu Leu Lys His Leu Ile Thr Ser Asp Tyr Ile Asn Thr Ser
2315                2320                2325

Leu Thr Ser Ile Asn Val Gln Ala Ser Ala Leu Phe Thr Leu Ala
2330                2335                2340

Arg Gly Phe Pro Phe Val Asp Val Gly Val Ser Ala Leu Leu Leu
2345                2350                2355

Ala Ala Gly Cys Trp Gly Gln Val Thr Leu Thr Val Thr Val Thr
2360                2365                2370

Ala Ala Thr Leu Leu Phe Cys His Tyr Ala Tyr Met Val Pro Gly
2375                2380                2385

Trp Gln Ala Glu Ala Met Arg Ser Ala Gln Arg Arg Thr Ala Ala
2390                2395                2400

Gly Ile Met Lys Asn Ala Val Val Asp Gly Ile Val Ala Thr Asp
2405                2410                2415

Val Pro Glu Leu Glu Arg Thr Thr Pro Ile Met Gln Lys Lys Val
2420                2425                2430

Gly Gln Ile Met Leu Ile Leu Val Ser Leu Ala Ala Val Val Val
2435                2440                2445
```

```
Asn Pro Ser Val Lys Thr Val Arg Glu Ala Gly Ile Leu Ile Thr
    2450            2455                2460

Ala Ala Ala Val Thr Leu Trp Glu Asn Gly Ala Ser Ser Val Trp
    2465            2470                2475

Asn Ala Thr Thr Ala Ile Gly Leu Cys His Ile Met Arg Gly Gly
    2480            2485                2490

Trp Leu Ser Cys Leu Ser Ile Thr Trp Thr Leu Ile Lys Asn Met
    2495            2500                2505

Glu Lys Pro Gly Leu Lys Arg Gly Gly Ala Lys Gly Arg Thr Leu
    2510            2515                2520

Gly Glu Val Trp Lys Glu Arg Leu Asn Gln Met Thr Lys Glu Glu
    2525            2530                2535

Phe Thr Arg Tyr Arg Lys Glu Ala Ile Ile Glu Val Asp Arg Ser
    2540            2545                2550

Ala Ala Lys His Ala Arg Lys Glu Gly Asn Val Thr Gly Gly His
    2555            2560                2565

Pro Val Ser Arg Gly Thr Ala Lys Leu Arg Trp Leu Val Glu Arg
    2570            2575                2580

Arg Phe Leu Glu Pro Val Gly Lys Val Ile Asp Leu Gly Cys Gly
    2585            2590                2595

Arg Gly Gly Trp Cys Tyr Tyr Met Ala Thr Gln Lys Arg Val Gln
    2600            2605                2610

Glu Val Arg Gly Tyr Thr Lys Gly Gly Pro Gly His Glu Glu Pro
    2615            2620                2625

Gln Leu Val Gln Ser Tyr Gly Trp Asn Ile Val Thr Met Lys Ser
    2630            2635                2640

Gly Val Asp Val Phe Tyr Arg Pro Ser Glu Cys Cys Asp Thr Leu
    2645            2650                2655

Leu Cys Asp Ile Gly Glu Ser Ser Ser Ser Ala Glu Val Glu Glu
    2660            2665                2670

His Arg Thr Ile Arg Val Leu Glu Met Val Glu Asp Trp Leu His
    2675            2680                2685

Arg Gly Pro Arg Glu Phe Cys Val Lys Val Leu Cys Pro Tyr Met
    2690            2695                2700

Pro Lys Val Ile Glu Lys Met Glu Leu Leu Gln Arg Arg Tyr Gly
    2705            2710                2715

Gly Gly Leu Val Arg Asn Pro Leu Ser Arg Asn Ser Thr His Glu
    2720            2725                2730

Met Tyr Trp Val Ser Arg Ala Ser Gly Asn Val Val His Ser Val
    2735            2740                2745

Asn Met Thr Ser Gln Val Leu Leu Gly Arg Met Glu Lys Arg Thr
    2750            2755                2760

Trp Lys Gly Pro Gln Tyr Glu Glu Asp Val Asn Leu Gly Ser Gly
    2765            2770                2775

Thr Arg Ala Val Gly Lys Pro Leu Leu Asn Ser Asp Thr Ser Lys
    2780            2785                2790

Ile Lys Asn Arg Ile Glu Arg Leu Arg Arg Glu Tyr Ser Ser Thr
    2795            2800                2805

Trp His His Asp Glu Asn His Pro Tyr Arg Thr Trp Asn Tyr His
    2810            2815                2820

Gly Ser Tyr Asp Val Lys Pro Thr Gly Ser Ala Ser Ser Leu Val
    2825            2830                2835

Asn Gly Val Val Arg Leu Leu Ser Lys Pro Trp Asp Thr Ile Thr
```

-continued

```
               2840                2845                2850

Asn Val Thr Thr Met Ala Met Thr Asp Thr Thr Pro Phe Gly Gln
    2855                2860                2865

Gln Arg Val Phe Lys Glu Lys Val Asp Thr Lys Ala Pro Glu Pro
    2870                2875                2880

Pro Glu Gly Val Lys Tyr Val Leu Asn Glu Thr Thr Asn Trp Leu
    2885                2890                2895

Trp Ala Phe Leu Ala Arg Glu Lys Arg Pro Arg Met Cys Ser Arg
    2900                2905                2910

Glu Glu Phe Ile Arg Lys Val Asn Ser Asn Ala Ala Leu Gly Ala
    2915                2920                2925

Met Phe Glu Glu Gln Asn Gln Trp Arg Ser Ala Arg Glu Ala Val
    2930                2935                2940

Glu Asp Pro Lys Phe Trp Glu Met Val Asp Glu Glu Arg Glu Ala
    2945                2950                2955

His Leu Arg Gly Glu Cys His Thr Cys Ile Tyr Asn Met Met Gly
    2960                2965                2970

Lys Arg Glu Lys Lys Pro Gly Glu Phe Gly Lys Ala Lys Gly Ser
    2975                2980                2985

Arg Ala Ile Trp Phe Met Trp Leu Gly Ala Arg Phe Leu Glu Phe
    2990                2995                3000

Glu Ala Leu Gly Phe Leu Asn Glu Asp His Trp Leu Gly Arg Lys
    3005                3010                3015

Asn Ser Gly Gly Gly Val Glu Gly Leu Gly Leu Gln Lys Leu Gly
    3020                3025                3030

Tyr Ile Leu Arg Glu Val Gly Thr Arg Pro Gly Gly Lys Ile Tyr
    3035                3040                3045

Ala Asp Asp Thr Ala Gly Trp Asp Thr Arg Ile Thr Arg Ala Asp
    3050                3055                3060

Leu Glu Asn Glu Ala Lys Val Leu Glu Leu Leu Asp Gly Glu His
    3065                3070                3075

Arg Arg Leu Ala Arg Ala Ile Ile Glu Leu Thr Tyr Arg His Lys
    3080                3085                3090

Val Val Lys Val Met Arg Pro Ala Ala Asp Gly Arg Thr Val Met
    3095                3100                3105

Asp Val Ile Ser Arg Glu Asp Gln Arg Gly Ser Gly Gln Val Val
    3110                3115                3120

Thr Tyr Ala Leu Asn Thr Phe Thr Asn Leu Ala Val Gln Leu Val
    3125                3130                3135

Arg Met Met Glu Gly Glu Gly Val Ile Gly Pro Asp Asp Val Glu
    3140                3145                3150

Lys Leu Thr Lys Gly Lys Gly Pro Lys Val Arg Thr Trp Leu Phe
    3155                3160                3165

Glu Asn Gly Glu Glu Arg Leu Ser Arg Met Ala Val Ser Gly Asp
    3170                3175                3180

Asp Cys Val Val Lys Pro Leu Asp Asp Arg Phe Ala Thr Ser Leu
    3185                3190                3195

His Phe Leu Asn Ala Met Ser Lys Val Arg Lys Asp Ile Gln Glu
    3200                3205                3210

Trp Lys Pro Ser Thr Gly Trp Tyr Asp Trp Gln Gln Val Pro Phe
    3215                3220                3225

Cys Ser Asn His Phe Thr Glu Leu Ile Met Lys Asp Gly Arg Thr
    3230                3235                3240
```

```
Leu Val  Val Pro Cys Arg Gly  Gln Asp Glu Leu Val  Gly Arg Ala
    3245                 3250                 3255

Arg Ile  Ser Pro Gly Ala Gly  Trp Asn Val Arg Asp  Thr Ala Cys
    3260                 3265                 3270

Leu Ala  Lys Ser Tyr Ala Gln  Met Trp Leu Leu Leu  Tyr Phe His
    3275                 3280                 3285

Arg Arg  Asp Leu Arg Leu Met  Ala Asn Ala Ile Cys  Ser Ala Val
    3290                 3295                 3300

Pro Val  Asn Trp Val Pro Thr  Gly Arg Thr Thr Trp  Ser Ile His
    3305                 3310                 3315

Ala Gly  Gly Glu Trp Met Thr  Thr Glu Asp Met Leu  Glu Val Trp
    3320                 3325                 3330

Asn Arg  Val Trp Ile Glu Glu  Asn Glu Trp Met Glu  Asp Lys Thr
    3335                 3340                 3345

Pro Val  Glu Lys Trp Ser Asp  Val Pro Tyr Ser Gly  Lys Arg Glu
    3350                 3355                 3360

Asp Ile  Trp Cys Gly Ser Leu  Ile Gly Thr Arg Ala  Arg Ala Thr
    3365                 3370                 3375

Trp Ala  Glu Asn Ile Gln Val  Ala Ile Asn Gln Val  Arg Ala Ile
    3380                 3385                 3390

Ile Gly  Asp Glu Lys Tyr Val  Asp Tyr Met Ser Ser  Leu Lys Arg
    3395                 3400                 3405

Tyr Glu  Asp Thr Thr Leu Val  Glu Asp Thr Val Leu
    3410                 3415                 3420

<210> SEQ ID NO 7
<211> LENGTH: 10996
<212> TYPE: DNA
<213> ORGANISM: Artificial Sequence
<220> FEATURE:
<223> OTHER INFORMATION: Recombinant West Nile virus/Dengue-4 virus
      chimera
<220> FEATURE:
<221> NAME/KEY: CDS
<222> LOCATION: (97)..(10362)

<400> SEQUENCE: 7
agtagttcgc ctgtgtgagc tgacaaactt agtagtgttt gtgaggatta acaacaatta      60
acacagtgcg agctgtttct tagcacgaag atctcg atg tct aag aaa cca gga       114
                                        Met Ser Lys Lys Pro Gly
                                        1               5 ggg ccc ggc aag agc cgg gct gtc aat atg cta aaa cgc gga atg ccc       162
Gly Pro Gly Lys Ser Arg Ala Val Asn Met Leu Lys Arg Gly Met Pro
            10                  15                  20 cgc gtg ttg tcc ttg att gga ctg aag agg gct atg ttg agc ctg atc       210
Arg Val Leu Ser Leu Ile Gly Leu Lys Arg Ala Met Leu Ser Leu Ile
        25                  30                  35 gac ggc aag ggg cca ata cga ttt gtg ttg gct ctc ttg gcg ttc ttc       258
Asp Gly Lys Gly Pro Ile Arg Phe Val Leu Ala Leu Leu Ala Phe Phe
    40                  45                  50 agg ttc aca gca att gct ccg acc cga gca gtg ctg gat cga tgg aga       306
Arg Phe Thr Ala Ile Ala Pro Thr Arg Ala Val Leu Asp Arg Trp Arg
55                  60                  65                  70 ggt gtg aac aaa caa aca gcg atg aaa cac ctt ctg agt ttt aag aag       354
Gly Val Asn Lys Gln Thr Ala Met Lys His Leu Leu Ser Phe Lys Lys
                75                  80                  85 gaa cta ggg acc ttg acc agt gct atc aat cgg cgg agc tca aaa caa       402
Glu Leu Gly Thr Leu Thr Ser Ala Ile Asn Arg Arg Ser Ser Lys Gln
            90                  95                  100

```
aag aaa aga tca acg ata aca ttg ctg tgc ttg att ccc acc gta atg      450
Lys Lys Arg Ser Thr Ile Thr Leu Leu Cys Leu Ile Pro Thr Val Met
        105                 110                 115 gcg ttt cac ttg tca aca aga gat ggc gaa ccc ctc atg ata gtg gca      498
Ala Phe His Leu Ser Thr Arg Asp Gly Glu Pro Leu Met Ile Val Ala
    120                 125                 130 aaa cat gaa agg ggg aga cct ctc ctg ttt aag aca aca gag ggg atc      546
Lys His Glu Arg Gly Arg Pro Leu Leu Phe Lys Thr Thr Glu Gly Ile
135                 140                 145                 150 aac aaa tgc act ctc att gcc atg gac ttg ggt gaa atg tgt gag gac      594
Asn Lys Cys Thr Leu Ile Ala Met Asp Leu Gly Glu Met Cys Glu Asp
            155                 160                 165 act gtc acg tac aaa tgc ccc tta ctg gtc aat acc gaa cct gaa gac      642
Thr Val Thr Tyr Lys Cys Pro Leu Leu Val Asn Thr Glu Pro Glu Asp
                170                 175                 180 att gat tgc tgg tgc aat ctc acg tct acc tgg gtc atg tat ggg aca      690
Ile Asp Cys Trp Cys Asn Leu Thr Ser Thr Trp Val Met Tyr Gly Thr
                    185                 190                 195 tgc acc cag agc gga gaa cgg aga cga gag aag cgc tca gta gct tta      738
Cys Thr Gln Ser Gly Glu Arg Arg Arg Glu Lys Arg Ser Val Ala Leu
        200                 205                 210 aca cca cat tca gga atg gga ttg gaa aca aga gct gag aca tgg atg      786
Thr Pro His Ser Gly Met Gly Leu Glu Thr Arg Ala Glu Thr Trp Met
215                 220                 225                 230 tca tcg gaa ggg gct tgg aag cat gct cag aga gta gag agc tgg ata      834
Ser Ser Glu Gly Ala Trp Lys His Ala Gln Arg Val Glu Ser Trp Ile
                235                 240                 245 ctc aga aac cca gga ttc gcg ctc ttg gca gga ttt atg gct tat atg      882
Leu Arg Asn Pro Gly Phe Ala Leu Leu Ala Gly Phe Met Ala Tyr Met
            250                 255                 260 att ggg caa aca gga atc cag cga act gtc ttc ttt gtc cta atg atg      930
Ile Gly Gln Thr Gly Ile Gln Arg Thr Val Phe Phe Val Leu Met Met
        265                 270                 275 ctg gtc gcc cca tcc tac gga atg cga tgc gta gga gta ggg aac aga      978
Leu Val Ala Pro Ser Tyr Gly Met Arg Cys Val Gly Val Gly Asn Arg
280                 285                 290 gac ttt gtg gaa gga gtc tca ggt gga gca tgg gtc gat ctg gtg cta     1026
Asp Phe Val Glu Gly Val Ser Gly Gly Ala Trp Val Asp Leu Val Leu
295                 300                 305                 310 gaa cat gga gga tgc gtc aca acc atg gcc cag gga aaa cca acc ttg     1074
Glu His Gly Gly Cys Val Thr Thr Met Ala Gln Gly Lys Pro Thr Leu
                315                 320                 325 gat ttt gaa ctg act aag aca aca gcc aag gaa gtg gct ctg tta aga     1122
Asp Phe Glu Leu Thr Lys Thr Thr Ala Lys Glu Val Ala Leu Leu Arg
            330                 335                 340 acc tat tgc att gaa gcc tca ata tca aac ata acc acg gca aca aga     1170
Thr Tyr Cys Ile Glu Ala Ser Ile Ser Asn Ile Thr Thr Ala Thr Arg
        345                 350                 355 tgt cca acg caa gga gag cct tat cta aaa gag gaa caa gac caa cag     1218
Cys Pro Thr Gln Gly Glu Pro Tyr Leu Lys Glu Glu Gln Asp Gln Gln
360                 365                 370 tac att tgc cgg aga gat gtg gta gac aga ggg tgg ggc aat ggc tgt     1266
Tyr Ile Cys Arg Arg Asp Val Val Asp Arg Gly Trp Gly Asn Gly Cys
375                 380                 385                 390 ggc ttg ttt gga aaa gga gga gtt gtg aca tgt gcg aag ttt tca tgt     1314
Gly Leu Phe Gly Lys Gly Gly Val Val Thr Cys Ala Lys Phe Ser Cys
                395                 400                 405 tcg ggg aag ata aca ggc aat ttg gtc caa att gag aac ctt gaa tac     1362
Ser Gly Lys Ile Thr Gly Asn Leu Val Gln Ile Glu Asn Leu Glu Tyr
            410                 415                 420
```

```
aca gtg gtt gta aca gtc cac aat gga gac acc cat gca gta gga aat    1410
Thr Val Val Val Thr Val His Asn Gly Asp Thr His Ala Val Gly Asn
        425                 430                 435 gac aca tcc aat cat gga gtt aca gcc acg ata act ccc agg tca cca    1458
Asp Thr Ser Asn His Gly Val Thr Ala Thr Ile Thr Pro Arg Ser Pro
    440                 445                 450 tcg gtg gaa gtc aaa ttg ccg gac tat gga gaa cta aca ctc gat tgt    1506
Ser Val Glu Val Lys Leu Pro Asp Tyr Gly Glu Leu Thr Leu Asp Cys
455                 460                 465                 470 gaa ccc agg tct gga att gac ttt aat gag atg att ctg atg aaa atg    1554
Glu Pro Arg Ser Gly Ile Asp Phe Asn Glu Met Ile Leu Met Lys Met
                475                 480                 485 aaa aag aaa aca tgg ctt gtg cat aag caa tgg ttt ttg gat cta cct    1602
Lys Lys Lys Thr Trp Leu Val His Lys Gln Trp Phe Leu Asp Leu Pro
            490                 495                 500 cta cca tgg aca gca gga gca gac aca tca gag gtt cac tgg aat tac    1650
Leu Pro Trp Thr Ala Gly Ala Asp Thr Ser Glu Val His Trp Asn Tyr
        505                 510                 515 aaa gag aga atg gtg aca ttt aag gtt cct cat gcc aag aga cag gat    1698
Lys Glu Arg Met Val Thr Phe Lys Val Pro His Ala Lys Arg Gln Asp
    520                 525                 530 gtg aca gtg ctg gga tct cag gaa gga gcc atg cat tct gcc ctc gct    1746
Val Thr Val Leu Gly Ser Gln Glu Gly Ala Met His Ser Ala Leu Ala
535                 540                 545                 550 gga gcc aca gaa gtg gac tcc ggt gat gga aat cac atg ttt gca gga    1794
Gly Ala Thr Glu Val Asp Ser Gly Asp Gly Asn His Met Phe Ala Gly
                555                 560                 565 cat ctc aag tgc aaa gtc cgt atg gag aaa ttg aga atc aag gga atg    1842
His Leu Lys Cys Lys Val Arg Met Glu Lys Leu Arg Ile Lys Gly Met
            570                 575                 580 tca tac acg atg tgt tca gga aag ttc tca att gac aaa gag atg gca    1890
Ser Tyr Thr Met Cys Ser Gly Lys Phe Ser Ile Asp Lys Glu Met Ala
        585                 590                 595 gaa aca cag cat ggg aca aca gtg gtg aaa gtc aag tat gaa ggt gct    1938
Glu Thr Gln His Gly Thr Thr Val Val Lys Val Lys Tyr Glu Gly Ala
    600                 605                 610 gga gct ccg tgt aaa gtc ccc ata gag ata aga gat gtg aac aag gaa    1986
Gly Ala Pro Cys Lys Val Pro Ile Glu Ile Arg Asp Val Asn Lys Glu
615                 620                 625                 630 aaa gtg gtt ggg cgt atc atc tca tcc acc cct ttg gct gag aat acc    2034
Lys Val Val Gly Arg Ile Ile Ser Ser Thr Pro Leu Ala Glu Asn Thr
                635                 640                 645 aac agt gca acc aac ata gag tta gaa ccc ccc ttt ggg gac agc tac    2082
Asn Ser Ala Thr Asn Ile Glu Leu Glu Pro Pro Phe Gly Asp Ser Tyr
            650                 655                 660 ata gtg ata ggt gtt gga aac agt gca tta aca ctc cat tgg ttc agg    2130
Ile Val Ile Gly Val Gly Asn Ser Ala Leu Thr Leu His Trp Phe Arg
        665                 670                 675 aaa ggg agt tcc att ggc aag atg ttt gag tcc aca tac aga ggt gca    2178
Lys Gly Ser Ser Ile Gly Lys Met Phe Glu Ser Thr Tyr Arg Gly Ala
    680                 685                 690 aaa cga atg gcc att cta ggt gaa aca gct tgg gat ttt ggt tcc gtt    2226
Lys Arg Met Ala Ile Leu Gly Glu Thr Ala Trp Asp Phe Gly Ser Val
695                 700                 705                 710 ggt gga ctg ttc aca tca ttg gga aag gct gtg cac cag gtt ttt gga    2274
Gly Gly Leu Phe Thr Ser Leu Gly Lys Ala Val His Gln Val Phe Gly
                715                 720                 725 agt gtg tat aca acc atg ttt gga gga gtc tca tgg atg att aga atc    2322
Ser Val Tyr Thr Thr Met Phe Gly Gly Val Ser Trp Met Ile Arg Ile
        730                 735                 740
```

```
cta att ggg ttc cta gtg ttg tgg att ggc acg aac tca agg aac act      2370
Leu Ile Gly Phe Leu Val Leu Trp Ile Gly Thr Asn Ser Arg Asn Thr
        745                 750                 755 tca atg gct atg acg tgc ata gct gtt gga gga atc act ctg ttt ctg      2418
Ser Met Ala Met Thr Cys Ile Ala Val Gly Gly Ile Thr Leu Phe Leu
760                 765                 770 ggc ttc aca gtt caa gca gac tcc gga tgt gcc ata gac atc agc cgg      2466
Gly Phe Thr Val Gln Ala Asp Ser Gly Cys Ala Ile Asp Ile Ser Arg
775                 780                 785                 790 caa gag ctg aga tgt gga agt gga gtg ttc ata cac aat gat gtg gag      2514
Gln Glu Leu Arg Cys Gly Ser Gly Val Phe Ile His Asn Asp Val Glu
            795                 800                 805 gct tgg atg gac cgg tac aag tat tac cct gaa acg cca caa ggc cta      2562
Ala Trp Met Asp Arg Tyr Lys Tyr Tyr Pro Glu Thr Pro Gln Gly Leu
        810                 815                 820 gcc aag atc att cag aaa gct cat aag gaa gga gtg tgc ggt cta cga      2610
Ala Lys Ile Ile Gln Lys Ala His Lys Glu Gly Val Cys Gly Leu Arg
    825                 830                 835 tca gtt tcc aga ctg gag cat caa atg tgg gaa gca gtg aag gac gag      2658
Ser Val Ser Arg Leu Glu His Gln Met Trp Glu Ala Val Lys Asp Glu
840                 845                 850 ctg aac act ctt ttg aag gag aat ggt gtg gac ctt agt gtc gtg gtt      2706
Leu Asn Thr Leu Leu Lys Glu Asn Gly Val Asp Leu Ser Val Val Val
855                 860                 865                 870 gag aaa cag gag gga atg tac aag tca gca cct aaa cgc ctc acc gcc      2754
Glu Lys Gln Glu Gly Met Tyr Lys Ser Ala Pro Lys Arg Leu Thr Ala
            875                 880                 885 acc acg gaa aaa ttg gaa att ggc tgg aag gcc tgg gga aag agt att      2802
Thr Thr Glu Lys Leu Glu Ile Gly Trp Lys Ala Trp Gly Lys Ser Ile
        890                 895                 900 tta ttt gca cca gaa ctc gcc aac aac acc ttt gtg gtt gat ggt ccg      2850
Leu Phe Ala Pro Glu Leu Ala Asn Asn Thr Phe Val Val Asp Gly Pro
    905                 910                 915 gag acc aag gaa tgt ccg act cag aat cgc gct tgg aat agc tta gaa      2898
Glu Thr Lys Glu Cys Pro Thr Gln Asn Arg Ala Trp Asn Ser Leu Glu
920                 925                 930 gtg gag gat ttt gga ttt ggt ctc acc agc act cgg atg ttc ctg aag      2946
Val Glu Asp Phe Gly Phe Gly Leu Thr Ser Thr Arg Met Phe Leu Lys
935                 940                 945                 950 gtc aga gag agc aac aca act gaa tgt gac tcg aag atc att gga acg      2994
Val Arg Glu Ser Asn Thr Thr Glu Cys Asp Ser Lys Ile Ile Gly Thr
            955                 960                 965 gct gtc aag aac aac ttg gcg atc cac agt gac ctg tcc tat tgg att      3042
Ala Val Lys Asn Asn Leu Ala Ile His Ser Asp Leu Ser Tyr Trp Ile
        970                 975                 980 gaa agc agg ctc aat gat acg tgg aag ctt gaa agg gca gtt ctg ggt      3090
Glu Ser Arg Leu Asn Asp Thr Trp Lys Leu Glu Arg Ala Val Leu Gly
    985                 990                 995 gaa gtc  aaa tca tgt acg tgg  cct gag acg cat acc  ttg tgg ggc       3135
Glu Val Lys Ser Cys Thr Trp Pro Glu Thr His Thr Leu Trp Gly
    1000                1005                1010 gat gga  atc ctt gag agt gac  ttg ata ata cca gtc  aca ctg gcg       3180
Asp Gly Ile Leu Glu Ser Asp Leu Ile Ile Pro Val Thr Leu Ala
    1015                1020                1025 gga cca  cga agc aat cac aat  cgg aga cct ggg tac  aag aca caa       3225
Gly Pro Arg Ser Asn His Asn Arg Arg Pro Gly Tyr Lys Thr Gln
    1030                1035                1040 aac cag  ggc cca tgg gac gaa  ggc cgg gta gag att  gac ttc gat       3270
Asn Gln Gly Pro Trp Asp Glu Gly Arg Val Glu Ile Asp Phe Asp
    1045                1050                1055
```

```
tac tgc cca gga act acg gtc acc ctg agt gag agc tgc gga cac        3315
Tyr Cys Pro Gly Thr Thr Val Thr Leu Ser Glu Ser Cys Gly His
1060                1065                1070 cgt gga cct gcc act cgc acc acc aca gag agc gga aag ttg ata        3360
Arg Gly Pro Ala Thr Arg Thr Thr Thr Glu Ser Gly Lys Leu Ile
1075                1080                1085 aca gat tgg tgc tgc agg agc tgc acc tta cca cca ctg cgc tac        3405
Thr Asp Trp Cys Cys Arg Ser Cys Thr Leu Pro Pro Leu Arg Tyr
1090                1095                1100 caa act gac agc ggc tgt tgg tat ggt atg gag atc aga cca cag        3450
Gln Thr Asp Ser Gly Cys Trp Tyr Gly Met Glu Ile Arg Pro Gln
1105                1110                1115 aga cat gat gaa aag acc ctc gtg cag tca caa gtg aat gct tat        3495
Arg His Asp Glu Lys Thr Leu Val Gln Ser Gln Val Asn Ala Tyr
1120                1125                1130 aat gct gat atg att gac cct ttt cag ttg ggc ctt ctg gtc gtg        3540
Asn Ala Asp Met Ile Asp Pro Phe Gln Leu Gly Leu Leu Val Val
1135                1140                1145 ttc ttg gcc acc cag gag gtc ctt cgc aag agg tgg aca gcc aag        3585
Phe Leu Ala Thr Gln Glu Val Leu Arg Lys Arg Trp Thr Ala Lys
1150                1155                1160 atc agc atg cca gct ata ctg att gct ctg cta gtc ctg gtg ttt        3630
Ile Ser Met Pro Ala Ile Leu Ile Ala Leu Leu Val Leu Val Phe
1165                1170                1175 ggg ggc att act tac act gat gtg tta cgc tat gtc atc ttg gtg        3675
Gly Gly Ile Thr Tyr Thr Asp Val Leu Arg Tyr Val Ile Leu Val
1180                1185                1190 ggg gca gct ttc gca gaa tct aat tcg gga gga gac gtg gta cac        3720
Gly Ala Ala Phe Ala Glu Ser Asn Ser Gly Gly Asp Val Val His
1195                1200                1205 ttg gcg ctc atg gcg acc ttc aag ata caa cca gtg ttt atg gtg        3765
Leu Ala Leu Met Ala Thr Phe Lys Ile Gln Pro Val Phe Met Val
1210                1215                1220 gca tcg ttt ctc aaa gcg aga tgg acc aac cag gag aac att ttg        3810
Ala Ser Phe Leu Lys Ala Arg Trp Thr Asn Gln Glu Asn Ile Leu
1225                1230                1235 ttg atg ttg gcg gct gtt ttc ttt caa atg gct tat tac gat gcc        3855
Leu Met Leu Ala Ala Val Phe Phe Gln Met Ala Tyr Tyr Asp Ala
1240                1245                1250 cgc caa att ctg ctc tgg gag atc cct gat gtg ttg aat tca ctg        3900
Arg Gln Ile Leu Leu Trp Glu Ile Pro Asp Val Leu Asn Ser Leu
1255                1260                1265 gcg gta gct tgg atg ata ctg aga gcc ata aca ttc aca acg aca        3945
Ala Val Ala Trp Met Ile Leu Arg Ala Ile Thr Phe Thr Thr Thr
1270                1275                1280 tca aac gtg gtt gtt ccg ctg cta gcc ctg cta aca ccc ggg ctg        3990
Ser Asn Val Val Val Pro Leu Leu Ala Leu Leu Thr Pro Gly Leu
1285                1290                1295 aga tgc ttg aat ctg gat gtg tac agg ata ctg ctg ttg atg gtc        4035
Arg Cys Leu Asn Leu Asp Val Tyr Arg Ile Leu Leu Leu Met Val
1300                1305                1310 gga ata ggc agc ttg atc agg gag aag agg agt gca gct gca aaa        4080
Gly Ile Gly Ser Leu Ile Arg Glu Lys Arg Ser Ala Ala Ala Lys
1315                1320                1325 aag aaa gga gca agt ctg cta tgc ttg gct cta gcc tca aca gga        4125
Lys Lys Gly Ala Ser Leu Leu Cys Leu Ala Leu Ala Ser Thr Gly
1330                1335                1340 ctt ttc aac ccc atg atc ctt gct gct gga ctg att gca tgt gat        4170
Leu Phe Asn Pro Met Ile Leu Ala Ala Gly Leu Ile Ala Cys Asp
1345                1350                1355
```

```
ccc aac cgt aaa cgc gga tgg ccc gca act gaa gtg atg aca gct      4215
Pro Asn Arg Lys Arg Gly Trp Pro Ala Thr Glu Val Met Thr Ala
    1360            1365                1370 gtc ggc cta atg ttt gcc atc gtc gga ggg ctg gca gag ctt gac      4260
Val Gly Leu Met Phe Ala Ile Val Gly Gly Leu Ala Glu Leu Asp
1375                1380                1385 att gac tcc atg gcc att cca atg act atc gcg ggg ctc atg ttt      4305
Ile Asp Ser Met Ala Ile Pro Met Thr Ile Ala Gly Leu Met Phe
    1390            1395                1400 gct gct ttc gtg att tct ggg aaa tca aca gat atg tgg att gag      4350
Ala Ala Phe Val Ile Ser Gly Lys Ser Thr Asp Met Trp Ile Glu
1405                1410                1415 aga acg gcg gac att tcc tgg gaa agt gat gca gaa att aca ggc      4395
Arg Thr Ala Asp Ile Ser Trp Glu Ser Asp Ala Glu Ile Thr Gly
    1420            1425                1430 tcg agc gaa aga gtt gat gtg cgg ctt gat gat gat gga aac ttc      4440
Ser Ser Glu Arg Val Asp Val Arg Leu Asp Asp Asp Gly Asn Phe
1435                1440                1445 cag ctc atg aat gat cca gga gca cct tgg aag ata tgg atg ctc      4485
Gln Leu Met Asn Asp Pro Gly Ala Pro Trp Lys Ile Trp Met Leu
    1450            1455                1460 aga atg gtc tgt ctc gcg att agt gcg tac acc ccc tgg gca atc      4530
Arg Met Val Cys Leu Ala Ile Ser Ala Tyr Thr Pro Trp Ala Ile
1465                1470                1475 ttg ccc tca gta gtt gga ttt tgg ata act ctc caa tac aca aag      4575
Leu Pro Ser Val Val Gly Phe Trp Ile Thr Leu Gln Tyr Thr Lys
    1480            1485                1490 aga gga ggc gtg ttg tgg gac act ccc tca cca aag gag tac aaa      4620
Arg Gly Gly Val Leu Trp Asp Thr Pro Ser Pro Lys Glu Tyr Lys
1495                1500                1505 aag ggg gac acg acc acc ggc gtc tac agg atc atg act cgt ggg      4665
Lys Gly Asp Thr Thr Thr Gly Val Tyr Arg Ile Met Thr Arg Gly
    1510            1515                1520 ctg ctc ggc agt tat caa gca gga gcg ggc gtg atg gtt gaa ggt      4710
Leu Leu Gly Ser Tyr Gln Ala Gly Ala Gly Val Met Val Glu Gly
1525                1530                1535 gtt ttc cac acc ctt tgg cat aca aca aaa gga gcc gct ttg atg      4755
Val Phe His Thr Leu Trp His Thr Thr Lys Gly Ala Ala Leu Met
    1540            1545                1550 agc gga gag ggc cgc ctg gac cca tac tgg ggc agt gtc aag gag      4800
Ser Gly Glu Gly Arg Leu Asp Pro Tyr Trp Gly Ser Val Lys Glu
1555                1560                1565 gat cga ctt tgt tac gga gga ccc tgg aaa ttg cag cac aag tgg      4845
Asp Arg Leu Cys Tyr Gly Gly Pro Trp Lys Leu Gln His Lys Trp
    1570            1575                1580 aac ggg cag gat gag gtg cag atg att gtg gtg gaa cct ggc agg      4890
Asn Gly Gln Asp Glu Val Gln Met Ile Val Val Glu Pro Gly Arg
1585                1590                1595 aac gtt aag aac gtc cag acg aaa cca ggg gtg ttc aaa aca cct      4935
Asn Val Lys Asn Val Gln Thr Lys Pro Gly Val Phe Lys Thr Pro
    1600            1605                1610 gaa gga gaa atc ggg gcc gtg act ttg gac ttc ccc act gga aca      4980
Glu Gly Glu Ile Gly Ala Val Thr Leu Asp Phe Pro Thr Gly Thr
1615                1620                1625 tca ggc tca cca ata gtg gac aaa aac ggt gat gtg att ggg ctt      5025
Ser Gly Ser Pro Ile Val Asp Lys Asn Gly Asp Val Ile Gly Leu
    1630            1635                1640 tat ggc aat gga gtc ata atg ccc aac ggc tca tac ata agc gcg      5070
Tyr Gly Asn Gly Val Ile Met Pro Asn Gly Ser Tyr Ile Ser Ala
1645                1650                1655
```

```
ata gtg cag ggt gaa agg atg gat gag cca atc cca gcc gga ttc    5115
Ile Val Gln Gly Glu Arg Met Asp Glu Pro Ile Pro Ala Gly Phe
    1660            1665                1670 gaa cct gag atg ctg agg aaa aaa cag atc act gta ctg gat ctc    5160
Glu Pro Glu Met Leu Arg Lys Lys Gln Ile Thr Val Leu Asp Leu
1675            1680                1685 cat ccc ggc gcc ggt aaa aca agg agg att ctg cca cag atc atc    5205
His Pro Gly Ala Gly Lys Thr Arg Arg Ile Leu Pro Gln Ile Ile
    1690            1695                1700 aaa gag gcc ata aac aga aga ctg aga aca gcc gtg cta gca cca    5250
Lys Glu Ala Ile Asn Arg Arg Leu Arg Thr Ala Val Leu Ala Pro
1705            1710                1715 acc agg gtt gtg gct gct gag atg gct gaa gca ctg aga gga ctg    5295
Thr Arg Val Val Ala Ala Glu Met Ala Glu Ala Leu Arg Gly Leu
    1720            1725                1730 ccc atc cgg tac cag aca tcc gca gtg ccc aga gaa cat aat gga    5340
Pro Ile Arg Tyr Gln Thr Ser Ala Val Pro Arg Glu His Asn Gly
1735            1740                1745 aat gag att gtt gat gtc atg tgt cat gct acc ctc acc cac agg    5385
Asn Glu Ile Val Asp Val Met Cys His Ala Thr Leu Thr His Arg
    1750            1755                1760 ctg atg tct cct cac agg gtg ccg aac tac aac ctg ttc gtg atg    5430
Leu Met Ser Pro His Arg Val Pro Asn Tyr Asn Leu Phe Val Met
1765            1770                1775 gat gag gct cat ttc acc gac cca gct agc att gca gca aga ggt    5475
Asp Glu Ala His Phe Thr Asp Pro Ala Ser Ile Ala Ala Arg Gly
    1780            1785                1790 tac att tcc aca aag gtc gag cta ggg gag gcg gcg gca ata ttc    5520
Tyr Ile Ser Thr Lys Val Glu Leu Gly Glu Ala Ala Ala Ile Phe
1795            1800                1805 atg aca gcc acc cca cca ggc act tca gat cca ttc cca gag tcc    5565
Met Thr Ala Thr Pro Pro Gly Thr Ser Asp Pro Phe Pro Glu Ser
    1810            1815                1820 aat tca cca att tcc gac tta cag act gag atc ccg gat cga gct    5610
Asn Ser Pro Ile Ser Asp Leu Gln Thr Glu Ile Pro Asp Arg Ala
1825            1830                1835 tgg aac tct gga tac gaa tgg atc aca gaa tac acc ggg aag acg    5655
Trp Asn Ser Gly Tyr Glu Trp Ile Thr Glu Tyr Thr Gly Lys Thr
    1840            1845                1850 gtt tgg ttt gtg cct agt gtc aag atg ggg aat gag att gcc ctt    5700
Val Trp Phe Val Pro Ser Val Lys Met Gly Asn Glu Ile Ala Leu
1855            1860                1865 tgc cta caa cgt gct gga aag aaa gta gtc caa ttg aac aga aag    5745
Cys Leu Gln Arg Ala Gly Lys Lys Val Val Gln Leu Asn Arg Lys
    1870            1875                1880 tcg tac gag acg gag tac cca aaa tgt aag aac gat gat tgg gac    5790
Ser Tyr Glu Thr Glu Tyr Pro Lys Cys Lys Asn Asp Asp Trp Asp
1885            1890                1895 ttt gtt atc aca aca gac ata tct gaa atg ggg gct aac ttc aag    5835
Phe Val Ile Thr Thr Asp Ile Ser Glu Met Gly Ala Asn Phe Lys
    1900            1905                1910 gcg agc agg gtg att gac agc cgg aag agt gtg aaa cca acc atc    5880
Ala Ser Arg Val Ile Asp Ser Arg Lys Ser Val Lys Pro Thr Ile
1915            1920                1925 ata aca gaa gga gaa ggg aga gtg atc ctg gga gaa cca tct gca    5925
Ile Thr Glu Gly Glu Gly Arg Val Ile Leu Gly Glu Pro Ser Ala
    1930            1935                1940 gtg aca gca gct agt gcc gcc cag aga cgt gga cgt atc ggt aga    5970
Val Thr Ala Ala Ser Ala Ala Gln Arg Arg Gly Arg Ile Gly Arg
1945            1950                1955
```

```
aat ccg tcg caa gtt ggt gat gag tac tgt tat ggg ggg cac acg      6015
Asn Pro Ser Gln Val Gly Asp Glu Tyr Cys Tyr Gly Gly His Thr
    1960            1965                1970 aat gaa gac gac tcg aac ttc gcc cat tgg act gag gca cga atc      6060
Asn Glu Asp Asp Ser Asn Phe Ala His Trp Thr Glu Ala Arg Ile
1975                1980                1985 atg ctg gac aac atc aac atg cca aac gga ctg atc gct caa ttc      6105
Met Leu Asp Asn Ile Asn Met Pro Asn Gly Leu Ile Ala Gln Phe
    1990            1995                2000 tac caa cca gag cgt gag aag gta tat acc atg gat ggg gaa tac      6150
Tyr Gln Pro Glu Arg Glu Lys Val Tyr Thr Met Asp Gly Glu Tyr
2005                2010                2015 cgg ctc aga gga gaa gag aga aaa aac ttt ctg gaa ctg ttg agg      6195
Arg Leu Arg Gly Glu Glu Arg Lys Asn Phe Leu Glu Leu Leu Arg
    2020            2025                2030 act gca gat ctg cca gtt tgg ctg gct tac aag gtt gca gcg gct      6240
Thr Ala Asp Leu Pro Val Trp Leu Ala Tyr Lys Val Ala Ala Ala
2035                2040                2045 gga gtg tca tac cac gac cgg agg tgg tgc ttt gat ggt cct agg      6285
Gly Val Ser Tyr His Asp Arg Arg Trp Cys Phe Asp Gly Pro Arg
    2050            2055                2060 aca aac aca att tta gaa gac aac aac gaa gtg gaa gtc atc acg      6330
Thr Asn Thr Ile Leu Glu Asp Asn Asn Glu Val Glu Val Ile Thr
2065                2070                2075 aag ctt ggt gaa agg aag att ctg agg ccg cgc tgg att gac gcc      6375
Lys Leu Gly Glu Arg Lys Ile Leu Arg Pro Arg Trp Ile Asp Ala
    2080            2085                2090 agg gtg tac tcg gat cac cag gca cta aag gcg ttc aag gac ttc      6420
Arg Val Tyr Ser Asp His Gln Ala Leu Lys Ala Phe Lys Asp Phe
2095                2100                2105 gcc tcg gga aaa cgt tct cag ata ggg ctc att gag gtt ctg gga      6465
Ala Ser Gly Lys Arg Ser Gln Ile Gly Leu Ile Glu Val Leu Gly
    2110            2115                2120 aag atg cct gag cac ttc atg ggg aag aca tgg gaa gca ctt gac      6510
Lys Met Pro Glu His Phe Met Gly Lys Thr Trp Glu Ala Leu Asp
2125                2130                2135 acc atg tac gtt gtg gcc act gca gag aaa gga gga aga gct cac      6555
Thr Met Tyr Val Val Ala Thr Ala Glu Lys Gly Gly Arg Ala His
    2140            2145                2150 aga atg gcc ctg gag gaa ctg cca gat gct ctt cag aca att gcc      6600
Arg Met Ala Leu Glu Glu Leu Pro Asp Ala Leu Gln Thr Ile Ala
2155                2160                2165 ttg att gcc tta ttg agt gtg atg acc atg gga gta ttc ttc ctc      6645
Leu Ile Ala Leu Leu Ser Val Met Thr Met Gly Val Phe Phe Leu
    2170            2175                2180 ctc atg cag cgg aag ggc att gga aag ata ggt ttg gga ggc gct      6690
Leu Met Gln Arg Lys Gly Ile Gly Lys Ile Gly Leu Gly Gly Ala
2185                2190                2195 gtc ttg gga gtc gcg acc ttt ttc tgt tgg atg gct gaa gtt cca      6735
Val Leu Gly Val Ala Thr Phe Phe Cys Trp Met Ala Glu Val Pro
    2200            2205                2210 gga acg aag atc gcc gga atg ttg ctg ctc tcc ctt ctc ttg atg      6780
Gly Thr Lys Ile Ala Gly Met Leu Leu Leu Ser Leu Leu Leu Met
2215                2220                2225 att gtg cta att cct gag cca gag aag caa cgt tcg cag aca gac      6825
Ile Val Leu Ile Pro Glu Pro Glu Lys Gln Arg Ser Gln Thr Asp
    2230            2235                2240 aac cag cta gcc gtg ttc ctg att tgt gtc atg acc ctt gtg agc      6870
Asn Gln Leu Ala Val Phe Leu Ile Cys Val Met Thr Leu Val Ser
2245                2250                2255
```

```
gca gtg gca gcc aac gag atg ggt tgg cta gat aag acc aag agt      6915
Ala Val Ala Ala Asn Glu Met Gly Trp Leu Asp Lys Thr Lys Ser
    2260            2265                2270 gac ata agc agt ttg ttt ggg caa aga att gag gtc aag gag aat      6960
Asp Ile Ser Ser Leu Phe Gly Gln Arg Ile Glu Val Lys Glu Asn
    2275            2280                2285 ttc agc atg gga gag ttt ctt ttg gac ttg agg cct gca aca gcc      7005
Phe Ser Met Gly Glu Phe Leu Leu Asp Leu Arg Pro Ala Thr Ala
    2290            2295                2300 tgg tca ctg tac gct gtg aca aca gcg gtc ctc act cca ctg cta      7050
Trp Ser Leu Tyr Ala Val Thr Thr Ala Val Leu Thr Pro Leu Leu
    2305            2310                2315 aag cat ttg atc acg tca gat tac atc aac acc tca ttg acc tca      7095
Lys His Leu Ile Thr Ser Asp Tyr Ile Asn Thr Ser Leu Thr Ser
    2320            2325                2330 ata aac gtt cag gca agt gca cta ttc aca ctc gcg cga ggc ttc      7140
Ile Asn Val Gln Ala Ser Ala Leu Phe Thr Leu Ala Arg Gly Phe
    2335            2340                2345 ccc ttc gtc gat gtt gga gtg tcg gct ctc ctg cta gca gcc gga      7185
Pro Phe Val Asp Val Gly Val Ser Ala Leu Leu Leu Ala Ala Gly
    2350            2355                2360 tgc tgg gga caa gtc acc ctc acc gtt acg gta aca gcg gca aca      7230
Cys Trp Gly Gln Val Thr Leu Thr Val Thr Val Thr Ala Ala Thr
    2365            2370                2375 ctc ctt ttt tgc cac tat gcc tac atg gtt ccc ggt tgg caa gct      7275
Leu Leu Phe Cys His Tyr Ala Tyr Met Val Pro Gly Trp Gln Ala
    2380            2385                2390 gag gca atg cgc tca gcc cag cgg cgg aca gcg gcc gga atc atg      7320
Glu Ala Met Arg Ser Ala Gln Arg Arg Thr Ala Ala Gly Ile Met
    2395            2400                2405 aag aac gct gta gtg gat ggc atc gtg gcc acg gac gtc cca gaa      7365
Lys Asn Ala Val Val Asp Gly Ile Val Ala Thr Asp Val Pro Glu
    2410            2415                2420 tta gag cgc acc aca ccc atc atg cag aag aaa gtt gga cag atc      7410
Leu Glu Arg Thr Thr Pro Ile Met Gln Lys Lys Val Gly Gln Ile
    2425            2430                2435 atg ctg atc ttg gtg tct cta gct gca gta gta gtg aac ccg tct      7455
Met Leu Ile Leu Val Ser Leu Ala Ala Val Val Val Asn Pro Ser
    2440            2445                2450 gtg aag aca gta cga gaa gcc gga att ttg atc acg gcc gca gcg      7500
Val Lys Thr Val Arg Glu Ala Gly Ile Leu Ile Thr Ala Ala Ala
    2455            2460                2465 gtg acg ctt tgg gag aat gga gca agc tct gtt tgg aac gca aca      7545
Val Thr Leu Trp Glu Asn Gly Ala Ser Ser Val Trp Asn Ala Thr
    2470            2475                2480 act gcc atc gga ctc tgc cac atc atg cgt ggg ggt tgg ttg tca      7590
Thr Ala Ile Gly Leu Cys His Ile Met Arg Gly Gly Trp Leu Ser
    2485            2490                2495 tgt cta tcc ata aca tgg aca ctc ata aag aac atg gaa aaa cca      7635
Cys Leu Ser Ile Thr Trp Thr Leu Ile Lys Asn Met Glu Lys Pro
    2500            2505                2510 gga cta aaa aga ggt ggg gca aaa gga cgc acc ttg gga gag gtt      7680
Gly Leu Lys Arg Gly Gly Ala Lys Gly Arg Thr Leu Gly Glu Val
    2515            2520                2525 tgg aaa gaa aga ctc aac cag atg aca aaa gaa gag ttc act agg      7725
Trp Lys Glu Arg Leu Asn Gln Met Thr Lys Glu Glu Phe Thr Arg
    2530            2535                2540 tac cgc aaa gag gcc atc atc gaa gtc gat cgc tca gcg gca aaa      7770
Tyr Arg Lys Glu Ala Ile Ile Glu Val Asp Arg Ser Ala Ala Lys
    2545            2550                2555
```

```
cac gcc agg aaa gaa ggc aat gtc act gga ggg cat cca gtc tct     7815
His Ala Arg Lys Glu Gly Asn Val Thr Gly Gly His Pro Val Ser
    2560                2565                2570 agg ggc aca gca aaa ctg aga tgg ctg gtc gaa cgg agg ttt ctc     7860
Arg Gly Thr Ala Lys Leu Arg Trp Leu Val Glu Arg Arg Phe Leu
    2575                2580                2585 gaa ccg gtc gga aaa gtg att gac ctt gga tgt gga aga ggc ggt     7905
Glu Pro Val Gly Lys Val Ile Asp Leu Gly Cys Gly Arg Gly Gly
    2590                2595                2600 tgg tgt tac tat atg gca acc caa aaa aga gtc caa gaa gtc aga     7950
Trp Cys Tyr Tyr Met Ala Thr Gln Lys Arg Val Gln Glu Val Arg
    2605                2610                2615 ggg tac aca aag ggc ggt ccc gga cat gaa gag ccc caa cta gtg     7995
Gly Tyr Thr Lys Gly Gly Pro Gly His Glu Glu Pro Gln Leu Val
    2620                2625                2630 caa agt tat gga tgg aac att gtc acc atg aag agt gga gtg gat     8040
Gln Ser Tyr Gly Trp Asn Ile Val Thr Met Lys Ser Gly Val Asp
    2635                2640                2645 gtg ttc tac aga cct tct gag tgt tgt gac acc ctc ctt tgt gac     8085
Val Phe Tyr Arg Pro Ser Glu Cys Cys Asp Thr Leu Leu Cys Asp
    2650                2655                2660 atc gga gag tcc tcg tca agt gct gag gtt gaa gag cat agg acg     8130
Ile Gly Glu Ser Ser Ser Ser Ala Glu Val Glu Glu His Arg Thr
    2665                2670                2675 att cgg gtc ctt gaa atg gtt gag gac tgg ctg cac cga ggg cca     8175
Ile Arg Val Leu Glu Met Val Glu Asp Trp Leu His Arg Gly Pro
    2680                2685                2690 agg gaa ttt tgc gtg aag gtg ctc tgc ccc tac atg ccg aaa gtc     8220
Arg Glu Phe Cys Val Lys Val Leu Cys Pro Tyr Met Pro Lys Val
    2695                2700                2705 ata gag aag atg gag ctg ctc caa cgc cgg tat ggg ggg gga ctg     8265
Ile Glu Lys Met Glu Leu Leu Gln Arg Arg Tyr Gly Gly Gly Leu
    2710                2715                2720 gtc aga aac cca ctc tca cgg aat tcc acg cac gag atg tat tgg     8310
Val Arg Asn Pro Leu Ser Arg Asn Ser Thr His Glu Met Tyr Trp
    2725                2730                2735 gtg agt cga gct tca ggc aat gtg gta cat tca gtg aat atg acc     8355
Val Ser Arg Ala Ser Gly Asn Val Val His Ser Val Asn Met Thr
    2740                2745                2750 agc cag gtg ctc cta gga aga atg gaa aaa agg acc tgg aag gga     8400
Ser Gln Val Leu Leu Gly Arg Met Glu Lys Arg Thr Trp Lys Gly
    2755                2760                2765 ccc caa tac gag gaa gat gta aac ttg gga agt gga acc agg gcg     8445
Pro Gln Tyr Glu Glu Asp Val Asn Leu Gly Ser Gly Thr Arg Ala
    2770                2775                2780 gtg gga aaa ccc ctg ctc aac tca gac acc agt aaa atc aag aac     8490
Val Gly Lys Pro Leu Leu Asn Ser Asp Thr Ser Lys Ile Lys Asn
    2785                2790                2795 agg att gaa cga ctc agg cgt gag tac agt tcg acg tgg cac cac     8535
Arg Ile Glu Arg Leu Arg Arg Glu Tyr Ser Ser Thr Trp His His
    2800                2805                2810 gat gag aac cac cca tat aga acc tgg aac tat cac ggc agt tat     8580
Asp Glu Asn His Pro Tyr Arg Thr Trp Asn Tyr His Gly Ser Tyr
    2815                2820                2825 gat gtg aag ccc aca ggc tcc gcc agt tcg ctg gtc aat gga gtg     8625
Asp Val Lys Pro Thr Gly Ser Ala Ser Ser Leu Val Asn Gly Val
    2830                2835                2840 gtc agg ctc ctc tca aaa cca tgg gac acc atc acg aat gtt acc     8670
Val Arg Leu Leu Ser Lys Pro Trp Asp Thr Ile Thr Asn Val Thr
    2845                2850                2855
```

```
acc atg gcc atg act gac act act ccc ttc ggg cag cag cga gtg      8715
Thr Met Ala Met Thr Asp Thr Thr Pro Phe Gly Gln Gln Arg Val
    2860            2865            2870 ttc aaa gag aag gtg gac acg aaa gct cct gaa ccg cca gaa gga      8760
Phe Lys Glu Lys Val Asp Thr Lys Ala Pro Glu Pro Pro Glu Gly
    2875            2880            2885 gtg aag tac gtg ctc aac gag acc acc aac tgg ttg tgg gcg ttt      8805
Val Lys Tyr Val Leu Asn Glu Thr Thr Asn Trp Leu Trp Ala Phe
    2890            2895            2900 ttg gcc aga gaa aaa cgt ccc aga atg tgc tct cga gag gaa ttc      8850
Leu Ala Arg Glu Lys Arg Pro Arg Met Cys Ser Arg Glu Glu Phe
    2905            2910            2915 ata aga aag gtc aac agc aat gca gct ttg ggt gcc atg ttt gaa      8895
Ile Arg Lys Val Asn Ser Asn Ala Ala Leu Gly Ala Met Phe Glu
    2920            2925            2930 gag cag aat caa tgg agg agc gcc aga gaa gca gtt gaa gat cca      8940
Glu Gln Asn Gln Trp Arg Ser Ala Arg Glu Ala Val Glu Asp Pro
    2935            2940            2945 aaa ttt tgg gag atg gtg gat gag gag cgc gag gca cat ctg cgg      8985
Lys Phe Trp Glu Met Val Asp Glu Glu Arg Glu Ala His Leu Arg
    2950            2955            2960 ggg gaa tgt cac act tgc att tac aac atg atg gga aag aga gag      9030
Gly Glu Cys His Thr Cys Ile Tyr Asn Met Met Gly Lys Arg Glu
    2965            2970            2975 aaa aaa ccc gga gag ttc gga aag gcc aag gga agc aga gcc att      9075
Lys Lys Pro Gly Glu Phe Gly Lys Ala Lys Gly Ser Arg Ala Ile
    2980            2985            2990 tgg ttc atg tgg ctc gga gct cgc ttt ctg gag ttc gag gct ctg      9120
Trp Phe Met Trp Leu Gly Ala Arg Phe Leu Glu Phe Glu Ala Leu
    2995            3000            3005 ggt ttt ctc aat gaa gac cac tgg ctt gga aga aag aac tca gga      9165
Gly Phe Leu Asn Glu Asp His Trp Leu Gly Arg Lys Asn Ser Gly
    3010            3015            3020 gga ggt gtc gag ggc ttg ggc ctc caa aaa ctg ggt tac atc ctg      9210
Gly Gly Val Glu Gly Leu Gly Leu Gln Lys Leu Gly Tyr Ile Leu
    3025            3030            3035 cgt gaa gtt ggc acc cgg cct ggg ggc aag atc tat gct gat gac      9255
Arg Glu Val Gly Thr Arg Pro Gly Gly Lys Ile Tyr Ala Asp Asp
    3040            3045            3050 aca gct ggc tgg gac acc cgc atc acg aga gct gac ttg gaa aat      9300
Thr Ala Gly Trp Asp Thr Arg Ile Thr Arg Ala Asp Leu Glu Asn
    3055            3060            3065 gaa gct aag gtg ctt gag ctg ctt gat ggg gaa cat cgg cgt ctt      9345
Glu Ala Lys Val Leu Glu Leu Leu Asp Gly Glu His Arg Arg Leu
    3070            3075            3080 gcc agg gcc atc att gag ctc acc tat cgt cac aaa gtt gtg aaa      9390
Ala Arg Ala Ile Ile Glu Leu Thr Tyr Arg His Lys Val Val Lys
    3085            3090            3095 gtg atg cgc ccg gct gct gat gga aga acc gtc atg gat gtt atc      9435
Val Met Arg Pro Ala Ala Asp Gly Arg Thr Val Met Asp Val Ile
    3100            3105            3110 tcc aga gaa gat cag agg ggg agt gga caa gtt gtc acc tac gcc      9480
Ser Arg Glu Asp Gln Arg Gly Ser Gly Gln Val Val Thr Tyr Ala
    3115            3120            3125 cta aac act ttc acc aac ctg gcc gtc cag ctg gtg agg atg atg      9525
Leu Asn Thr Phe Thr Asn Leu Ala Val Gln Leu Val Arg Met Met
    3130            3135            3140 gaa ggg gaa gga gtg att ggc cca gat gat gtg gag aaa ctc aca      9570
Glu Gly Glu Gly Val Ile Gly Pro Asp Asp Val Glu Lys Leu Thr
    3145            3150            3155
```

```
aaa ggg aaa gga ccc aaa gtc agg acc tgg ctg ttt gag aat ggg    9615
Lys Gly Lys Gly Pro Lys Val Arg Thr Trp Leu Phe Glu Asn Gly
    3160            3165                3170 gaa gaa aga ctc agc cgc atg gct gtc agt gga gat gac tgt gtg    9660
Glu Glu Arg Leu Ser Arg Met Ala Val Ser Gly Asp Asp Cys Val
    3175            3180                3185 gta aag ccc ctg gac gat cgc ttt gcc acc tcg ctc cac ttc ctc    9705
Val Lys Pro Leu Asp Asp Arg Phe Ala Thr Ser Leu His Phe Leu
    3190            3195                3200 aat gct atg tca aag gtt cgc aaa gac atc caa gag tgg aaa ccg    9750
Asn Ala Met Ser Lys Val Arg Lys Asp Ile Gln Glu Trp Lys Pro
    3205            3210                3215 tca act gga tgg tat gat tgg cag cag gtt cca ttt tgc tca aac    9795
Ser Thr Gly Trp Tyr Asp Trp Gln Gln Val Pro Phe Cys Ser Asn
    3220            3225                3230 cat ttc act gaa ttg atc atg aaa gat gga aga aca ctg gtg gtt    9840
His Phe Thr Glu Leu Ile Met Lys Asp Gly Arg Thr Leu Val Val
    3235            3240                3245 cca tgc cga gga cag gat gaa ttg gta ggc aga gct cgc ata tct    9885
Pro Cys Arg Gly Gln Asp Glu Leu Val Gly Arg Ala Arg Ile Ser
    3250            3255                3260 cca ggg gcc gga tgg aac gtc cgc gac act gct tgt ctg gct aag    9930
Pro Gly Ala Gly Trp Asn Val Arg Asp Thr Ala Cys Leu Ala Lys
    3265            3270                3275 tct tat gcc cag atg tgg ctg ctt ctg tac ttc cac aga aga gac    9975
Ser Tyr Ala Gln Met Trp Leu Leu Leu Tyr Phe His Arg Arg Asp
    3280            3285                3290 ctg cgg ctc atg gcc aac gcc att tgc tcc gct gtc cct gtg aat   10020
Leu Arg Leu Met Ala Asn Ala Ile Cys Ser Ala Val Pro Val Asn
    3295            3300                3305 tgg gtc cct acc gga aga acc acg tgg tcc atc cat gca gga gga   10065
Trp Val Pro Thr Gly Arg Thr Thr Trp Ser Ile His Ala Gly Gly
    3310            3315                3320 gag tgg atg aca aca gag gac atg ttg gag gtc tgg aac cgt gtt   10110
Glu Trp Met Thr Thr Glu Asp Met Leu Glu Val Trp Asn Arg Val
    3325            3330                3335 tgg ata gag gag aat gaa tgg atg gaa gac aaa acc cca gtg gag   10155
Trp Ile Glu Glu Asn Glu Trp Met Glu Asp Lys Thr Pro Val Glu
    3340            3345                3350 aaa tgg agt gac gtc cca tat tca gga aaa cga gag gac atc tgg   10200
Lys Trp Ser Asp Val Pro Tyr Ser Gly Lys Arg Glu Asp Ile Trp
    3355            3360                3365 tgt ggc agc ctg att ggc aca aga gcc cga gcc acg tgg gca gaa   10245
Cys Gly Ser Leu Ile Gly Thr Arg Ala Arg Ala Thr Trp Ala Glu
    3370            3375                3380 aac atc cag gtg gct atc aac caa gtc aga gca atc atc gga gat   10290
Asn Ile Gln Val Ala Ile Asn Gln Val Arg Ala Ile Ile Gly Asp
    3385            3390                3395 gag aag tat gtg gat tac atg agt tca cta aag aga tat gaa gac   10335
Glu Lys Tyr Val Asp Tyr Met Ser Ser Leu Lys Arg Tyr Glu Asp
    3400            3405                3410 aca act ttg gtt gag gac aca gta ctg tagatattta atcaattgta     10382
Thr Thr Leu Val Glu Asp Thr Val Leu
    3415            3420 aatagacaat ataagtatgc ataaaagtgt agttttatag tagtatttag tggtgttagt   10442
gtaaatagtt aagaaaattt tgaggagaaa gtcaggccgg gaagttcccg ccaccggaag   10502
ttgagtagac ggtgctgcct gcgactcaac cccaggagga ctgggtgaac aaagccgcga   10562
agtgatccat gtaagccctc agaaccgtct cggaaggagg accccacatg ttgtaacttc   10622
```

-continued

```
aaagcccaat gtcagaccac gctacggcgt gctactctgc ggagagtgca gtctgcgata    10682 gtgcccagg  aggactgggt taacaaaggc aaaccaacgc cccacgcggc cctagccccg    10742
gtaatggtgt taaccagggc gaaaggacta gaggttagag gagaccccgc ggtttaaagt    10802
gcacggccca gcctggctga agctgtaggt caggggaagg actagaggtt agtggagacc    10862
ccgtgccaca aaacaccaca acaaaacagc atattgacac ctgggataga ctaggagatc    10922
ttctgctctg cacaaccagc cacacggcac agtgcgccga caatggtggc tggtggtgcg    10982
agaacacagg atct                                                     10996
```

<210> SEQ ID NO 8
<211> LENGTH: 3422
<212> TYPE: PRT
<213> ORGANISM: Artificial Sequence
<220> FEATURE:
<223> OTHER INFORMATION: Synthetic Construct

<400> SEQUENCE: 8

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Ser Thr Ile Thr Leu Leu Cys
            100                 105                 110

Leu Ile Pro Thr Val Met Ala Phe His Leu Ser Thr Arg Asp Gly Glu
        115                 120                 125

Pro Leu Met Ile Val Ala Lys His Glu Arg Gly Arg Pro Leu Leu Phe
    130                 135                 140

Lys Thr Thr Glu Gly Ile Asn Lys Cys Thr Leu Ile Ala Met Asp Leu
145                 150                 155                 160

Gly Glu Met Cys Glu Asp Thr Val Thr Tyr Lys Cys Pro Leu Leu Val
                165                 170                 175

Asn Thr Glu Pro Glu Asp Ile Asp Cys Trp Cys Asn Leu Thr Ser Thr
            180                 185                 190

Trp Val Met Tyr Gly Thr Cys Thr Gln Ser Gly Glu Arg Arg Arg Glu
        195                 200                 205

Lys Arg Ser Val Ala Leu Thr Pro His Ser Gly Met Gly Leu Glu Thr
    210                 215                 220

Arg Ala Glu Thr Trp Met Ser Ser Glu Gly Ala Trp Lys His Ala Gln
225                 230                 235                 240

Arg Val Glu Ser Trp Ile Leu Arg Asn Pro Gly Phe Ala Leu Leu Ala
                245                 250                 255

Gly Phe Met Ala Tyr Met Ile Gly Gln Thr Gly Ile Gln Arg Thr Val
            260                 265                 270

Phe Phe Val Leu Met Met Leu Val Ala Pro Ser Tyr Gly Met Arg Cys
        275                 280                 285

Val Gly Val Gly Asn Arg Asp Phe Val Glu Gly Val Ser Gly Gly Ala
    290                 295                 300
```

```
Trp Val Asp Leu Val Leu Glu His Gly Gly Cys Val Thr Thr Met Ala
305                 310                 315                 320

Gln Gly Lys Pro Thr Leu Asp Phe Glu Leu Thr Lys Thr Thr Ala Lys
                325                 330                 335

Glu Val Ala Leu Leu Arg Thr Tyr Cys Ile Glu Ala Ser Ile Ser Asn
            340                 345                 350

Ile Thr Thr Ala Thr Arg Cys Pro Thr Gln Gly Glu Pro Tyr Leu Lys
        355                 360                 365

Glu Glu Gln Asp Gln Gln Tyr Ile Cys Arg Arg Asp Val Val Asp Arg
370                 375                 380

Gly Trp Gly Asn Gly Cys Gly Leu Phe Gly Lys Gly Val Val Thr
385                 390                 395                 400

Cys Ala Lys Phe Ser Cys Ser Gly Lys Ile Thr Gly Asn Leu Val Gln
                405                 410                 415

Ile Glu Asn Leu Glu Tyr Thr Val Val Val Thr Val His Asn Gly Asp
            420                 425                 430

Thr His Ala Val Gly Asn Asp Thr Ser Asn His Gly Val Thr Ala Thr
        435                 440                 445

Ile Thr Pro Arg Ser Pro Ser Val Glu Val Lys Leu Pro Asp Tyr Gly
450                 455                 460

Glu Leu Thr Leu Asp Cys Glu Pro Arg Ser Gly Ile Asp Phe Asn Glu
465                 470                 475                 480

Met Ile Leu Met Lys Met Lys Lys Thr Trp Leu Val His Lys Gln
                485                 490                 495

Trp Phe Leu Asp Leu Pro Leu Pro Trp Thr Ala Gly Ala Asp Thr Ser
                500                 505                 510

Glu Val His Trp Asn Tyr Lys Glu Arg Met Val Thr Phe Lys Val Pro
        515                 520                 525

His Ala Lys Arg Gln Asp Val Thr Val Leu Gly Ser Gln Glu Gly Ala
                530                 535                 540

Met His Ser Ala Leu Ala Gly Ala Thr Glu Val Asp Ser Gly Asp Gly
545                 550                 555                 560

Asn His Met Phe Ala Gly His Leu Lys Cys Lys Val Arg Met Glu Lys
                565                 570                 575

Leu Arg Ile Lys Gly Met Ser Tyr Thr Met Cys Ser Gly Lys Phe Ser
                580                 585                 590

Ile Asp Lys Glu Met Ala Glu Thr Gln His Gly Thr Thr Val Val Lys
            595                 600                 605

Val Lys Tyr Glu Gly Ala Gly Ala Pro Cys Lys Val Pro Ile Glu Ile
        610                 615                 620

Arg Asp Val Asn Lys Glu Lys Val Val Gly Arg Ile Ile Ser Ser Thr
625                 630                 635                 640

Pro Leu Ala Glu Asn Thr Asn Ser Ala Thr Asn Ile Glu Leu Glu Pro
                645                 650                 655

Pro Phe Gly Asp Ser Tyr Ile Val Ile Gly Val Gly Asn Ser Ala Leu
            660                 665                 670

Thr Leu His Trp Phe Arg Lys Gly Ser Ser Ile Gly Lys Met Phe Glu
        675                 680                 685

Ser Thr Tyr Arg Gly Ala Lys Arg Met Ala Ile Leu Gly Glu Thr Ala
        690                 695                 700

Trp Asp Phe Gly Ser Val Gly Gly Leu Phe Thr Ser Leu Gly Lys Ala
705                 710                 715                 720

Val His Gln Val Phe Gly Ser Val Tyr Thr Thr Met Phe Gly Gly Val
                725                 730                 735
```

-continued

```
Ser Trp Met Ile Arg Ile Leu Ile Gly Phe Leu Val Leu Trp Ile Gly
            740                 745                 750

Thr Asn Ser Arg Asn Thr Ser Met Ala Met Thr Cys Ile Ala Val Gly
            755                 760                 765

Gly Ile Thr Leu Phe Leu Gly Phe Thr Val Gln Ala Asp Ser Gly Cys
770                 775                 780

Ala Ile Asp Ile Ser Arg Gln Glu Leu Arg Cys Gly Ser Gly Val Phe
785                 790                 795                 800

Ile His Asn Asp Val Glu Ala Trp Met Asp Arg Tyr Lys Tyr Tyr Pro
            805                 810                 815

Glu Thr Pro Gln Gly Leu Ala Lys Ile Ile Gln Lys Ala His Lys Glu
            820                 825                 830

Gly Val Cys Gly Leu Arg Ser Val Ser Arg Leu Glu His Gln Met Trp
            835                 840                 845

Glu Ala Val Lys Asp Glu Leu Asn Thr Leu Leu Lys Glu Asn Gly Val
            850                 855                 860

Asp Leu Ser Val Val Glu Lys Gln Glu Gly Met Tyr Lys Ser Ala
865                 870                 875                 880

Pro Lys Arg Leu Thr Ala Thr Thr Glu Lys Leu Glu Ile Gly Trp Lys
            885                 890                 895

Ala Trp Gly Lys Ser Ile Leu Phe Ala Pro Glu Leu Ala Asn Asn Thr
            900                 905                 910

Phe Val Val Asp Gly Pro Glu Thr Lys Glu Cys Pro Thr Gln Asn Arg
            915                 920                 925

Ala Trp Asn Ser Leu Glu Val Glu Asp Phe Gly Phe Gly Leu Thr Ser
            930                 935                 940

Thr Arg Met Phe Leu Lys Val Arg Glu Ser Asn Thr Thr Glu Cys Asp
945                 950                 955                 960

Ser Lys Ile Ile Gly Thr Ala Val Lys Asn Asn Leu Ala Ile His Ser
            965                 970                 975

Asp Leu Ser Tyr Trp Ile Glu Ser Arg Leu Asn Asp Thr Trp Lys Leu
            980                 985                 990

Glu Arg Ala Val Leu Gly Glu Val Lys Ser Cys Thr Trp Pro Glu Thr
            995                 1000                1005

His Thr Leu Trp Gly Asp Gly Ile Leu Glu Ser Asp Leu Ile Ile
    1010                1015                    1020

Pro Val Thr Leu Ala Gly Pro Arg Ser Asn His Asn Arg Arg Pro
    1025                1030                    1035

Gly Tyr Lys Thr Gln Asn Gln Gly Pro Trp Asp Glu Gly Arg Val
    1040                1045                    1050

Glu Ile Asp Phe Asp Tyr Cys Pro Gly Thr Thr Val Thr Leu Ser
    1055                1060                    1065

Glu Ser Cys Gly His Arg Gly Pro Ala Thr Arg Thr Thr Thr Glu
    1070                1075                    1080

Ser Gly Lys Leu Ile Thr Asp Trp Cys Cys Arg Ser Cys Thr Leu
    1085                1090                    1095

Pro Pro Leu Arg Tyr Gln Thr Asp Ser Gly Cys Trp Tyr Gly Met
    1100                1105                    1110

Glu Ile Arg Pro Gln Arg His Asp Glu Lys Thr Leu Val Gln Ser
    1115                1120                    1125

Gln Val Asn Ala Tyr Asn Ala Asp Met Ile Asp Pro Phe Gln Leu
    1130                1135                    1140

Gly Leu Leu Val Val Phe Leu Ala Thr Gln Glu Val Leu Arg Lys
    1145                1150                    1155
```

```
Arg Trp Thr Ala Lys Ile Ser Met Pro Ala Ile Leu Ile Ala Leu
1160                1165                1170

Leu Val Leu Val Phe Gly Ile Thr Tyr Thr Asp Val Leu Arg
1175                1180                1185

Tyr Val Ile Leu Val Gly Ala Ala Phe Ala Glu Ser Asn Ser Gly
1190                1195                1200

Gly Asp Val Val His Leu Ala Leu Met Ala Thr Phe Lys Ile Gln
1205                1210                1215

Pro Val Phe Met Val Ala Ser Phe Leu Lys Ala Arg Trp Thr Asn
1220                1225                1230

Gln Glu Asn Ile Leu Leu Met Leu Ala Ala Val Phe Phe Gln Met
1235                1240                1245

Ala Tyr Tyr Asp Ala Arg Gln Ile Leu Leu Trp Glu Ile Pro Asp
1250                1255                1260

Val Leu Asn Ser Leu Ala Val Ala Trp Met Ile Leu Arg Ala Ile
1265                1270                1275

Thr Phe Thr Thr Thr Ser Asn Val Val Pro Leu Leu Ala Leu
1280                1285                1290

Leu Thr Pro Gly Leu Arg Cys Leu Asn Leu Asp Val Tyr Arg Ile
1295                1300                1305

Leu Leu Leu Met Val Gly Ile Gly Ser Leu Ile Arg Glu Lys Arg
1310                1315                1320

Ser Ala Ala Ala Lys Lys Lys Gly Ala Ser Leu Leu Cys Leu Ala
1325                1330                1335

Leu Ala Ser Thr Gly Leu Phe Asn Pro Met Ile Leu Ala Ala Gly
1340                1345                1350

Leu Ile Ala Cys Asp Pro Asn Arg Lys Arg Gly Trp Pro Ala Thr
1355                1360                1365

Glu Val Met Thr Ala Val Gly Leu Met Phe Ala Ile Val Gly Gly
1370                1375                1380

Leu Ala Glu Leu Asp Ile Asp Ser Met Ala Ile Pro Met Thr Ile
1385                1390                1395

Ala Gly Leu Met Phe Ala Ala Phe Val Ile Ser Gly Lys Ser Thr
1400                1405                1410

Asp Met Trp Ile Glu Arg Thr Ala Asp Ile Ser Trp Glu Ser Asp
1415                1420                1425

Ala Glu Ile Thr Gly Ser Ser Glu Arg Val Asp Val Arg Leu Asp
1430                1435                1440

Asp Asp Gly Asn Phe Gln Leu Met Asn Asp Pro Gly Ala Pro Trp
1445                1450                1455

Lys Ile Trp Met Leu Arg Met Val Cys Leu Ala Ile Ser Ala Tyr
1460                1465                1470

Thr Pro Trp Ala Ile Leu Pro Ser Val Val Gly Phe Trp Ile Thr
1475                1480                1485

Leu Gln Tyr Thr Lys Arg Gly Gly Val Leu Trp Asp Thr Pro Ser
1490                1495                1500

Pro Lys Glu Tyr Lys Lys Gly Asp Thr Thr Thr Gly Val Tyr Arg
1505                1510                1515

Ile Met Thr Arg Gly Leu Leu Gly Ser Tyr Gln Ala Gly Ala Gly
1520                1525                1530

Val Met Val Glu Gly Val Phe His Thr Leu Trp His Thr Thr Lys
1535                1540                1545

Gly Ala Ala Leu Met Ser Gly Glu Gly Arg Leu Asp Pro Tyr Trp
1550                1555                1560
```

```
Gly Ser Val Lys Glu Asp Arg Leu Cys Tyr Gly Gly Pro Trp Lys
    1565                1570                1575

Leu Gln His Lys Trp Asn Gly Gln Asp Glu Val Gln Met Ile Val
    1580                1585                1590

Val Glu Pro Gly Arg Asn Val Lys Asn Val Gln Thr Lys Pro Gly
    1595                1600                1605

Val Phe Lys Thr Pro Glu Gly Glu Ile Gly Ala Val Thr Leu Asp
    1610                1615                1620

Phe Pro Thr Gly Thr Ser Gly Ser Pro Ile Val Asp Lys Asn Gly
    1625                1630                1635

Asp Val Ile Gly Leu Tyr Gly Asn Gly Val Ile Met Pro Asn Gly
    1640                1645                1650

Ser Tyr Ile Ser Ala Ile Val Gln Gly Glu Arg Met Asp Glu Pro
    1655                1660                1665

Ile Pro Ala Gly Phe Glu Pro Glu Met Leu Arg Lys Lys Gln Ile
    1670                1675                1680

Thr Val Leu Asp Leu His Pro Gly Ala Gly Lys Thr Arg Arg Ile
    1685                1690                1695

Leu Pro Gln Ile Ile Lys Glu Ala Ile Asn Arg Arg Leu Arg Thr
    1700                1705                1710

Ala Val Leu Ala Pro Thr Arg Val Val Ala Ala Glu Met Ala Glu
    1715                1720                1725

Ala Leu Arg Gly Leu Pro Ile Arg Tyr Gln Thr Ser Ala Val Pro
    1730                1735                1740

Arg Glu His Asn Gly Asn Glu Ile Val Asp Val Met Cys His Ala
    1745                1750                1755

Thr Leu Thr His Arg Leu Met Ser Pro His Arg Val Pro Asn Tyr
    1760                1765                1770

Asn Leu Phe Val Met Asp Glu Ala His Phe Thr Asp Pro Ala Ser
    1775                1780                1785

Ile Ala Ala Arg Gly Tyr Ile Ser Thr Lys Val Glu Leu Gly Glu
    1790                1795                1800

Ala Ala Ala Ile Phe Met Thr Ala Thr Pro Pro Gly Thr Ser Asp
    1805                1810                1815

Pro Phe Pro Glu Ser Asn Ser Pro Ile Ser Asp Leu Gln Thr Glu
    1820                1825                1830

Ile Pro Asp Arg Ala Trp Asn Ser Gly Tyr Glu Trp Ile Thr Glu
    1835                1840                1845

Tyr Thr Gly Lys Thr Val Trp Phe Val Pro Ser Val Lys Met Gly
    1850                1855                1860

Asn Glu Ile Ala Leu Cys Leu Gln Arg Ala Gly Lys Lys Val Val
    1865                1870                1875

Gln Leu Asn Arg Lys Ser Tyr Glu Thr Glu Tyr Pro Lys Cys Lys
    1880                1885                1890

Asn Asp Asp Trp Asp Phe Val Ile Thr Thr Asp Ile Ser Glu Met
    1895                1900                1905

Gly Ala Asn Phe Lys Ala Ser Arg Val Ile Asp Ser Arg Lys Ser
    1910                1915                1920

Val Lys Pro Thr Ile Ile Thr Glu Gly Glu Gly Arg Val Ile Leu
    1925                1930                1935

Gly Glu Pro Ser Ala Val Thr Ala Ala Ser Ala Ala Gln Arg Arg
    1940                1945                1950

Gly Arg Ile Gly Arg Asn Pro Ser Gln Val Gly Asp Glu Tyr Cys
    1955                1960                1965
```

-continued

Tyr Gly Gly His Thr Asn Glu Asp Asp Ser Asn Phe Ala His Trp
1970                1975                1980

Thr Glu Ala Arg Ile Met Leu Asp Asn Ile Asn Met Pro Asn Gly
1985                1990                1995

Leu Ile Ala Gln Phe Tyr Gln Pro Glu Arg Glu Lys Val Tyr Thr
2000                2005                2010

Met Asp Gly Glu Tyr Arg Leu Arg Gly Glu Glu Arg Lys Asn Phe
2015                2020                2025

Leu Glu Leu Leu Arg Thr Ala Asp Leu Pro Val Trp Leu Ala Tyr
2030                2035                2040

Lys Val Ala Ala Ala Gly Val Ser Tyr His Asp Arg Arg Trp Cys
2045                2050                2055

Phe Asp Gly Pro Arg Thr Asn Thr Ile Leu Glu Asp Asn Asn Glu
2060                2065                2070

Val Glu Val Ile Thr Lys Leu Gly Glu Arg Lys Ile Leu Arg Pro
2075                2080                2085

Arg Trp Ile Asp Ala Arg Val Tyr Ser Asp His Gln Ala Leu Lys
2090                2095                2100

Ala Phe Lys Asp Phe Ala Ser Gly Lys Arg Ser Gln Ile Gly Leu
2105                2110                2115

Ile Glu Val Leu Gly Lys Met Pro Glu His Phe Met Gly Lys Thr
2120                2125                2130

Trp Glu Ala Leu Asp Thr Met Tyr Val Val Ala Thr Ala Glu Lys
2135                2140                2145

Gly Gly Arg Ala His Arg Met Ala Leu Glu Glu Leu Pro Asp Ala
2150                2155                2160

Leu Gln Thr Ile Ala Leu Ile Ala Leu Leu Ser Val Met Thr Met
2165                2170                2175

Gly Val Phe Phe Leu Leu Met Gln Arg Lys Gly Ile Gly Lys Ile
2180                2185                2190

Gly Leu Gly Gly Ala Val Leu Gly Val Ala Thr Phe Phe Cys Trp
2195                2200                2205

Met Ala Glu Val Pro Gly Thr Lys Ile Ala Gly Met Leu Leu Leu
2210                2215                2220

Ser Leu Leu Leu Met Ile Val Leu Ile Pro Glu Pro Glu Lys Gln
2225                2230                2235

Arg Ser Gln Thr Asp Asn Gln Leu Ala Val Phe Leu Ile Cys Val
2240                2245                2250

Met Thr Leu Val Ser Ala Val Ala Ala Asn Glu Met Gly Trp Leu
2255                2260                2265

Asp Lys Thr Lys Ser Asp Ile Ser Ser Leu Phe Gly Gln Arg Ile
2270                2275                2280

Glu Val Lys Glu Asn Phe Ser Met Gly Glu Phe Leu Leu Asp Leu
2285                2290                2295

Arg Pro Ala Thr Ala Trp Ser Leu Tyr Ala Val Thr Thr Ala Val
2300                2305                2310

Leu Thr Pro Leu Leu Lys His Leu Ile Thr Ser Asp Tyr Ile Asn
2315                2320                2325

Thr Ser Leu Thr Ser Ile Asn Val Gln Ala Ser Ala Leu Phe Thr
2330                2335                2340

Leu Ala Arg Gly Phe Pro Phe Val Asp Val Gly Val Ser Ala Leu
2345                2350                2355

Leu Leu Ala Ala Gly Cys Trp Gly Gln Val Thr Leu Thr Val Thr
2360                2365                2370

```
Val Thr Ala Ala Thr Leu Leu Phe Cys His Tyr Ala Tyr Met Val
2375                2380                2385

Pro Gly Trp Gln Ala Glu Ala Met Arg Ser Ala Gln Arg Arg Thr
2390                2395                2400

Ala Ala Gly Ile Met Lys Asn Ala Val Val Asp Gly Ile Val Ala
2405                2410                2415

Thr Asp Val Pro Glu Leu Glu Arg Thr Thr Pro Ile Met Gln Lys
2420                2425                2430

Lys Val Gly Gln Ile Met Leu Ile Leu Val Ser Leu Ala Ala Val
2435                2440                2445

Val Val Asn Pro Ser Val Lys Thr Val Arg Glu Ala Gly Ile Leu
2450                2455                2460

Ile Thr Ala Ala Ala Val Thr Leu Trp Glu Asn Gly Ala Ser Ser
2465                2470                2475

Val Trp Asn Ala Thr Thr Ala Ile Gly Leu Cys His Ile Met Arg
2480                2485                2490

Gly Gly Trp Leu Ser Cys Leu Ser Ile Thr Trp Thr Leu Ile Lys
2495                2500                2505

Asn Met Glu Lys Pro Gly Leu Lys Arg Gly Gly Ala Lys Gly Arg
2510                2515                2520

Thr Leu Gly Glu Val Trp Lys Glu Arg Leu Asn Gln Met Thr Lys
2525                2530                2535

Glu Glu Phe Thr Arg Tyr Arg Lys Glu Ala Ile Ile Glu Val Asp
2540                2545                2550

Arg Ser Ala Ala Lys His Ala Arg Lys Glu Gly Asn Val Thr Gly
2555                2560                2565

Gly His Pro Val Ser Arg Gly Thr Ala Lys Leu Arg Trp Leu Val
2570                2575                2580

Glu Arg Arg Phe Leu Glu Pro Val Gly Lys Val Ile Asp Leu Gly
2585                2590                2595

Cys Gly Arg Gly Gly Trp Cys Tyr Tyr Met Ala Thr Gln Lys Arg
2600                2605                2610

Val Gln Glu Val Arg Gly Tyr Thr Lys Gly Gly Pro Gly His Glu
2615                2620                2625

Glu Pro Gln Leu Val Gln Ser Tyr Gly Trp Asn Ile Val Thr Met
2630                2635                2640

Lys Ser Gly Val Asp Val Phe Tyr Arg Pro Ser Glu Cys Cys Asp
2645                2650                2655

Thr Leu Leu Cys Asp Ile Gly Glu Ser Ser Ser Ala Glu Val
2660                2665                2670

Glu Glu His Arg Thr Ile Arg Val Leu Glu Met Val Glu Asp Trp
2675                2680                2685

Leu His Arg Gly Pro Arg Glu Phe Cys Val Lys Val Leu Cys Pro
2690                2695                2700

Tyr Met Pro Lys Val Ile Glu Lys Met Glu Leu Leu Gln Arg Arg
2705                2710                2715

Tyr Gly Gly Gly Leu Val Arg Asn Pro Leu Ser Arg Asn Ser Thr
2720                2725                2730

His Glu Met Tyr Trp Val Ser Arg Ala Ser Gly Asn Val Val His
2735                2740                2745

Ser Val Asn Met Thr Ser Gln Val Leu Leu Gly Arg Met Glu Lys
2750                2755                2760

Arg Thr Trp Lys Gly Pro Gln Tyr Glu Glu Asp Val Asn Leu Gly
2765                2770                2775
```

```
Ser Gly Thr Arg Ala Val Gly Lys Pro Leu Leu Asn Ser Asp Thr
    2780            2785                2790

Ser Lys Ile Lys Asn Arg Ile Glu Arg Leu Arg Arg Glu Tyr Ser
    2795            2800                2805

Ser Thr Trp His His Asp Glu Asn His Pro Tyr Arg Thr Trp Asn
    2810            2815                2820

Tyr His Gly Ser Tyr Asp Val Lys Pro Thr Gly Ser Ala Ser Ser
    2825            2830                2835

Leu Val Asn Gly Val Val Arg Leu Leu Ser Lys Pro Trp Asp Thr
    2840            2845                2850

Ile Thr Asn Val Thr Thr Met Ala Met Thr Asp Thr Thr Pro Phe
    2855            2860                2865

Gly Gln Gln Arg Val Phe Lys Glu Lys Val Asp Thr Lys Ala Pro
    2870            2875                2880

Glu Pro Pro Glu Gly Val Lys Tyr Val Leu Asn Glu Thr Thr Asn
    2885            2890                2895

Trp Leu Trp Ala Phe Leu Ala Arg Glu Lys Arg Pro Arg Met Cys
    2900            2905                2910

Ser Arg Glu Glu Phe Ile Arg Lys Val Asn Ser Asn Ala Ala Leu
    2915            2920                2925

Gly Ala Met Phe Glu Glu Gln Asn Gln Trp Arg Ser Ala Arg Glu
    2930            2935                2940

Ala Val Glu Asp Pro Lys Phe Trp Glu Met Val Asp Glu Glu Arg
    2945            2950                2955

Glu Ala His Leu Arg Gly Glu Cys His Thr Cys Ile Tyr Asn Met
    2960            2965                2970

Met Gly Lys Arg Glu Lys Lys Pro Gly Glu Phe Gly Lys Ala Lys
    2975            2980                2985

Gly Ser Arg Ala Ile Trp Phe Met Trp Leu Gly Ala Arg Phe Leu
    2990            2995                3000

Glu Phe Glu Ala Leu Gly Phe Leu Asn Glu Asp His Trp Leu Gly
    3005            3010                3015

Arg Lys Asn Ser Gly Gly Gly Val Glu Gly Leu Gly Leu Gln Lys
    3020            3025                3030

Leu Gly Tyr Ile Leu Arg Glu Val Gly Thr Arg Pro Gly Gly Lys
    3035            3040                3045

Ile Tyr Ala Asp Asp Thr Ala Gly Trp Asp Thr Arg Ile Thr Arg
    3050            3055                3060

Ala Asp Leu Glu Asn Glu Ala Lys Val Leu Glu Leu Leu Asp Gly
    3065            3070                3075

Glu His Arg Arg Leu Ala Arg Ala Ile Ile Glu Leu Thr Tyr Arg
    3080            3085                3090

His Lys Val Val Lys Val Met Arg Pro Ala Ala Asp Gly Arg Thr
    3095            3100                3105

Val Met Asp Val Ile Ser Arg Glu Asp Gln Arg Gly Ser Gly Gln
    3110            3115                3120

Val Val Thr Tyr Ala Leu Asn Thr Phe Thr Asn Leu Ala Val Gln
    3125            3130                3135

Leu Val Arg Met Met Glu Gly Glu Gly Val Ile Gly Pro Asp Asp
    3140            3145                3150

Val Glu Lys Leu Thr Lys Gly Lys Gly Pro Lys Val Arg Thr Trp
    3155            3160                3165

Leu Phe Glu Asn Gly Glu Glu Arg Leu Ser Arg Met Ala Val Ser
    3170            3175                3180
```

```
Gly  Asp  Asp  Cys  Val  Val  Lys  Pro  Leu  Asp  Asp  Arg  Phe  Ala  Thr
     3185                3190                     3195

Ser  Leu  His  Phe  Leu  Asn  Ala  Met  Ser  Lys  Val  Arg  Lys  Asp  Ile
     3200                3205                     3210

Gln  Glu  Trp  Lys  Pro  Ser  Thr  Gly  Trp  Tyr  Asp  Trp  Gln  Gln  Val
     3215                3220                     3225

Pro  Phe  Cys  Ser  Asn  His  Phe  Thr  Glu  Leu  Ile  Met  Lys  Asp  Gly
     3230                3235                     3240

Arg  Thr  Leu  Val  Val  Pro  Cys  Arg  Gly  Gln  Asp  Glu  Leu  Val  Gly
     3245                3250                     3255

Arg  Ala  Arg  Ile  Ser  Pro  Gly  Ala  Gly  Trp  Asn  Val  Arg  Asp  Thr
     3260                3265                     3270

Ala  Cys  Leu  Ala  Lys  Ser  Tyr  Ala  Gln  Met  Trp  Leu  Leu  Leu  Tyr
     3275                3280                     3285

Phe  His  Arg  Arg  Asp  Leu  Arg  Leu  Met  Ala  Asn  Ala  Ile  Cys  Ser
     3290                3295                     3300

Ala  Val  Pro  Val  Asn  Trp  Val  Pro  Thr  Gly  Arg  Thr  Thr  Trp  Ser
     3305                3310                     3315

Ile  His  Ala  Gly  Gly  Glu  Trp  Met  Thr  Thr  Glu  Asp  Met  Leu  Glu
     3320                3325                     3330

Val  Trp  Asn  Arg  Val  Trp  Ile  Glu  Glu  Asn  Glu  Trp  Met  Glu  Asp
     3335                3340                     3345

Lys  Thr  Pro  Val  Glu  Lys  Trp  Ser  Asp  Val  Pro  Tyr  Ser  Gly  Lys
     3350                3355                     3360

Arg  Glu  Asp  Ile  Trp  Cys  Gly  Ser  Leu  Ile  Gly  Thr  Arg  Ala  Arg
     3365                3370                     3375

Ala  Thr  Trp  Ala  Glu  Asn  Ile  Gln  Val  Ala  Ile  Asn  Gln  Val  Arg
     3380                3385                     3390

Ala  Ile  Ile  Gly  Asp  Glu  Lys  Tyr  Val  Asp  Tyr  Met  Ser  Ser  Leu
     3395                3400                     3405

Lys  Arg  Tyr  Glu  Asp  Thr  Thr  Leu  Val  Glu  Asp  Thr  Val  Leu
     3410                3415                     3420

<210> SEQ ID NO 9
<211> LENGTH: 75
<212> TYPE: DNA
<213> ORGANISM: Artificial Sequence
<220> FEATURE:
<223> OTHER INFORMATION: Dengue 2 virus C protien/prM protein junction
<220> FEATURE:
<221> NAME/KEY: CDS
<222> LOCATION: (1)..(75)

<400> SEQUENCE: 9 aga  cgc  aga  tct  gca  ggc  atg  atc  att  atg  ctg  att  cca  aca  gtg  atg      48
Arg  Arg  Arg  Ser

```
<400> SEQUENCE: 10

Arg Arg Arg Ser Ala Gly Met Ile Ile Met Leu Ile Pro Thr Val Met
1               5                   10                  15

Ala Phe His Leu Thr Thr Arg Asn Gly
            20                  25

<210> SEQ ID NO 11
<211> LENGTH: 75
<212> TYPE: DNA
<213> ORGANISM: Artificial Sequence
<220> FEATURE:
<223> OTHER INFORMATION: West Nile virus/Dengue 2 virus chimera C
      protein/prM protein junction
<220> FEATURE:
<221> NAME/KEY: CDS
<222> LOCATION: (1)..(75)

<400> SEQUENCE: 11 aag aaa aga tcc gcg ggc atg atc att atg ctg att cca aca gtg atg      48
Lys Lys Arg Ser Ala Gly Met Ile Ile Met Leu Ile Pro Thr Val Met
1               5                   10                  15 gcg ttc cat tta acc aca cgt aac gga                                  75
Ala Phe His Leu Thr Thr Arg Asn Gly
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Lys Lys Arg Ser Ala Gly Met Ile Ile Met Leu Ile Pro Thr Val Met
1               5                   10                  15

Ala Phe His Leu Thr Thr Arg Asn Gly
            20                  25

<210> SEQ ID NO 13
<211> LENGTH: 87
<212> TYPE: DNA
<213> ORGANISM: Artificial Sequence
<220> FEATURE:
<223> OTHER INFORMATION: West Nile virus C protein/prM protein junction
<220> FEATURE:
<221> NAME/KEY: CDS
<222> LOCATION: (1)..(87)

<400> SEQUENCE: 13 aag aaa aga gga gga aag acc gga att gca gtc atg att ggc ctg atc      48
Lys Lys Arg Gly Gly Lys Thr Gly Ile Ala Val Met Ile Gly Leu Ile
1               5                   10                  15 gcc agc gta gga gca gtt acc ctc tct aac ttc caa ggg                  87
Ala Ser Val Gly Ala Val Thr Leu Ser Asn Phe Gln Gly
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic Construct
```

```
<400> SEQUENCE: 14

Lys Lys Arg Gly Gly Lys Thr Gly Ile Ala Val Met Ile Gly Leu Ile
1               5                   10                  15

Ala Ser Val Gly Ala Val Thr Leu Ser Asn Phe Gln Gly
            20                  25

<210> SEQ ID NO 15
<211> LENGTH: 75
<212> TYPE: DNA
<213> ORGANISM: Artificial Sequence
<220> FEATURE:
<223> OTHER INFORMATION: West Nile virus/Dengue 1 virus chimera C
      protein/prM protein junction
<220> FEATURE:
<221> NAME/KEY: CDS
<222> LOCATION: (1)..(75)

<400> SEQUENCE: 15 aag aaa aga tcc gtg acc atg ctc ctt atg ctg ctg ccc aca gcc ctg       48
Lys Lys Arg Ser Val Thr Met Leu Leu Met Leu Leu Pro Thr Ala Leu
1               5                   10                  15 gcg ttc cat ctg acg aca cga ggg gga                                   75
Ala Phe His Leu Thr Thr Arg Gly Gly
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct

<400> SEQUENCE: 16

Lys Lys Arg Ser Val Thr Met Leu Leu Met Leu Leu Pro Thr Ala Leu
1               5                   10                  15

Ala Phe His Leu Thr Thr Arg Gly Gly
            20                  25

<210> SEQ ID NO 17
<211> LENGTH: 75
<212> TYPE: DNA
<213> ORGANISM: Artificial Sequence
<220> FEATURE:
<223> OTHER INFORMATION: West Nile virus/Dengue 3 virus chimera C
      protein/prM protein chimera
<220> FEATURE:
<221> NAME/KEY: CDS
<222> LOCATION: (1)..(75)

<400> SEQUENCE: 17 aag aaa aga aca tcg ctc tgt ctc atg atg atg tta cca gca aca ctt       48
Lys Lys Arg Thr Ser Leu Cys Leu Met Met Met Leu Pro Ala Thr Leu
1               5                   10                  15 gct ttc cac tta act tca cga gat gga                                   75
Ala Phe His Leu Thr Ser Arg Asp Gly
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Construct
```

```
<400> SEQUENCE: 18

Lys Lys Arg Thr Ser Leu Cys Leu Met Met Met Leu Pro Ala Thr Leu
1               5                   10                  15

Ala Phe His Leu Thr Ser Arg Asp Gly
            20                  25

<210> SEQ ID NO 19
<211> LENGTH: 75
<212> TYPE: DNA
<213> ORGANISM: Artificial Sequence
<220> FEATURE:
<223> OTHER INFORMATION: West Nile virus/Dengue 4 virus C protein/prM
      protein junction
<220> FEATURE:
<221> NAME/KEY: CDS
<222> LOCATION: (1)..(75)

<400> SEQUENCE: 19 aag aaa aga tca acg ata aca ttg ctg tgc ttg att ccc acc gta atg     48
Lys Lys Arg Ser Thr Ile Thr Leu Leu Cys Leu Ile Pro Thr Val Met
1               5                   10                  15 gcg ttt cac ttg tca aca aga gat ggc                                 75
Ala Phe His Leu Ser Thr Arg Asp Gly
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Lys Lys Arg Ser Thr Ile Thr Leu Leu Cys Leu Ile Pro Thr Val Met
1               5                   10                  15

Ala Phe His Leu Ser Thr Arg Asp Gly
            20                  25
```